US011312990B2

(12) United States Patent
Abate et al.

(10) Patent No.: US 11,312,990 B2
(45) Date of Patent: *Apr. 26, 2022

(54) PCR-ACTIVATED SORTING (PAS)

(71) Applicant: The Regents of the University of California, Oakland, CA (US)

(72) Inventors: Adam R. Abate, San Francisco, CA (US); Dennis Jay Eastburn, Burlingame, CA (US); Adam R. Sciambi, San Francisco, CA (US); Shaun Lim, Singapore (SG)

(73) Assignee: The Regents of the University of California, Oakland, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/856,343

(22) Filed: Apr. 23, 2020

(65) Prior Publication Data
US 2021/0002697 A1 Jan. 7, 2021

Related U.S. Application Data

(63) Continuation of application No. 15/317,393, filed as application No. PCT/US2015/037822 on Jun. 25, 2015, now Pat. No. 10,697,007.

(60) Provisional application No. 62/018,400, filed on Jun. 27, 2014.

(51) Int. Cl.
| *C12Q 1/686* | (2018.01) |
| *C12Q 1/70* | (2006.01) |
| *C12Q 1/689* | (2018.01) |
| *C12Q 1/6886* | (2018.01) |

(52) U.S. Cl.
CPC ............ *C12Q 1/686* (2013.01); *C12Q 1/689* (2013.01); *C12Q 1/6886* (2013.01); *C12Q 1/70* (2013.01); *C12Q 2600/156* (2013.01); *C12Q 2600/158* (2013.01)

(58) Field of Classification Search
CPC . C12Q 1/686; C12Q 1/6886; C12Q 2600/156
See application file for complete search history.

(56) References Cited

U.S. PATENT DOCUMENTS

| 7,638,276 | B2 | 12/2009 | Griffiths et al. |
| RE41,780 | E | 9/2010 | Anderson et al. |
| 8,067,159 | B2 | 11/2011 | Brown et al. |
| 8,257,925 | B2 | 9/2012 | Brown et al. |
| 8,765,485 | B2 | 7/2014 | Link et al. |
| 9,150,852 | B2 | 10/2015 | Samuels et al. |
| 10,161,007 | B2 | 12/2018 | Abate et al. |
| 10,745,762 | B2 | 8/2020 | Abate et al. |
| 2002/0086042 | A1 | 7/2002 | Delrieu et al. |
| 2003/0156993 | A1 | 8/2003 | Staats |
| 2003/0180737 | A1 | 9/2003 | Gu et al. |
| 2005/0019902 | A1 | 1/2005 | Mathies et al. |
| 2005/0112639 | A1 | 5/2005 | Wang et al. |
| 2005/0172476 | A1 | 8/2005 | Stone et al. |
| 2007/0039866 | A1 | 2/2007 | Schroeder et al. |
| 2007/0077572 | A1 | 4/2007 | Tawfik et al. |
| 2007/0141593 | A1 | 6/2007 | Lee et al. |
| 2007/0231880 | A1 | 10/2007 | Chang-yen et al. |
| 2008/0014589 | A1 | 1/2008 | Link et al. |
| 2009/0045064 | A1 | 2/2009 | Simmons et al. |
| 2009/0098555 | A1 | 4/2009 | Roth et al. |
| 2010/0015614 | A1 | 1/2010 | Beer et al. |
| 2010/0028915 | A1 | 2/2010 | Gualberto et al. |
| 2010/0055677 | A1 | 3/2010 | Colston, Jr. et al. |
| 2010/0137163 | A1 | 6/2010 | Link et al. |
| 2010/0173394 | A1 | 7/2010 | Colston, Jr. et al. |
| 2010/0248237 | A1* | 9/2010 | Froehlich ............ C12Q 1/6846 435/6.14 |
| 2010/0285975 | A1 | 11/2010 | Mathies et al. |
| 2011/0053798 | A1* | 3/2011 | Hindson ................ G01N 21/75 506/12 |
| 2011/0056575 | A1 | 3/2011 | Hong et al. |
| 2011/0059556 | A1 | 3/2011 | Strey et al. |
| 2011/0086352 | A1 | 4/2011 | Bashir et al. |
| 2011/0103176 | A1 | 5/2011 | Van Dam et al. |
| 2011/0104816 | A1 | 5/2011 | Pollack et al. |
| 2011/0118151 | A1 | 5/2011 | Eshoo et al. |
| 2011/0160078 | A1 | 6/2011 | Fodor et al. |
| 2011/0217736 | A1 | 9/2011 | Hindson |

(Continued)

FOREIGN PATENT DOCUMENTS

| AU | 2013203624 | 5/2013 |
| AU | 2013302867 | 2/2015 |

(Continued)

OTHER PUBLICATIONS

Extended European Search Report received for European Patent Application Serial No. 17840230.1 dated Apr. 30, 2020, 12 pages.
Extended European Search Report received for European Patent Application Serial No. 17885180.4 dated Jul. 20, 2020, 11 pages.
Extended European Search Report received for European Patent Application Serial No. 13829925.0 dated Feb. 8, 2016, 7 pages.
Extended European Search Report received for European Patent Application Serial No. 15812857.9 dated Oct. 17, 2017, 7 pages.
Integrated DNA Technologies "Molecular Facts and Figures", 2011, pp. 1-9.
Abate, Adam R., et al., (2013) "DNA sequence analysis with droplet-based microfluids", Lab Chip, vol. 13(24), pp. 4864-4869.

(Continued)

*Primary Examiner* — Sahana S Kaup
(74) *Attorney, Agent, or Firm* — Edward J. Baba; Bozicevic, Field & Francis LLP

(57) ABSTRACT

The methods described herein, referred to as PCR-Activated Sorting (PAS), allow nucleic acids contained in biological systems to be sorted based on their sequence as detected with nucleic acid amplification techniques, e.g., PCR. The nucleic acids can be free floating or contained within living or nonliving structures, including particles, viruses, and cells. The nucleic acids can include, e.g., DNA or RNA. Systems and devices for use in practicing methods of the invention are also provided.

20 Claims, 85 Drawing Sheets

Specification includes a Sequence Listing.

(56) References Cited

U.S. PATENT DOCUMENTS

| | | |
|---|---|---|
| 2011/0311978 A1 | 12/2011 | Makarewicz, Jr. et al. |
| 2012/0010086 A1 | 1/2012 | Froehlich et al. |
| 2012/0045765 A1 | 2/2012 | Curran et al. |
| 2012/0122714 A1 | 5/2012 | Samuels et al. |
| 2012/0132288 A1 | 5/2012 | Weitz et al. |
| 2012/0190032 A1 | 7/2012 | Ness et al. |
| 2012/0190033 A1 | 7/2012 | Ness et al. |
| 2012/0196288 A1 | 8/2012 | Beer |
| 2012/0219947 A1 | 8/2012 | Yurkovetsky et al. |
| 2012/0220494 A1 | 8/2012 | Samuels et al. |
| 2012/0258870 A1 | 10/2012 | Schwartz et al. |
| 2012/0264646 A1 | 10/2012 | Link et al. |
| 2012/0270739 A1 | 10/2012 | Rava et al. |
| 2012/0309002 A1 | 12/2012 | Link |
| 2012/0316074 A1 | 12/2012 | Saxonov |
| 2013/0032235 A1 | 2/2013 | Johnstone et al. |
| 2013/0046030 A1 | 2/2013 | Rotem et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0236901 A1 | 9/2013 | Potier et al. |
| 2013/0295567 A1 | 11/2013 | Link et al. |
| 2013/0295587 A1 | 11/2013 | Sjobom |
| 2014/0057799 A1 | 2/2014 | Johnson et al. |
| 2014/0154695 A1 | 6/2014 | Miller et al. |
| 2014/0155295 A1 | 6/2014 | Hindson et al. |
| 2014/0179544 A1 | 6/2014 | Steenblock et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378345 A1 | 12/2014 | Hindson et al. |
| 2014/0378349 A1 | 12/2014 | Hindson et al. |
| 2015/0232942 A1 | 8/2015 | Abate et al. |
| 2015/0298091 A1 | 10/2015 | Weitz et al. |
| 2016/0064755 A1 | 3/2016 | Hubner et al. |
| 2016/0177375 A1 | 6/2016 | Abate et al. |
| 2016/0265043 A1 | 9/2016 | Geng et al. |
| 2017/0009274 A1 | 1/2017 | Abate et al. |
| 2017/0022538 A1 | 1/2017 | Abate et al. |
| 2017/0121756 A1 | 5/2017 | Abate et al. |
| 2018/0056288 A1 | 3/2018 | Abate et al. |
| 2018/0216160 A1 | 8/2018 | Abate et al. |
| 2018/0237836 A1 | 8/2018 | Abate et al. |
| 2019/0127789 A1 | 5/2019 | Weitz et al. |
| 2019/0169700 A1 | 6/2019 | Abate et al. |
| 2019/0218594 A1 | 7/2019 | Abate et al. |
| 2019/0241965 A1 | 8/2019 | Abate et al. |
| 2019/0330701 A1 | 10/2019 | Abate et al. |

FOREIGN PATENT DOCUMENTS

| | | | |
|---|---|---|---|
| AU | 2016215298 | 8/2017 | |
| AU | 2016215304 | 8/2017 | |
| AU | 2017382905 | 7/2019 | |
| AU | 2019226236 | 9/2019 | |
| CA | 2881783 | 2/2014 | |
| CA | 3001986 | 4/2016 | |
| CA | 2974299 | 8/2016 | |
| CA | 2974306 | 8/2016 | |
| CA | 3047328 | 6/2018 | |
| CN | 1693478 | 11/2005 | |
| CN | 104736725 | 6/2015 | |
| CN | 107107058 | 8/2017 | |
| CN | 107429426 | 12/2017 | |
| CN | 107530654 | 1/2018 | |
| CN | 108350488 | 7/2018 | |
| CN | 110088290 | 8/2019 | |
| CN | 110462053 | 11/2019 | |
| DE | 10339452 | 3/2005 | |
| EP | 1547677 | 6/2005 | |
| EP | 2145955 | 2/2012 | |
| EP | 2565650 | 3/2013 | |
| EP | 2882872 | 6/2015 | |
| EP | 3160654 | 5/2017 | |
| EP | 3209419 | 8/2017 | |
| EP | 3253479 | 12/2017 | |
| EP | 3253910 | 12/2017 | |
| EP | 3337907 | 6/2018 | |
| EP | 3497228 | 6/2019 | |
| EP | 3571308 | 11/2019 | |
| GB | 2519906 | 5/2015 | |
| GB | 2539836 | 12/2016 | |
| JP | 2013503630 | 2/2013 | |
| JP | 2014521334 A | 8/2014 | |
| JP | 2015533079 | 11/2015 | |
| JP | 2018505671 | 3/2018 | |
| JP | 2018508198 | 3/2018 | |
| JP | 2018525004 | 9/2018 | |
| WO | WO 9412216 | 6/1994 | |
| WO | WO 2007140015 | 12/2007 | |
| WO | WO 2009050512 | 4/2009 | |
| WO | WO 2009054870 | 4/2009 | |
| WO | WO 2009111014 | 9/2009 | |
| WO | WO 2010148039 | 12/2010 | |
| WO | WO 2011047307 | 4/2011 | |
| WO | WO 2012011091 | 1/2012 | |
| WO | WO 2012048341 | 4/2012 | |
| WO | WO 2012083225 | 6/2012 | |
| WO | 2012106385 A2 | 8/2012 | |
| WO | WO 2012109600 | 8/2012 | |
| WO | WO 2012142213 | 10/2012 | |
| WO | WO 2012162267 | 11/2012 | |
| WO | WO 2013015793 | 1/2013 | |
| WO | WO 2013095469 | 6/2013 | |
| WO | WO 2013119753 | 8/2013 | |
| WO | WO 2013126741 | 8/2013 | |
| WO | WO 2013130512 | 9/2013 | |
| WO | WO 2013134261 | 9/2013 | |
| WO | WO-2013134261 A1 * | 9/2013 | .......... B01F 13/0071 |
| WO | WO 2013173394 | 11/2013 | |
| WO | WO 2014028378 | 2/2014 | |
| WO | WO 2014028537 | 2/2014 | |
| WO | WO 2014047556 | 3/2014 | |
| WO | WO 2014083435 | 6/2014 | |
| WO | WO 2014093676 | 6/2014 | |
| WO | WO 2014108323 | 7/2014 | |
| WO | WO 2014138132 | 9/2014 | |
| WO | WO 2014151658 | 9/2014 | |
| WO | WO 2014153071 | 9/2014 | |
| WO | WO 2015031691 | 3/2015 | |
| WO | WO 2015069798 | 5/2015 | |
| WO | WO 2015120398 | 8/2015 | |
| WO | WO 2015157369 | 10/2015 | |
| WO | WO2015179848 A1 | 11/2015 | |
| WO | WO 2015189336 | 12/2015 | |
| WO | WO 2015200717 | 12/2015 | |
| WO | WO 2016064755 | 4/2016 | |
| WO | WO 2016065056 | 4/2016 | |
| WO | WO 2016126865 | 8/2016 | |
| WO | WO 2016126871 | 8/2016 | |
| WO | WO 2017031125 | 2/2017 | |
| WO | WO2018031691 A1 | 2/2018 | |
| WO | WO 2018119301 | 6/2018 | |
| WO | WO2019099908 A1 | 5/2019 | |

OTHER PUBLICATIONS

Abate, Adam R., et al., (2009) "Beating Poisson encapsulation statistics using close-packed ordering", Lab Chip, vol. 9, pp. 2628-2631.

Abbaspourrad, et al., (2015) "Label-free single-cell protein quantification using a dropbased mix-and-read system", Sci. Rep., 5, p. 12756.

Agargel, (2019) "Agar-Agar", retrieved on Jun. 6, 2019 from https://web.archive.org/web/20170527222040/http://www.agargel.com.br/agar-tecen. html, 3 pages.

Autour, et al., (2017) "Ultrahigh-throughput improvement and discovery of enzymes using droplet-based microfluidic screening" Micromachines, vol. 8(128), pp. 1-21.

(56) References Cited

OTHER PUBLICATIONS

Baker, (2012) "Digital PCR hits its stride", Nat. Methods, vol. 9(6), pp. 541-544.
Bjork, et al., (2012) "Metabolite profiling of microfluidic cell culture conditions for droplet based screening", Biomicrojluidics, vol. 9, p. 044128.
Blainey, et al., (2014) "Dissecting genomic diversity, one cell at a time" Nat. Methods, vol. 11(1), pp. 19-21.
Chang, et al., (2012) "Single Molecule Enzyme-Linked Immunosorbent Assays: Theoretical Considerations", J Immunol Methods, vol. 378(1-2), pp. 102-115.
Chen et al., (2017) "Centrifugal micro-channel array droplet generation for highly parallel digital PCR", Lab Chip, 17, pp. 235-240.
Chen et al., (2016) "Spinning micropipette liquid emulsion generator for single cell whole genome amplification", Lab Chip, 16, pp. 4512-4516.
Civelek et al., (2014) "Systems genetics approaches to understand complex traits", Nat. Rev. Genet., 15(1), pp. 34-48.
Collins et al., (2015) "The Poisson distribution and beyond: methods for microfluidic droplet production and single cell encapsulation", Lab on a Chip, 15, pp. 3439-3459.
Costa et al., (2008) "Complex networks: The key to systems biology", Genet. Mol. Biol., 31(3), pp. 591-601.
Elnifro, et al., (2000) "Multiplex PCR: Optimization and Application in Diagnostic Virology", Clin. Microbial. Rev., 13, pp. 559-570.
Fritzsch et al., (2012), "Single-Cell Analysis in Biotechnology, Systems Biology, and Biocatalysis", Annu. Rev. Chem. Biomol. Eng. 3, pp. 129-155.
Gielen, et al., (2016) "Ultrahigh-throughput-directed enzyme evolution by absorbance activated droplet sorting (AADS)", PNAS, pp. E7383-E7389.
Griffiths, et al., (2006) "Miniaturising the laboratory in emulsion droplets Trends" Biotechnol., 24, pp. 395-402.
Guo, et al., (2012) "Droplet microfluidics for highthroughput biological assays.", Lab Chip, pp. 2146-2155.
Halldorsson et al., (2015) "Advantages and challenges of microfluidic cell culture in polydimethylsiloxane devices", Biosens. Bioelectron., 63, pp. 218-231.
Huang, et al., (2017) "Collective generation of milliemulsions by step-emulsification", RSC Advances, 7, pp. 14932-14938.
Joanicot, et al., (2005) "Droplet control for microfluidics", Science, 309(5736), pp. 887-888.
Katepalli, et al., (2014) "Bose, A. Response of Surfactant Stabilized Oil-in-Water Emulsions to the Addition of Particles in an Aqueous Suspension", Langmuir, 30(43), p. 12736-12742.
Kim, et al., (2017) "Measurement of copy number variation in single cancer cells using rapid-emulsification digital droplet MPA", Microsystems & Nanoengineering 3:17018, pp. 1-7.
Kim, et al., (2014) "Droplet Microfluidics for Producing Functional Microparticles", Langmuir, 30, pp. 1473-1488.
Kimmerling et al., (2016) "A microfluidic platform enabling single-cell RNA-seq of multigenerational lineages", Nature Commun., 7, p. 10220.
Kolodziejczyk, et al., (2015) "The Technology and Biology of Single-Cell RNA Sequencing", Mol. Cell, 58(4), pp. 610-620.
Lage, J. M.., et al., (2003) "Whole Genome Analysis of Genetic Alterations in Small DNA Samples Using Hyperbranched Strand Displacement Amplification and Array-CGH", Genome Res., 13, pp. 294-307.
Lance, et al., (2016) "Peering below the diffraction limit: robust and specific sorting of viruses with flow cytometry", Viral J, 13, p. 201.
Macosko, et al., (2015) "Highly parallel genome-wide expression profiling of individual cells using nanoliter droplets" Cell, 161, pp. 1202-1214.
Margulies, et al., (2005) "Genome sequencing in microfabricated high-density picolitre reactors", Nature, 437, pp. 376-380.
Mashaghi, et al., (2016) "Droplet microfluidics: A tool for biology, chemistry and nanotechnology", TrAC-Trends Anal. Chem., 82, pp. 118-125.
Morimoto, et al., (2013) "Three-dimensional cell culture based on microfluidic techniques to mimic living tissues", Biomaterials Science, vol. 1, No. 3, pp. 257-264.
Morimoto, et al., (2009) "Reconstruction of 3D Hierarchic Micro-Tissues using Monodisperse Collagen Microbeads", Micro Electro Mechanical Systems, IEEE 22nd International Conference, pp. 56-59.
Pinheiro, et al., (2012) Evaluation of a droplet digital polymerase chain reaction format for DNA copy number quantification, Anal. Chem., 84, pp. 1003-1011.
Romero, et al., (2015) "Dissecting enzyme function with microfluidic-based deep mutational scanning", PNAS, 112(23), pp. 7159-7164.
Sandberg, et al., (2009) "Flow cytometry for enrichment and titration in massively parallel DNA sequencing", Nucleic Acids Res, 37(8), p. e63.
Song, et al., (2006) "On-Chip Titration of an Anticoagulant Argatroban and Determination of the Clotting Time within Whole Blood or Plasma Using a Plug-Based Microfluidic System", Anal. Chem., 78(14), pp. 4839-4849.
Soon, et al., (2013) "High-throughput sequencing for biology and medicine", Mol. Syst. Biol., 9(64), pp. 1-14.
Spencer, Sarah J., et al. (2016), "Massively parallel sequencing of single cells by epicPCR links functional genes with phylogenetic markers", The ISME Journal 10, pp. 427-436.
Spies, et al., (2017) "Genome-wide reconstruction of complex structural variants using read clouds", Nat. Methods, 14(9), pp. 915-920.
Sukovich, et al., (2017) "Sequence specific sorting of DNA molecules with FACS using 3dPCR", Sci. Rep., 7, p. 39385.
Taly, et al., (2013) "Multiplex picodroplet digital PCR to detect KRAS mutations in circulating DNA from the plasma of colorectal cancer patients", Clin. Chern., 59, pp. 1722-1731.
Tran, et al., (2013) "From tubes to drops: dropletbased biology microfluidics for ultrahigh-throughput", J Phys. D. Appl. Phys., 46, p. 114004.
Weaver, et al., (2014) "Advances in high-throughput single-cell microtechnologies", Curr. Opin. Biotechnol., 0, pp. 114-123.
Yan, et al., (2017) "Intestinal Enteroendocrine Lineage Cells Possess Homeostatic and Injury-Inducible Stem Cell Activity", Cell Stem Cell, 21, pp. 78-90.
Zhu, et al., (2017) "Hydrogel Droplet Microfluidics for High-Throughput Single Molecule/Cell Analysis", Ace. Chem. Res., 50(1), pp. 22-31.
Zilionis, et al., (2017) "Single-cell barcoding and sequencing using droplet microfluidics", Nat. Protoc., 12(1), pp. 44-73.
Extended European Search Report received for European Patent Application Serial No. 15853268.9 dated Sep. 3, 2018, 12 pages.
Extended European Search Report received for European Patent Application Serial No. 16747224.0 dated May 24, 2018, 9 pages.
Extended European Search Report received for European Patent Application Serial No. 16747229.9 dated Sep. 10, 2019, 8 pages.
Extended European Search Report received for European Patent Application Serial No. 16837703.4 dated Nov. 29, 2018, 9 pages.
First search received for Chinese Patent Application Serial No. 2013800532581 dated Feb. 22, 2016, 2 pages.
First search received for Chinese Patent Application Serial No. 2015800704110 dated Dec. 13, 2018, 2 pages.
International Preliminary Report on Patentability received for PCT Application Serial No. PCT/US2013/054517 dated Feb. 26, 2015, 14 pages.
International Preliminary Report on Patentability received for PCT Application Serial No. PCT/US2015/037822 dated Jan. 5, 2017, 7 pages.
International Preliminary Report on Patentability received for PCT Application Serial No. PCT/US2015/056743 dated May 4, 2017, 9 pages.
International Preliminary Report on Patentability received for PCT Application Serial No. PCT/US2016/016438 dated Aug. 17, 2017, 10 pages.
International Preliminary Report on Patentability received for PCT Application Serial No. PCT/US2016/016444 dated Aug. 17, 2017, 40 pages.

(56) References Cited

OTHER PUBLICATIONS

International Preliminary Report on Patentability received for PCT Application Serial No. PCT/US2016/047199 dated Mar. 1, 2018, 8 pages.
International Preliminary Report on Patentability received for PCT Application Serial No. PCT/US2017/046159 dated Feb. 21, 2019, 9 pages.
International Preliminary Report on Patentability received for PCT Application Serial No. PCT/US2017/068006 dated Jul. 4, 2019, 7 pages.
International Preliminary Report on Patentability received for PCT Application Serial No. PCT/US2017/68006 dated Jul. 4, 2019, 7 pages.
International Search Report and Written Opinion received for PCT Application Serial No. PCT/US2013/054517 dated Feb. 21, 2014, 19 pages.
International Search Report and Written Opinion received for PCT Application Serial No. PCT/US2015/037822 dated Feb. 2, 2016, 9 pages.
International Search Report and Written Opinion received for PCT Application Serial No. PCT/US2015/056743 dated Mar. 3, 2016, 12 pages.
International Search Report and Written Opinion received for PCT Application Serial No. PCT/US2016/016438 dated Jun. 10, 2016, 14 pages.
International Search Report and Written Opinion received for PCT Application Serial No. PCT/US2016/016444 dated Jul. 27, 2016, 43 pages.
International Search Report and Written Opinion received for PCT Application Serial No. PCT/US2016/047199 dated Dec. 12, 2016, 10 pages.
International Search Report and Written Opinion received for PCT Application Serial No. PCT/US2017/046159 dated Nov. 21, 2017, 12 pages.
International Search Report and Written Opinion received for PCT Application Serial No. PCT/US2017/068006 dated Mar. 26, 2018, 9 pages.
Abate, Adam R, et al., "Efficient encapsulation with plug-triggered drop formation", vol. 84(3), Phys Rev E Stat Nonlin Soft Matter Phys., Sep. 22, 2011, 031502.
Abate, Adam R, et al., "Faster multiple emulsification with drop splitting", vol. 11(11), Lab Chip, Jun. 7, 2011, 1911-1915.
Abate, Adam R, et al., "High-throughput injection with microfluidics using picoinjectors", PNAS vol. 107(45), Nov. 9, 2010, 19163-19166.
Abate, Adam R, et al., "Microfluidic sorting with high-speed single-layer membrane valves", Applied Physics Letters 96, 2010, 03509-1-203509-3.
Abate, Adam R, et al., "One-step formation of multiple emulsions in microfluidics", vol. 11(2) Lab on a Chip, Oct. 2010, 253-258.
Abate, Adam R, et al., "Photoreactive coating for high-contrast spatial patterning of microfluidic device wettability", vol. 8(12), Lab on a Chip, Oct. 17, 2008, 2157-2160.
Agresti, Jeremy J, et al., "Ultrahigh-throughput screening in drop-based microfluidics for directed evolution", See Corrected Version—Proc Natl Acad Sci USA, 107, 2010, 4004-4009.
Agresti, Jeremy J, et al., "Ultrahigh-throughput screening in drop-based microfluidics for directed evolution", Corrected Version—Proc Natl Acad Sci USA, 107(14), 2010, 6550-6551.
Ahn, Keunho, et al., "Electrocoalescence of drops synchronized by size-dependent flow in microfluidic channels", vol. 88, Applied Physics Letters, 264105-1-264105-3.
Ali, M Monsur, et al., "Rolling circle amplification: a versatile tool for chemical biology, materials science and medicine", vol. 43(10), Chem Soc Rev., Mar. 18, 2014, 3324-3341.
Allen, Lisa Z, et al., "Single virus genomics: a new tool for virus discovery", PLoS ONE vol. 6(3), Mar. 23, 2011, e17722.
Arriaga, Laura R, et al., "Ultrathin Shell Double Emulsion Templated Giant Unilamellar Lipid Vesicles with Controlled Microdomain Formation", vol. 10(5), Mar. 12, 2014, 950-956.

Atten, P, "Electrocoalescence of Water Droplets in an Insulating Liquid", vol. 30, 259-269.
Barenholz, Y, et al., "A simple method for the preparation of homogeneous phospholipid vesicles", Biochemistry 16(12), 2806-2810.
Baret, Jean C, et al., "Fluorescence-activated droplet sorting (FADS): efficient microfluidic cell sorting based on enzymatic activity", vol. 9(13), Lab on a Chip, Apr. 23, 2009, 1850-1858.
Battaglia, Giuseppe, et al., "Polymeric vesicle permeability: a facile chemical assay", vol. 22(11), Langmuir, 4910-4913.
Beer, NR, et al., "On-chip single-copy real-time reverse-transcription PCR in isolated picoliter droplets", Anal Chem., vol. 80(6), 1854-1858.
Bernath, K, et al., "In vitro compartmentalization by double emulsions: sorting and gene enrichment by fluorescence activated cell sorting", vol. 325(1), Analytical Biochemistry, 151-157.
Bird, R E, et al., "Single-chain antigen-binding proteins", vol. 242 (4877), Science, Oct. 21, 1988, 423-426.
Blainey, Paul C, "The future is now: single-cell genomics of bacteria and archaea", FEMS microbiology reviews 37(3), May 2013, 407-427.
Brouzes, E, et al., "Droplet microfluidic technology for single-cell high-throughput screening", vol. 106(34), Proc Natl Acad Sci U S A., 14195-14200.
Brown, Robert B, et al., "Current techniques for single-cell lysis", J R Soc Interface, 5 Suppl 2, Oct. 6, 2008, S131-S138.
Caron, G. Nebe-Von, et al., "Assessment of bacterial viability status by flow cytometry and single cell sorting", vol. 84(6), Journal of Applied Microbiology, Jul. 17, 1997, 988-998.
Caruccio, N. (2011) "Preparation of Next-Generation Sequencing Libraries Using Nextera" Technology: Simultaneous DNA Fragmentation and Adaptor Tagging by in Vitro TranspositionMethods in Molecular Biology, 733-:241-255.
Chabert, M, et al., "Droplet fusion by alternating current (AC) field electrocoalescence in microchannels", Electrophoresis vol. 26(19), 3706-3715.
Chaffer, Christine L, et al., "A Perspective on Cancer Cell Metastasis", Science vol. 331(6024), Mar. 25, 2011, 1559-1564.
Chen, Chin-Ming, et al., "Influence of pH on the stability of oil-in-water emulsions stabilized by a splittable surfactant", Colloids and Surfaces A: Physicochemical and Engineering Aspects, vol. 170 (2-3), 173-179.
Chung, Changkwon, et al., "Droplet dynamics passing through obstructions in confined microchannel flow", Microfluidics and Nanofluidics, vol. 9(6), 1151-1163.
Clausell-Tormos, J., et al., "Droplet-based microfluidic platforms for the encapsulation and screening of Mammalian cells and multicellular organisms", Chemistry and Biology, vol. 15(5), 427-437.
Demaree et al., (2018) "An Ultranigh-throughput Microfluidic Platform for Single-cell Genome Sequencing", Journal of Visualized Experiments, No. 135.
Dejournette, Cheryl J, et al., "Creating Biocompatible Oil-Water Interfaces without Synthesis: Direct Interactions between Primary Amines and Carboxylated Perfluorocarbon Surfactants", Analytical chemistry, vol. 85 (21), Sep. 26, 2013, 10556-10564.
Dietrich, G J, et al., "Effects of UV irradiation and hydrogen peroxide on DNA fragmentation, motility and fertilizing ability of rainbow trout (*Oncorhynchus mykiss*) spermatozoa", Theriogenology vol. 64(8), Nov. 2005, 1809-1822.
Duffy, David C, et al., "Rapid Prototyping of Microfluidic Systems in Poly(dimethylsiloxane)", Anal. Chem., vol. 70(23), Oct. 24, 1998, 4974-4984.
Eastburn, Dennis J, et al., "Picoinjection enables digital detection of RNA with droplet rt-PCR", PLoS One vol. 8(4), Apr. 26, 2013, e62961.
Eastburn, Dennis J, et al., "Ultrahigh-Throughput Mammalian Single-Cell Reverse-Transcriptase Polymerase Chain Reaction in Microfluidic Drops", Anal. Chem. 85 (16), Jul. 26, 2013, 8016-8021.
Edd, Jon F, et al., "Controlled encapsulation of single-cells into monodisperse picolitre drops", Lab Chip, vol. 8(8), Aug. 2008, 1262-1264.

(56) References Cited

OTHER PUBLICATIONS

Freeman et al., (2017) "Single-cell genome sequencing at ultra-high-throughput with microfluidic droplet barcoding, (includes Online Methods)", Nature Biotechnology, vol. 35, No. 7, pp. 640-646.
Frenz, Lucas, et al., "Reliable microfluidic on-chip incubation of droplets in delay-lines", Lab on a Chip vol. 9(10), 1344-1348.
Fu, Yusi, et al., "Uniform and accurate single-cell sequencing based on emulsion whole-genome amplification", Proc. Nall. Acad. Sci. USA, vol. 112(38), 11923-11928.
Garstecki, Piotr, et al., "Formation of droplets and bubbles in a microfluidic T-junction-scaling and mechanism of break-up", Lab on a Chip, vol. 6(3), 437-446.
Gevensleben, Heidrun, et al., "Non-invasive Detection of HER2 Amplification with Plasma DNA Digital PCR", Clinical Cancer Research, vol. 19(12), 3276-3284.
Gong, Jian, et al., "Characterization and Design of Digitizing Processes for Uniform and controllable droplet volume in Ewod Digital Microfluidics, Solid-State Sensor, Actuator and Microsystem Workshop", Jun. 5, 2006.
Gribskov, M, et al., "Sigma factors from *E. coli*, B. subtilis, phage SP01, and phage T4 are homologous proteins", Nucleic Acids Res., vol. 14(16), 6745-6763.
Grover, Alka, et al., "Multiple displacement amplification as a pre-polymerase chain reaction (pre-PCR) to detect ultra low population of Ralstonia solanacearum (Smith 1896) Yabuchi et al. (1996)", Letters in Applied Microbiology, vol. 49(5), 539-543.
Hayward, Ryan C, et al., "Dewetting instability during the formation of polymersomes from block-copolymer-stabilized double emulsions", Langmuir, vol. 22(10), Apr. 11, 2006, 4457-4461.
Herminghaus, S, "Dynamical Instability of Thin Liquid Films Between Conducting Media", Physical Review Letter, vol. 83(12), 2359-2361.
Hindson, et al., (2011) High-ghroughput droplet digital PCR system for absolute quantitation of DNA copy number. Analytical Chemistry, 83(22), pp. 8604-8610.
Holland, P M, et al., "Detection of specific polymerase chain reaction product by utilizing the 5'----3' exonuclease activity of Thermus aquaticus DNA polymerase", Proc Natl Acad Sci USA, 88 (16), Aug. 15, 1991, 7276-7280.
Holtze, C, et al., "Biocompatible surfactants for water-in-fluorocarbon emulsions", Lab Chip 8(10), 1632-1639.
Horton, Robert M, et al., "Gene splicing by overlap extension: tailor-made genes using the polymerase chain reaction", Biotechniques, vol. 54, Mar. 2013, 129-133.
Hu, Hoa, et al., "Mutation screening in 86 known X-linked mental retardation genes by droplet-based multiplex PCR and massive parallel sequencing", Hugo J., vol. 3 (1-4), 41-49.
Huebner, Ansgar, et al., "Microdroplets: A sea of applications?", Lab on a Chip, vol. 8(8), 1244-1254.
Hunkapiller, Tim, et al., "Immunology: The growing immunoglobulin gene superfamily", Nature vol. 323, 15-16.
Hunt, Josephine A, et al., "Effect of pH on the stability and surface composition of emulsions made with whey protein isolate", Journal of Agricultural and Food Chemistry, vol. 42(10), Oct. 1, 1994, 2131-2135.
Huston, J S, et al., "Protein engineering of antibody binding sites: recovery of specific activity in an anti-digoxin single-chain Fv analogue produced in *Escherichia coli*", Proc. Natl. Acad. Sci. U.S.A. vol. 85(16), Aug. 1988, 5879-5883.
Ichii et al., (2010) Amplification of RNA in Growing and Dividing Micro-Droplets, 2010, 14th International Conference on Miniaturized Systems for Chemistry and Life Sciences, pp. 2089-2091.
Kawasaki, Ernest S, "Sample Preparation From Blood, Cells, and Other Fluids", Chapter 18 of PCR Protocols: A guide to methods and Applications, 1990, 146-152.
Ki, Jang-Seu, et al. "Integrated Method for Single-Cell DNA Extraction, PCR Amplification, and Sequencing of Ribosomal DNA from Harmful Dinoflagellates Cochlodinium polykrikoides and Alexandrium catenella", Marine Biotechnology, vol. 6, 587-593.

Kiss, Margaret M, et al., "High-Throughput Quantitative Polymerase Chain Reaction in Picoliter Droplets", Anal Chem vol. 80(23), Dec. 1, 2008, 8975-8981.
Kritikou, Ekat, "It's cheaper in the Picolab", Nat Rev Genet, vol. 6, 668.
Kumaresan P, Yang CJ, Cronier SA, Blazej Rg, Mathies RA, "High-throughput single copy DNA amplification and cell analysis in engineered nanoliter droplets". Analytical chemistry, May 15, 2008; (10), 3522-9.
Kuster, Simon K, et al., "Interfacing Droplet Microfluidics with Matrix-Assisted Laser Desorption/Ionization Mass Spectrometry: Label-Free Content Analysis of Single Droplets", Anal Chem vol. 85(3), Jan. 5, 2013, 1285-1289.
Lagally, E T, et al., "Single-Molecule DNA Amplification and Analysis in an Integrated Microfluidic Device", Analytical Chemistry, vol. 73(3), Jan. 3, 2001, 565-570.
Lanzavecchia, Antonio, et al., "The use of hybrid hybridomas to target human cytotoxic T lymphocytes", Eur. J. Immunology, vol. 17(1), 105-111.
Leary, James F, "Strategies for rare cell detection and isolation", Methods Cell Biol., vol. 42, 1994, 331-358.
Le Goff et al., (2015) Hydrogel microparticles for biosensing, European Polymer Journal 2015; 72: 386-412.
Lim, Shaun W, et al., "Ultrahigh-throughput sorting of microfluidic drops with flow cytometry", Lab on a Chip, vol. 13, Oct. 8, 2013, 4563-4572.
Link, D R, et al., "Geometrically mediated breakup of drops in microfluidic devices", Phys. Rev. Lett., vol. 92(5), Feb. 6, 2004, 054503.
Livak, K J, et al., "Analysis of Relative Gene Expression Data Using Real-Time Quantitative PCR and the 2(-Delta Delta C(T)) Method", Methods, vol. 25(4), Dec. 2001, 402-408.
Longo, M C, et al., "Use of uracil DNA glycosylase to control carry-over contamination in polymerase chain reactions", Gene, vol. 93(1), Sep. 1, 1990, 125-128.
Malloggi, Florent, et al., "Electrowetting-controlled droplet generation in a microfluidic flow-focusing device", Journal of Physics Condensed Matter, vol. 19(46), 462101, 1-7.
Marcus, Joshua S, et al., "Parallel Picoliter rt-PCR Assays Using Microfluidics", Analytical Chemistry, vol. 78(3), Feb. 1, 2006, 956-958.
Markou, Athina, et al., "Molecular Characterization of Circulating Tumor Cells in Breast Cancer by a Liquid Bead Array Hybridization Assay", Clinical Chemistry vol. 57(3), 421-430.
Mary, Pascaline, et al., "Controlling droplet incubation using close-packed plug flow", Biomicrofluidics, vol. 5(2), 24101.
Mazutis, Linas, et al., "Single-cell analysis and sorting using droplet-based microfluidics", Nature protocols, vol. 8(5), 870-891.
McDonald, J C, et al., "Fabrication of microfluidic systems in poly(dimethylsiloxane)", Electrophoresis, vol. 21(1), Jan. 2000, 27-40.
Medkov, Martina, et al., "Analyzing Cancer at Single Cell Resolution with Droplet Technology", American Association of Cancer Research (AACR), 1 page.
Metzker, Michael L, "Sequencing technologies—the next generation", Nature Reviews Genetics, vol. 11, Jan. 2010, 31-46.
Miyazaki, Kentaro, "Random DNA fragmentation with endonuclease V: application to DNA shuffling", vol. 30(24), pp. 139.
Miyazaki, Ryo, et al., "A new large-DNA-fragment delivery system based on integrase activity from an integrative and conjugative element", Appl Environ Microbiol vol. 79(14), 4440-4447.
Moon, Sangjun, et al., "Drop-on-Demand Single Cell Isolation and Total RNA Analysis", vol. 6 Issues, pp. 1-10.
Morton, Keith J, et al., "Crossing microfluidic streamlines to lyse, label and wash cells", Lab Chip vol. 8(9), Sep. 2008, 1448-1453.
Mui, B. L, et al., "Osmotic properties of large unilamellar vesicles prepared by extrusion", vol. 64(2), Feb. 1993, 443-453.
Nagrath, Sunitha, et al., "Isolation of rare circulating tumour cells in cancer patients by microchip technology", Nature, vol. 450, 1235-1239.
Nakano, Michihiko, et al., "Single-molecule reverse transcription polymerase chain reaction using water-in-oil emulsion", vol. 99(3), pp. 293-295.

(56) References Cited

OTHER PUBLICATIONS

Nikolova, Albena N, et al., "Effect of grafted PEG-2000 on the size and permeability of vesicles", vol. 1304(2), Nov. 22, 1996, pp. 120-128.

Nishikawa, Yohei, et al., "Monodisperse Picoliter Droplets for Low-Bias and Contamination-Free Reactions in Single-Cell Whole Genome Amplification", PLoS One vol. 10(9), e0138733.

Novak, Richard, et al., "Single-cell multiplex gene detection and sequencing with microfluidically generated agarose emulsions", Angew Chem Int Ed Engl., vol. 50(2), 390-395.

Nunes, J K, et al., "Dripping and jetting in microfluidic multiphase flows applied to particle and fibre synthesis", Journal of Physics D: Applied Physics, vol. 46(11), Feb. 22, 2013.

Oberholzer, Thomas, et al., "Polymerase chain reaction in liposomes", vol. 2(10), 677-682.

O'Donovan, Brian, et al., "Electrode-free picoinjection of microfluidic drops", Lab on a chip, vol. 12, 4029-4032.

Okochi, Mina, et al., "Droplet-based gene expression analysis using a device with magnetic force-based-droplet-handling system", Journal of Bioscience and Bioengineering, vol. 109(2), 193-197.

Pekin D, Skhiri Y, Baret JC, Le Corre D, Mazutis L, Ben Salem C, Millot F, El Harrak A, Hutchison JB, Larson JW, Link DR, Laurent-Puig P, Griffiths AD, Taly V, (2011) Lap Chip 11:2156-2166.

Perry, David J, "Solid-Phase Sequencing of Biotinylated PCR Products with Streptavidin-Coated Magnetic Beads", Hemostasis and Thrombosis Protocols, vol. 31, 1999, 49-54.

Piatek, Amy S, et al., "Molecular beacon sequence analysis for detecting drug resistance in *Mycobacterium tuberculosis*", Nature Biotechnology, vol. 16(4), Apr. 1998, 359-363.

Priest, Craig, et al., "Controlled electrocoalescence in microfluidics: Targeting a single lamella", Appl Phys Lett, vol. 89, 134101.

Rakszewska et al, (2014) "One drop at a time: toward droplet microfluidics as a versatile tool for single-cell analysis", NPG Asia Materials, vol. 6, No. 10, pp. 1-11.

Roche, "emPCR Amplification Method Manual—Lib L LV for GS FLX+ Series—XL+", 454 Sequencing, Life Science Corp., May 2011, 1-12.

Rolando, Monica, et al., "Legionella pneumophila Effector RomA Uniquely Modifies Host Chromatin to Repress Gene Expression and Promote Intracellular Bacterial Replication", Cell Host & Microbe, vol. 13(4), 395-405.

Sciambi, Adam, et al., "Adding reagent to droplets with controlled rupture of encapsulated double emulsions", Biomicrofluidics, vol. 7(4), 044112-1-044112-6.

Sciambia, Adam, et al., "Accurate microfluidic sorting of droplets at 30 kHz", Lab Chip vol. 15(1), 47-51.

Seemann, Ralf, et al., "Droplet based microfluidics", IOP Science, vol. 75, 016601.

Shembekar et al, (2016) "Droplet-based microfluidics in drug discovery, transcriptomics and high-throughput molecular genetics", Lab on a Chip, vol. 16, No. 8, pp. 1314-1331.

Shui, Lingling, et al., "Microfluidic DNA fragmentation for on-chip genomic analysis", Nanotechnology, vol. 22(49), 494013.

Sidore, Angus M, et al., "Enhanced sequencing coverage with digital droplet multiple displacement amplification", Nucleic Acids Res., vol. 44(7), Apr. 20, 2016, e66.

Siegel, Adam, et al., "Microsolidics: Fabrication of Three-Dimensional Metallic Microstructures in Poly (dimethylsiloxane)", Advanced Materials, vol. 19(5), 727-733.

Song, Helen, et al., "Reactions in droplets in microfluidic channels", Angew Chem Int Ed Engl, vol. 45(44), 7336-7356.

Squires, Tom M, et al., "Microfluidics: Fluid physics at the nanoliter scale", Reviews of modern physics, vol. 77(3), Oct. 6, 2005, 977-1026.

Stone, H. A, et al., "Engineering flows in small devices: microfluidics toward a lab-on-achip", vol. 36, Jan. 21, 2004, pp. 381-411.

Stott, Shannon L, et al., "Isolation of circulating tumor cells using a microvortex-generating herringbone-chip", Proc Natl Acad Sci USA, vol. 107(43), Oct. 26, 2010, pp. 18392-18397.

Syed, F, et al., "Next-generation sequencing library preparation: simultaneous fragmentation and tagging using in vitro transposition", vol. 6, pp. 1-2.

Tadmorad, Arbel D, et al., "Probing individual environmental bacteria for viruses by using microfluidic digital PGR", vol. 333-(6038), 2011, pp. 58-62.

Takagi, Junya, et al., "Continuous particle separation in a microchannel having asymmetrically arranged multiple branches", Lab on a Chip, vol. 5(7), pp. 778-784.

Tamminen, Manu V, et al., "Single gene-based distinction of individual microbial genomes from a mixed population of microbial cells", Front Microbiol., vol. 6(195), Mar. 11, 2015, 1-10.

Teh, Shia-Yen, et al., "Droplet microfluidics", Lab on a chip, vol. 8, Issue 2, 198-220.

Tewhey, Ryan, et al., "Microdroplet-based PGR enrichment for large-scale targeted sequencing", Nature Biotechnology, vol. 27, 1025-1031.

Thomann, Yi, et al., "PMMA Gradient Materials and in situ Nanocoating via Self-Assembly of Semifluorinated Hyperbranched Amphiphiles", Macromolecular Chemistry and Physics, vol. 206(1), 135-141.

Thorsen, Todd, et al., "Dynamic pattern formation in a vesicle-generating microfluidic device", Physical Review Letter, vol. 86(18), 4163-4166.

Tsai, Scott S H, et al., "Microfluidic immunomagnetic multi-target sorting—a model for controlling deflection of paramagnetic beads", Lab on a Chip, vol. 11(15), Aug. 7, 2011, 2577-2582.

Ullal, Adeeti V, et al., "Cancer cell profiling by barcoding allows multiplexed protein analysis in fine needle aspirates", Science Translation Medicine, vol. 6, Issue 219, Jan. 15, 2014, pp. 1-22.

Utada, Andrew S, et al., "Dripping to jetting transitions in co flowing liquid streams", Physical Review Letters, vol. 99(9), Aug. 31, 2007, pp. 094502-1-094502-4.

Vanapalli, Siva A, et al., "Hydrodynamic resistance of single confined moving drops in rectangnlar microchannels", Lab on a Chip, vol. 9, 2009, 982-990.

Vickers, Jonathan A, et al., "Generation of Hydrophilic Poly(dimethylsiloxane) for High-Performance Microchip Electrophoresis", Anal. Chem, vol. 78(21), Oct. 5, 2006, 7446-7452.

Wang, Chao, et al., "Amphiphilic building blocks for self-assembly: from amphiphiles to supra-amphiphiles", Accounts of Chemical Research, vol. 45(4), 608-618.

Wheeler, Aaron R, et al., "Digital microfluidics with in-line sample purification for proteomics analyses with MALDI-MS", Anal Chem. Volume 77(2), 2005, 534-540.

Whitcombe, David, et al., "Detection of PGR products using self-probing amplicons and fluorescence", Nature biotechnology, vol. 17(8), 804-807.

Whitesides, George M, "The origins and the future of microfluidics", Nature vol. 442, 2006, 368-373.

Xia, Younan, et al., "Soft lithography", Annual Review of Materials Science, vol. 37, 551-575.

Yu, Zhenming, et al., "Mung bean nuclease treatment increases capture specificity of microdroplet-PCR based targeted DNA enrichment", PLoS One vol. 9(7), e103491, 1-7.

Zeng, Yong, et al., "High-Performance Single Cell Genetic Analysis Using Microfluidic Emulsion Generator Arrays", Anal Chem, vol. 82(8), 3183-3190.

Zheng, Bo, et al., "Formation of droplets of in microfluidic channels alternating composition and applications to indexing of concentrations in droplet-based assays", Anal Chem., vol. 76, 4977-4982.

Zhong, Qun, et al., "Multiplex digital PCR: breaking the one target per color barrier of quantitative PCR", Lab on a Chip, vol. 11 (13), 2167-2174.

Zhu, Y Y, et al., "Reverse transcriptase template switching: a SMART approach for full-length cDNA library Construction", BioTechniques, vol. 30(4), Apr. 2001, 892-897.

Zhu, Zhi, et al., "Highly sensitive and quantitative detection of rare pathogens through agarose droplet microfluidic emulsion PCR at the single-cell level", Lab on a Chip, vol. 12(20), 3907-3913.

(56) References Cited

OTHER PUBLICATIONS

Zien, Tse-Fou, "Hydrodynamics of bolus flow—an analytical approach to blood flow in capillaries", Bull Math Biophys, vol. 31 (4), 681-694.

* cited by examiner

FIG. 4
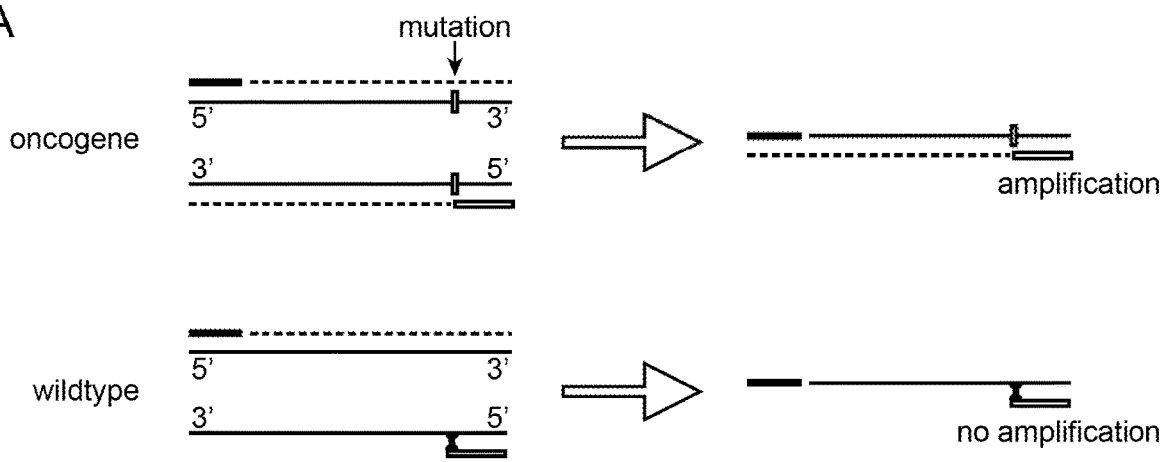
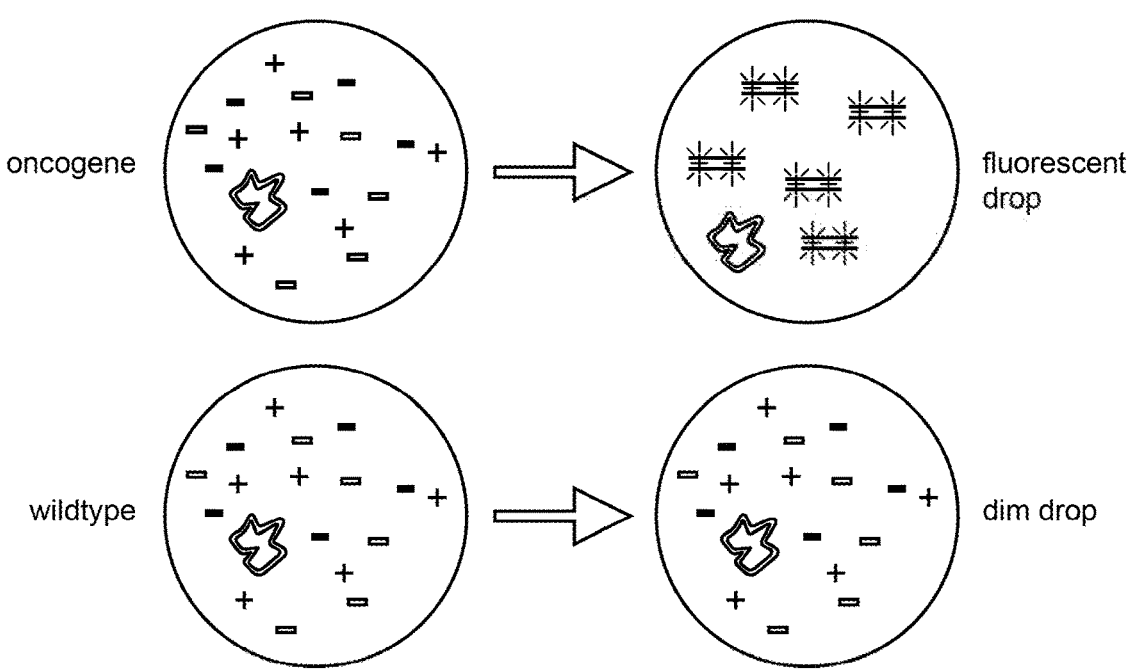

Taqman PCR on drop encapsulated MCF7 cells

FIG. 12 (Cont.)
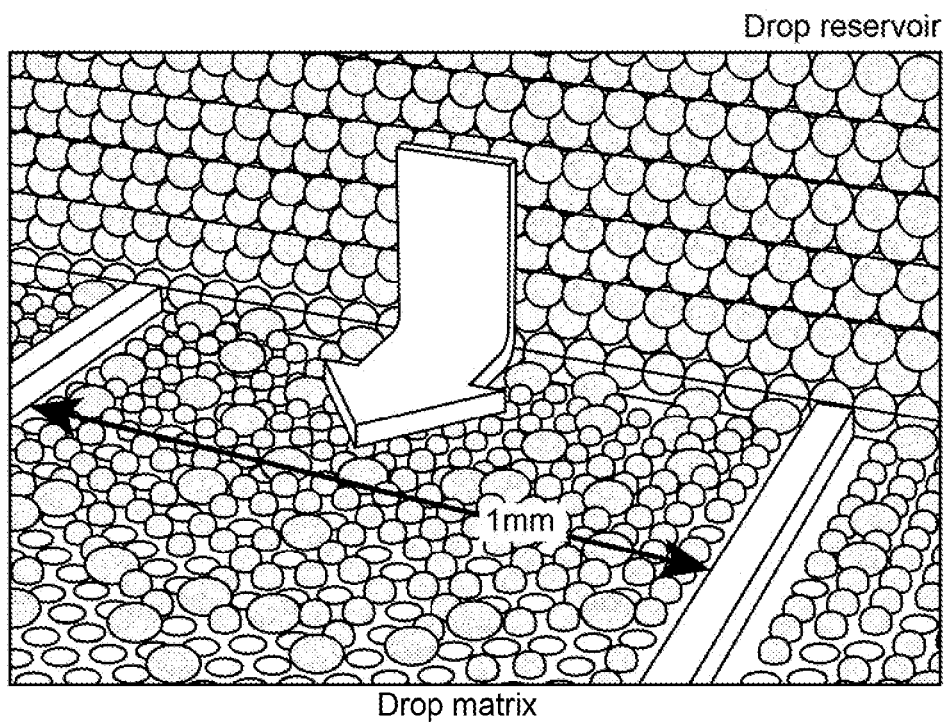
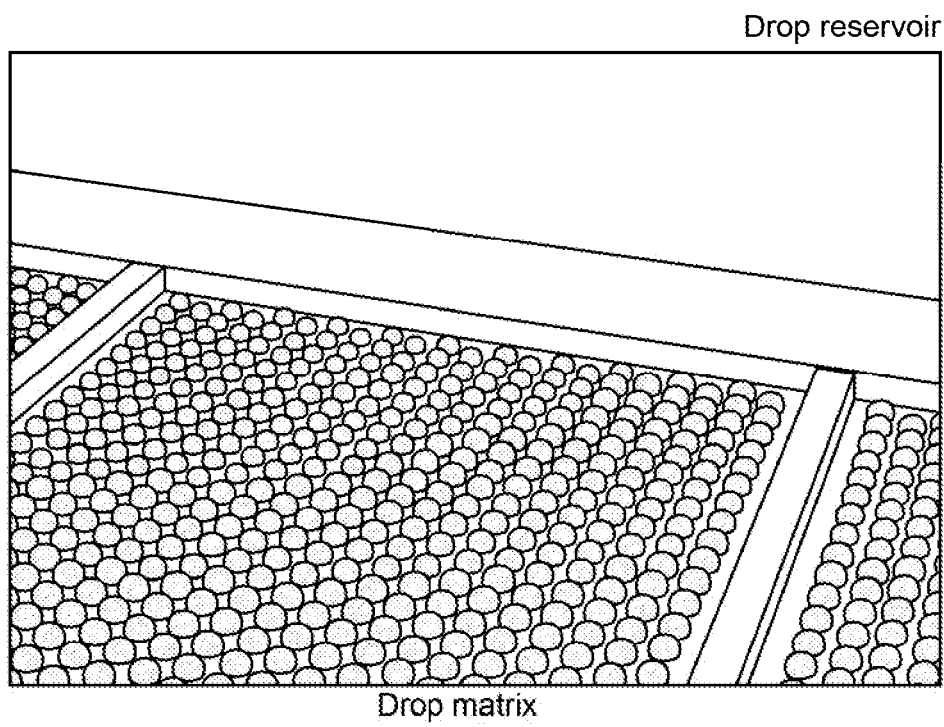

FIG. 13
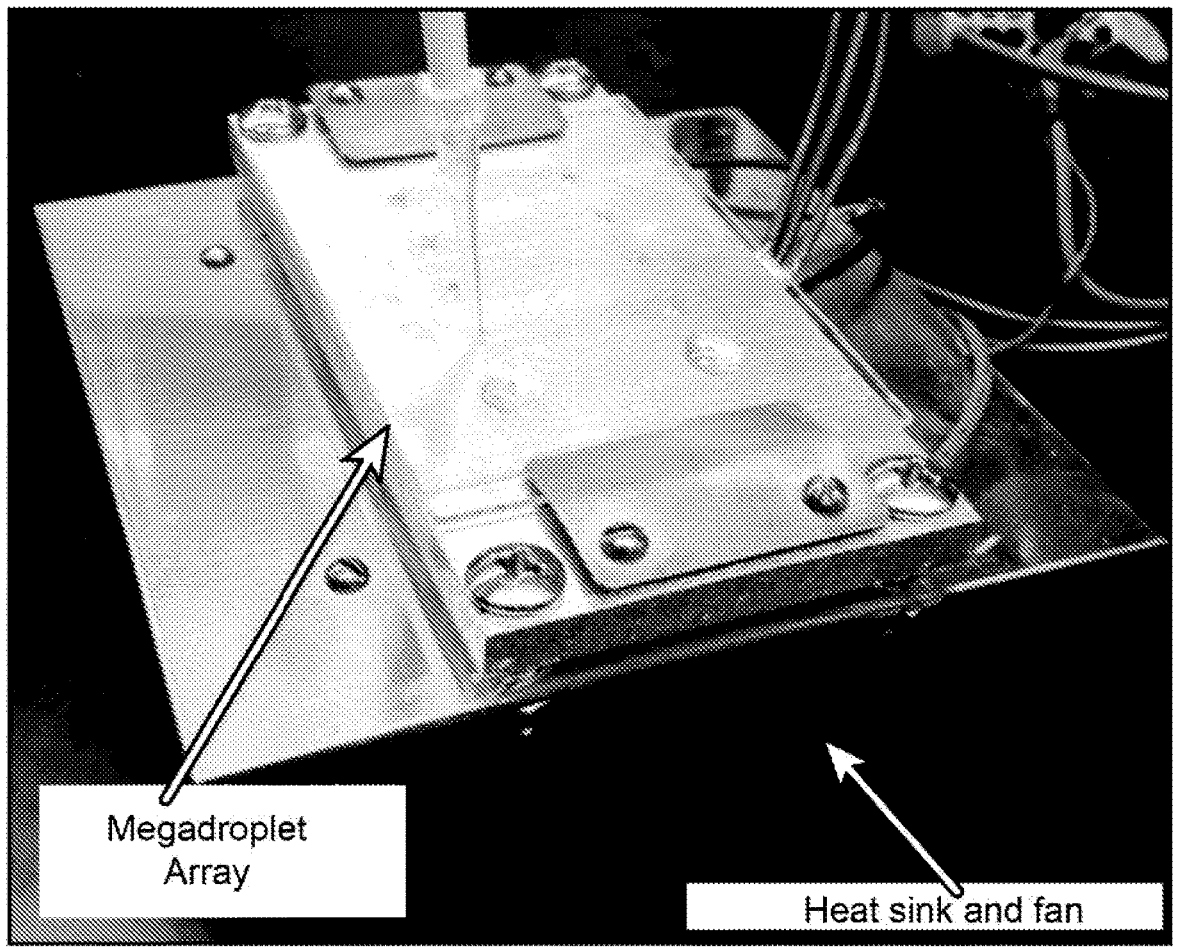
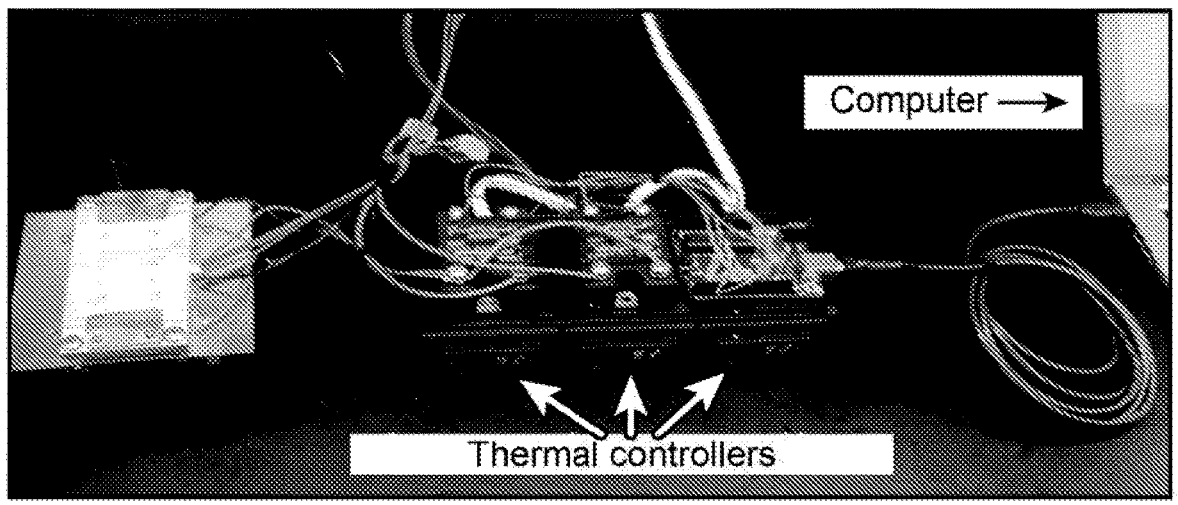

FIG. 14
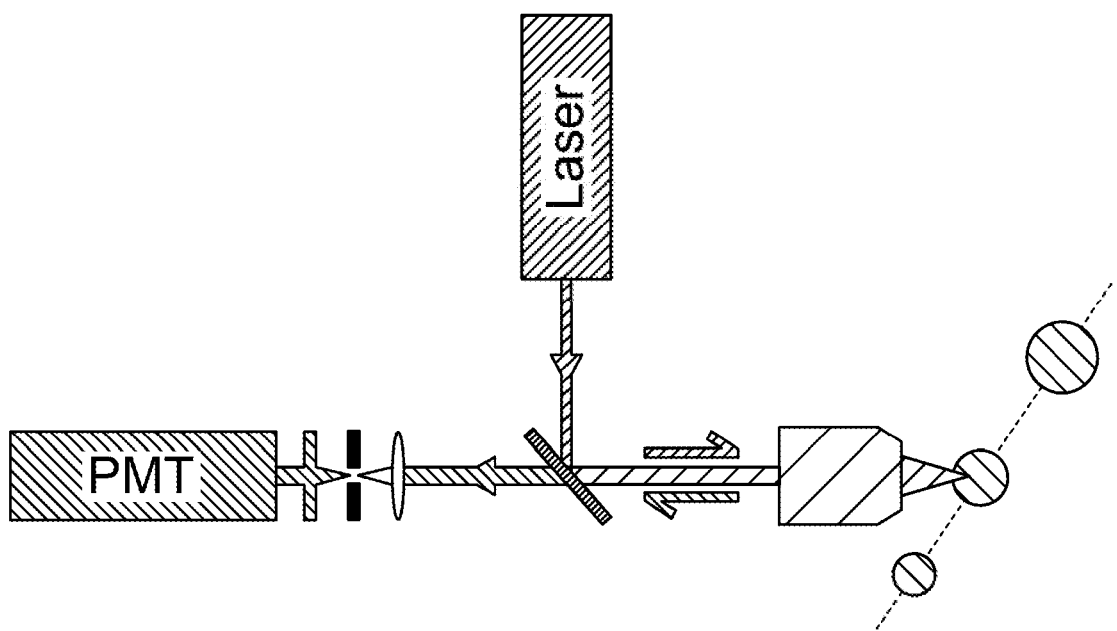
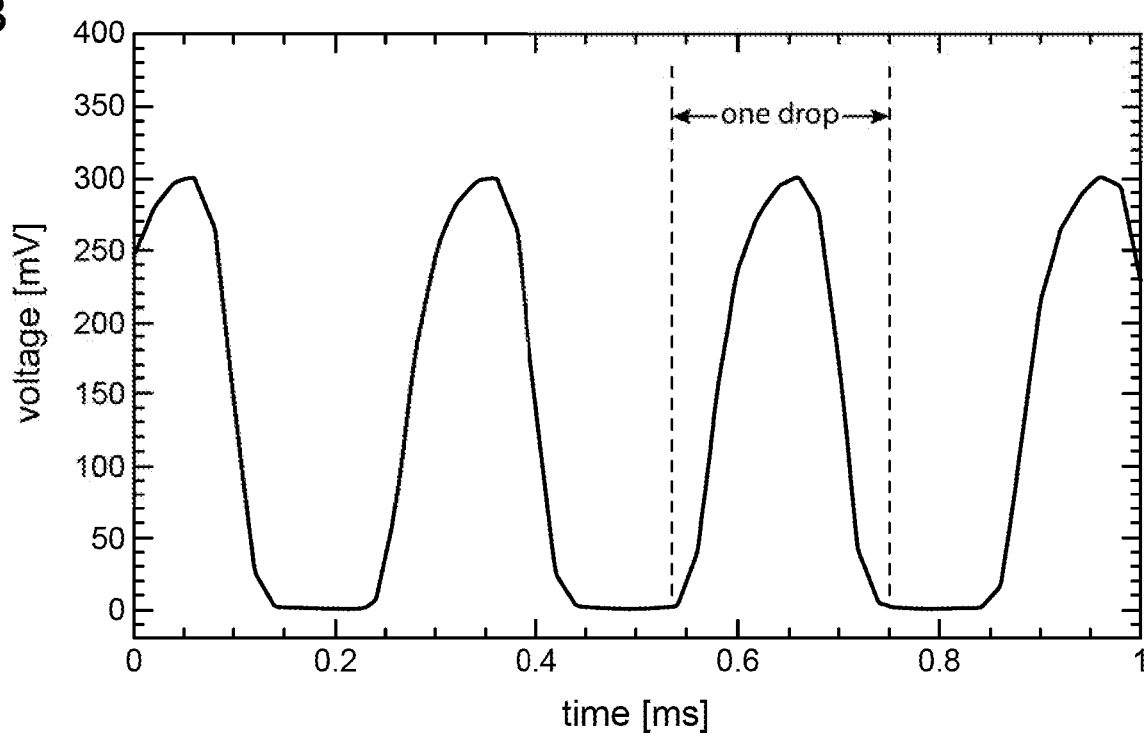

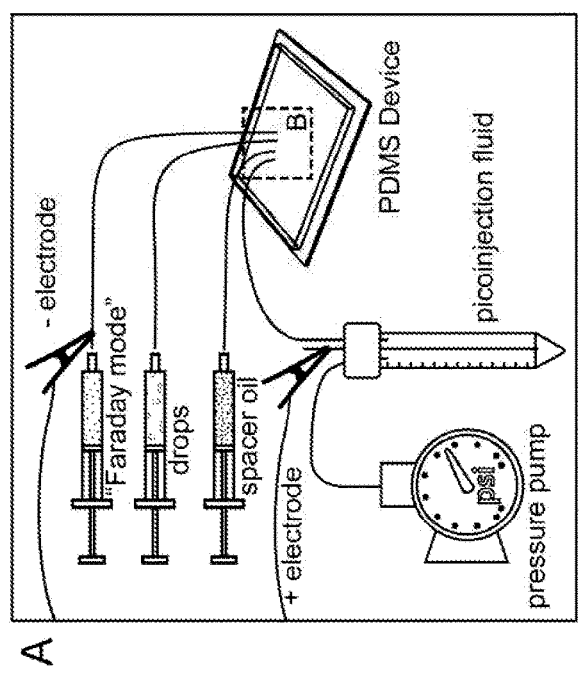
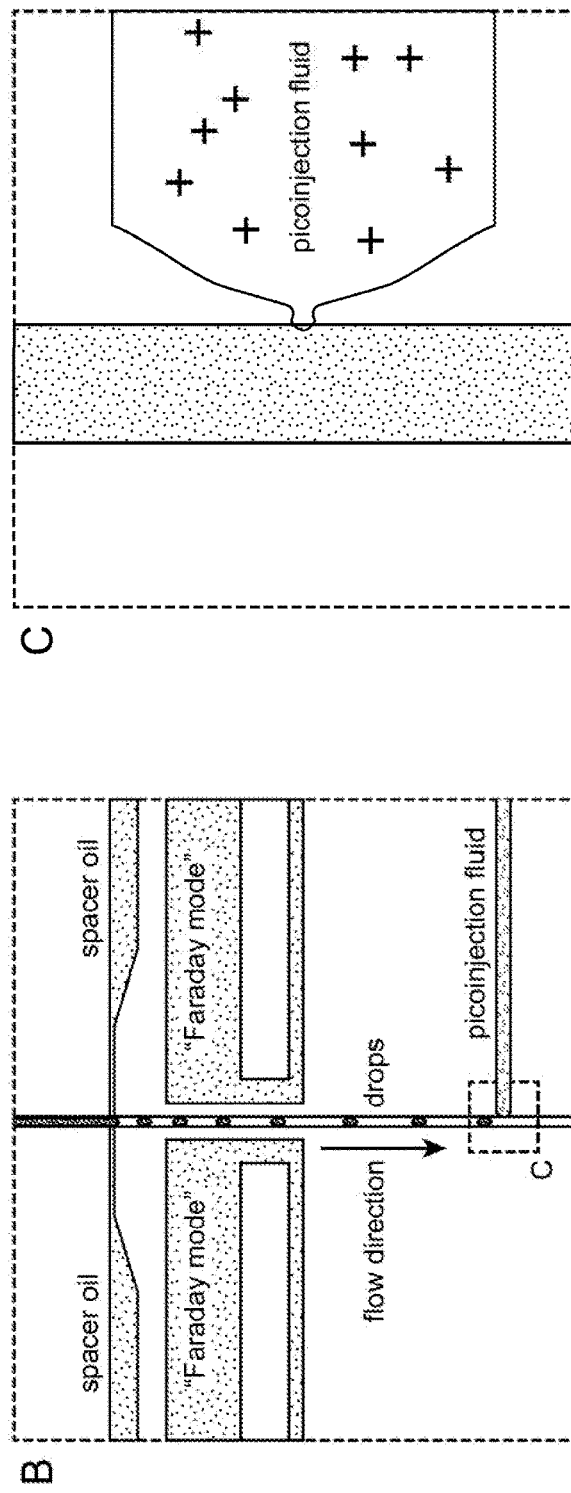
FIG. 15

FIG. 16
A
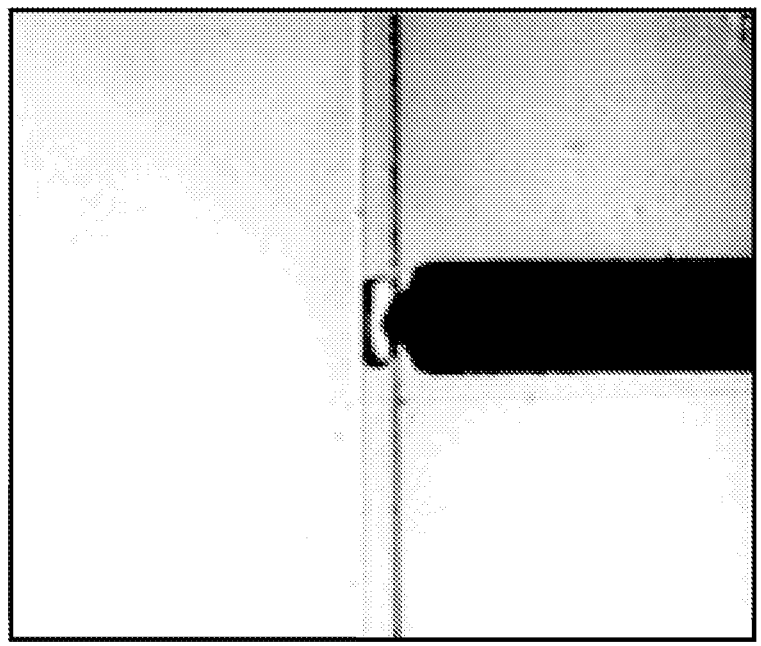
B
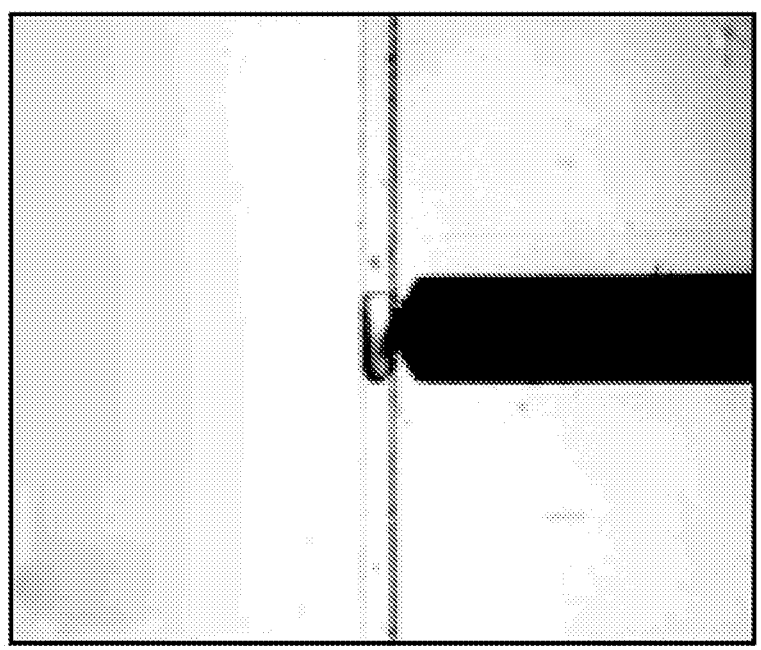

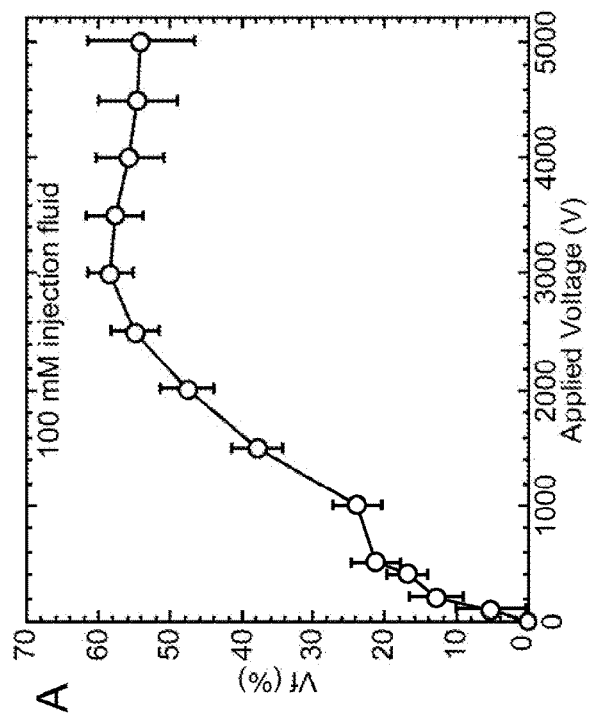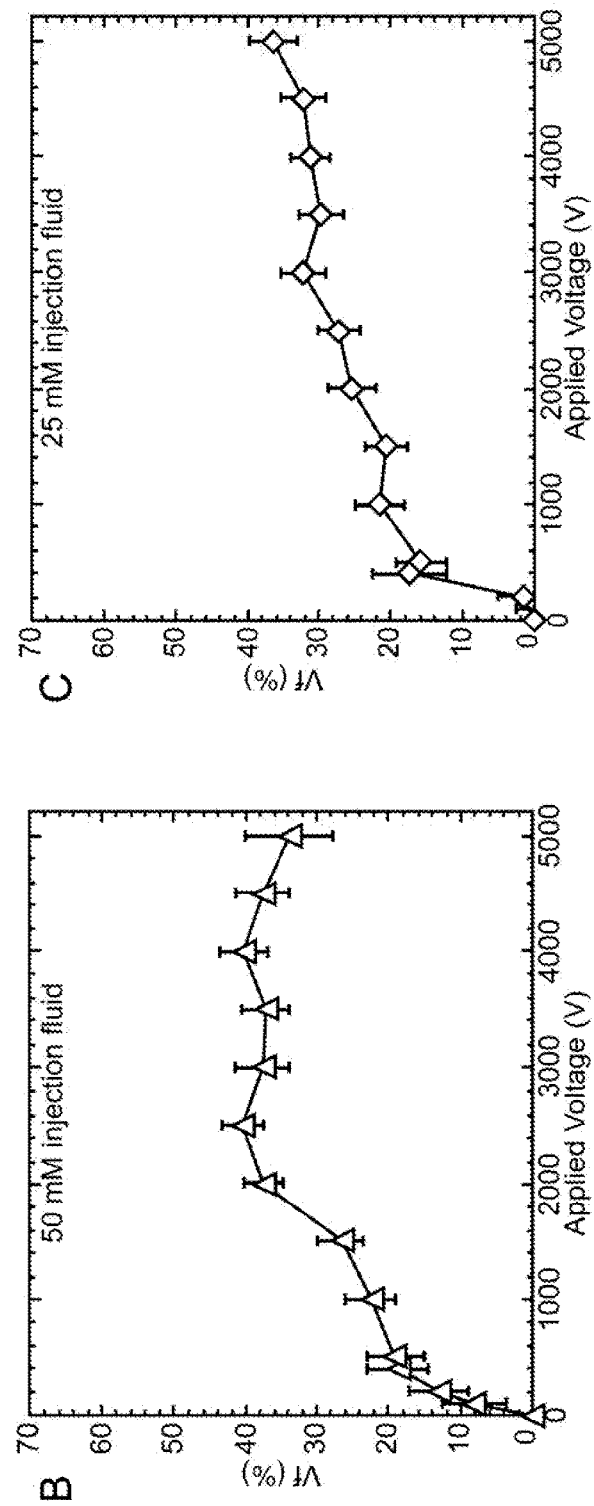
FIG. 17

FIG. 20
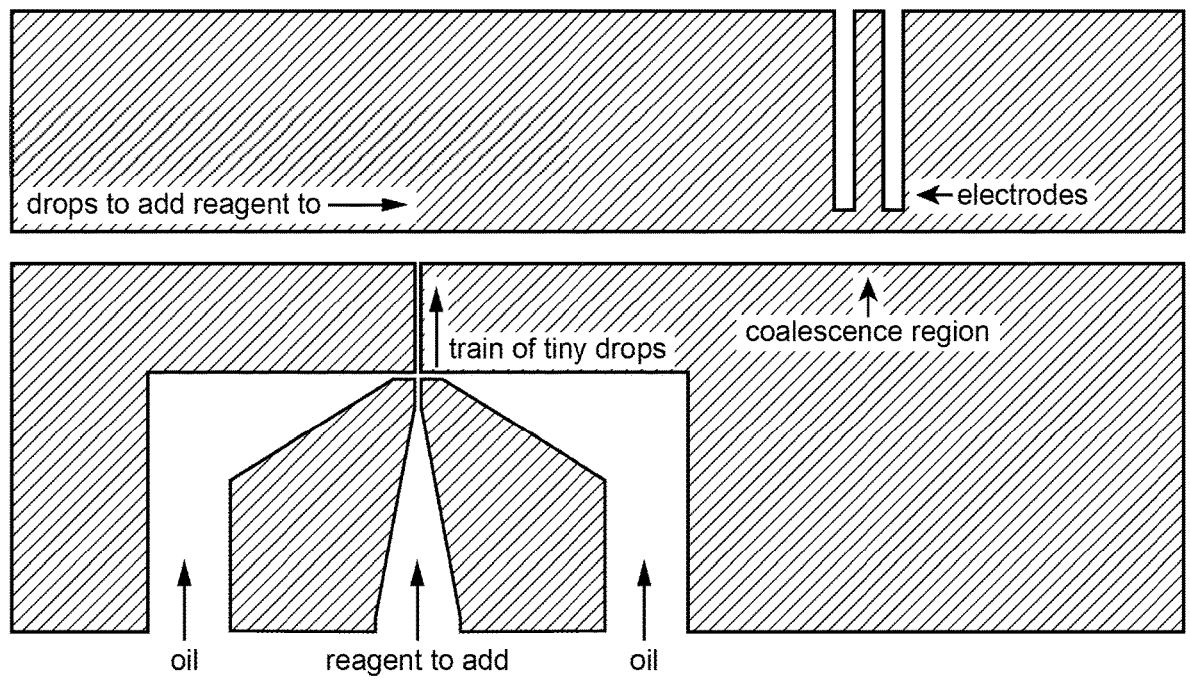
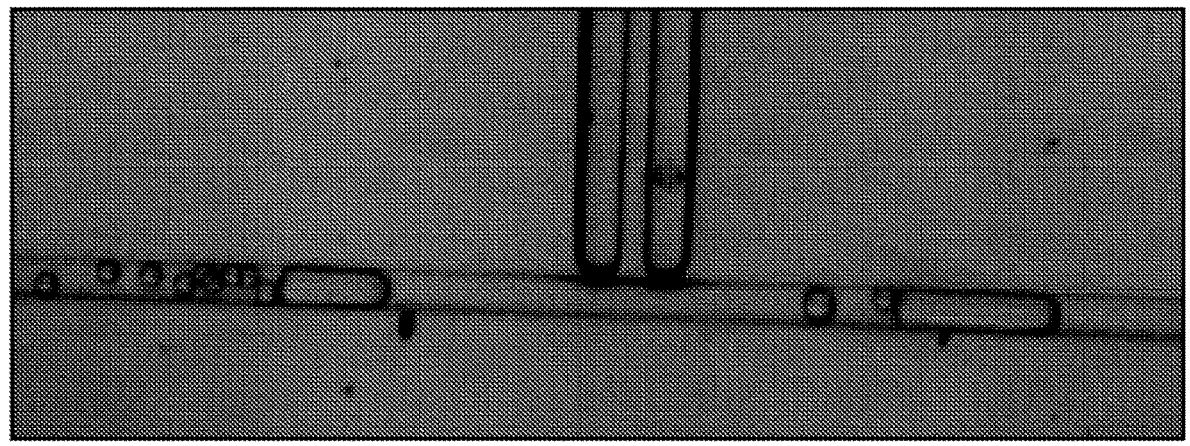

FIG. 22
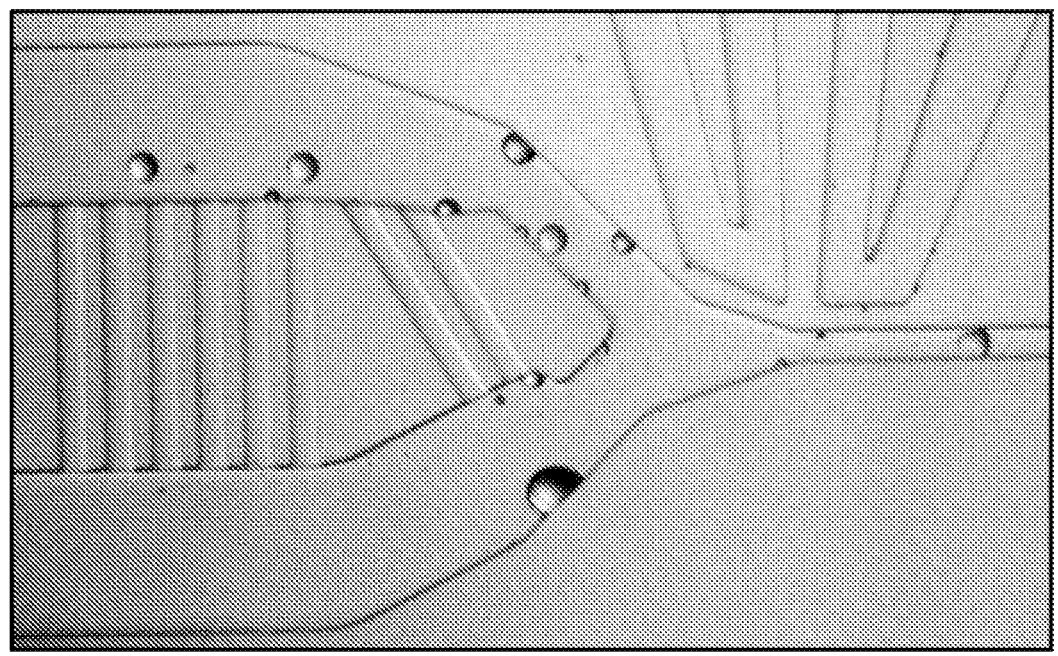
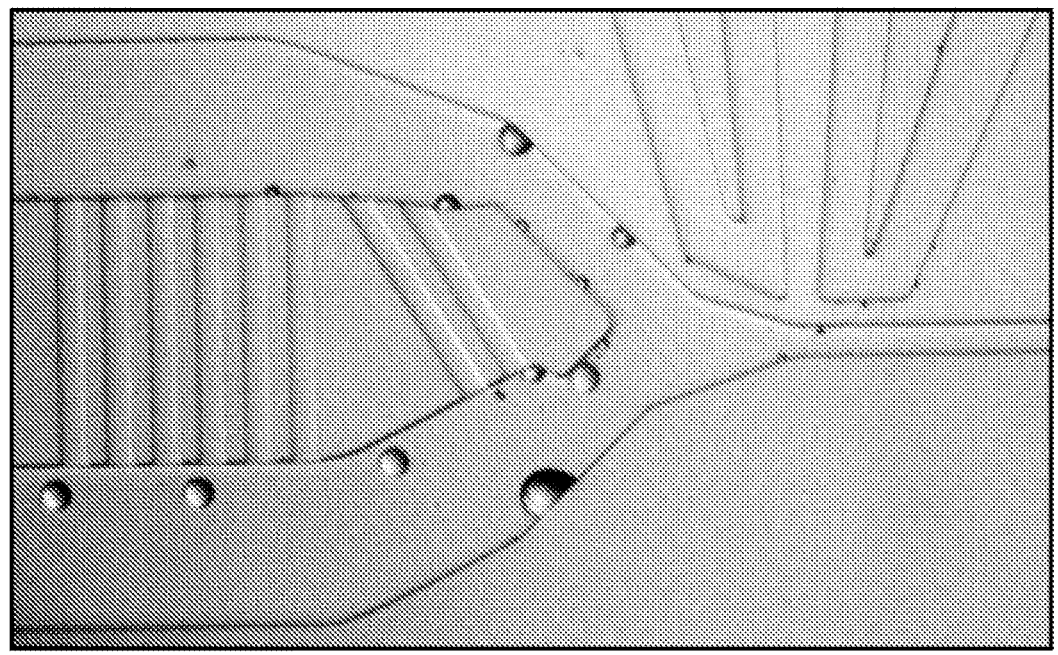

FIG. 26
A
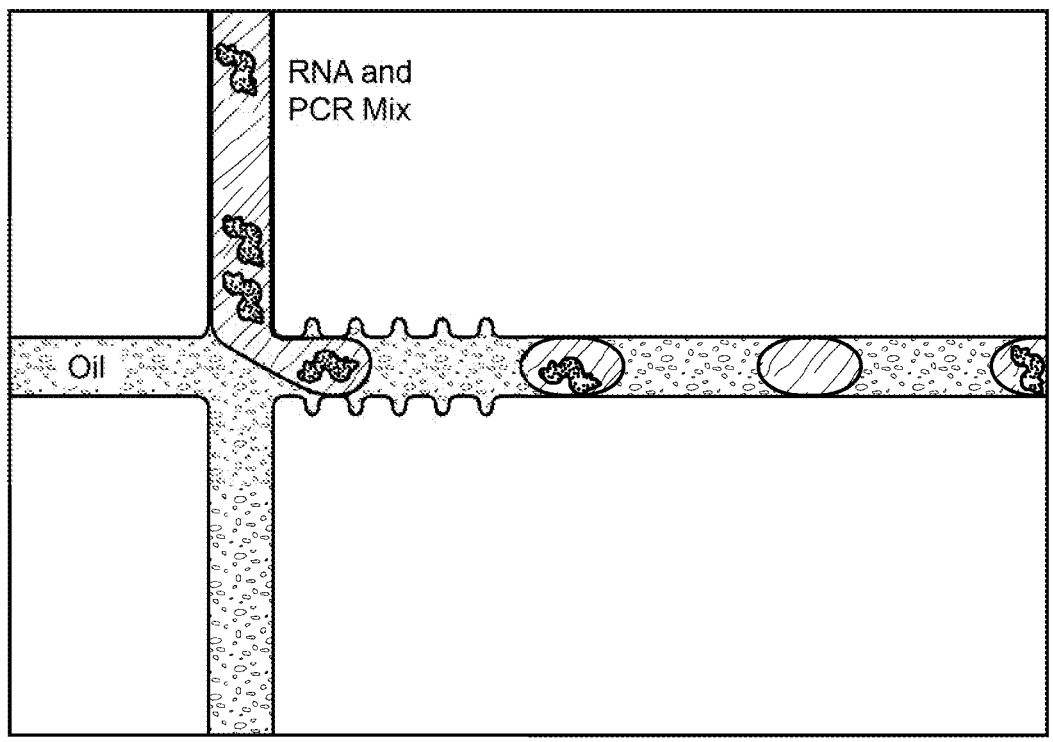
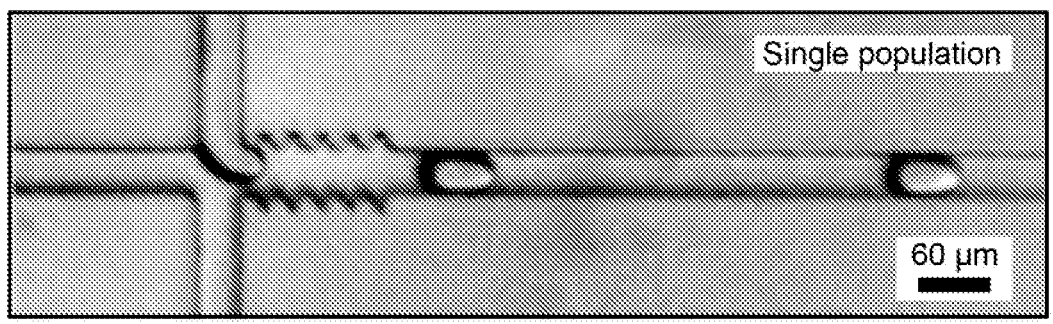
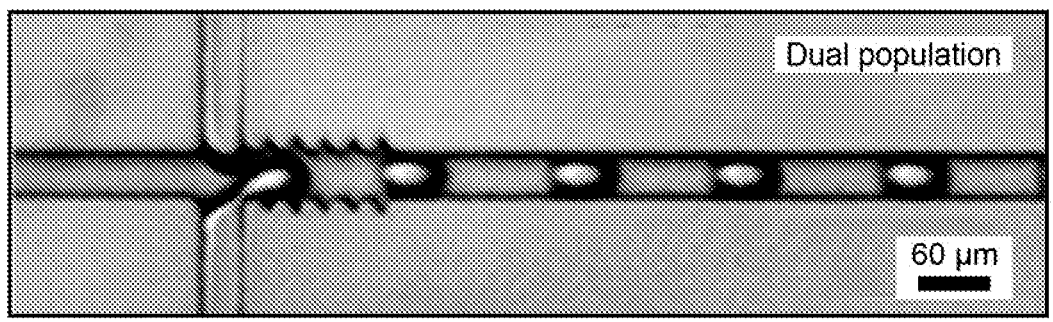

FIG. 26 (Cont.)
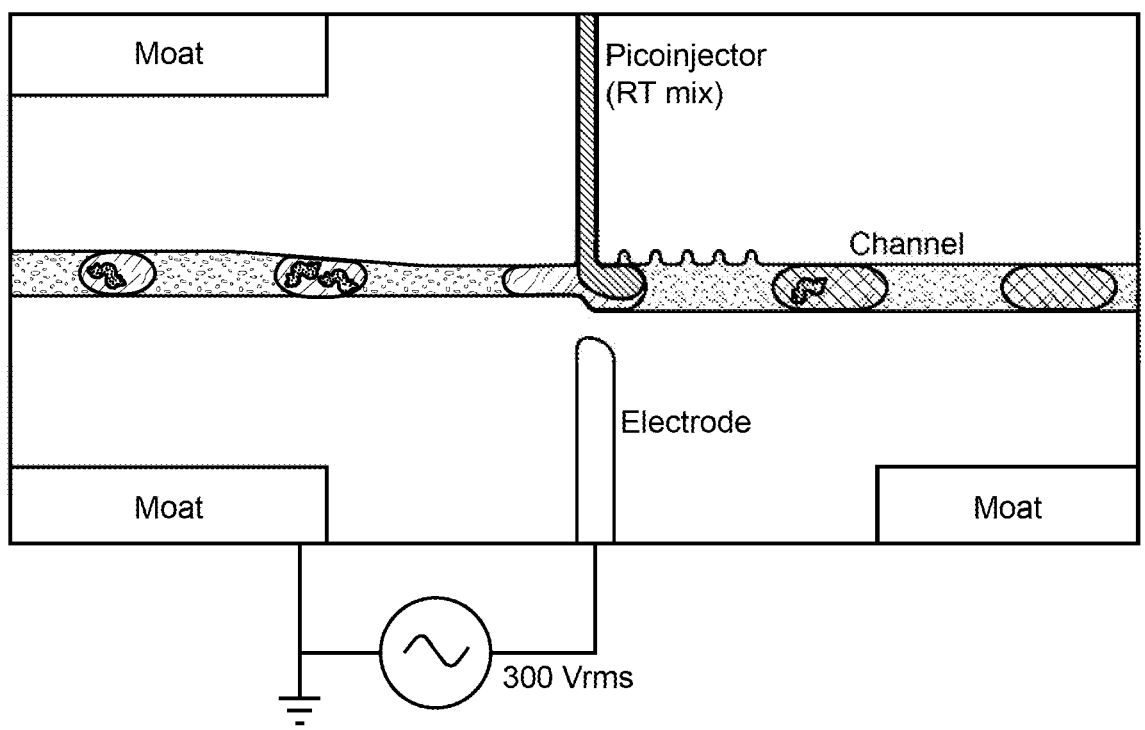
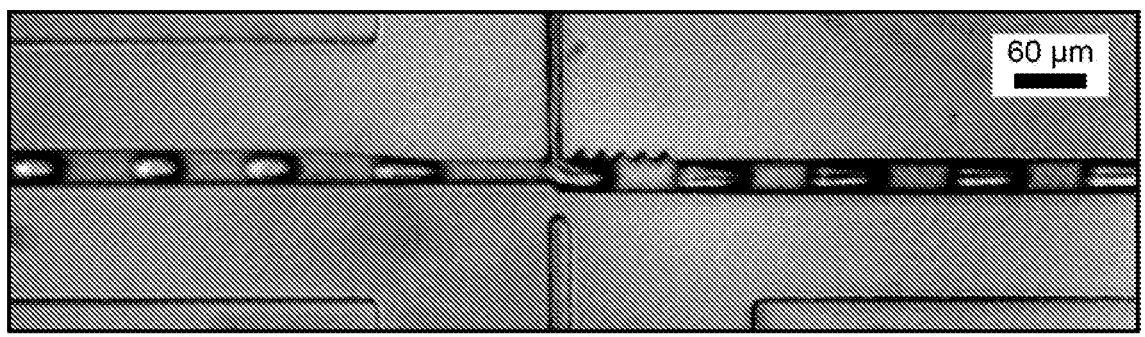

C

Collect, Thermocycle, and Image

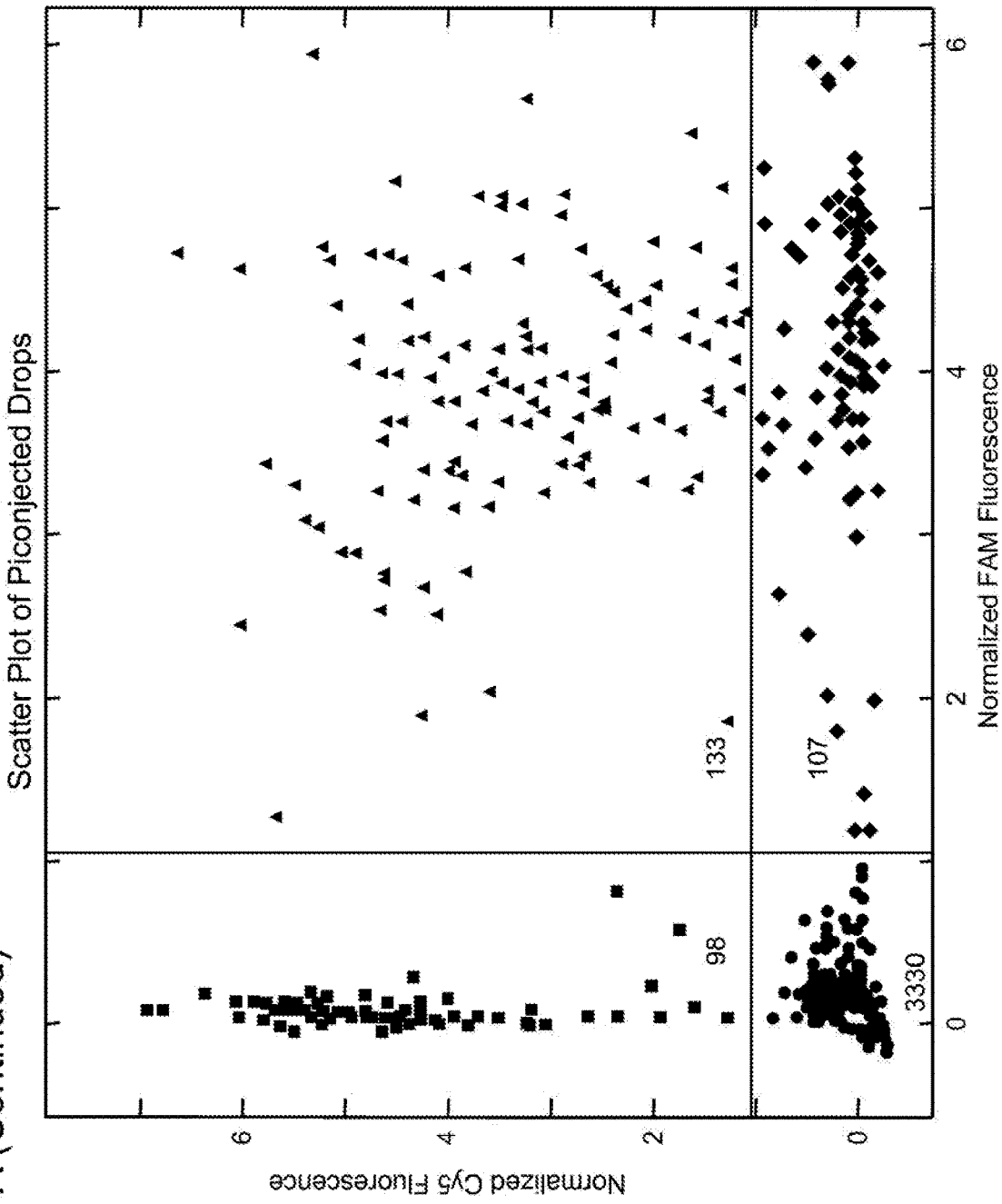

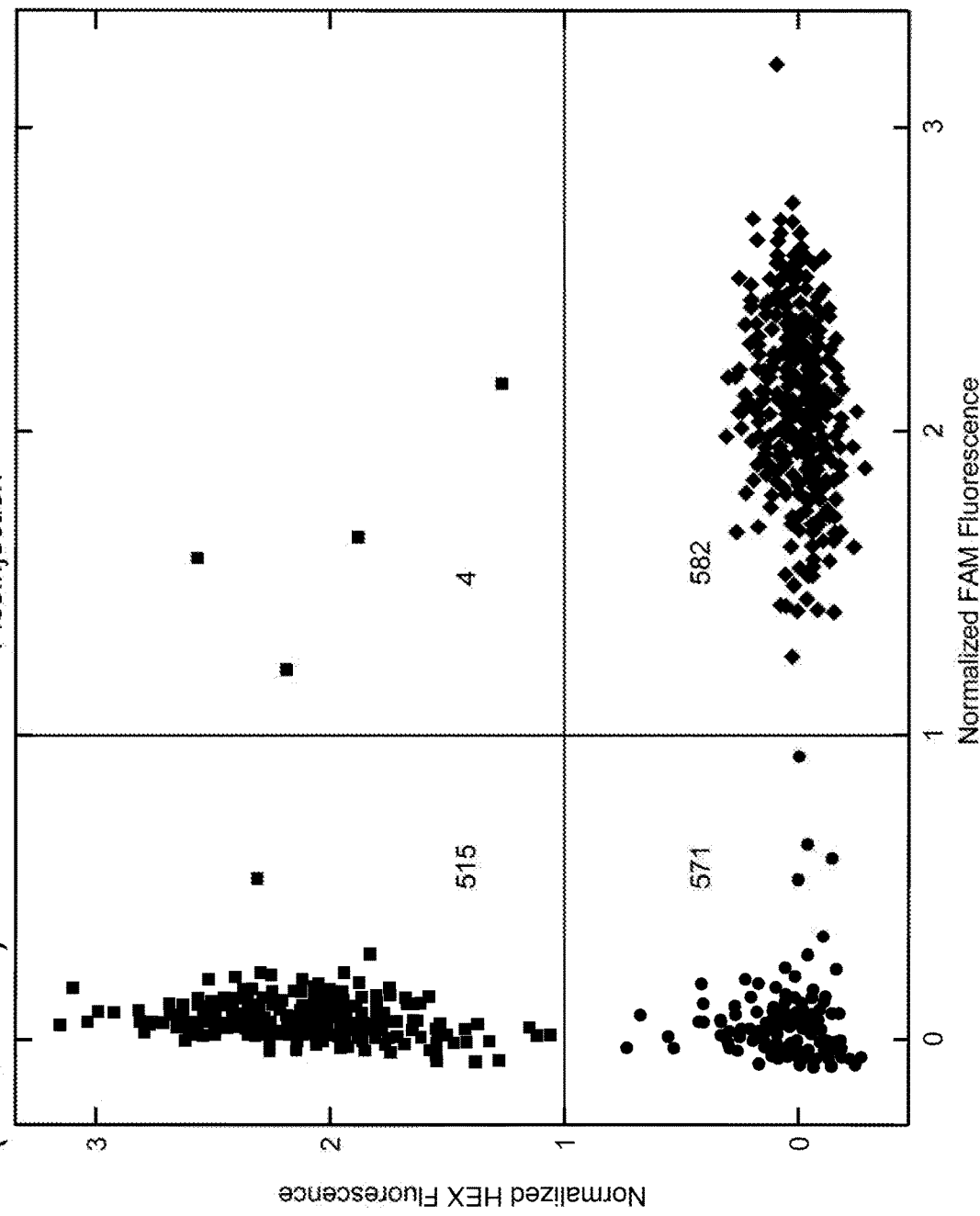
FIG. 30 (Cont.) A (Continued)

FIG. 41
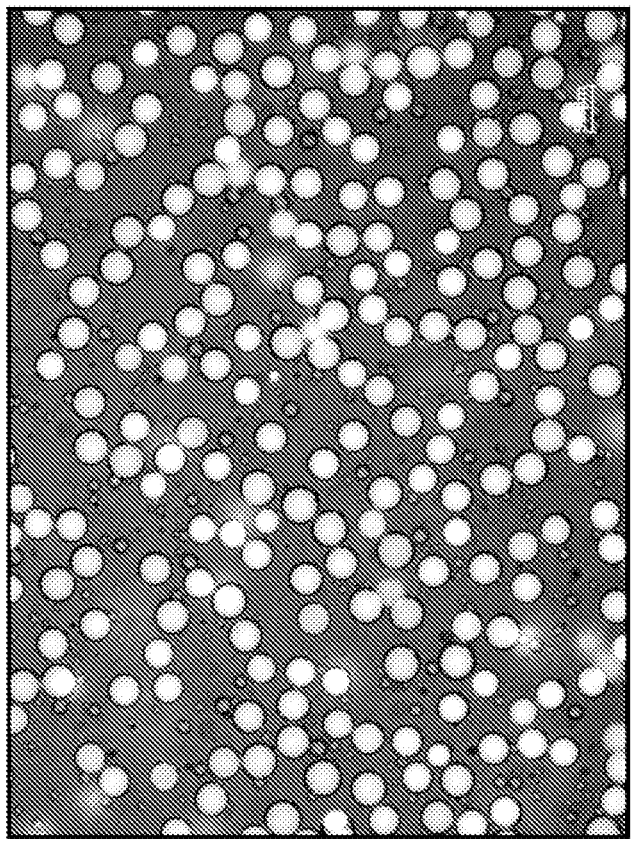
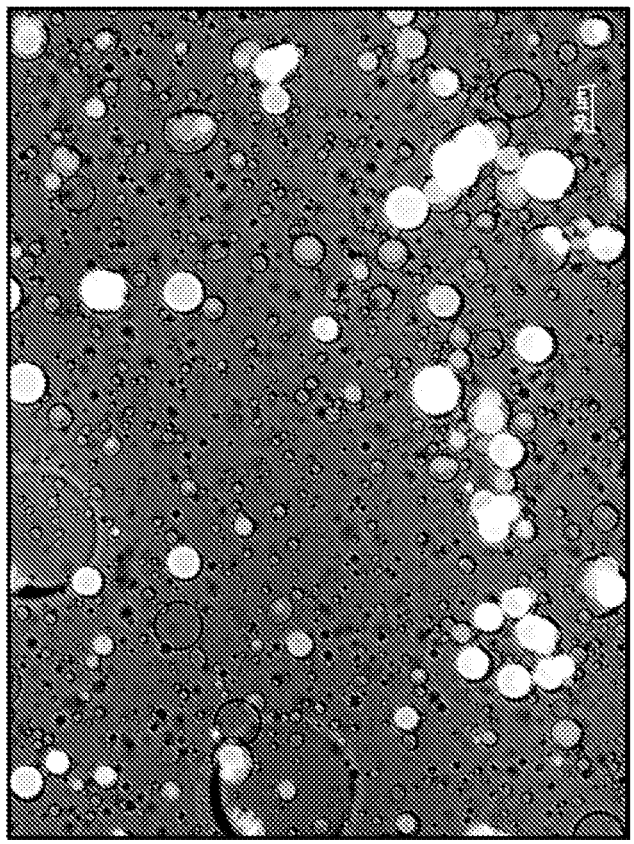

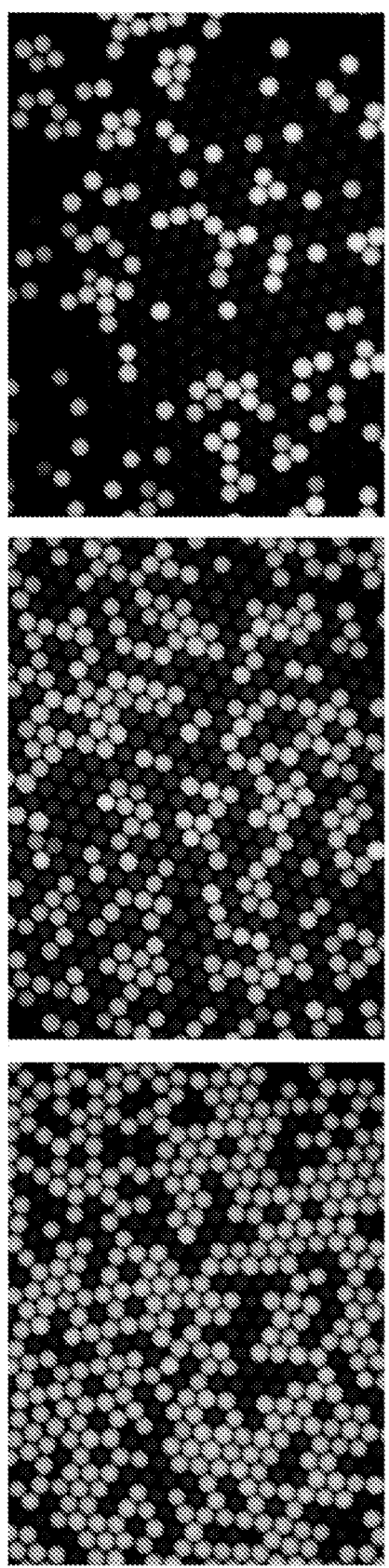
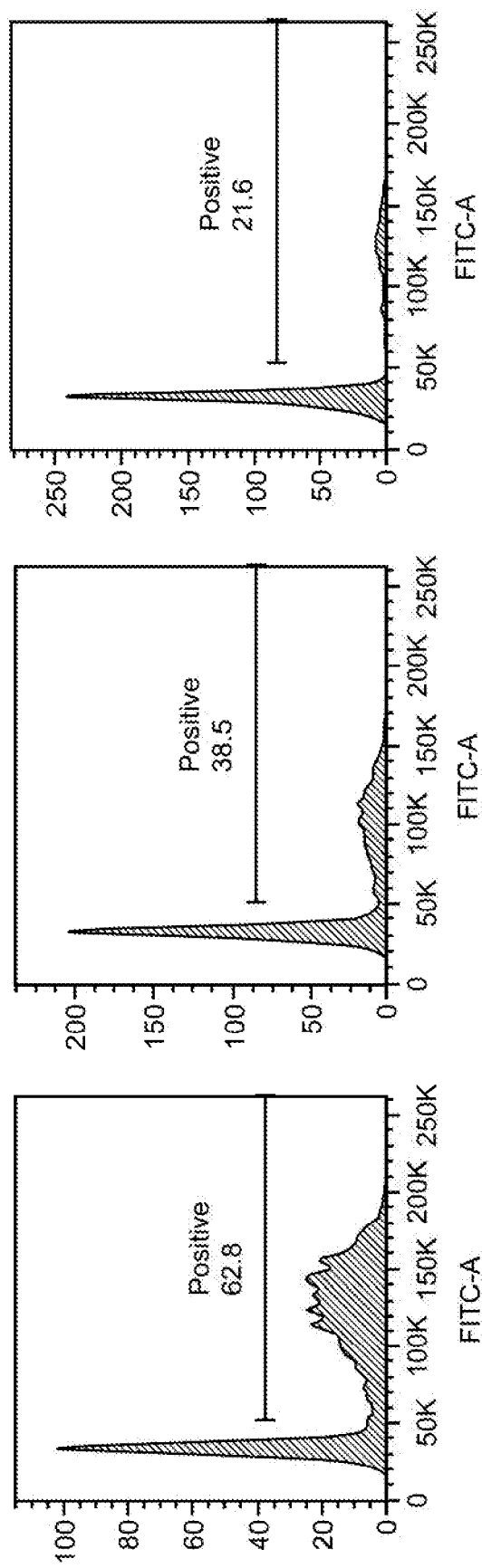
FIG. 47

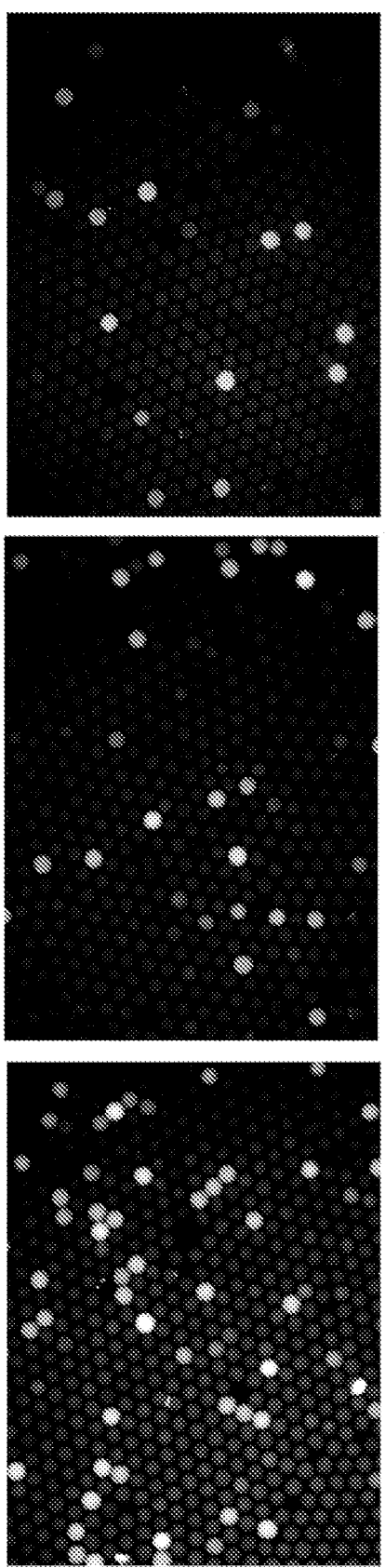
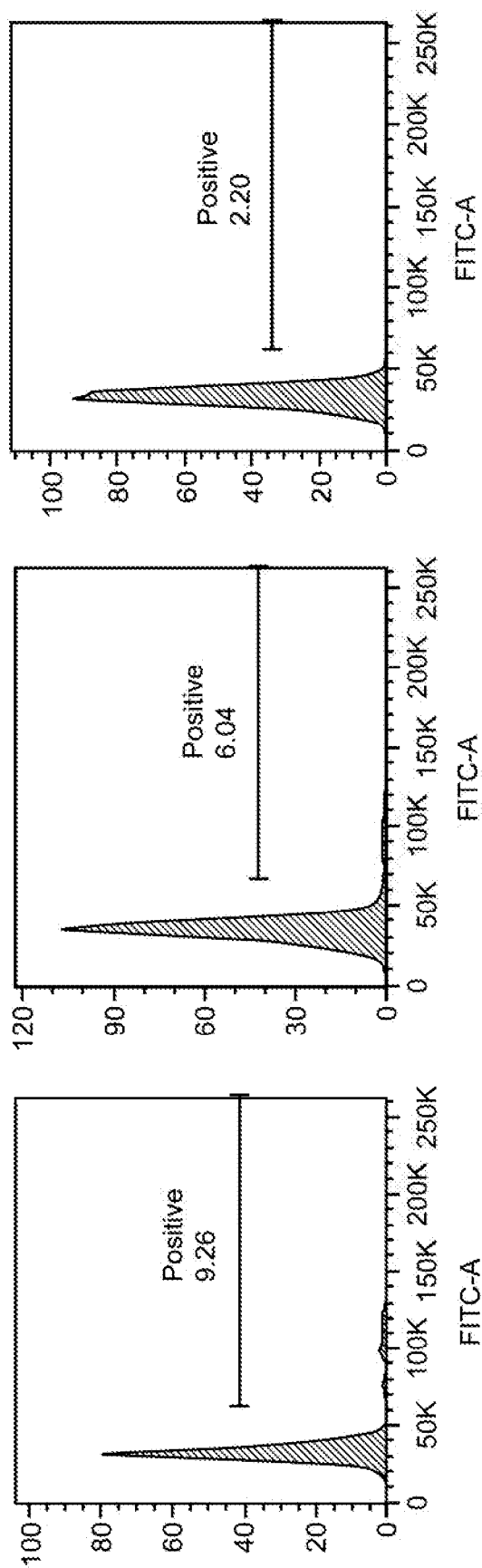
FIG. 48

FIG. 49
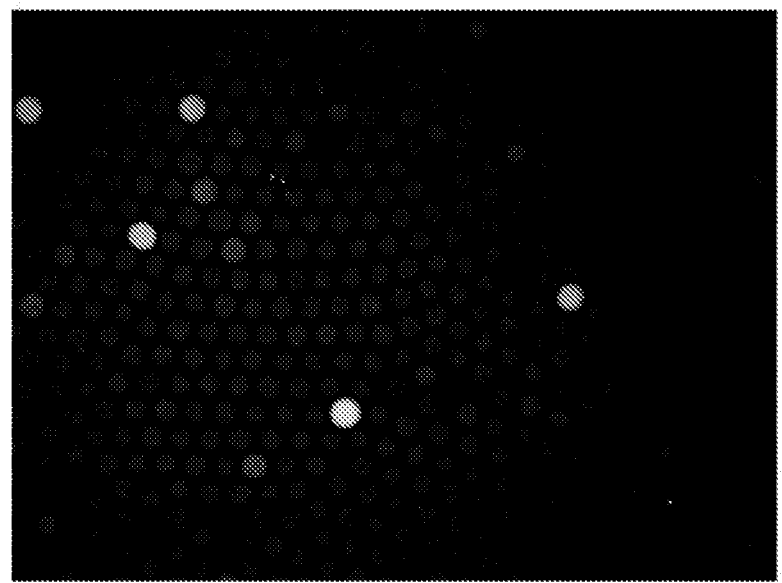
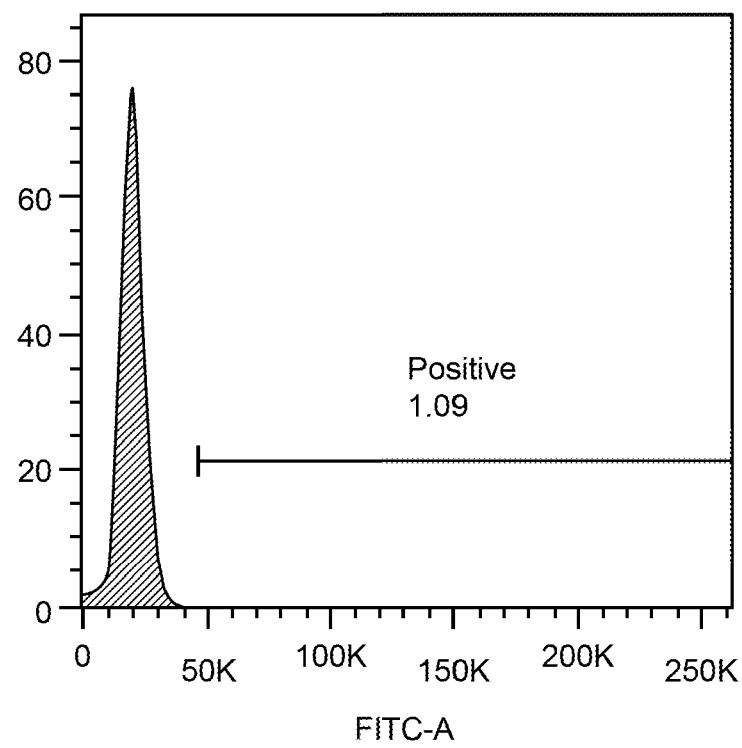

A

FIG. 62
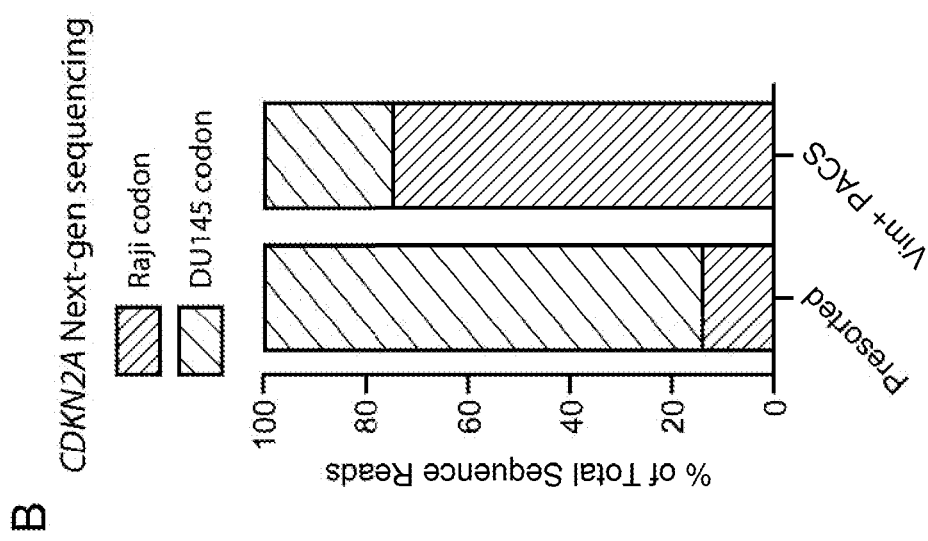
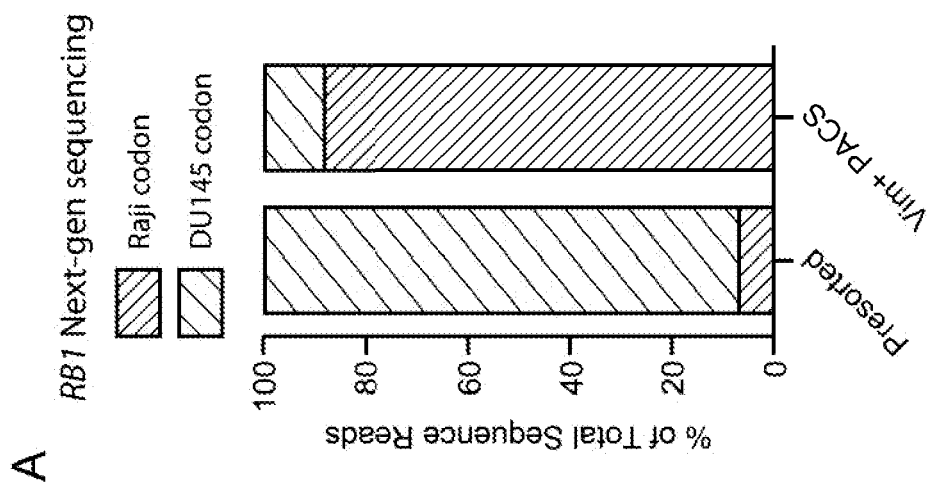

FIG. 64 (Cont.)
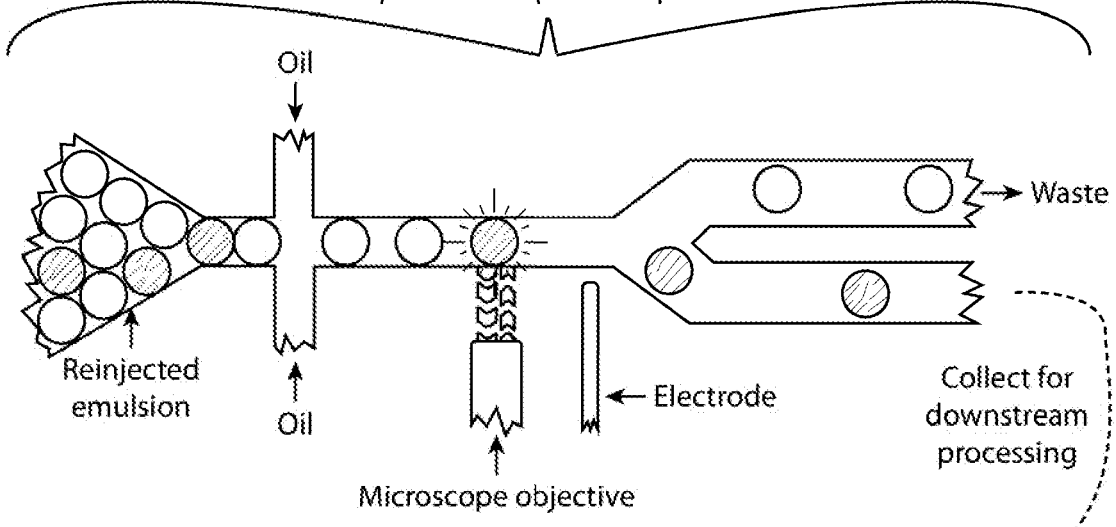
E — Dielectrophoretic sorting to isolate positive Taqman droplets
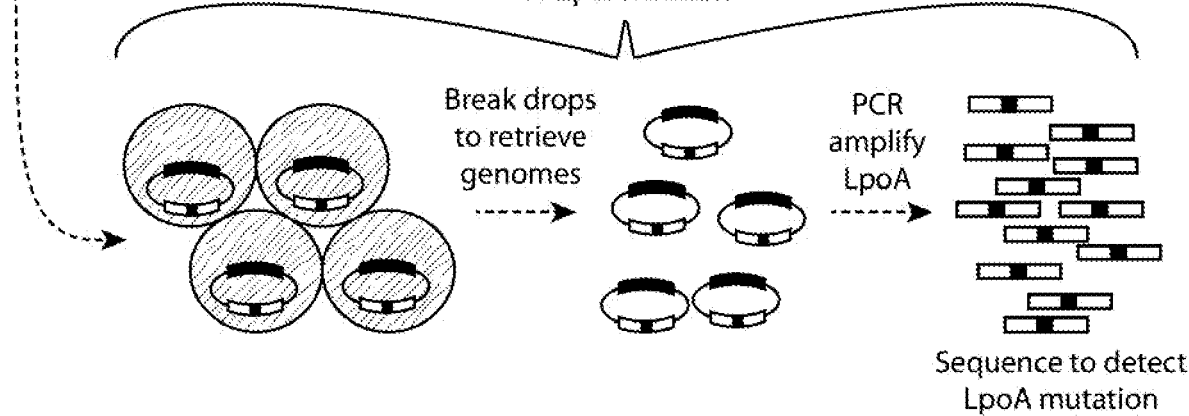
F — Check for sort purity via sequencing of LpoA mutant FIG. 65
A
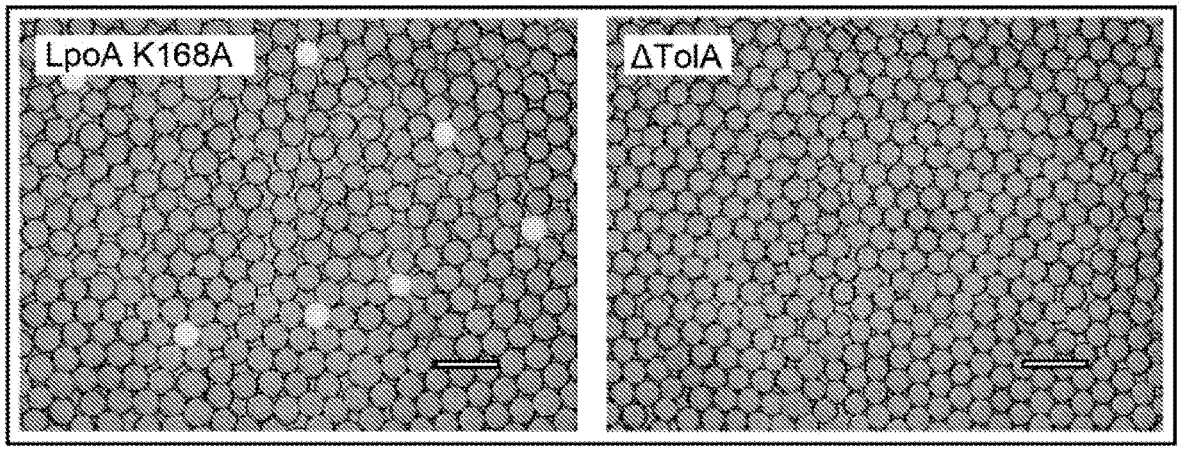
B
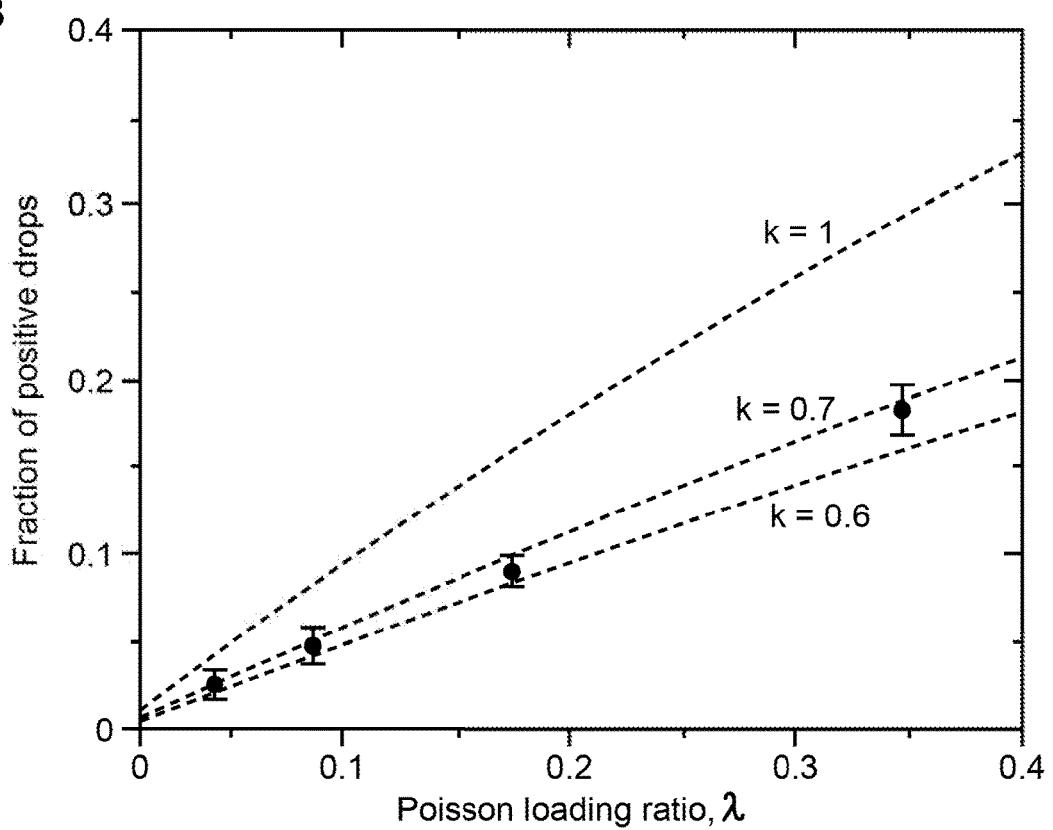

FIG. 69
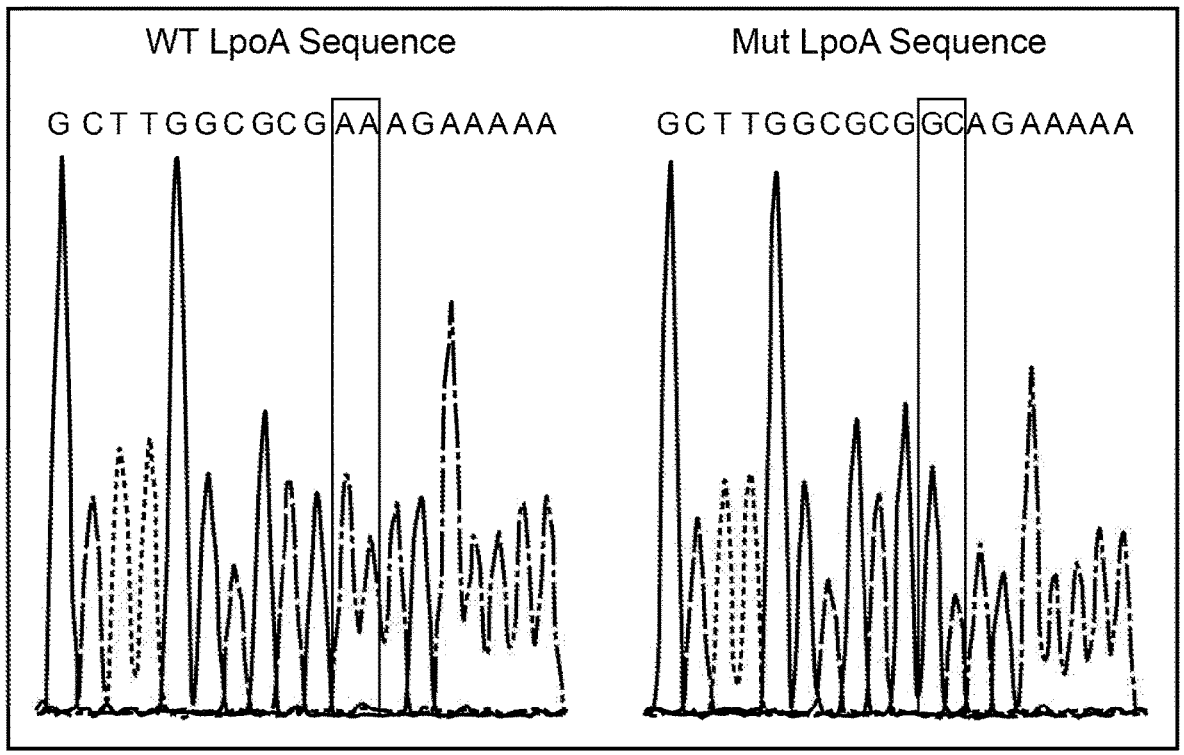
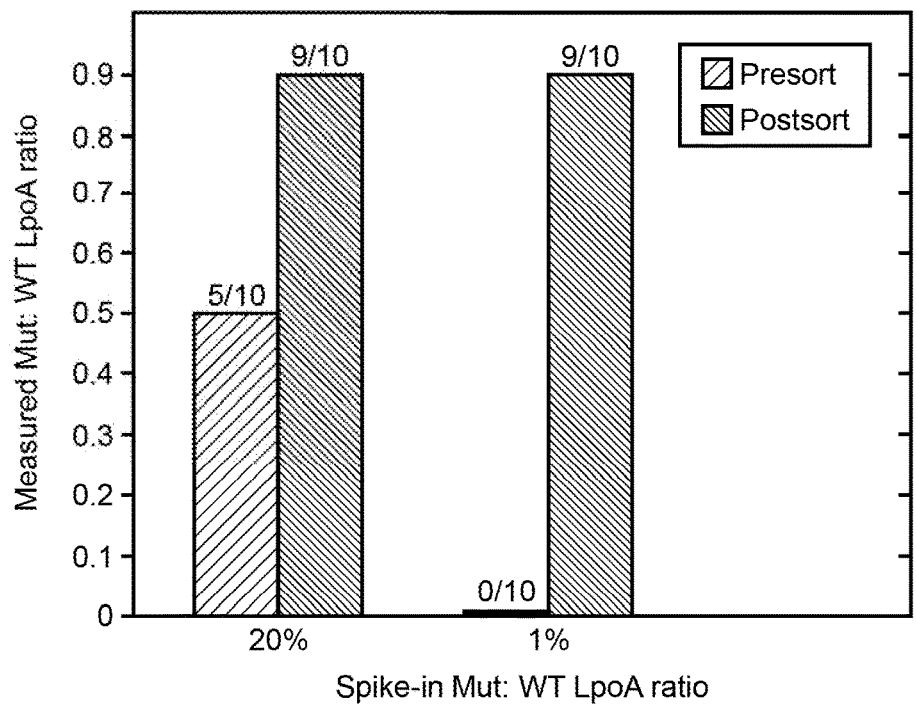

```
                         SEQUENCE LISTING

<160> NUMBER OF SEQ ID NOS: 30

<210> SEQ ID NO 1
    <211> LENGTH: 21
    <212> TYPE: DNA
    <213> ORGANISM: Artificial sequence
    <220> FEATURE:
    <223> OTHER INFORMATION: synthetic oligonucleotide

<400> SEQUENCE: 1
cctatgcatc tcacccatct c                                                  21

<210> SEQ ID NO 2
    <211> LENGTH: 22
    <212> TYPE: DNA
    <213> ORGANISM: Artificial sequence
    <220> FEATURE:
    <223> OTHER INFORMATION: synthetic oligonucleotide

<400> SEQUENCE: 2
agttgttgct ggaattgttg tg                                                 22

<210> SEQ ID NO 3
    <211> LENGTH: 27
    <212> TYPE: DNA
    <213> ORGANISM: Artificial sequence
    <220> FEATURE:
    <223> OTHER INFORMATION: synthetic oligonucleotide

<400> SEQUENCE: 3
acggttaaca atagttatgg taattgg                                            27

<210> SEQ ID NO 4
    <211> LENGTH: 21
    <212> TYPE: DNA
    <213> ORGANISM: Artificial sequence
    <220> FEATURE:
    <223> OTHER INFORMATION: synthetic oligonucleotide

<400> SEQUENCE: 4
caacacctcc cagtatgaca c                                                  21

<210> SEQ ID NO 5
    <211> LENGTH: 23
    <212> TYPE: DNA
    <213> ORGANISM: Artificial sequence
    <220> FEATURE:
    <223> OTHER INFORMATION: synthetic oligonucleotide

<400> SEQUENCE: 5
ccatatgttt gctttccttc tcc                                                23
```

<210> SEQ ID NO 6
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 6
tggtgacttt tggcagatga                                           20

<210> SEQ ID NO 7
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 7
atctcagcct tctcatactt tgccattctc                                30

<210> SEQ ID NO 8
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 8
tgcttcaatg cttcagctcc acct                                      24

<210> SEQ ID NO 9
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 9
cctggtctcc atgtttcagt tctgtca                                   27

<210> SEQ ID NO 10
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 10
gtgaatccag attagtttcc ctca                                      24

<210> SEQ ID NO 11
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 11
caagacctgc tcaatgttaa gatg                                      24

<210> SEQ ID NO 12
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 12
cgccttccag cagcttcctg ta                                              22

<210> SEQ ID NO 13
<211> LENGTH: 69
<212> TYPE: DNA
<213> ORGANISM: Artificial sequence
<220> FEATURE:
<223> OTHER INFORMATION: synthetic oligonucleotide

<400> SEQUENCE: 13
tgccgattta atattgagca ttgcgtaaaa aaatatcac tggatacatt gcccgtagtc      60
tgcaaatcc                                                             69

<210> SEQ ID NO 14
<211> LENGTH: 69
<212> TYPE: DNA
<213> ORGANISM: Artificial sequence
<220> FEATURE:
<223> OTHER INFORMATION: synthetic oligonucleotide

<400> SEQUENCE: 14
cagccagcga cgcgcttgtg cttcccacgc atcgccggtc tgtttggtgg ccatgacccg     60
ggaattacg                                                             69

<210> SEQ ID NO 15
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 15
cgcaaacaac cgggcattaa tc                                              22

<210> SEQ ID NO 16
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 16
tttgctgcgg gtcacactg                                                  19

<210> SEQ ID NO 17
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 17
gctgcttggc gcggcagaaa aacagcag                                        28

<210> SEQ ID NO 18
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 18

```
ctgctgttttt tctgccgcgc caagcagc                                      28

<210> SEQ ID NO 19
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 19
gttgattcag gtgcggtagt t                                              21

<210> SEQ ID NO 20
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 20
gcctgctgtt ccttcatctt                                                20

<210> SEQ ID NO 21
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 21
atcaaacctg aaggtggcga tccc                                           24

<210> SEQ ID NO 22
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 22
tttactgcgc gcgttaattg                                                20

<210> SEQ ID NO 23
<211> LENGTH: 17
<212> TYPE: DNA
<213> ORGANISM: Artificial sequence
<220> FEATURE:
<223> OTHER INFORMATION: synthetic oligonucleotide

<400> SEQUENCE: 23
ttgcggctga ggttgtt                                                   17

<210> SEQ ID NO 24
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 24
gtaaaacgac ggccag                                                    16

<210> SEQ ID NO 25
<211> LENGTH: 21
<212> TYPE: DNA
<213> ORGANISM: Homo sapiens
```

-continued

```
<400> SEQUENCE: 25
tgcaaagtga agaatataga c                                              21

<210> SEQ ID NO 26
<211> LENGTH: 21
<212> TYPE: DNA
<213> ORGANISM: Homo sapiens

<400> SEQUENCE: 26
tgcaaagtgt agaatataga c                                              21

<210> SEQ ID NO 27
<211> LENGTH: 21
<212> TYPE: DNA
<213> ORGANISM: Homo sapiens

<400> SEQUENCE: 27
cccgtgcacg acgctgcccg g                                              21

<210> SEQ ID NO 28
<211> LENGTH: 21
<212> TYPE: DNA
<213> ORGANISM: Homo sapiens

<400> SEQUENCE: 28
cccgtgcact acgctgcccg g                                              21

<210> SEQ ID NO 29
<211> LENGTH: 19
<212> TYPE: DNA
<213> ORGANISM: Escherichia coli

<400> SEQUENCE: 29
gcttggcgcg aaagaaaaa                                                 19

<210> SEQ ID NO 30
<211> LENGTH: 19
<212> TYPE: DNA
<213> ORGANISM: Escherichia coli

<400> SEQUENCE: 30
gcttggcgcg gcagaaaaa                                                 19
```

PCR-ACTIVATED SORTING (PAS)

CROSS-REFERENCE

The present application is a continuation of U.S. patent application Ser. No. 15/317,393, filed Dec. 8, 2016, which is a continuation of PCT/US2015/037822, filed Jun. 25, 2015 which claims the benefit of U.S. Provisional Patent Application No. 62/018,400, filed Jun. 27, 2014, the disclosures of which are herein incorporated by reference.

GOVERNMENT SUPPORT

This invention was made with government support under grant no. HG007233 awarded by the National Institutes of Health. The government has certain rights in the invention.

INTRODUCTION

Biological systems often contain large and diverse collections of organisms. Interrogating the nucleic acids in these systems is a valuable method for studying what genes and species are present and understanding the system's overall properties. However, the diversity of the nucleic acids and organisms in common biological systems often makes direct study of the system through sequencing of all nucleic acids present challenging or impossible, since the very large numbers of sequences obtained tend to convolute the analysis process.

By way of example, microbial communities, which play important roles in geochemistry, exist in staggeringly diverse ecosystems. Understanding the genetics of the cells that inhabit an ecosystem may be critical to understanding how microbes function individually and in the complex networks that make up the natural environment. Studying the genetics of individual microbes, however, is difficult because most cannot be cultured in the laboratory and comprise uncultivable "microbial dark matter". To study uncultivable microbes, cultivation-free methods like shotgun sequencing have been utilized. In this approach, nucleic acids are purified out of a heterogeneous sample via chemical means, sheared into short fragments, and sequenced. To assemble the resulting compilation of short sequences into a larger coherent dataset, computational algorithms are utilized, but this process is often hampered by the lack of sequencing depth and the complexity of the diverse set of sequences obtained. As a result, next-generation sequencing of diverse communities commonly yields information about the genes present in a system but is unable to tell how those genes are bundled into genomes and packaged into individual cells. The inability to correlate sequences present within a single microbe prevents the association of distinct biosynthetic pathways that interact to form important phenotypes that can impact the global ecology of the system. Moreover, in such analyses, the genes of rare microbes are difficult to detect since they tend to be swamped out by the sequences of the off-target microbes that greatly outnumber them. This makes studying low-abundance microbes with interesting phenotypes particularly difficult.

One strategy for obtaining the genomic sequences of rare microbes in a diverse population is target enrichment. In this approach, fragments of the genomes of the target microbes are recovered by hybridization to capture probes. Sequence complementarity between the probes and targets allows the molecules to anneal, so that the target fragments can be recovered via probe enrichment. A limitation of probe capture, however, is that recovering whole microbial genomes requires hundreds or thousands of overlapping capture probes, necessitating substantial knowledge of the target sequence, which may not be available. Moreover, even when capture probes can be designed, the fragments captured are limited to those near the sequences targeted by the probes, biasing what can be detected by what is already known; this precludes recovery of whole genomes in many instances and, thus, prevents complete genetic characterization of the species of interest. This is particularly problematic when the horizontal transfer of genetic elements occurs because, in such unpredictable instances, these sequences are not known to exist in the species of interest and, thus, it may not possible to construct probes with which to capture them. Horizontal gene transfer is an important method by which microbes transfer genetic information and generate phenotypic diversity, which is why detecting such events is important for increased understanding of microbe evolution.

To overcome the limitations of probe hybridization capture, a superior method would be to label the target microbes with a specific reporter; the labeled cells could then be recovered, together with their whole genome, using ultra-high-throughput fluorescence-activated cell sorting (FACS). One method for accomplishing this is to chemically fix and permeabilize microbes and then bind to their nucleic acids probes labeled with fluorescent dyes; the then fluorescent cells can be sorted with FACS, a method known as fluorescence in-situ hybridization, fluorescence-activated cell sorting (FISH-FACS). FISH-FACS has enormous benefits over probe hybridization capture because it allows cultivation-free enrichment of the whole genome of the microbe of interest. However, FISH-FACS also has drawbacks that significantly limit its applicability for sequencing microbes. For example, fixation can chemically modify DNA and introduce sequencing bias and errors into the genomes recovered, yielding poor sequence data. More importantly, achieving bright, specific labeling of the cell type of interest requires substantial trial-and-error optimization of the fixation and permeabilization procedure, something that may not be possible when seeking to recover the genome of a cell that cannot be cultured in the lab. This is particularly challenging when screening natural samples containing large numbers of different microbes with distinct cell wall and membrane properties. Consequently, while FISH-FACS holds enormous utility for the in-situ identification of nucleic acid sequences in uncultivable microbes, it does have drawbacks which limit its routine use for sequencing purposes. To enable the robust whole-genome sequencing of rare, uncultivable microbes, a new method for enriching intact microbial genomes out of a diverse ecosystem is needed.

The present disclosure addresses the above issues and provides related advantages.

SUMMARY

This application incorporates herein by reference the entire disclosure of PCT Application No. PCT/US2013/054517, published as WO/2014/028378.

The methods and systems described herein, referred to as PCR-Activated Sorting (PAS), allow nucleic acids contained in biological systems to be sorted based on their sequence as detected with nucleic acid amplification techniques, e.g., PCR. This sorting allows for the enrichment of target sequences of interest from a sample while large amounts of off-target "background" DNA are discarded such that when the material is sequenced the majority of the reads obtained are from the target molecules of interest. The nucleic acids can be free floating or contained within living or nonliving structures, including particles, viruses, and cells. The nucleic acids can include, e.g., DNA or RNA. Systems and devices for use in practicing methods of the invention are also provided.

Generally, the disclosed methods include encapsulating an aqueous sample, which may include a heterogeneous population of cells, viruses, and/or nucleic acids, in a plurality of microdroplets, wherein each microdroplet includes an aqueous phase fluid in an immiscible phase carrier fluid. In some embodiments, the sample may be diluted prior to encapsulation, e.g., so as to encapsulate a controlled number of cells, viruses, and/or nucleic acids in the microdroplets. PCR reagents may be added to the microdroplets at the time of encapsulation or added to the microdroplets at a later time using one or more of the methods described herein, e.g., picoinjection, droplet merger, etc. The microdroplets are then subjected to PCR amplification conditions, such that if a microdroplet contains a nucleic acid corresponding to a target of interest, e.g., a cell, virus, or nucleic acid of interest, the microdroplet becomes detectably labeled, e.g., fluorescently labeled as a result of a fluorogenic assay, such as Sybr staining of amplified DNA or TaqMan PCR. To recover the target nucleic acids or entities comprising the target nucleic acids, the detectably labeled droplets may be sorted using microfluidic (e.g., dielectrophoresis, membrane valves, etc.) or non-microfluidic techniques (e.g., FACS).

In some embodiments, a method for sorting samples including nucleic acids, is provided, wherein the method includes encapsulating a sample including nucleic acids in a plurality of microdroplets, each microdroplet including a first aqueous phase fluid in an immiscible phase carrier fluid; introducing polymerase chain reaction (PCR) reagents and a plurality of PCR primers into the microdroplets; incubating the microdroplets under conditions sufficient for PCR amplification to produce PCR amplification products, wherein the plurality of PCR primers include one or more primers that each hybridize to one or more oligonucleotides; introducing a detection component into the microdroplets either before or after the incubating; detecting the presence or absence of the PCR amplification products by detection of the detection component, wherein detection of the detection component indicates the presence of PCR amplification products; and sorting the microdroplets based on detection of the detection component, wherein the sorting separates microdroplets including the PCR amplification products, when present, from microdroplets which do not include the PCR amplification products. One or more of these steps may be performed under microfluidic control.

In some embodiments of the above method, after the incubating, and before or after the detecting, the microdroplets may be positioned in an aqueous phase carrier fluid, e.g., by flowing the microdroplets through a double emulsion droplet maker, to provide aqueous phase-in-immiscible phase-in aqueous phase microdroplets. The aqueous phase-in-immiscible phase-in aqueous phase microdroplets may then be sorted based on detection of the detection component, wherein the sorting separates aqueous phase-in-immiscible phase-in aqueous phase microdroplets comprising the PCR amplification products, when present, from aqueous phase-in-immiscible phase-in aqueous phase microdroplets which do not comprise the PCR amplification products. One or more steps of the method may be performed under microfluidic control.

In some embodiments, referred to herein as PCR-Activated Virus Sorting (PAVS), a sample including viruses is encapsulated in microdroplets and subjected to PCR conditions, e.g., droplet PCR. In some embodiments, the encapsulated viruses are subjected to one or more virus lysing techniques, such as proteinase k digestion or thermal lysis. PCR assays specific to the viruses of interest can cause microdroplets containing the viruses of interest to become detectably labeled, e.g., fluorescently labeled. The viruses are then recovered by sorting the microdroplets and recovering their contents via microdroplet rupture, e.g., through chemical or electrical means.

In some embodiments, referred to herein as PCR-Activated Cell Sorting (PACS), a sample including cells is encapsulated in microdroplets and subjected to PCR conditions, e.g., droplet PCR. In some embodiments, the encapsulated cells are subjected to one or more cell lysing techniques, such as proteinase k digestion or thermal lysis. PCR assays specific to the cells of interest can cause microdroplets containing the cells of interest to become detectably labeled, e.g., fluorescently labeled. The cells are then recovered by sorting the microdroplets and recovering their contents via microdroplet rupture, e.g., through chemical or electrical means.

In some embodiments, referred to herein as PCR-Activated Nucleic Acid Sorting (PANS), a sample including nucleic acids (e.g., DNA and/or RNA) is encapsulated in microdroplets and subjected to PCR conditions, e.g., RT-PCR conditions, e.g., droplet PCR (or RT-PCR). PCR, e.g., RT-PCR, assays specific to the nucleic acids of interest can cause droplets containing the nucleic acids of interest to become detectably labeled, e.g., fluorescently labeled. The nucleic acids of interest are then recovered by sorting the microdroplets and recovering their contents via microdroplet rupture, e.g., through chemical or electrical means.

In one aspect of PANS, a method for enriching for a target nucleic acid sequence is provided, wherein the method includes encapsulating a sample including nucleic acids in a plurality of microdroplets, each microdroplet including a first aqueous phase fluid in an immiscible phase carrier fluid; introducing polymerase chain reaction (PCR) reagents and a plurality of PCR primers into the microdroplets; incubating the microdroplets under conditions sufficient for PCR amplification to produce PCR amplification products, wherein the plurality of PCR primers include one or more primers that each hybridize to one or more oligonucleotides comprised by the target nucleic acid sequence, and wherein the PCR amplification products do not include the entire target nucleic acid sequence; introducing a detection component into the microdroplets either before or after the incubating; detecting the presence or absence of the PCR amplification products by detection of the detection component, wherein detection of the detection component indicates the presence of PCR amplification products and the target nucleic acid sequence; and sorting the microdroplets based on detection of the detection component, wherein the sorting separates microdroplets including the PCR amplification products and the target nucleic acid sequence, when present, from microdroplets which do not include the PCR amplification products and the target nucleic acid sequence; and pooling the nucleic acid sequences from the sorted microdroplets to provide an enriched pool of target nucleic acid sequences, when present. One or more of these steps may be performed under microfluidic control.

In some embodiments of the above method, after the incubating, and before or after the detecting, the method can include positioning the microdroplets in an aqueous phase carrier fluid to provide aqueous phase-in-immiscible phase-in aqueous phase microdroplets. In such embodiments, the sorting may include sorting the aqueous phase-in-immiscible phase-in aqueous phase microdroplets based on detection of the detection component, wherein the sorting separates aqueous phase-in-immiscible phase-in aqueous phase microdroplets including the PCR amplification products and the target nucleic acid, when present, from aqueous phase-in-immiscible phase-in aqueous phase microdroplets which do not include the PCR amplification products and the target nucleic acid. In such embodiments, the pooling may include pooling the target nucleic acids from the sorted aqueous phase-in-immiscible phase-in aqueous phase microdroplets to provide an enriched pool of the target nucleic acids, when present. One or more of these steps may be performed under microfluidic control.

In practicing the subject methods, several variations may be employed. For example, a wide range of different PCR-based assays may be employed, such as quantitative PCR (qPCR). The number and nature of primers used in such assays may vary, based at least in part on the type of assay being performed, the nature of the biological sample, and/or other factors. In certain aspects, the number of primers that may be added to a microdroplet may be 1 to 100 or more, and/or may include primers to detect from about 1 to 100 or more different genes (e.g., oncogenes). In addition to, or instead of, such primers, one or more probes (e.g., TaqMan® probes) may be employed in practicing the subject methods.

The microdroplets themselves may vary, including in size, composition, contents, and the like. Microdroplets may generally have an internal volume of from about 0.001 to 1000 picoliters or more, e.g., from about 0.001 picoliters to about 0.01 picoliters, from about 0.01 picoliters to about 0.1 picoliters, from about 0.1 picoliters to about 1 picoliter, from about 1 picoliter to about 10 picoliters, from about 10 picoliters to about 100 picoliters, or from about 100 picoliters to about 1000 picoliters or more. Further, microdroplets may or may not be stabilized by surfactants and/or particles.

The means by which reagents are added to a microdroplet may vary greatly. Reagents may be added in one step or in multiple steps, such as 2 or more steps, 4 or more steps, or 10 or more steps. In certain aspects, reagents may be added using techniques including droplet coalescence, picoinjection, multiple droplet coalescence, and the like, as shall be described more fully herein. In certain embodiments, reagents are added by a method in which the injection fluid itself acts as an electrode. The injection fluid may contain one or more types of dissolved electrolytes that permit it to be used as such. Where the injection fluid itself acts as the electrode, the need for metal electrodes in the microfluidic chip for the purpose of adding reagents to a droplet may be obviated. In certain embodiments, the injection fluid does not act as an electrode, but one or more liquid electrodes are utilized in place of metal electrodes.

Various ways of detecting the absence or presence of PCR products may be employed, using a variety of different detection components. Detection components of interest include, but are not limited to, fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Detection components may include beads (e.g., magnetic or fluorescent beads, such as Luminex beads) and the like. In certain aspects, detection may involve holding a microdroplet at a fixed position during thermal cycling so it can be repeatedly imaged. Such repeated imaging may involve the use of a Megadroplet Array, as shall be described more fully herein. In certain aspects, detection may involve fixing and/or permeabilizing one or more cells in one or more microdroplets.

Suitable subjects for the methods disclosed herein include mammals, e.g., humans. The subject may be one that exhibits clinical presentations of a disease condition, or has been diagnosed with a disease. In certain aspects, the subject may be one that has been diagnosed with cancer, exhibits clinical presentations of cancer, or is determined to be at risk of developing cancer due to one or more factors such as family history, environmental exposure, genetic mutation(s), lifestyle (e.g., diet and/or smoking), the presence of one or more other disease conditions, and the like. In certain aspects, the subject may be one that has been diagnosed with a microbial infection, exhibits clinical presentations of a microbial infection, or is determined to be at risk of developing a microbial infection due to one or more factors such as family history, environmental exposure, genetic mutation(s), lifestyle (e.g., diet and/or travel), the presence of one or more other disease conditions, and the like. In certain aspects, the subject may be one that has been diagnosed with a viral infection, exhibits clinical presentations of a viral infection, or is determined to be at risk of developing a viral infection due to one or more factors such as family history, environmental exposure, genetic mutation(s), lifestyle (e.g., diet and/or travel), the presence of one or more other disease conditions, and the like.

Microfluidic systems and devices are also provided by the present disclosure. In certain aspects, the microfluidic devices include a sample loading region, e.g., a cell loading region, to encapsulate, e.g., a cell to be analyzed in a microdroplet; a first chamber in fluidic communication with the sample loading region, the first chamber having a means for adding a first reagent to the microdroplet, and a heating element; a second chamber in fluidic communication with the first chamber, the second chamber having a means for adding a second reagent to the microdroplet, and a heating element, wherein the heating element may heat the microdroplet at one or more temperatures; a detection region, in fluidic communication with the second chamber, which detects the presence or absence of reaction products from the first or second chamber; and a sorting region, in fluid communication with the detection region, which sorts microdroplets based on the detection of the presence or absence of reaction products from the first or second chamber. In some embodiments, alternatively or in addition to an "on-chip" sorting region, sorting of the microdroplets may occur "off-chip". For example, in the case of aqueous phase-in immiscible phase-in aqueous phase double emulsions, an off chip flow cytometry device, e.g., a FACS device, may be utilized for sorting.

BRIEF DESCRIPTION OF THE DRAWINGS

The invention may be best understood from the following detailed description when read in conjunction with the accompanying drawings. Included in the drawings are the following figures:

FIG. 4, Panels A-B, depict a binary PCR reaction to detect CTCs. Panel A: Forward and reverse primers are encapsulated in the drops that target an oncogenic sequence. If the oncogenic sequence is present, the PCR reaction produces double-stranded PCR products (Panel A, upper), whereas, if it is not, no products are produced (Panel A, lower). An intercalating stain (e.g., SybrGreen) may also be present in the drop. Panel B: If double-stranded products are produced, the dye intercalates into them, becoming fluorescent, and turning the drop fluorescent (Panel B, upper); by contrast, if no double-stranded products are produced, the dye remains non-fluorescent, producing a dim drop (Panel B, lower).

FIG. 13 depicts a Megadroplet Array for multiplexed qPCR analysis, of the type depicted in FIG. 12, Panels A-C. Drops are pipetted and sealed in a clear glass/epoxy chamber and fixed in place using a microfabricated well array (top). The entire chip is clamped to a metal block and thermocycled using Peltier heaters under the copper blocks. Thermometers, a heat sink, a fan (top), and digital controllers are used to regulate and cycle the temperature (bottom). Amplification is monitored in real time by imaging the array through the transparent plates that make up the top of the device.

FIG. 14, Panels A-B, depict the use of a one-color flow-cytometer used to detect PCR amplification products in drops, via fluorescence. Panel A: Schematic of detector, consisting of a 488 nm laser directed into the back of an objective, and focused onto a microfluidic channel through which the droplets flow. The laser excites fluorescent dyes within the drops, and any emitted light is captured by the objective and imaged onto a photomultiplier tube (PMT) after it is filtered through a dichroic mirror and 520 f 5 nm band pass filter. Panel B: The drops appear as peaks in intensity as a function of time, as shown by the output voltage of a PMT, which is proportional to the intensity of the emitted light, as a function of time for detected fluorescent drops.

FIG. 15, Panels A-C, show a schematic of device setup. Panel A: Drops, spacer oil, and 1 M NaCl are introduced to the PDMS device via syringe pumps. The picoinjection fluid is introduced using an air pressure control pump. Electrodes from the high voltage amplifier are connected to a wire submerged in the picoinjection fluid and to the metal needle of the syringe containing the 1 M NaCl "Faraday Mote." Panel B: A magnified view of the droplet spacer and picoinjection site. Panel C: Further magnified view of the picoinjection site showing the fluid bulge at the injection orifice.

FIG. 16, Panels A-B, show bright field microscopy images of the picoinjection site. In the absence of an electric field (Panel A), surfactants prevent coalescence with the injection fluid and a distinct boundary is visible at the droplet/injection fluid interface. When the electric field is applied, the boundary disappears and reagent is injected as the droplet passes (Panel B).

FIG. 17, Panels A-C, show the volume fraction increase (Vf) of drop size after injection for (Panel A) 100 mM, (Panel B) 50 mM, and (Panel C) 25 mM injection fluids. A stronger electric field more readily ruptures the oil/water interfaces allowing injection over a larger length of the passing droplets, and larger injection volumes. Higher molarities of dissolved electrolytes produce stronger electric fields at the injection site for a given voltage, also increasing injection volume. The error bars represent 1 standard deviation in either direction for >1200 drops sampled at each point.

FIG. 20, Panels A-B, show adding reagents via multiple droplet coalescence. Panel A: A schematic of a microfluidic device for adding reagents via multiple droplet coalescence. The reagent to add is introduced from below, along with oil, into a very small drop maker. This leads to the production of a train of very small drops at a high frequency. The drops to which the reagent is to be added are injected, spaced by oil, from the left and then the streams combine where the channel intersects with the outlet of the tiny drop maker. Because the reagent drops are much smaller than the target drops, they are introduced at a high rate frequency, and so many (tens or more) of these drops are injected for every one target drop. Due to their small size they flow faster than the larger drops and collect behind them so that, by the time the reach the electrode channels they are in contact and can be coalesced by the electric field. Panel B: Close-up of the coalescence region in such a microfluidic device. Drops flow from left to the right. A train of tiny droplets form behind the droplet to which they are to be added. Once the tiny droplets and the droplet pass through the coalescence region, the electrodes cause the tiny droplets to merge into the droplet. The resulting output on the right is a droplet that contains the reagent(s) that were present in the tiny droplets.

FIG. 22, Panels A-B, show sorting. Droplets enter from the right and flow to the left, passing by the electrodes. The drops are thus sorted on the presence (Panel A; droplets flow into the top output) or absence of a particular property (Panel B; droplets flow into the bottom output).

FIG. 41 provides fluorescent microscope images of fluorescent double emulsions. The image on the left shows double emulsions formed by shaking the fluids, which results in a large amount of polydispersity and a small number of drops of the appropriate size for FACS sorting. The image on the right shows double emulsions made with the microfluidic process disclosed herein, which are much more monodisperse.

FIG. 47 shows emulsions containing three different concentrations of DNA. All drops contain TaqMan® probes for the DNA target, but the target is encapsulated at limiting concentration, so that only the drops that get a target undergo amplification. When the target concentration is reduced, the fraction of fluorescent drops goes down. The lower plots show the drops after being encapsulated in double emulsions and screed on FACS.

FIG. 48 shows emulsions containing three concentrations of DNA lower than those in the previous Figure. All drops contain TaqMan® probes for the DNA target, but the target is encapsulated at limiting concentration, so that only the drops that get a target undergo amplification. When the target concentration is reduced, the fraction of fluorescent drops goes down. The lower plots show the drops after being encapsulated in double emulsions and screed on FACS.

FIG. 49 shows emulsions as for FIGS. 47 and 48 at the lowest DNA concentration of the three Figures. The lower plot shows the drops after being encapsulated in double emulsions and screed on FACS.

FIG. 56, Panels a and b, show that, e.g., Raji and DU145 cells are isolated into aqueous microdroplets in an oil-based emulsion and lysed. Only DU145 cells express vimentin mRNA and have genetic mutations in RB1 and CDKN2A genes. FIG. 56, Panel c, shows a microfluidic chip processing the cells, readying the lysate for PCR. Single-cell TaqMan PCR reactions targeting vimentin mRNA are thermocycled and droplets are sorted based on positive TaqMan probe fluorescence. FIG. 56, Panel d, shows cell lysate being recovered for downstream nucleic acid analysis following microfluidic droplet sorting.

FIG. 57, Panel a, depicts merged brightfield and fluorescence images showing amplified vimentin TaqMan probe (red), calcein violet DU145 (blue) and calcein green Raji (green) lysate in droplets. The presence of a purple-violet color indicates droplets where both DU145 calcein violet stain and HEX from the vimentin TaqMan probe were detected. Individual fluorescence channels from the dashed region are shown. Scale bar is 100 nm. FIG. 57, Panel b, shows Vimentin TaqMan detection rates of individual DU145 and Raji cells processed with the single-cell RT-PCR microfluidic workflow. Data was compiled from replicate experiments analyzed with a MATLAB script.

FIG. 59, Panel a, shows a photograph of a dielectrophoretic microfluidic sorter. Reinjected emulsion entered the device from the left and was interrogated for fluorescence at the laser spot. A voltage was applied to the sorting electrode when a droplet was positive for both calcein and HEX above the specified thresholds. This pulled the specified droplets into the lower channel for collection. Scale bar is 100 nm. FIG. 59, Panel b, shows a Scatterplot diagram of single-cell RT-PCR sorted droplets showing the calcein violet cell stain fluorescence used to mark Raji and DU145 cells on the x axis and HEX fluorescence from the TaqMan positive reactions on the y axis. Dashed red lines indicate where the sorting thresholds were applied. Only droplets in the upper right quadrant were selected for sorting. This PACS data was generated from an initial 80% Raji and 20% DU145 heterogeneous cell suspension. FIG. 59, Panel c, shows imaged pre-sorted and sorted droplets to evaluate sorting efficiency. Arrowheads in the pre-sorted emulsion image point to two droplets positive for both calcein and HEX. The rest of the droplets are either empty or only calcein positive. Nearly all of the droplets following sorting are positive for both calcein and HEX.

FIG. 60 shows that 95.8% of positively-sorted droplets had significant calcein and HEX fluorescence.

FIG. 61, Panel a, shows a portion of the RB1 locus was amplified from genomic DNA isolated from individual cell lines and Sanger sequenced as a control (top two sequences). Raji cell RB1 encodes for a lysine at amino acid position 715 (black box). DU145 genomic DNA has a nonsense mutation at this position (red box). Sequencing of genomic DNA amplified from droplets prior to vimentin-positive PACS sorting (Pre-sorted) produces a Raji cell sequence with lysine at position 715. This is expected based on the initial encapsulation of a 90% Raji cell and 10% DU145 cell suspension. Following vimentin-positive droplet sorting (Vimentin+PACS), sequencing shows that the genomic DNA is dramatically enriched for the DU145-specific stop codon. (SEQ ID NO:25 on left, SEQ ID NO:26 on right).

FIG. 61, Panel b, shows sequencing of CDKN2A amplicons from control cell genomic DNA (top two sequences) Amino acid 84 is mutated from an aspartic acid to a tyrosine in DU145 cells (red box). Sequencing of the pre-sorted single-cell RT-PCR emulsion DNA yields a Raji-specific aspartic acid. Following vimentin-positive PACS sorting, the genomic DNA is enriched for tyrosine encoding sequence. Arrows indicate the position of the SNPs. (SEQ ID NO: 27 on left, SEQ ID NO:28 on right).

FIG. 62, Panels a-b, show quantitative analysis of PACS genome enrichment with next-generation sequencing according to certain embodiments. Analysis of RB1 and CDKN2A genomic loci for the presence of DU145-specific SNPs. Sequencing libraries from RB1 and CDKN2A amplicons were generated using Nextera XT reagents. FIG. 62, Panel a, depicts quantitative analysis of RB1 sequence reads demonstrated that the DU145-specific nonsense mutation, AAG to TAG, was found in 6.2% of the sequence reads generated from pre-sorted cell lysate. Following PACS sorting (Vim+PACS) the presence of this mutation relative to the Raji-specific codon was enriched to 87.7%. FIG. 62, Panel b, shows that similar data was obtained upon sequence analysis of CDKN2A amplicons generated from pre-sorted and Vim+PACS sorted cell lysate. The DU145 specific missense mutation, GAC to TAC, went from including 13.5% of the sequence reads to 74.2% of the sequence reads upon PACS enrichment. More than 15,000 sequence reads were analyzed for each of the 4 samples.

FIG. 63, Panel a, depicts qRT-PCR amplification curves from GAPDH or CD9 performed on cell line isolated total RNA control samples. CD9 was expressed significantly higher in DU145 cells than in Raji cells. FIG. 63, Panel b shows RNA from pre-sorted and vimentin-positive PACS (Vim sorted) droplets was analyzed for CD9 expression following normalization of input levels with GAPDH. CD9 was only detected in the vimentin-positive sorted droplets indicating that PACS enriched for DU145 expressed transcripts. Three replicate amplification curves are shown for each qRT-PCR experiment.

FIG. 64, Panel a, depicts a microbial sample including, e.g., K-12 E. coli harboring wild type TolA and a spike-in variant (ΔTolA) is created from growth cultures. FIG. 64, Panel b, shows the sample of FIG. 64, Panel a, encapsulated together with PCR reagent to form a single emulsion. FIG. 64, Panel c-d, depicts collecting and thermal cycling the emulsion with PCR-positive droplets experiencing an increase in TaqMan fluorescence. FIG. 64, Panel e, depicts DEP sorting for bright drops. FIG. 64, Panel f, depicts rupturing the drops to release genomic content which is sequenced to verify sorting efficacy.

FIG. 65, Panels a-b, depict TaqMan PCR detection of TolA gene in E. coli bacteria. E. coli bacteria are encapsulated with PCR reagents in droplets and are thermalcycled. FIG. 65, Panel a (upper), depicts that drops containing bacteria with the TolA gene are bright, whereas this is absent in FIG. 65, Panel a (lower), which depicts E. coli without this gene. FIG. 65, Panel b, shows the dependency of the fraction of loading drops which are bright versus the poisson loading ratio. The different curves represent different calculated curves if the E. coli lysis factor k was varied.

FIG. 67, upper, shows the device layout, with the salt "moat" insulating the drops from any stray electric fields potentially originating from the salt electrode. This device includes a reinjection junction, FIG. 67, left, at which the reinjected emulsion is spaced out, as well as a sorting junction, FIG. 67, middle, which is, e.g., where detection and sorting occurs. FIG. 67, right, shows positive and negative droplet sorting events.

FIG. 68, Panel a, depicts a PMT timetrace of recorded signals from an optical droplet detection setup. There is a clear peak at 32.5 ms, which corresponds to a bright drop that is sorted. FIG. 68, Panel b, shows fluorescence images of thermalcycled drops before and after DEP sorting.

FIG. 69, Panels a-b, illustrate sequencing verification and genome enrichment according to certain embodiments. FIG. 69, Panel a, depicts an electropherogram of the LpoA gene and its mutant counterpart after Sanger sequencing LpoA from sorted bacterial genomes. FIG. 69, Panel b, shows sequencing results, with enrichments for the TolA/ALpoA bacterial strain for both spike-in ratios. (SEQ ID NO:29 on left, SEQ ID NO:30 on right).

DETAILED DESCRIPTION

Figure 1:
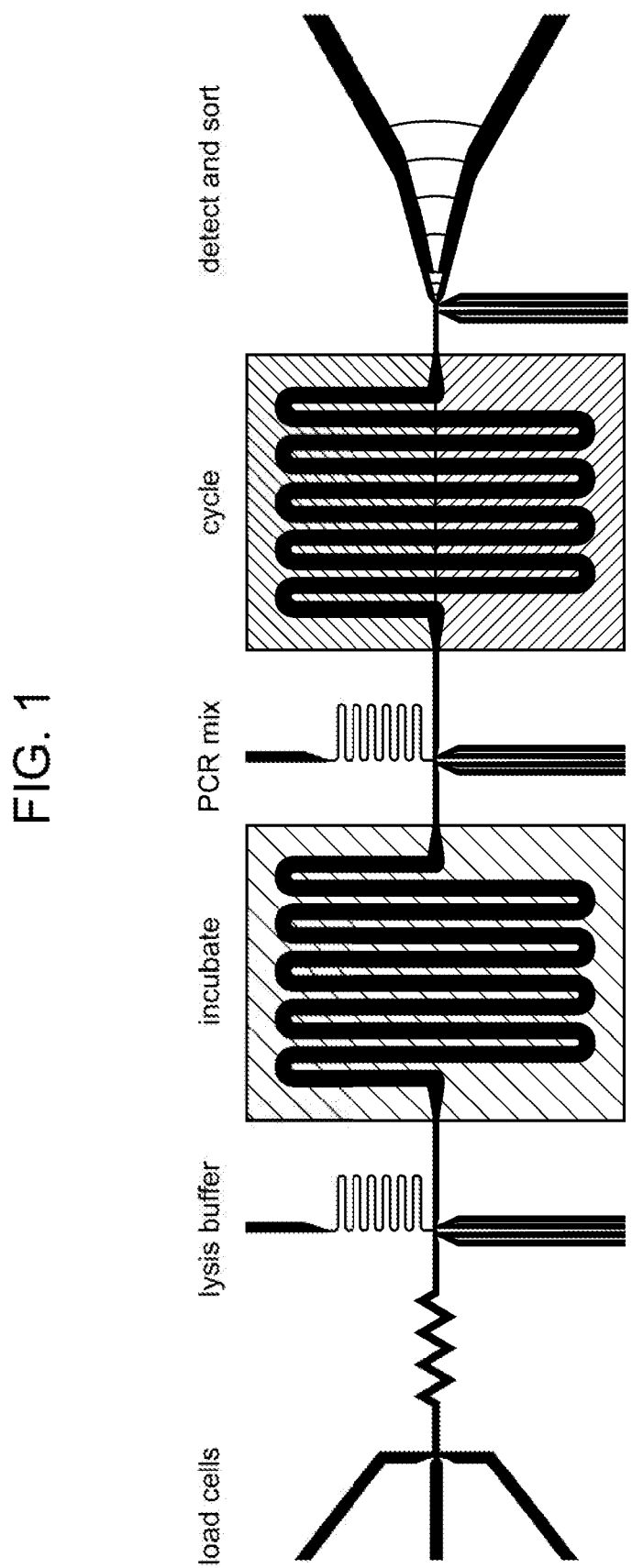
FIG. 1 is a simplified depiction of an embodiment of a microfluidic system of the instant disclosure. In the depicted system, the microfluidic system may be used, among a variety of other applications, for detecting and/or genotyping a component of a biological sample. For example, as applied to the detection of tumor cells, nucleated blood cells are encapsulated into individual microdroplets using an encapsulation device (left). The microdroplets are injected with a lysis buffer and incubated at 37° C. to accelerate cell lysis. They are injected with PCR mix containing primers targeting characteristic oncogenic mutations (center). The microdroplets are flowed through a channel snaking over zones maintained at 65° C. and 95° C. As the microdroplets move through the zones, their temperature cycles, as needed for some PCR reactions. During this PCR reaction, if a microdroplet contains a genome of a tumor cell with a mutation for which the primers are designed to detect, amplification will be initiated, producing a fluorescent output that turns the microdroplet fluorescent. The microdroplets are then optically scanned using flow cytometry and sorted using microdroplet sorting to recover them (right). The microdroplets may be stored or used for further analysis, such as being subjected to sequencing (e.g., used as input for a next-gen sequencer, or provided to a sequencing facility).

The methods described herein, referred to as PCR-Activated Sorting (PAS), allow nucleic acids contained in biological systems to be sorted based on their sequence as detected with PCR. The nucleic acids can be free floating or contained within living or nonliving structures, including particles, viruses, and cells. The nucleic acids can include, e.g., DNA or RNA. Systems and devices for use in practicing methods of the invention are also provided.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a microdroplet" includes a plurality of such microdroplets and reference to "the microdroplet" includes reference to one or more microdroplets, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the present disclosure include methods for the detection and sorting of components from biological samples. Aspects include methods for the detection, quantification, and/or genotyping of cells, e.g. normal mammalian cells (e.g., non-tumor cells), tumor cells, CTCs, or microbial cells. Additional embodiments of interest include PCR-based sorting of viral particles and PCR-based sorting of nucleic acids from a heterogeneous population of nucleic acids.

As used herein, the term "biological sample" encompasses a variety of sample types obtained from a variety of sources, which sample types contain biological material. For example, the term includes biological samples obtained from a mammalian subject, e.g., a human subject, and biological samples obtained from a food, water, or other environmental source, etc. The definition encompasses blood and other liquid samples of biological origin, as well as solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, cells, serum, plasma, biological fluid, and tissue samples. "Biological sample" includes cells; biological fluids such as blood, cerebrospinal fluid, semen, saliva, and the like; bile; bone marrow; skin (e.g., skin biopsy); and antibodies obtained from an individual.

As described more fully herein, in various aspects the subject methods may be used to detect a variety of components from such biological samples. Components of interest include, but are not necessarily limited to, cells (e.g., circulating cells and/or circulating tumor cells), viruses, polynucleotides (e.g., DNA and/or RNA), polypeptides (e.g., peptides and/or proteins), and many other components that may be present in a biological sample.

"Polynucleotides" or "oligonucleotides" as used herein refer to linear polymers of nucleotide monomers, and may be used interchangeably. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999).

The terms "polypeptide," "peptide," and "protein," used interchangeably herein, refer to a polymeric form of amino acids of any length. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-3559 is used.

In certain aspects, methods are provided for counting and/or genotyping cells, including normal cells or tumor cells, such as CTCs. A feature of such methods is the use of microfluidics.

Figure 3:
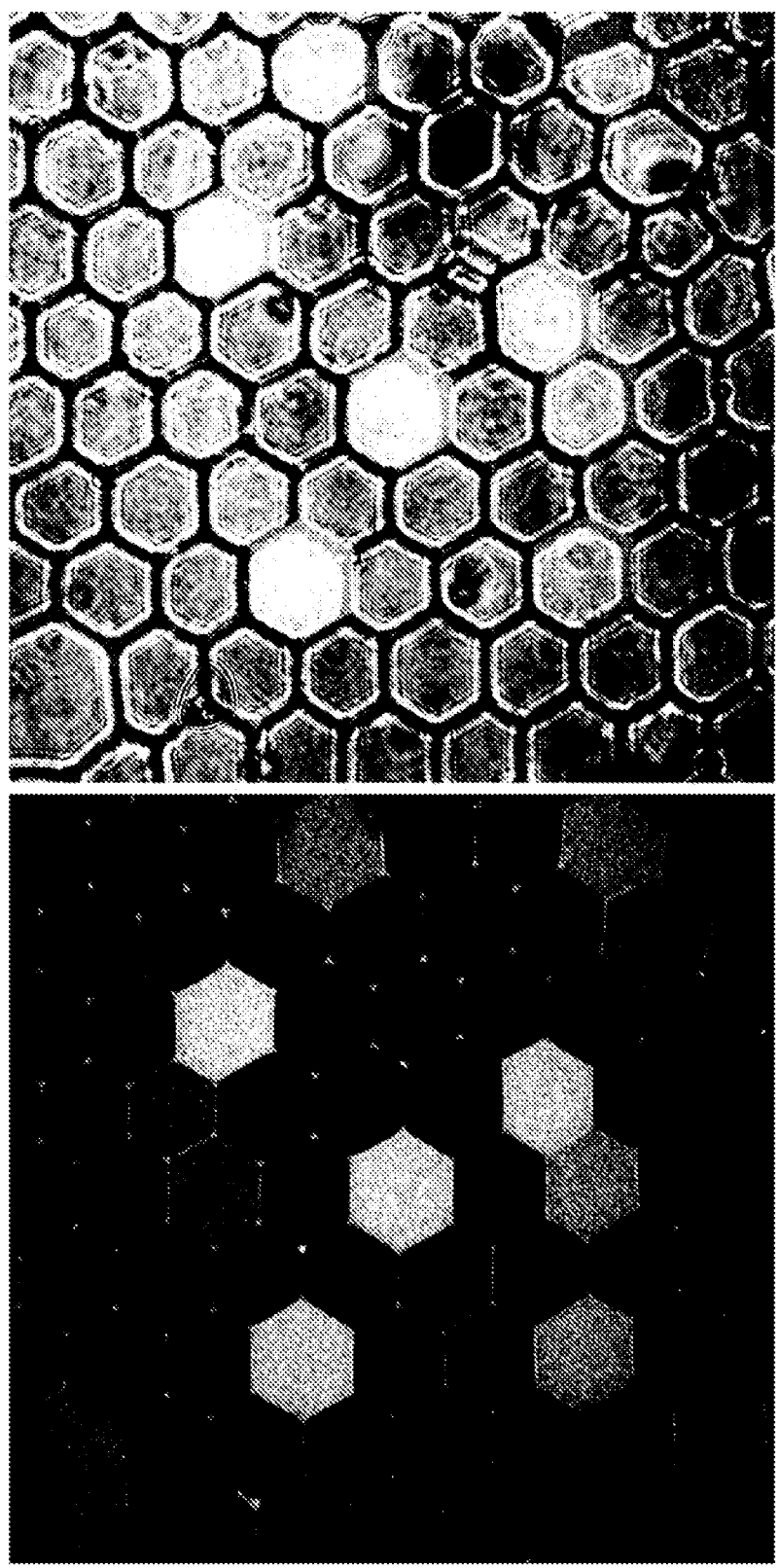
FIG. 3 depicts digital detection of BRAF using a TaqMan® PCR probe labeled with the fluorophore FAM that is complementary to an amplicon from a portion of the human BRAF gene. Fluorescent drops indicate amplification of the BRAF gene from purified human genomic DNA, while non-fluorescent drops were devoid of the gene.

FIG. 1 presents a non-limiting, simplified representation of one type of a microfluidics system and method of the present disclosure. The particular application depicted in FIG. 1 may be utilized in the detection and/or genotyping of cells, e.g., tumor cells, from a biological sample. In one such method, nucleated blood cells may be obtained from a biological sample from a subject. The nucleated blood cells are encapsulated into individual microdroplets using an encapsulation device (left). The microdroplets may then be injected with a lysis buffer and incubated at conditions that accelerate cell lysis (e.g., at 37° C.). The microdroplets may be injected with a PCR mix that includes one or more primers targeting characteristic oncogenic mutations (center). The microdroplets containing the PCR mix may be flowed through a channel that incubates the droplets under conditions effective for PCR. In the figure, this is achieved by flowing the microdroplets through a channel that snakes over various zones maintained at 65° C. and 95° C. As the microdroplets move through the zones, their temperature cycles, as needed for PCR. During the PCR reaction, if a microdroplet contains a genome of a cell with a mutation for which the primer(s) are designed to detect, amplification is initiated. The presence of these particular PCR products may be detected by, for example, a fluorescent output that turns the microdroplets fluorescent (FIGS. 3-4). The microdroplets may thus be scanned, such as by using flow cytometry, to detect the presence of fluorescent drops (FIG. 14, Panels A-B). In certain aspects, the drops may also be sorted using, for example, droplet sorting to recover drops of interest (right). Using the nomenclature of the current disclosure, the steps described above are thus performed "under microfluidic control." That is, the steps are performed on one or more microfluidics devices, or at least in part on one or more microfluidic devices.

Figure 2:
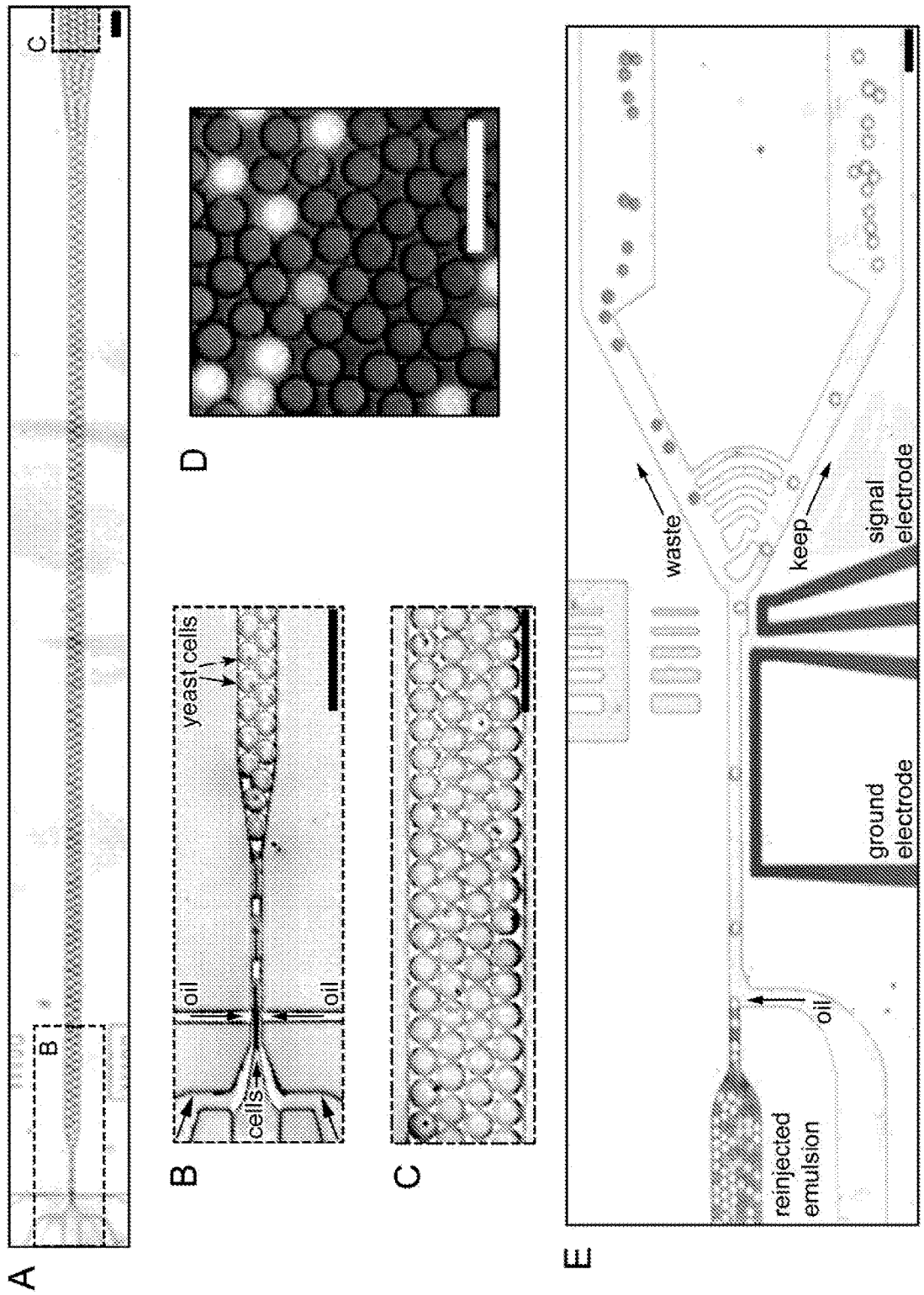
FIG. 2, Panels A-E, depict single cells enclosed in microdroplets, using a fluorescence assay. Yeast cells (black specks) enter from the far left and are encapsulated into drops, shown at low (4× objective; Panel A) and high magnification (10× objective; Panel B). The drops are incubated allowing the yeast to secrete a product (Panel C); this produces a fluorescent compound in the drops, so that drops containing efficient producers quickly become fluorescent (Panel D). The drops are then sorted to extract the most efficient yeast using a microfluidic sorter (Panel E). The scale bars denote 80 mm.

FIG. 2, Panels A-E depict a microfluidics system involving many of the general principles and steps described above. Here, yeast cells (black specks) enter from the far left and are encapsulated into drops, shown at low (4× objective; Panel A) and high magnification (10× objective; Panel B). The drops are incubated to allow the yeast to produce a secreted product (Panel C); this produces a fluorescent compound in the drops, so that drops containing efficient producers quickly become fluorescent (Panel D). The drops are then sorted to extract the most efficient yeast using a microfluidic sorter (Panel E).

Figure 5:
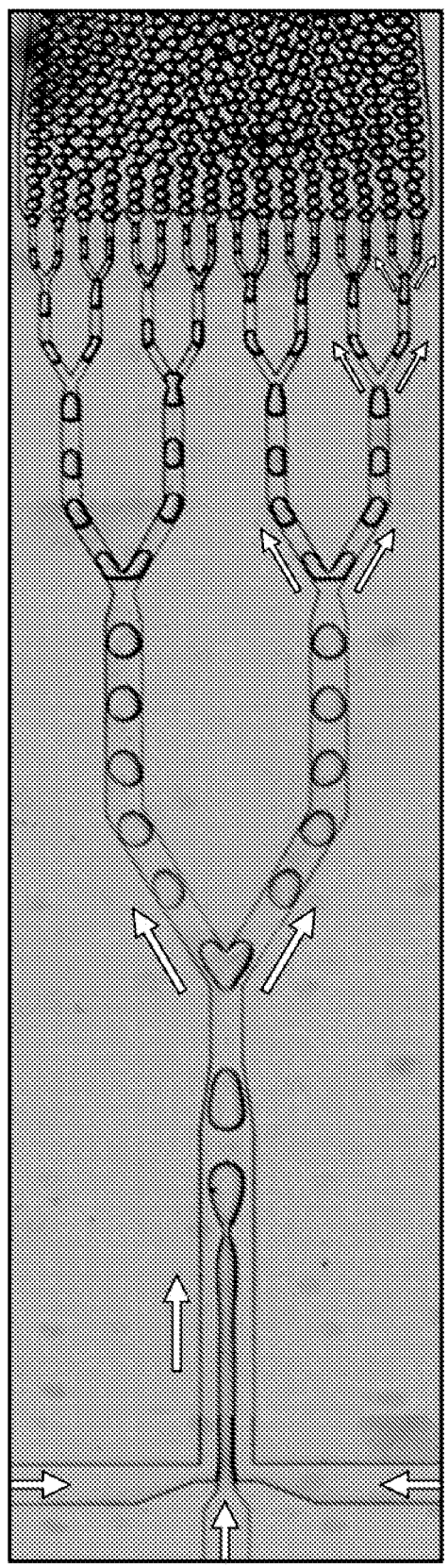
FIG. 5 is an optical microscopy image of massively parallel drop formation in a serial bisection device. DI water that does not contain cells is injected from the left. The solution flowing in along the top and bottom arrows is HFE-7500 fluorocarbon oil with a fluorocarbon surfactant at 2% by weight. After serial bisection, the resulting drops shown to the far right are 25 µm in diameter.

Encapsulating a component from a biological sample may be achieved by any convenient means. FIG. 5 presents but one possible example, in which droplets are formed in a massively parallel fashion a serial bisection device. For instance, cell-containing solution may be injected from the left and formed into large drops, which flow into the serial bisection array and are split into small drops; drops shown to the far right are 25 mm in diameter. Encapsulation approaches of interest also include, but are not limited to, hydrodynamically-triggered drop formation and those described by Link, et al., *Phys. Rev. Lett.* 92, 054503 (2004), the disclosure of which is incorporated herein by reference.

Figure 6:
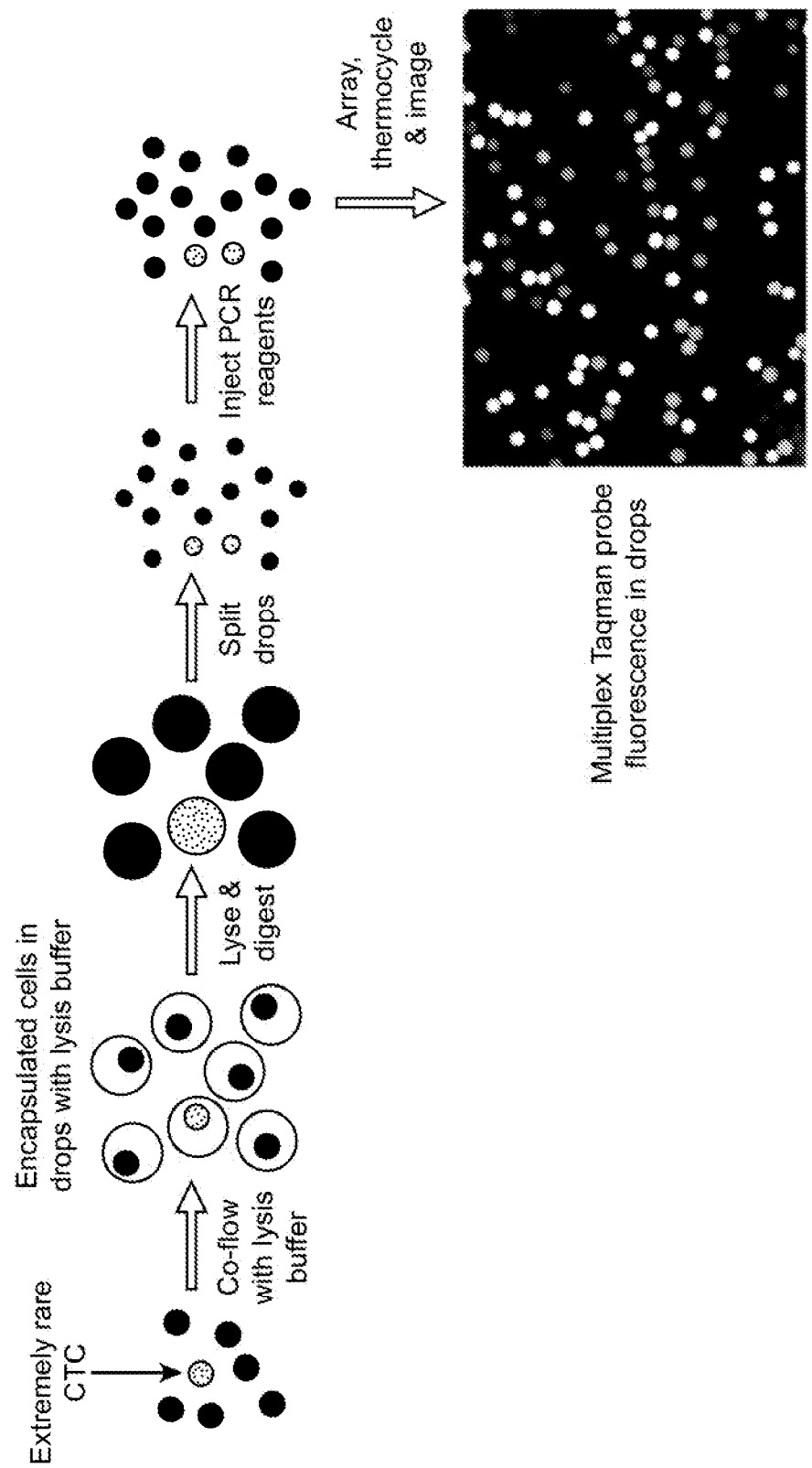
FIG. 6 is a schematic microfluidic device and data showing procedure for droplet-based detection of CTCs. Blood cells and rare CTCs are encapsulated in microdrops with lysis buffer containing Proteinase K. The drops are incubated at 55° C. to lyse cells and digest cellular proteins. Drops are then split to a size optimal for imaging, and the Proteinase K is heat-inactivated. The drops are then picoinjected with PCR reagents and TaqMan® probes, followed by thermocycling and imaging on a Megadroplet Array. CTCs are identified based on the presence of CTC-specific transcripts, detected by multiplexed TaqMan® probe fluorescence.

As evidenced by FIGS. 1, 4, and 6, a feature of certain methods of the present disclosure is the use of a polymerase chain reaction (PCR)-based assay to detect the presence of certain oligonucleotides and/or oncogene(s) present in cells. Examples of PCR-based assays of interest include, but are not limited to, quantitative PCR (qPCR), quantitative fluorescent PCR (QF-PCR), multiplex fluorescent PCR (MF-PCR), single cell PCR, PCR-RFLP/real time-PCR-RFLP, hot start PCR, nested PCR, in situ polony PCR, in situ rolling circle amplification (RCA), bridge PCR, picotiter PCR, emulsion PCR and reverse transcriptase PCR (RT-PCR). Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA).

A PCR-based assay may be used to detect the presence of certain gene(s), such as certain oncogene(s). FIG. 4, Panels A-B depict a PCR-based assay to detect oncogenes. In this assay, one or more primers specific to each oncogene of interest are reacted with the genome of each cell. These primers have sequences specific to the particular oncogene, so that they will only hybridize and initiate PCR when they are complimentary to the genome of the cell. If an oncogene is present and the primer is a match, large many copies of the oncogene are created. To determine whether an oncogene is present, the PCR products may be detected through an assay probing the liquid of the drop, such as by staining the solution with an intercalating dye, like SybrGreen or ethidium bromide, hybridizing the PCR products to a solid substrate, such as a bead (e.g., magnetic or fluorescent beads, such as Luminex beads), or detecting them through an intermolecular reaction, such as FRET. These dyes, beads, and the like are each examples of a "detection component," a term that is used broadly and generically herein to refer to any component that is used to detect the presence or absence of PCR product(s).

A great number of variations of these basic approaches will now be outlined in greater detail below.

Detecting Rare Cells (e.g., Tumor Cells)

Aspects of the subject methods involve detecting the presence of one or more subset of cells (e.g., tumor cells) in a biological sample. An example of such a scheme is depicted in FIG. 6. To use this approach for the detection of, e.g., tumor cells, a biological sample (e.g., whole blood) may be recovered from a subject using any convenient means. The biological sample may be processed to remove components other than cells using, for example, processing steps such as centrifugation, filtration, and the like.

Each cell in the biological sample is then encapsulated into a microdroplet using a microfluidic device, such as that shown in FIGS. 5 and/or 8. Using the example from FIG. 5, the cell-containing solution is injected from the left and formed into large drops, which flow into the serial bisection array and are split into smaller droplets. Other methods of encapsulating cells into droplets are known in the art. Where desired, the cells may be stained with one or more antibodies and/or probes prior to encapsulating them into microdroplets. As used herein, the terms "drop," "droplet," and "microdroplet" may be used interchangeably to refer to tiny, generally spherical, microcompartments containing at least a first fluid phase, e.g., an aqueous phase (e.g., water), bounded by a second fluid phase (e.g., oil) which is immiscible with the first fluid phase. In some embodiments, the second fluid phase will be an immiscible phase carrier fluid. Microdroplets generally range from 0.1 to 1000 µm in diameter, and may be used to encapsulate cells, DNA, enzymes, and other components. Accordingly, the above terms may be used to refer to a droplet produced in, on, or by a microfluidics device.

One or more lysing agents may also be added to the microdroplets containing a cell, under conditions in which the cell(s) may be caused to burst, thereby releasing their genomes. The lysing agents may be added after the cells are encapsulated into microdroplets. Any convenient lysing agent may be employed, such as proteinase K or cytotoxins. In particular embodiments, cells may be co-encapsulated in microdroplets with lysis buffer containing detergents such as Triton X100 and/or proteinase K. The specific conditions in which the cell(s) may be caused to burst will vary depending on the specific lysing agent used. For example, if proteinase K is incorporated as a lysing agent, the microdroplets may be heated to about 37-60° C. for about 20 min to lyse the cells and to allow the proteinase K to digest cellular proteins, after which they may be heated to about 95° C. for about 5-10 min to deactivate the proteinase K.

In certain aspects, cell lysis may also, or instead, rely on techniques that do not involve addition of lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient means of effecting cell lysis may be employed in the methods described herein.

Primers may be introduced into the microdroplet for each of the genes and/or genetic markers, e.g., oncogenes, to be detected. Hence, in certain aspects, primers for a variety of genes and/or genetic markers, e.g., all oncogenes may be present in the microdroplet at the same time, thereby providing a multiplexed assay. The microdroplets are temperature-cycled so that microdroplets containing cancerous cells, for example, will undergo PCR. During this time, only the primers corresponding to oncogenes and/or genetic markers present in the genome will induce amplification, creating many copies of these oncogenes and/or genetic markers in the microdroplet. Detecting the presence of these PCR products may be achieved by a variety of ways, such as by using FRET, staining with an intercalating dye, or attaching them to a bead. For more information on the different options for this, see the section describing variations of the technique. The microdroplet may be optically probed to detect the PCR products (FIG. 14). Optically probing the microdroplet may involve counting the number of tumor cells present in the initial population, and/or allowing for the identification of the oncogenes present in each tumor cell.

The subject methods may be used to determine whether a biological sample contains particular cells of interest, e.g., tumor cells, or not. In certain aspects, the subject methods may include quantifying the number of cells of interest, e.g., tumor cells, present in a biological sample. Quantifying the number of cells of interest, e.g., tumor cells, present in a biological sample may be based at least in part on the number of microdroplets in which PCR amplification products were detected. For example, microdroplets may be produced under conditions in which the majority of microdroplets are expected to contain zero or one cell. Those microdroplets that do not contain any cells may be removed, using techniques described more fully herein. After performing the PCR steps outlined above, the total number of microdroplets that are detected to contain PCR products may be counted, so as to quantify the number of cells of interest, e.g., tumor cells, in the biological sample. In certain aspects, the methods may also include counting the total number of microdroplets so as to determine the fraction or percentage of cells from the biological sample that are cells of interest, e.g., tumor cells.

PCR-Activated Virus Sorting (PAVS)

In some embodiments, referred to herein as PCR-Activated Virus Sorting (PAVS), a biological sample including viruses is encapsulated in microdroplets and subjected to PCR conditions, e.g., droplet PCR. The viruses may be encapsulated in microdroplets using any of the suitable methods and/or devices described herein or known in the art. Where desired, the viruses may be detectably labeled prior to encapsulating them into microdroplets.

One or more lysing agents may also be added to the microdroplets containing virus, under conditions in which the virus(es) may be lysed, thereby releasing their genomes. The lysing agents may be added after the viruses are encapsulated into microdroplets. Any convenient lysing agent may be employed, such as proteinase K or guanidine thiocyanate, provided that it is compatible with the microdroplet structure. In particular embodiments, viruses may be co-encapsulated in microdroplets with lysis buffer containing detergents such as Triton X100 and/or proteinase K. The specific conditions in which the viruses may be caused to release their genomic material will vary depending on the specific lysing agent used.

In certain aspects, lysis of virus particles may also, or instead, rely on techniques that do not involve the addition of a lysing agent. For example, suitable thermal lysis techniques may be utilized. Any convenient means of effecting lysis of viral particles may be employed in the methods described herein.

Primers may be introduced into the microdroplets for each of the viral nucleic acids to be detected. The microdroplets are then temperature-cycled so that microdroplets containing the target viral nucleic acids will undergo PCR. During this time, only the primers corresponding to the target viral nucleic acids will induce amplification, creating many copies of these nucleic acids in the microdroplet. Detecting the presence of these PCR products may be achieved in a variety of ways, such as by using FRET, staining with an intercalating dye, or attaching them to a bead. For more information on the different options for this, see the section describing variations of the technique. The microdroplet may be optically probed to detect the PCR products.

The subject methods may be used to determine whether a biological sample contains particular viruses of interest, or not. In certain aspects, the subject methods may include quantifying the number of viruses of interest present in a biological sample. Quantifying the number of viruses of interest present in a biological sample may be based at least in part on the number of microdroplets in which PCR amplification products were detected. For example, microdroplets may be produced under conditions in which the majority of microdroplets are expected to contain zero or one virus. Those microdroplets that do not contain any viruses may be removed, using techniques described more fully herein. After performing the PCR steps outlined above, the total number of microdroplets that are detected to contain PCR products may be counted, so as to quantify the number of viruses of interest in the biological sample. In certain aspects, the methods may also include counting the total number of microdroplets so as to determine the fraction or percentage of viruses from the biological sample that are viruses of interest.

The viruses of interest are then recovered by sorting the microdroplets and recovering their contents via microdroplet rupture, e.g., through chemical, electrical, or mechanical means as described in greater detail herein. A variety of suitable sorting techniques and related devices may be utilized sort and separate the microdroplets containing PCR amplification products including those described herein.

PCR-Activated Cell Sorting (PACS)

In some embodiments, referred to herein as PCR-Activated Cell Sorting (PACS), a biological sample including cells is encapsulated in microdroplets and subjected to PCR conditions, e.g., droplet PCR. The cells may be encapsulated in microdroplets using any of the suitable methods and/or devices described herein or known in the art. Where desired, the cells may be detectably labeled, e.g., with one or more antibodies and/or probes, prior to encapsulating them into microdroplets.

One or more lysing agents may also be added to the microdroplets containing a cell, under conditions in which the cell(s) may be lysed, thereby releasing their genomes. The lysing agents may be added after the cells are encapsulated into microdroplets. Any convenient lysing agent may be employed, such as proteinase K or cytotoxis, provided that it is compatible with the microdroplet structure. In particular embodiments, cells may be co-encapsulated in microdroplets with lysis buffer containing detergents such as Triton X100 and/or proteinase K. The specific conditions in which the cell(s) may be caused to release their genomic material will vary depending on the specific lysing agent used. For example, if proteinase K is incorporated as a lysing agent, the microdroplets may be heated to about 37-60° C. for about 20 min to lyse the cells and to allow the proteinase K to digest cellular proteins, after which they may be heated to about 95° C. for about 5-10 min to deactivate the proteinase K.

In certain aspects, cell lysis may also, or instead, rely on techniques that do not involve the addition of a lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient means of effecting cell lysis may be employed in the methods described herein.

Primers may be introduced into the microdroplets for each of the nucleic acids to be detected for a cell of interest. The microdroplets are then temperature-cycled so that microdroplets containing the target nucleic acids for the target cells will undergo PCR. During this time, only the primers corresponding to the target cellular nucleic acids will induce amplification, creating many copies of these nucleic acids in the microdroplet. Detecting the presence of these PCR products may be achieved in a variety of ways, such as by using FRET, staining with an intercalating dye, or attaching them to a bead. For more information on the different options for this, see the section describing variations of the technique. The microdroplet may be optically probed to detect the PCR products.

The subject methods may be used to determine whether a biological sample contains particular cells of interest, or not. In certain aspects, the subject methods may include quantifying the number of cells of interest present in a biological sample. Quantifying the number of cells of interest present in a biological sample may be based at least in part on the number of microdroplets in which PCR amplification products were detected. For example, microdroplets may be produced under conditions in which the majority of microdroplets are expected to contain zero or one cell. Those microdroplets that do not contain any cells may be removed, using techniques described more fully herein. After performing the PCR steps outlined above, the total number of microdroplets that are detected to contain PCR products may be counted, so as to quantify the number of cells of interest in the biological sample. In certain aspects, the methods may also include counting the total number of microdroplets so as to determine the fraction or percentage of cells from the biological sample that are cells of interest.

The cells and/or cellular material of interest are then recovered by sorting the microdroplets and recovering their contents via microdroplet rupture, e.g., through chemical, electrical, or mechanical means as described in greater detail herein. A variety of suitable sorting techniques and related devices may be utilized sort and separate the microdroplets containing PCR amplification products including those described herein.

PACS may be utilized, e.g., for the cultivation-free enrichment and sequencing of rare microbes and/or cells, e.g., as described in greater detail in Example 11.

PCR-Activated Nucleic Acid Sorting (PANS)

In some embodiments, referred to herein as PCR-Activated Nucleic Acid Sorting (PANS), a sample including nucleic acids (e.g., DNA and/or RNA) is encapsulated in microdroplets and subjected to PCR conditions, e.g., RT-PCR conditions, PCR (or RT-PCR). PCR, e.g., RT-PCR, assays specific to the nucleic acids of interest cause microdroplets containing the nucleic acids of interest to become detectably labeled, e.g., fluorescently labeled. The nucleic acids of interest are then recovered by sorting the microdroplets and recovering their contents via microdroplet rupture, e.g., through chemical or electrical means.

In one aspect of PANS, a method for enriching for a target nucleic acid sequence is provided, wherein the method includes encapsulating a sample including nucleic acids in a plurality of microdroplets, each microdroplet including a first aqueous phase fluid in an immiscible phase carrier fluid; introducing polymerase chain reaction (PCR) reagents and a plurality of PCR primers into the microdroplets; incubating the microdroplets under conditions sufficient for PCR amplification to produce PCR amplification products, wherein the plurality of PCR primers include one or more primers that each hybridize to one or more oligonucleotides comprised by the target nucleic acid sequence, and wherein the PCR amplification products do not include the entire target nucleic acid sequence; introducing a detection component into the microdroplets either before or after the incubating; detecting the presence or absence of the PCR amplification products by detection of the detection component, wherein detection of the detection component indicates the presence of PCR amplification products and the target nucleic acid sequence; and sorting the microdroplets based on detection of the detection component, wherein the sorting separates microdroplets including the PCR amplification products and the target nucleic acid sequence, when present, from microdroplets which do not include the PCR amplification products and the target nucleic acid sequence; and pooling the nucleic acid sequences from the sorted microdroplets to provide an enriched pool of target nucleic acid sequences, when present. One or more of these steps may be performed under microfluidic control.

The above method allows, for example, for the enrichment of DNA molecules out of a heterogeneous system based on the presence of PCR-detectable subsequences. The DNA molecules can be short (e.g., hundreds of bases) or long (e.g., megabases or longer). The sample may be encapsulated in microdroplets such that target molecules are detected in the microdroplets digitally—i.e., each microdroplet contains 0 or 1 target molecule. The microdroplets may then be sorted based on, e.g., fluorescence, to recover the target molecules. This method can be used to enrich for a large genomic region, e.g., on the order of megabases in length, in a heterogeneous sample of DNA fragments.

The above method enables a sufficient amount of DNA to be recovered without the need to perform PCR to amplify the DNA for sequencing. Amplification-free DNA sample prep is valuable, for example, where PCR does not preserve the sequences or epigenetic factors of interest, or cannot recover sequences that are of the needed length (e.g., >about 10 kb, the practical limit of long-range PCR).

Another application is to apply PANS to enrich DNA for epigenetic sequencing. Epigenetic marks on DNA are not preserved by PCR, so sequencing them requires unamplified DNA from the host nucleic acids. With PANS, a sufficient amount of DNA can be obtained for sequencing without needing to perform PCR, and thus preserving the epigenetic marks.

Figure 71:
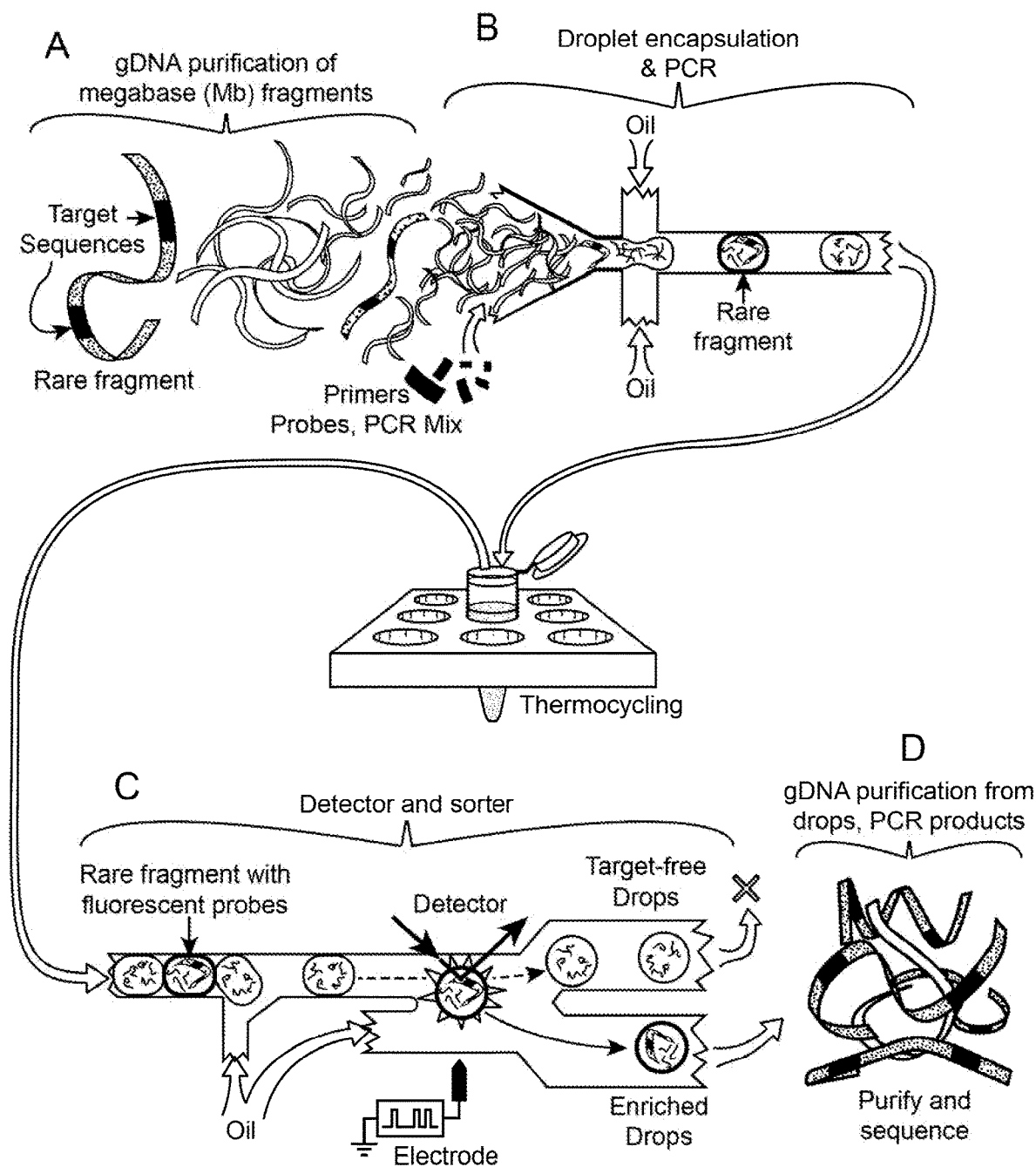
FIG. 71 provides a schematic of an embodiment of a PCR-Activated Nucleic Acid Sorting method according to the present disclosure.

An embodiment of the PANS method is depicted generally in FIG. 71. Briefly, megabase size fragments of genomic DNA may be encapsulated into microdroplets, e.g., along with suitable PCR reagents, including, e.g., PCR primers which hybridize to one or more oligonucleotides including a target nucleic acid sequence. The microdroplets may then be thermocycled (either on-chip or off) to produce PCR amplification products which identify, e.g., via a detectable label, microdroplets which contain the target nucleic acid sequences, but which do not contain amplicons of the complete target nucleic acid sequence. Microdroplets which contain the target nucleic acid sequences may then be sorted using any suitable method, e.g., dielectrophoresis or flow cytometry, and separated from microdroplets which do not include the target nucleic acid sequences, thereby enriching for the target nucleic acid sequences without directly amplifying the complete target nucleic acid sequences. The enriched target nucleic acid may then be purified and sequenced as desired using any suitable method. As discussed above, this embodiment of the PANS method has particular utility where the length of the target nucleic acid exceeds the practical limits of long-range PCR, e.g., where the nucleic acid is greater than about 10 kb, and/or where it is desirable to preserve epigenetic marks on the DNA. In some embodiments, the target nucleic acid to be enriched is greater than about 100 kb in length, e.g., greater than about 1 megabase in length. In some embodiments, the target nucleic acid to be enriched is from about 10 kb to about 100 kb, from about 100 kb to about 500 kb, or from about 500 kb to about 1 megabase in length.

PCR

As summarized above, in practicing methods of the invention a PCR-based assay may be used to detect the presence of certain genes of interest and/or genetic markers, e.g., oncogene(s), present in cells or a heterogeneous sample of nucleic acids. The conditions of such PCR-based assays may vary in one or more ways.

For instance, the number of PCR primers that may be added to a microdroplet may vary. The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The number of PCR primers that may be added to a microdroplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

These primers may contain primers for one or more gene of interest, e.g. oncogenes. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more. Genes and oncogenes of interest include, but are not limited to, BAX, BCL2L1, CASP8, CDK4, ELK1, ETS1, HGF, JAK2, JUNB, JUND, KIT, KITLG, MCL1, MET, MOS, MYB, NFKBIA, EGFR, Myc, EpCAM, NRAS, PIK3CA, PML, PRKCA, RAF1, RARA, REL, ROS1, RUNX1, SRC, STAT3, CD45, cytokeratins, CEA, CD133, HER2, CD44, CD49f, CD146, MUC1/2, and ZHX2.

Such primers and/or reagents may be added to a microdroplet in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent.

Once primers have been added to a microdroplet the microdroplet may be incubated under conditions allowing for PCR. The microdroplet may be incubated on the same microfluidic device as was used to add the primer(s), or may be incubated on a separate device. In certain embodiments, incubating the microdroplet under conditions allowing for PCR amplification is performed on the same microfluidic device used to encapsulate the cells and lyse the cells. Incubating the microdroplets may take a variety of forms. In certain aspects, the drops containing the PCR mix may be flowed through a channel that incubates the microdroplets under conditions effective for PCR. Flowing the microdroplets through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the drops move through such zones, their temperature cycles, as needed for PCR. The precise number of zones, and the respective temperature of each zone, may be readily determined by those of skill in the art to achieve the desired PCR amplification.

Figure 12:
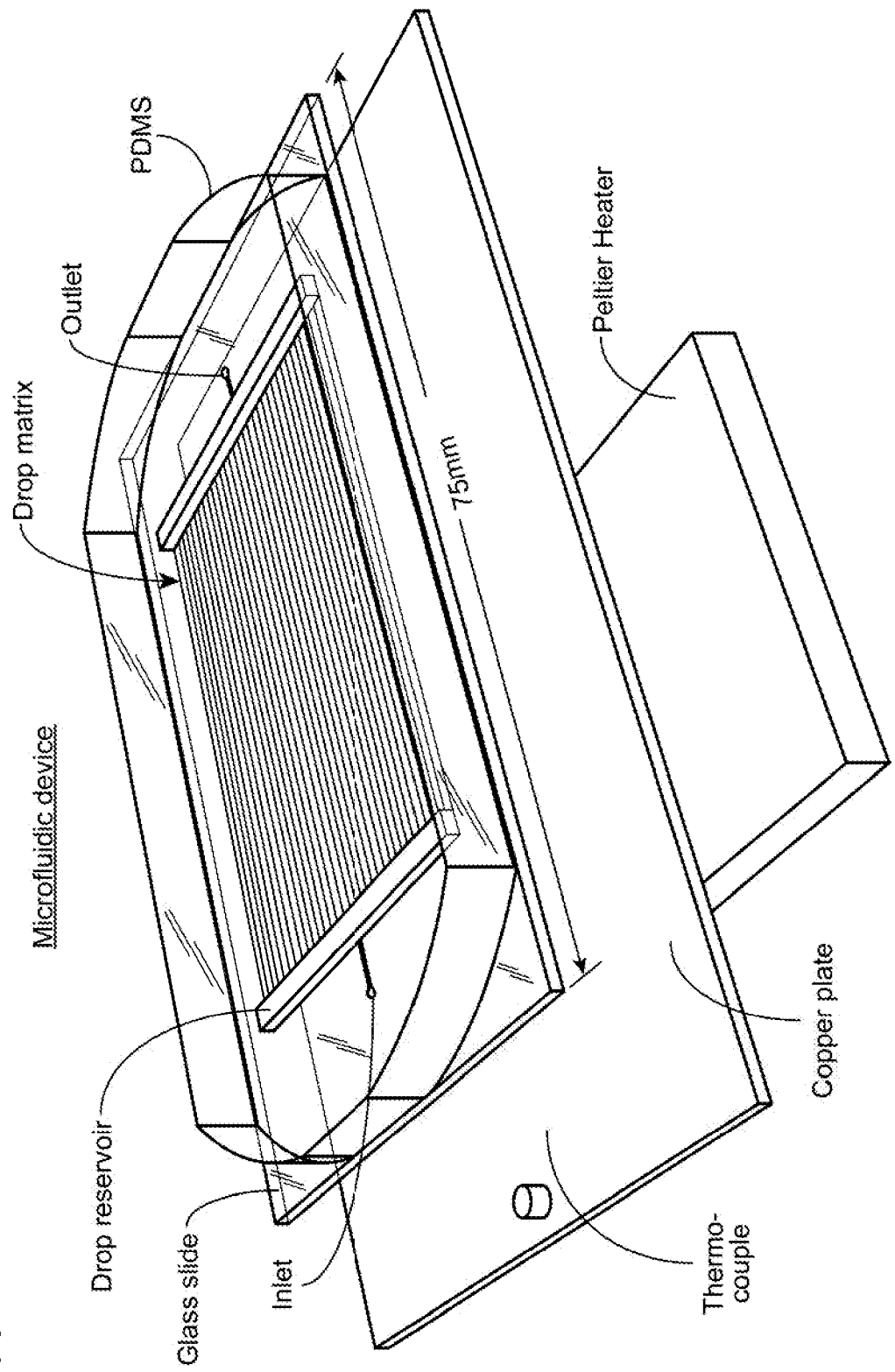
FIG. 12, Panels A-C, show a schematic illustration of a device for performing multiplexed qPCR analysis on cells individually. The device consists of an array of about 10 million traps indented into a PDMS channel that sits above a thermal system (Panel A). The height of the microfluidic channel is smaller than the diameter of the drops, causing drops to adopt a flattened pancake shape. When a drop flows over an unoccupied indentation, it adopts a lower, more energetically favorable, radius of curvature, leading to a force that pulls the drop entirely into the trap (Panel B). By flowing drops as a close pack, it is ensured that all traps on the array are occupied, as illustrated in Panel C. The entire device is thermal cycled and imaged between cycles using a microarray scanner.

In other embodiments, incubating the microdroplets may involve the use of a device of the general types depicted in FIG. 12, Panels A-C, and FIG. 13; a device of this general type may be referred to herein as a "Megadroplet Array." In such a device, an array of hundreds, thousands, or millions of traps indented into a channel (e.g., a PDMS channel) sit above a thermal system (FIG. 12, Panel A). The channel may be pressurized, thereby preventing gas from escaping. The height of the microfluidic channel is smaller than the diameter of the drops, causing drops to adopt a flattened pancake shape. When a drop flows over an unoccupied indentation, it adopts a lower, more energetically favorable, radius of curvature, leading to a force that pulls the drop entirely into the trap (FIG. 12, Panel B). By flowing drops as a close pack, it is ensured that all traps on the array are occupied, as illustrated in FIG. 12, Panel C. The entire device may be thermal cycled using a heater.

In certain aspects, the heater includes a Peltier plate, heat sink, and control computer. The Peltier plate allows for the heating or cooling of the chip above or below room temperature by controlling the applied current. To ensure controlled and reproducible temperature, a computer may monitor the temperature of the array using integrated temperature probes, and may adjust the applied current to heat and cool as needed. A metallic (e.g. copper) plate allows for uniform application of heat and dissipation of excess heat during cooling cycles, enabling cooling from about 95° C. to about 60° C. in under about one minute.

Methods of the invention may also include introducing one or more probes to the microdroplet. As used herein with respect to nucleic acids, the term "probe" refers to a labeled oligonucleotide which forms a duplex structure with a sequence in the target nucleic acid, due to complementarity of at least one sequence in the probe with a sequence in the target region. In some embodiments, the probe does not contain a sequence complementary to sequence(s) used to prime the polymerase chain reaction. The number of probes that are added may be from about one to 500, e.g., about 1 to 10 probes, about 10 to 20 probes, about 20 to 30 probes, about 30 to 40 probes, about 40 to 50 probes, about 50 to 60 probes, about 60 to 70 probes, about 70 to 80 probes, about 80 to 90 probes, about 90 to 100 probes, about 100 to 150 probes, about 150 to 200 probes, about 200 to 250 probes, about 250 to 300 probes, about 300 to 350 probes, about 350 to 400 probes, about 400 to 450 probes, about 450 to 500 probes, or about 500 probes or more. The probe(s) may be introduced into the microdroplet prior to, subsequent with, or after the addition of the one or more primer(s). Probes of interest include, but are not limited to, TaqMan® probes (e.g., as described in Holland, P. M.; Abramson, R. D.; Watson, R.; Gelfand, D. H. (1991). "Detection of specific polymerase chain reaction product by utilizing the 5'---3' exonuclease activity of *Thermus aquaticus* DNA polymerase". PNAS, 88 (16): 7276-7280).

In certain embodiments, an RT-PCR based assay may be used to detect the presence of certain transcripts of interest, e.g., oncogene(s), present in cells. In such embodiments, reverse transcriptase and any other reagents necessary for cDNA synthesis are added to the microdroplet in addition to the reagents used to carry out PCR described herein (collectively referred to as the "RT-PCR reagents"). The RT-PCR reagents are added to the microdroplet using any of the methods described herein. Once reagents for RT-PCR have been added to a microdroplet, the microdroplet may be incubated under conditions allowing for reverse transcription followed by conditions allowing for PCR as described herein. The microdroplet may be incubated on the same microfluidic device as was used to add the RT-PCR reagents, or may be incubated on a separate device. In certain embodiments, incubating the microdroplet under conditions allowing for RT-PCR is performed on the same microfluidic device used to encapsulate the cells and lyse the cells.

In certain embodiments, the reagents added to the microdroplet for RT-PCR or PCR further includes a fluorescent DNA probe capable of detecting RT-PCR or PCR products. Any suitable fluorescent DNA probe can be used including, but not limited to SYBR Green, TaqMan®, Molecular Beacons and Scorpion probes. In certain embodiments, the reagents added to the microdroplet include more than one DNA probe, e.g., two fluorescent DNA probes, three fluorescent DNA probes, or four fluorescent DNA probes. The use of multiple fluorescent DNA probes allows for the concurrent measurement of RT-PCR or PCR products in a single reaction.

Double PCR

To amplify rare transcripts, a microdroplet that has undergone a first-step RT-PCR or PCR reaction as described herein may be further subjected to a second step PCR reaction. In some embodiments, a portion of a microdroplet that has undergone a first-step RT-PCR or PCR reaction is extracted from the microdroplet and coalesced with a droplet containing additional PCR reagents, including, but not limited to enzymes (e.g. DNA polymerase), DNA probes (e.g. fluorescent DNA probes) and primers. In certain embodiments, the droplet containing the additional PCR reagents is larger than the microdroplet that has undergone the first step RT-PCR or PCR reaction. This may be beneficial, for example, because it allows for the dilution of cellular components that may be inhibitory to the second step PCR. The second step PCR reaction may be carried out on the same microfluidic device used to carry out the first-step reaction or on a different microfluidic device.

In some embodiments, the primers used in the second step PCR reaction are the same primers used in the first step RT-PCR or PCR reaction. In other embodiments, the primers used in the second step PCR reaction are different than the primers used in the first step reaction.

Multiplexing

In certain embodiments of the subject methods, multiple biomarkers may be detected and analyzed for a particular cell. Biomarkers detected may include, but are not limited to, one or more proteins, transcripts and/or genetic signatures in the cell's genome or combinations thereof. With standard fluorescence based detection, the number of biomarkers that can be simultaneously interrogated may be limited to the number of fluorescent dyes that can be independently visualized within each microdrop. In certain embodiments, the number of biomarkers that can be individually detected within a particular microdroplet can be increased. For example, this may be accomplished by segregation of dyes to different parts of the microdroplet. In particular embodiments, beads (e.g. LUMINEX® beads) conjugated with dyes and probes (e.g., nucleic acid or antibody probes) may be encapsulated in the microdroplet to increase the number of biomarkers analyzed. In another embodiment, fluorescence polarization may be used to achieve a greater number of detectable signals for different biomarkers for a single cell. For example, fluorescent dyes may be attached to various probes and the microdroplet may be visualized under different polarization conditions. In this way, the same colored dye can be utilized to provide a signal for different probe targets for a single cell. The use of fixed and/or permeabilized cells (as discussed in greater detail below) also allows for increased levels of multiplexing. For example, labeled antibodies may be used to target protein targets localized to cellular components while labeled PCR and/or RT-PCR products are free within a microdroplet. This allows for dyes of the same color to be used for antibodies and for amplicons produced by RT-PCR.

Types of Microdroplets

In practicing the methods of the present invention, the composition and nature of the microdroplets may vary. For instance, in certain aspects, a surfactant may be used to stabilize the microdroplets. Accordingly, a microdroplet may involve a surfactant stabilized emulsion. Any convenient surfactant that allows for the desired reactions to be performed in the drops may be used. In other aspects, a microdroplet is not stabilized by surfactants or particles.

The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox FSH). If, however, the oil was switched to be a hydrocarbon oil, for example, the surfactant would instead be chosen so that it had a hydrophobic hydrocarbon block, like the surfactant ABIL EM90. In selecting a surfactant, desirable properties that may be considered in choosing the surfactant may include one or more of the following: (1) the surfactant has low viscosity; (2) the surfactant is immiscible with the polymer used to construct the device, and thus it doesn't swell the device; (3) biocompatibility; (4) the assay reagents are not soluble in the surfactant; (5) the surfactant exhibits favorable gas solubility, in that it allows gases to come in and out; (6) the surfactant has a boiling point higher than the temperature used for PCR (e.g., 95 C); (7) the emulsion stability; (8) that the surfactant stabilizes drops of the desired size; (9) that the surfactant is soluble in the carrier phase and not in the droplet phase; (10) that the surfactant has limited fluorescence properties; and (11) that the surfactant remains soluble in the carrier phase over a range of temperatures.

Other surfactants can also be envisioned, including ionic surfactants. Other additives can also be included in the oil to stabilize the drops, including polymers that increase droplet stability at temperatures above 35° C.

The microdroplets described herein may be prepared as emulsions, e.g., as an aqueous phase fluid dispersed in an immiscible phase carrier fluid (e.g., a fluorocarbon oil or a hydrocarbon oil) or vice versa. In some embodiments, where a particular sorting technique benefits from or requires that the microdroplets be provided in an aqueous phase fluid, e.g., in the case of sorting via FACS, the microdroplets may be provided as double-emulsions following a nucleic acid amplification step, e.g., as an aqueous phase fluid in an immiscible phase fluid, dispersed in an aqueous phase carrier fluid; quadruple emulsions, e.g., an aqueous phase fluid in an immiscible phase fluid, in an aqueous phase fluid, in an immiscible phase fluid, dispersed in an aqueous phase carrier fluid; and so on. The nature of the microfluidic channel (or a coating thereon), e.g., hydrophilic or hydrophobic, may be selected so as to be compatible with the type of emulsion being utilized at a particular point in a microfluidic work flow. See, e.g., FIG. 23 in which a hydrophilic channel is utilized in connection with a double emulsion stage whereas a hydrophobic channel is utilized in connection with a triple emulsion stage.

Adding Reagents to Microdroplets

In practicing the subject methods, a number of reagents may need to be added to the microdroplets, in one or more steps (e.g., about 2, about 3, about 4, or about 5 or more steps). The means of adding reagents to the microdroplets may vary in a number of ways. Approaches of interest include, but are not limited to, those described by Ahn, et al., Appl. Phys. Lett. 88, 264105 (2006); Priest, et al., Appl. Phys. Lett. 89, 134101 (2006); Abate, et al., PNAS, Nov. 9, 2010 vol. 107 no. 45 19163-19166; and Song, et al., Anal. Chem., 2006, 78 (14), pp 4839-4849; the disclosures of which are incorporated herein by reference.

For instance, a reagent may be added to a microdroplet, e.g., a droplet, by a method involving merging a microdroplet with a second microdroplet that contains the reagent(s). The reagent(s) that are contained in the second microdroplet may be added by any convenient means, specifically including those described herein. This microdroplet may be merged with the first microdroplet to create a microdroplet that includes the contents of both the first microdroplet and the second microdroplet.

One or more reagents may also, or instead, be added using techniques such as droplet coalescence, or picoinjection. In droplet coalescence, a target microdroplet may be flowed alongside a microdroplet containing the reagent(s) to be added to the target microdroplet. The two microdroplets may be flowed such that they are in contact with each other, but not touching other microdroplets. These microdroplets may then be passed through electrodes or other means of applying an electrical field, wherein the electric field may destabilize the microdroplets such that they are merged together.

Reagents may also, or instead, be added using picoinjection. In this approach, a target microdroplet may be flowed past a channel containing the reagent(s) to be added, wherein the reagent(s) are at an elevated pressure. Due to the presence of the surfactants, however, in the absence of an electric field, the microdroplet will flow past without being injected, because surfactants coating the microdroplet may prevent the fluid(s) from entering. However, if an electric field is applied to the microdroplet as it passes the injector, fluid containing the reagent(s) will be injected into the microdroplet. The amount of reagent added to the microdroplet may be controlled by several different parameters, such as by adjusting the injection pressure and the velocity of the flowing drops, by switching the electric field on and off, and the like.

In other aspects, one or more reagents may also, or instead, be added to a microdroplet by a method that does not rely on merging two microdroplets together or on injecting liquid into a microdroplet. Rather, one or more reagents may be added to a microdroplet by a method involving the steps of emulsifying a reagent into a stream of very small drops, and merging these small drops with a target microdroplet (FIG. 20, Panels A-B). Such methods shall be referred to herein as "reagent addition through multiple-drop coalescence." These methods take advantage of the fact that due to the small size of the drops to be added compared to that of the target microdroplet, the small drops will flow faster than the target microdroplets and collect behind them. The collection can then be merged by, for example, applying an electric field. This approach can also, or instead, be used to add multiple reagents to a microdroplet by using several co-flowing streams of small drops of different fluids. To enable effective merger of the tiny and target microdroplets, it is important to make the tiny drops smaller than the channel containing the target microdroplets, and also to make the distance between the channel injecting the target microdroplets from the electrodes applying the electric field sufficiently long so as to give the tiny drops time to "catch up" to the target microdroplets. If this channel is too short, not all tiny drops will merge with the target microdroplet and less than the desired amount of reagent may be added. To a certain degree, this can be compensated for by increasing the magnitude of the electric field, which tends to allow drops that are farther apart to merge. In addition to making the tiny drops on the same microfluidic device, as is shown in FIG. 20, Panels A-B, they can also, or instead, be made offline using another microfluidic drop maker or through homogenization and then injecting them into the device containing the target microdroplets.

Accordingly, in certain aspects a reagent is added to a microdroplet by a method involving emulsifying the reagent into a stream of droplets, wherein the droplets are smaller than the size of the microdroplet; flowing the droplets together with the microdroplet; and merging a droplet with the microdroplet. The diameter of the droplets contained in the stream of droplets may vary ranging from about 75% or less than that of the diameter of the microdroplet, e.g., the diameter of the flowing droplets is about 75% or less than that of the diameter of the microdroplet, about 50% or less than that of the diameter of the microdroplet, about 25% or less than that of the diameter of the microdroplet, about 15% or less than that of the diameter of the microdroplet, about 10% or less than that of the diameter of the microdroplet, about 5% or less than that of the diameter of the microdroplet, or about 2% or less than that of the diameter of the microdroplet. In certain aspects, a plurality of flowing droplets may be merged with the microdroplet, such as 2 or more droplets, 3 or more, 4 or more, or 5 or more. Such merging may be achieved by any convenient means, including but not limited to by applying an electric field, wherein the electric field is effective to merge the flowing droplet with the microdroplet.

As a variation of the above-described methods, the fluids may be jetting. That is, rather than emulsifying the fluid to be added into flowing droplets, a long jet of this fluid can be formed and flowed alongside the target microdroplet. These two fluids can then be merged by, for example, applying an electric field. The result is a jet with bulges where the microdroplets are, which may naturally break apart into droplets of roughly the size of the target microdroplets before the merger, due to the Rayleigh plateau instability. A number of variants are contemplated. For instance, one or more agents may be added to the jetting fluid to make it easier to jet, such as gelling agents and/or surfactants. Moreover, the viscosity of the continuous fluid could also be adjusted to enable jetting, such as that described by Utada, et al., *Phys. Rev. Lett.* 99, 094502 (2007), the disclosure of which is incorporated herein by reference.

In other aspects, one or more reagents may be added using a method that uses the injection fluid itself as an electrode, by exploiting dissolved electrolytes in solution (FIGS. 15-19). Methods of this general type are described more fully herein in Example 3.

In another aspect, a reagent is added to a microdroplet formed at an earlier time by enveloping the microdroplet to which the reagent is to be added (i.e., the "target microdroplet") inside a drop containing the reagent to be added (the "target reagent"). In certain embodiments such a method is carried out by first encapsulating the target microdroplet in a shell of a suitable hydrophobic phase, e.g., oil, to form a double emulsion. The double emulsion is then encapsulated by a microdroplet containing the target reagent to form a triple emulsion. To combine the target drop with the drop containing the target reagent, the double emulsion is then burst open using any suitable method, including, but not limited to, applying an electric field, adding chemicals that destabilizes the microdroplet interface, flowing the triple emulsion through constrictions and other microfluidic geometries, applying mechanical agitation or ultrasound, increasing or reducing temperature, or by encapsulating magnetic particles in the microdroplet that can rupture the double emulsion interface when pulled by a magnetic field.

Methods of making a triple emulsion and combining a target drop with a target reagent are described in Example 4 provided herein.

Detecting PCR Products

In practicing the subject methods, the manner in which PCR products may be detected may vary. For example, if the goal is simply to count the number of a particular cell type, e.g., tumor cells, present in a population, this may be achieved by using a simple binary assay in which Sybr-Green, or any other stain and/or intercalating stain, is added to each microdroplet so that in the event a characterizing gene, e.g., an oncogene, is present and PCR products are produced, the microdroplet will become fluorescent. The change in fluorescence may be due to fluorescence polarization. The detection component may include the use of an intercalating stain (e.g., SybrGreen).

A variety of different detection components may be used in practicing the subject methods, including using fluorescent dyes known in the art. Fluorescent dyes may typically be divided into families, such as fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va.

FIG. 14, Panels A-B depict the use of a one-color flow-cytometer, which can be used, for example, to detect tumor cell containing microdroplets. Panel A presents a schematic of a detector, consisting of a 488 nm laser directed into the back of an objective, and focused onto a microfluidic channel through which the microdroplets flow. The laser may excite fluorescent dyes within the microdroplets, and any emitted light is captured by the objective and imaged onto a PMT after it is filtered through a dichroic mirror and 520 f 5 nm band pass filter. Turning to Panel B, microdroplet appear as peaks in intensity as a function of time, as shown by the output voltage of a PMT, which is proportional to the intensity of the emitted light, as a function of time for detected fluorescent microdroplets.

FIGS. 3 and 4, Panels A-B further illustrate such a concept. FIG. 3, for example, is a non-limiting example that depicts digital detection of BRAF using TaqMan® PCR assays in arrayed microdroplets. Fluorescent microdroplets indicate amplification of the BRAF gene from human genomic DNA, while non-fluorescent microdroplets were devoid of the gene. Turning to FIG. 4, Panels A-B, this scheme is generalized. In FIG. 4, Panel A, a schematic is presented showing forward and reverse primers being encapsulated in the microdroplets that target an oncogenic sequence. If the oncogenic sequence is present, the PCR reaction produces double-stranded PCR products (Panel A, upper), whereas, if it is not, no products are produced (Panel A, lower). SybrGreen, or any other type of intercalating stain, is also present in the microdroplet. The results are depicted by the images in FIG. 4, Panel B, in that if double-stranded products are produced, the dye intercalates into them, becoming fluorescent, and turning the microdroplet fluorescent (FIG. 4, Panel B, upper); by contrast, if no double-stranded products are produced, the dye remains non-fluorescent, producing a dim microdroplet (FIG. 4, Panel B, lower).

In other aspects, particularly if a goal is to further characterize the oncogenes present, additional testing may be needed. For instance, in the case of the multiplex assays described more fully herein (Example 2), this may be achieved by having optical outputs that relate which of the gene(s) are amplified in the microdroplet. An alternative approach would be to use a binary output, for example, with an intercalated stain, to simply determine which microdroplets have any oncogenes. These can then be sorted to recover these microdroplets so that they could be analyzed in greater detail to determine which oncogenes they contain. To determine the oncogenes present in such a microdroplet, microfluidic techniques or nonmicrofluidic techniques could be used. Using non-microfluidic techniques, a microdroplet identified as containing an oncogene can be placed into a well on a wellplate where will be diluted into a larger volume, releasing all of the PCR products that were created during the multiplexed PCR reaction. Samples from this well can then be transferred into other wells, into each of which would be added primers for one of the oncogenes. These wells would then be temperature-cycled to initiate PCR, at which point an intercalating stain would be added to cause wells that have matching oncogenes and primers to light up.

In practicing the subject methods, therefore, a component may be detected based upon, for example, a change in fluorescence. In certain aspects, the change in fluorescence is due to fluorescence resonance energy transfer (FRET). In this approach, a special set of primers may be used in which the 5' primer has a quencher dye and the 3' primer has a fluorescent dye. These dyes can be arranged anywhere on the primers, either on the ends or in the middles. Because the primers are complementary, they will exist as duplexes in solution, so that the emission of the fluorescent dye will be quenched by the quencher dye, since they will be in close proximity to one another, causing the solution to appear dark. After PCR, these primers will be incorporated into the long PCR products, and will therefore be far apart from one another. This will allow the fluorescent dye to emit light, causing the solution to become fluorescent. Hence, to detect if a particular oncogene is present, one may measure the intensity of the droplet at the wavelength of the fluorescent dye. To detect if different oncogenes are present, this would be done with different colored dyes for the different primers. This would cause the droplet to become fluorescent at all wavelengths corresponding to the primers of the oncogenes present in the cell.

Sorting

In practicing the methods of the present disclosure, one or more sorting steps may be employed. Sorting approaches of interest include, by are not necessarily limited to, approaches that involve the use of membrane valves, bifurcating channels, surface acoustic waves, and/or dielectrophoresis. Sorting approaches of interest further include those depicted in FIGS. 2 and 22, Panels A-B, and those described by Agresti, et al., PNAS vol. 107, no 9, 4004-4009; the disclosure of which is incorporated herein by reference. A population may be enriched by sorting, in that a population containing a mix of members having or not having a desired property may be enriched by removing those members that do not have the desired property, thereby producing an enriched population having the desired property.

Sorting may be applied before or after any of the steps described herein. Moreover, two or more sorting steps may be applied to a population of microdroplets, e.g., about 2 or more sorting steps, about 3 or more, about 4 or more, or about 5 or more, etc. When a plurality of sorting steps is applied, the steps may be substantially identical or different in one or more ways (e.g., sorting based upon a different property, sorting using a different technique, and the like).

Figure 21:
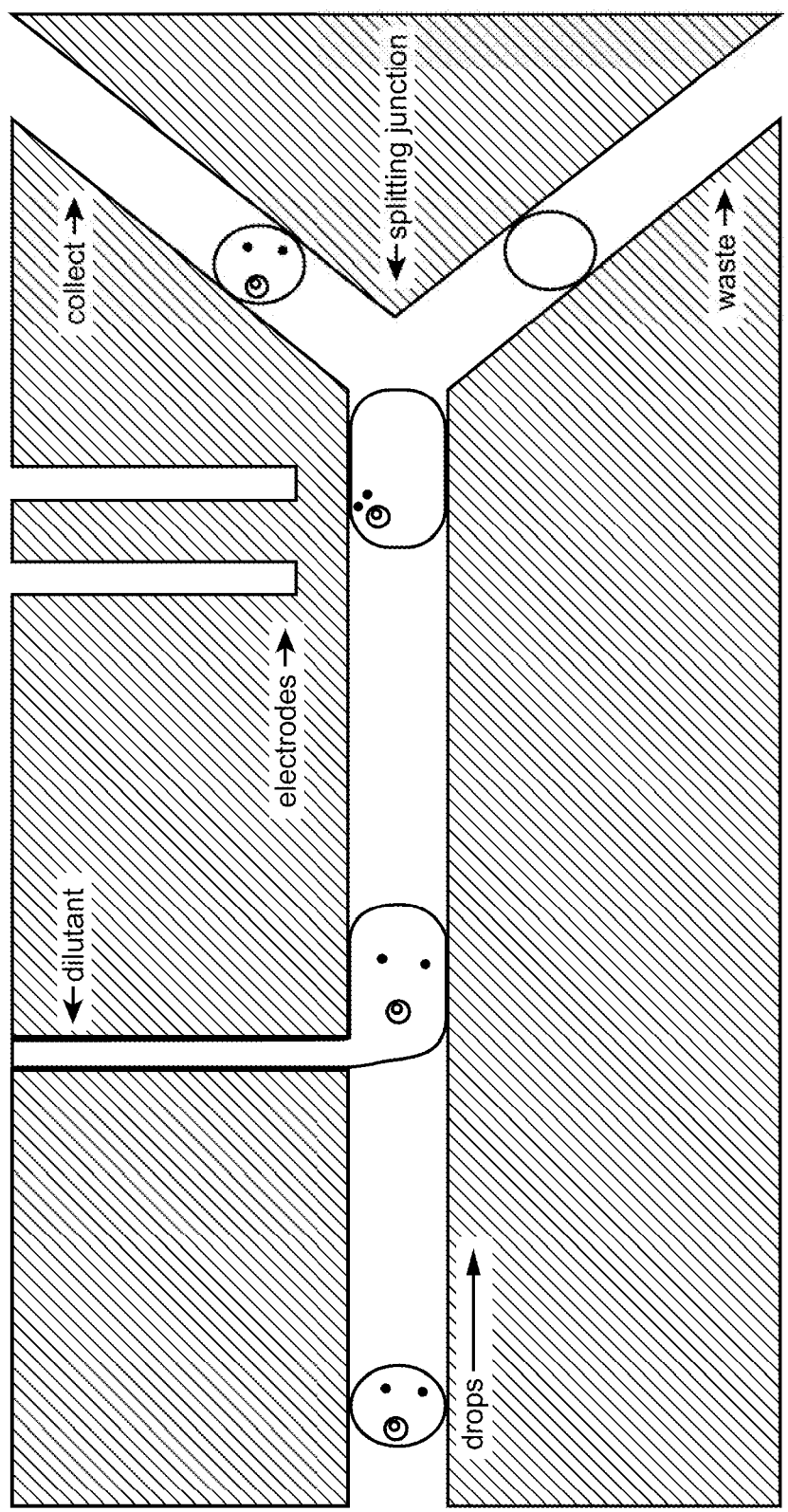
FIG. 21 shows a schematic of a microfluidic device whereby a microdroplet may be purified. That is, a majority of the fluid in the drop is replaced it with a purified solution, without removing any discrete reagents that may be encapsulated in the drop, such a cells or beads. The microdroplet is first injected with a solution to dilute any impurities within it. The diluted microdroplet is then flowed through a microfluidic channel on which an electric field is being applied using electrodes. Due to the dielectrophoretic forces generated by the field, as the cells or other discrete reagents pass through the field they will be displaced in the flow. The drops are then split, so that all the objects end up in one microdroplet. Accordingly, the initial microdroplet has been washed, in that the contaminants may be removed while the presence and/or concentration of discrete reagents, such as beads or cells, that may be encapsulated within the droplet are maintained in the resulting microdroplet.

Moreover, microdroplets may be purified prior to, or after, any sorting step. FIG. 21 presents a schematic of a microfluidic device whereby a microdroplet may be purified. That is, a majority of the fluid in the microdroplet is replaced it with a purified solution, without removing any discrete reagents that may be encapsulated in the microdroplet, such a cells or beads. The microdroplet is first injected with a solution to dilute any impurities within it. The diluted microdroplet is then flowed through a microfluidic channel on which an electric field is being applied using electrodes. Due to the dielectrophoretic forces generated by the field, as the cells or other discrete reagents pass through the field they will be displaced in the flow. The microdroplets are then split, so that all the objects end up in one microdroplet. Accordingly, the initial microdroplet has been purified, in that the contaminants may be removed while the presence and/or concentration of discrete reagents, such as beads or cells, that may be encapsulated within the microdroplet are maintained in the resulting microdroplet.

Microdroplets may be sorted based on one or more properties. Properties of interest include, but are not limited to, the size, viscosity, mass, buoyancy, surface tension, electrical conductivity, charge, magnetism, and/or presence or absence of one or more components. In certain aspects, sorting may be based at least in part upon the presence or absence of a cell in the microdroplet. In certain aspects, sorting may be based at least in part based upon the detection of the presence or absence of PCR amplification products.

Microdroplet sorting may be employed, for example, to remove microdroplets in which no cells are present. Encapsulation may result in one or more microdroplets, including a majority of the microdroplets, in which no cell is present. If such empty microdroplets were left in the system, they would be processed as any other microdroplet, during which reagents and time would be wasted. To achieve the highest speed and efficiency, these empty microdroplets may be removed with microdroplets sorting. For example, as described in Example 1, a drop maker may operate close to the dripping-to-jetting transition such that, in the absence of a cell, 8 μm drops are formed; by contrast, when a cell is present the disturbance created in the flow will trigger the breakup of the jet, forming drops 25 μm in diameter. The device may thus produce a bi-disperse population of empty 8 μm drops and single-cell containing 25 μm drops, which may then be sorted by size using, e.g., a hydrodynamic sorter to recover only the larger, single-cell containing drops.

Passive sorters of interest include hydrodynamic sorters, which sort microdroplets into different channels according to size, based on the different ways in which small and large microdroplets travel through the microfluidic channels. Also of interest are bulk sorters, a simple example of which is a tube containing microdroplets of different mass in a gravitational field. By centrifuging, agitating, and/or shaking the tube, lighter microdroplets that are more buoyant will naturally migrate to the top of the container. Microdroplets that have magnetic properties could be sorted in a similar process, except by applying a magnetic field to the container, towards which microdroplets with magnetic properties will naturally migrate according to the magnitude of those properties. A passive sorter as used in the subject methods may also involve relatively large channels that will sort large numbers of microdroplets simultaneously based on their flow properties.

Picoinjection can also be used to change the electrical properties of the microdroplets, e.g., drops. This could be used, for example, to change the conductivity of the microdroplets by adding ions, which could then be used to sort them, for example, using dielectrophoresis. Alternatively, picoinjection can also be used to charge the microdroplets, e.g., drops. This could be achieved by injecting a fluid into the microdroplets that is charged, so that after injection, the microdroplets would be charged. This would produce a collection of microdroplets in which some were charged and others not, and the charged microdroplets could then be extracted by flowing them through a region of electric field, which will deflect them based on their charge amount. By injecting different amounts of liquid by modulating the piocoinjection, or by modulating the voltage to inject different charges for affixed injection volume, the final charge on the microdroplets could be adjusted, to produce microdroplets with different charge. These would then be deflected by different amounts in the electric field region, allowing them to be sorted into different containers.

Flow cytometry (FC) may be utilized as an alternative to on-chip microdroplet sorting in any of the methods described herein. Such a method, along with devices which may be utilized in the practice of the method, are described in Lim and Abate, *Lab Chip,* 2013, 13, 4563-4572; the disclosure of which is incorporated herein by reference in its entirety and for all purposes. Briefly, microdroplets, e.g., drops, may be formed and manipulated, e.g., using techniques like splitting and picoinjection as described herein, resulting in single emulsions. These single emulsions may then be double emulsified, e.g., using one or more devices as described in Lim and Abate, *Lab Chip,* 2013, 13, 4563-4572. The double emulsions may then be analyzed via FC, e.g., FACS.

Figure 70:
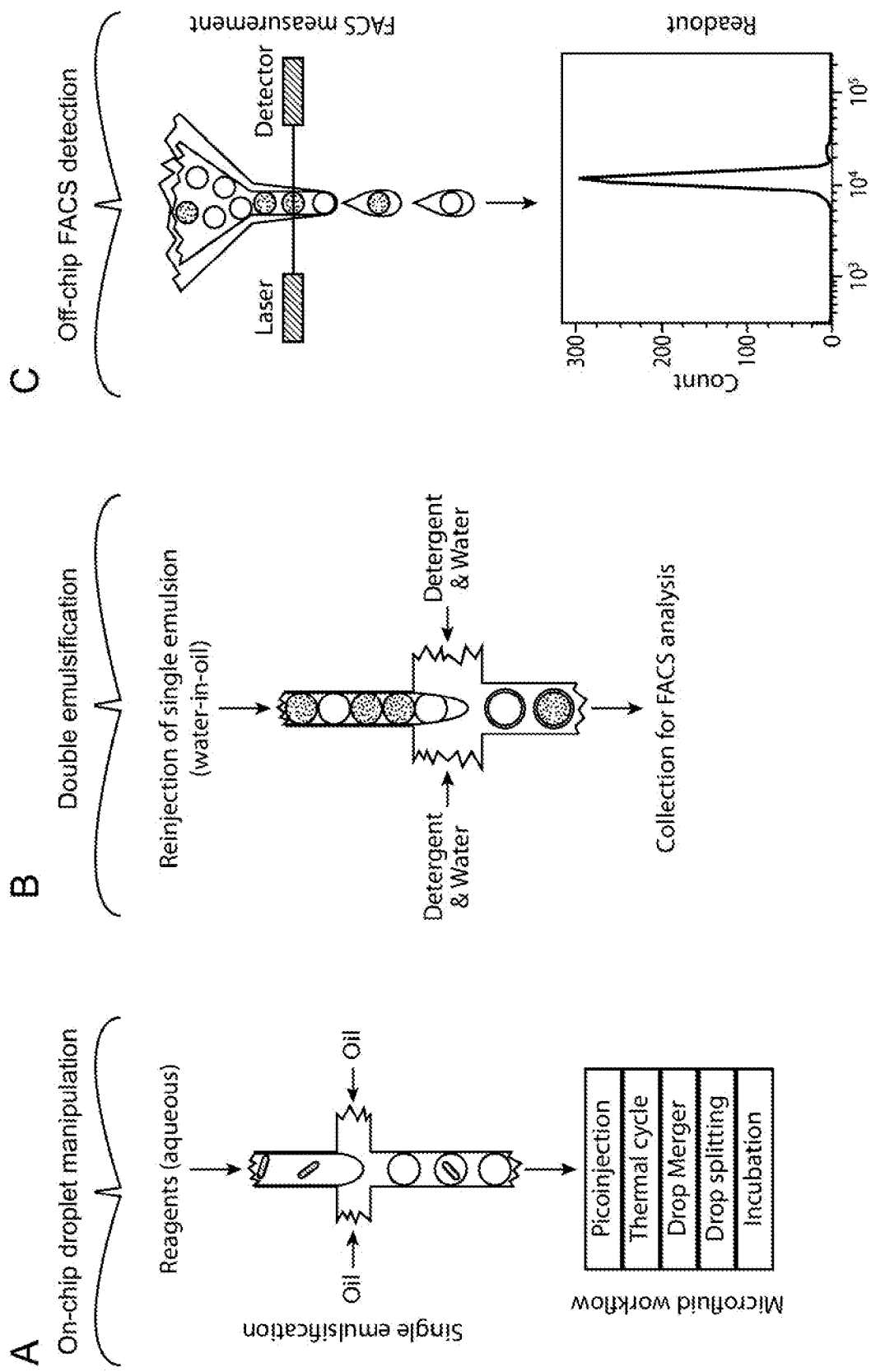
FIG. 70, Panels a-c, provides a schematic of a microfluidic double emulsion FACS analysis according to certain embodiments. A coaxial flow-focusing device, e.g., as shown in FIGS. 38-40, is utilized to encapsulate drops in double emulsions for subsequent FACS analysis.

A device which may be utilized to form double emulsions suitable for FC analysis and the characterization and application thereof is described in greater detail herein with reference to FIGS. 38-55 and Example 9. A general workflow scheme for an embodiment including sorting via FACS is provided in FIG. 70. Although specific microfluidic steps are listed, e.g., picoinjection, drop merger, etc., these are merely exemplary and it should be noted that any of the microfluidic manipulations described herein may be utilized in connection with such a double-emulsion/FACS sorting scheme.

Figure 38:
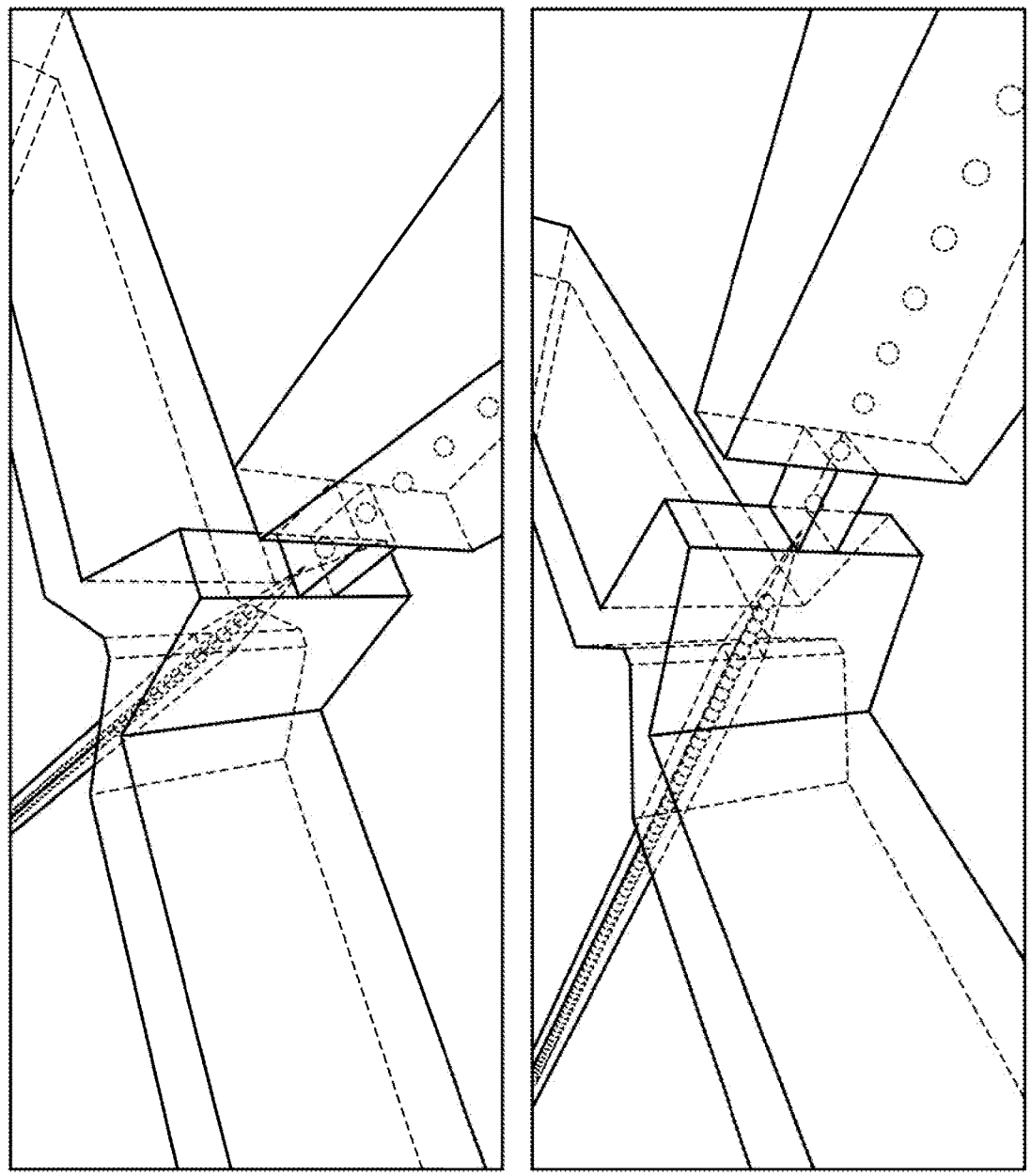
FIG. 38 provides two different views of a three dimensions schematic showing a device which may be used to encapsulate single emulsions in double emulsions. It includes a channel in which the single emulsions are introduced, which channel opens up into a large channel in which additional aqueous phase is added. This focuses the injected drops through an orifice, causing them to be encapsulated in oil drops and forming water-in-oil-in-water double emulsions.
Figure 39:
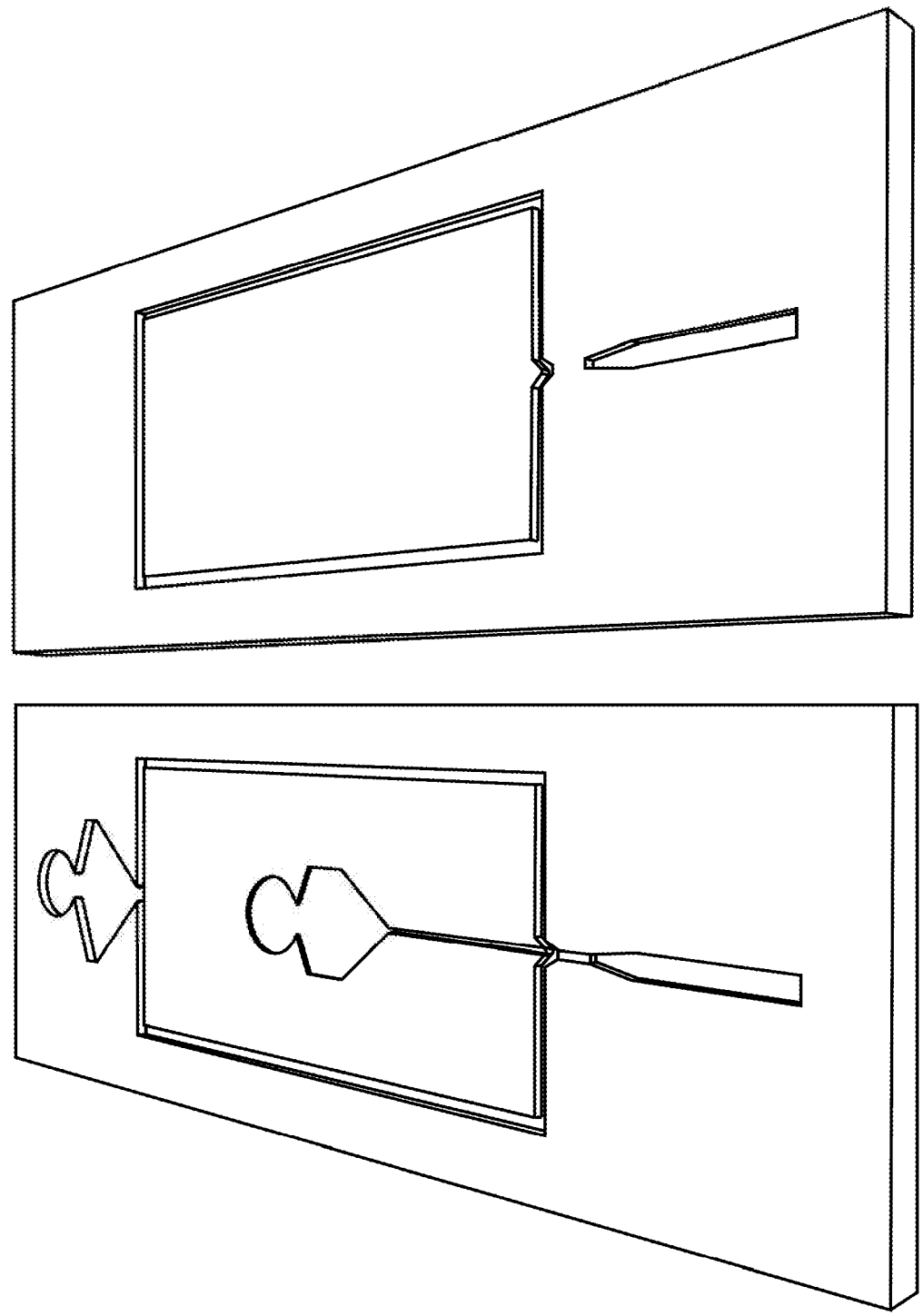
FIG. 39 provides two schematics of PDMS slabs that may be used to construct a double emulsification device. The slab on the left has channels with two heights—short channels for the droplet reinjection and constriction channels (see previous Figure) and tall channels for the aqueous phase and outlets. The slab on the right has only the tall channels. To complete the device, the slabs are aligned and sealed together so that the channels are facing. The devices are bonded using plasma oxidation.
Figure 40:
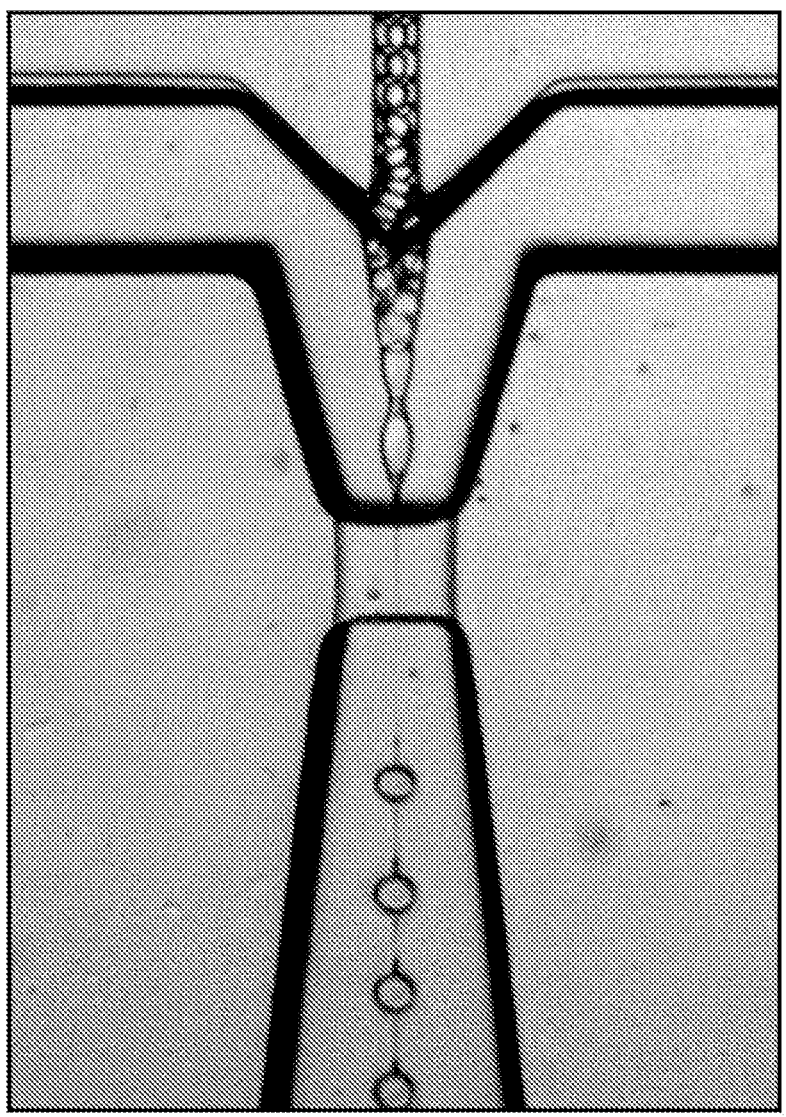
FIG. 40 provides a microscope image of a double emulsification device encapsulating a reinjected single emulsions in double emulsions. The reinjected single emulsions enter from above and are encapsulated in the constriction shown in the center of the device. They then exit as double emulsions, four of which are shown towards the bottom of the device.
Figure 42:
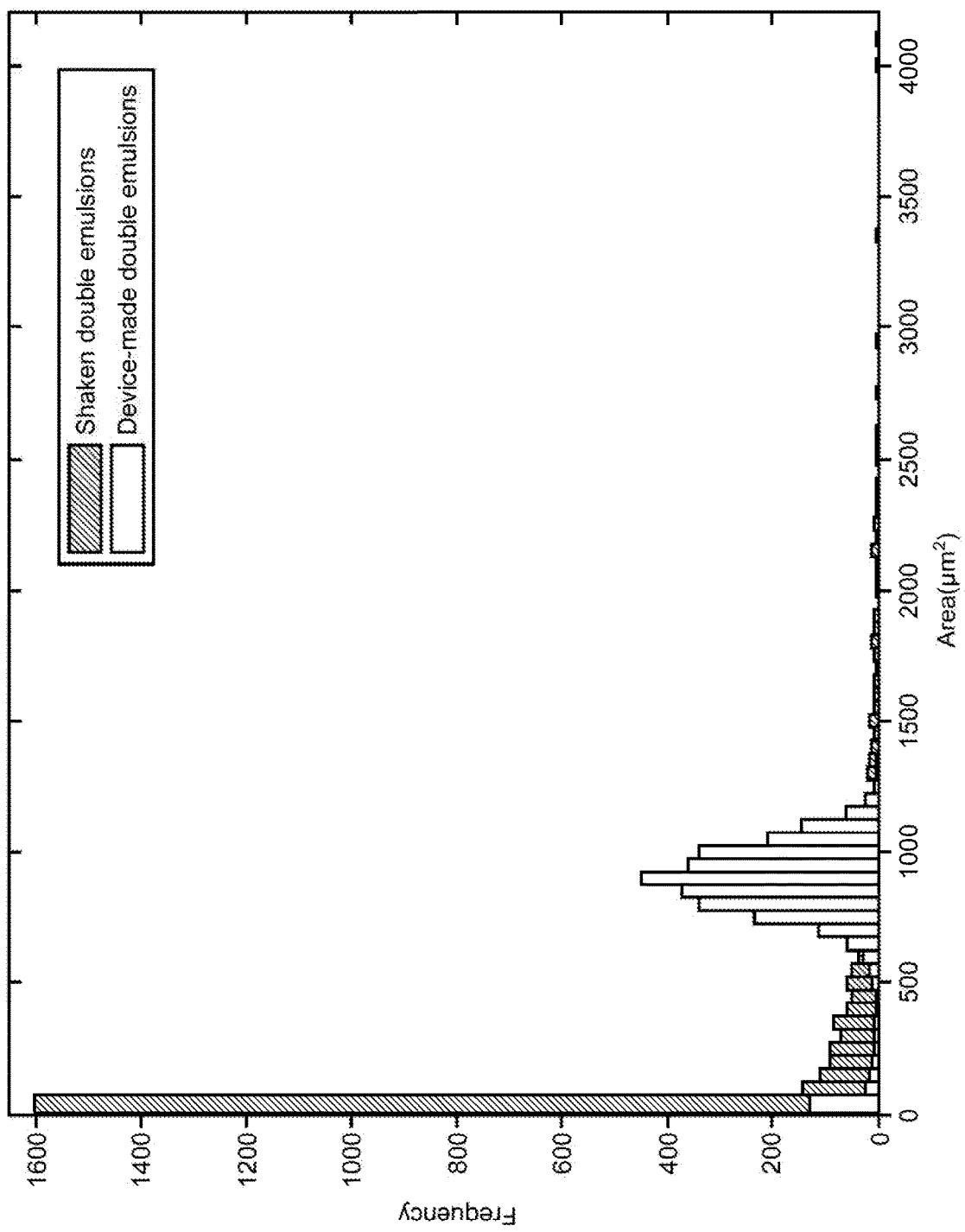
FIG. 42 provides a histogram of the drop areas for shaken vs. device-created double emulsions. The device-created double emulsions are much more monodisperse, as demonstrated by the peak.
Figure 43:
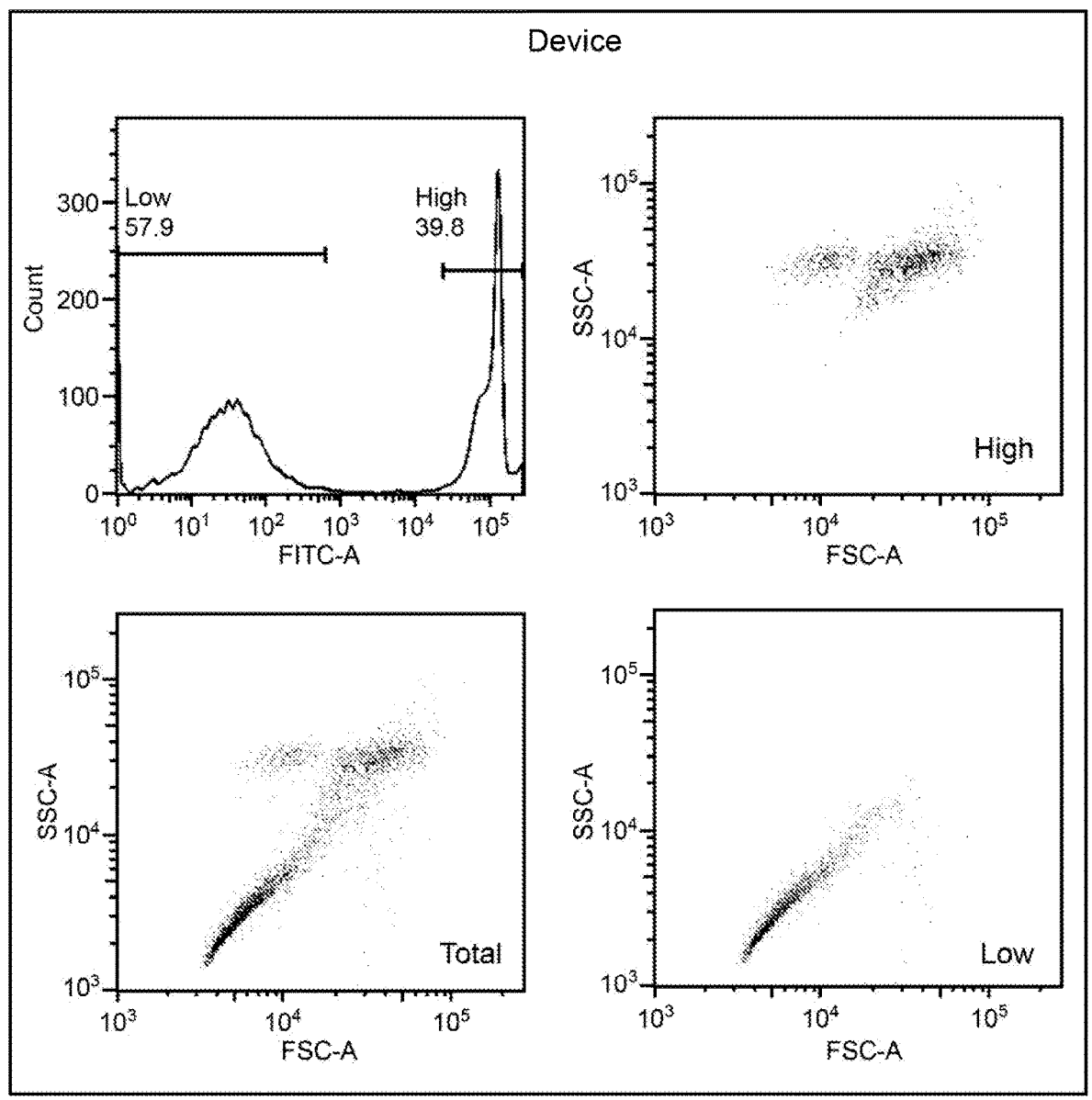
FIG. 43 shows FACS fluorescence and scattering data for microfluidic device generated double emulsions according to the present disclosure. The upper plot shows the intensity histogram of the population as measured with the FITC channel (~520 nm) of the FACS. The plots below show the forward and side scattering of the drops, gated according to FITC signal.
Figure 44:
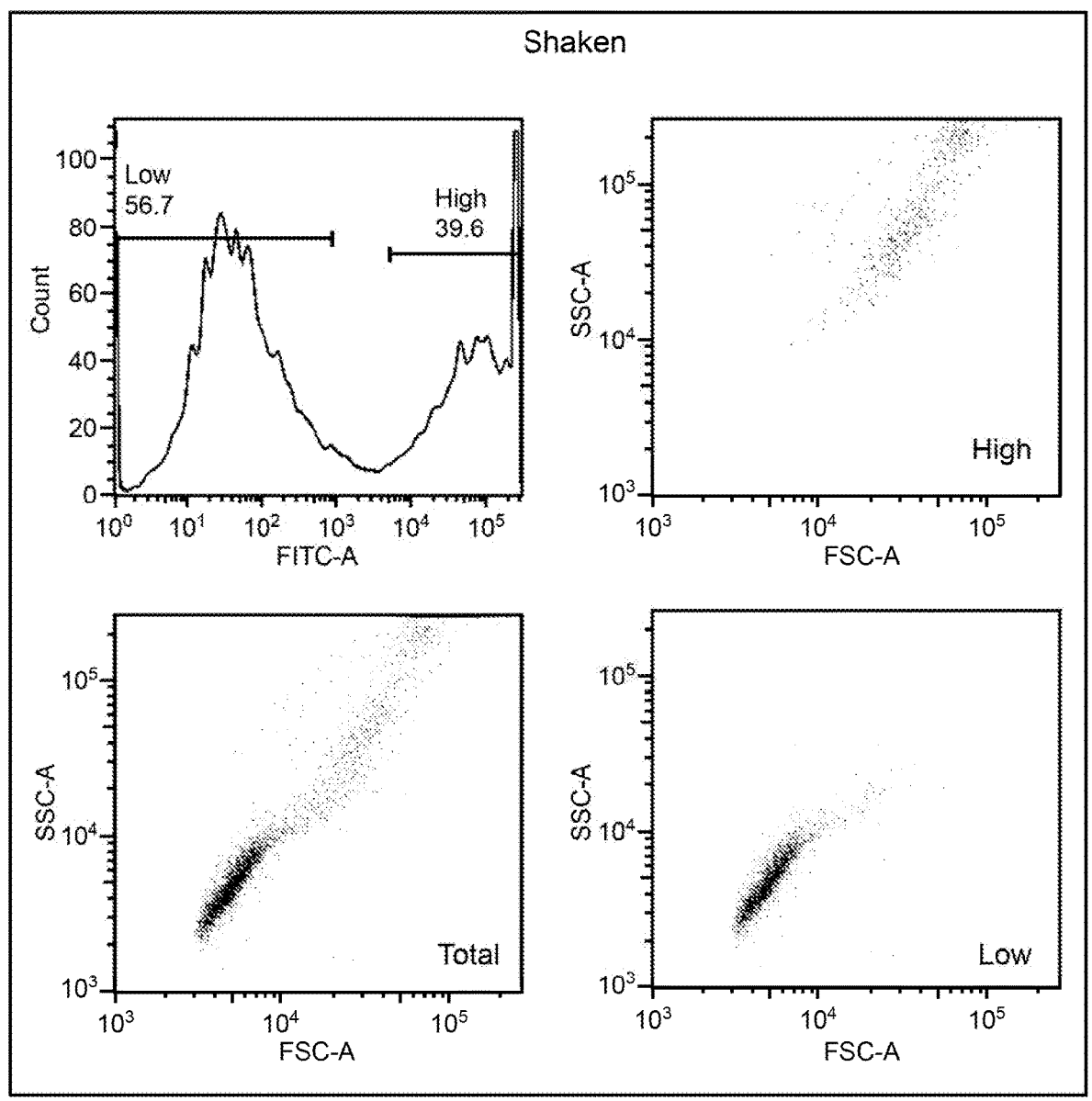
FIG. 44 shows FACS fluorescence and scattering data for shaken double emulsions. The upper plot shows the intensity histogram of the population as measured with the FITC channel (~520 nm) of the FACS. The plots below show the forward and side scattering of the drops, gated according to FITC signal.
Figure 45:
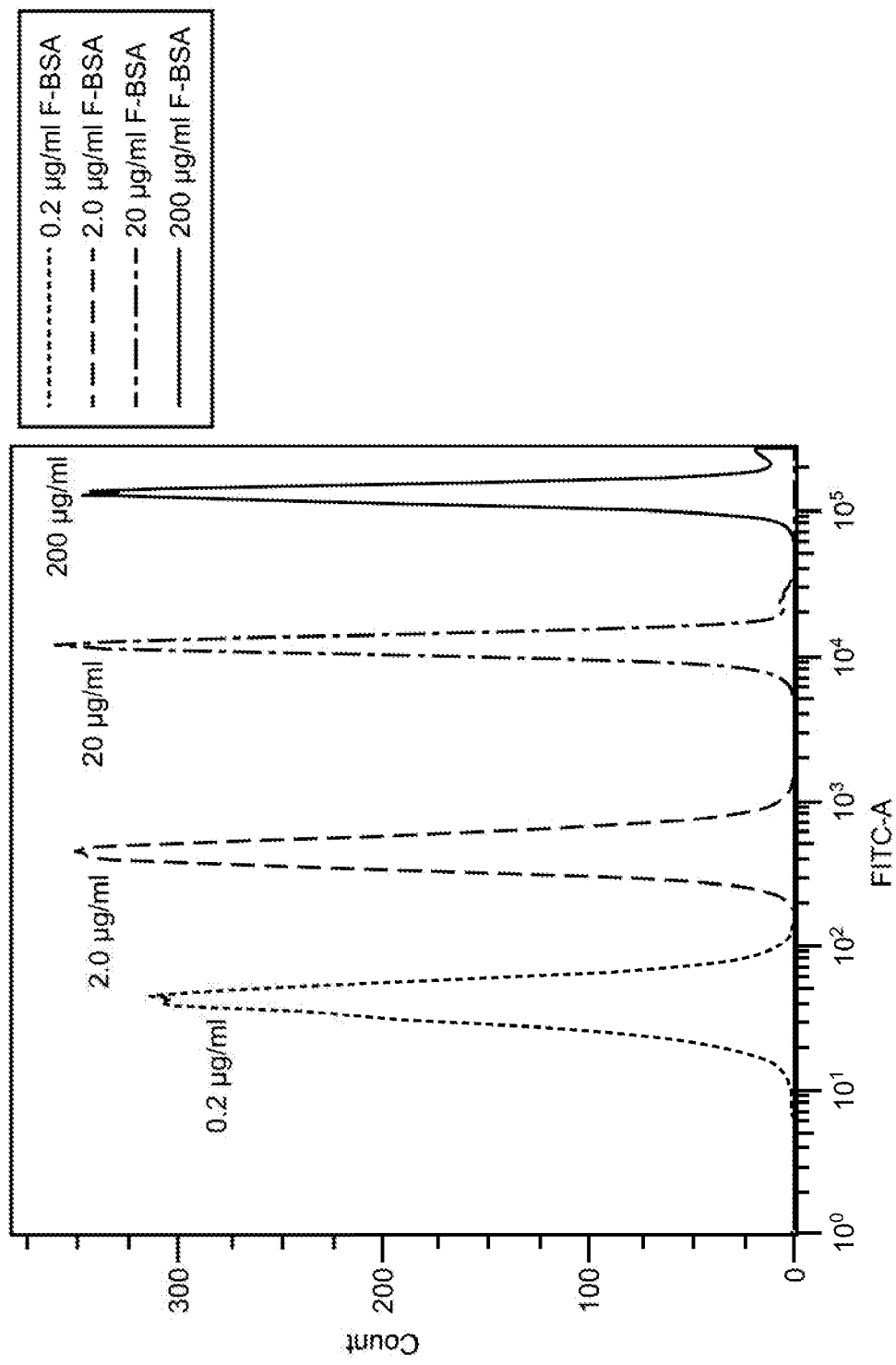
FIG. 45 provides a histogram of droplet intensity as read out with the FACS (FITC channel) for four different concentrations of encapsulated dye. The dye is composed of fluorescently-labeled BSA.
Figure 46:
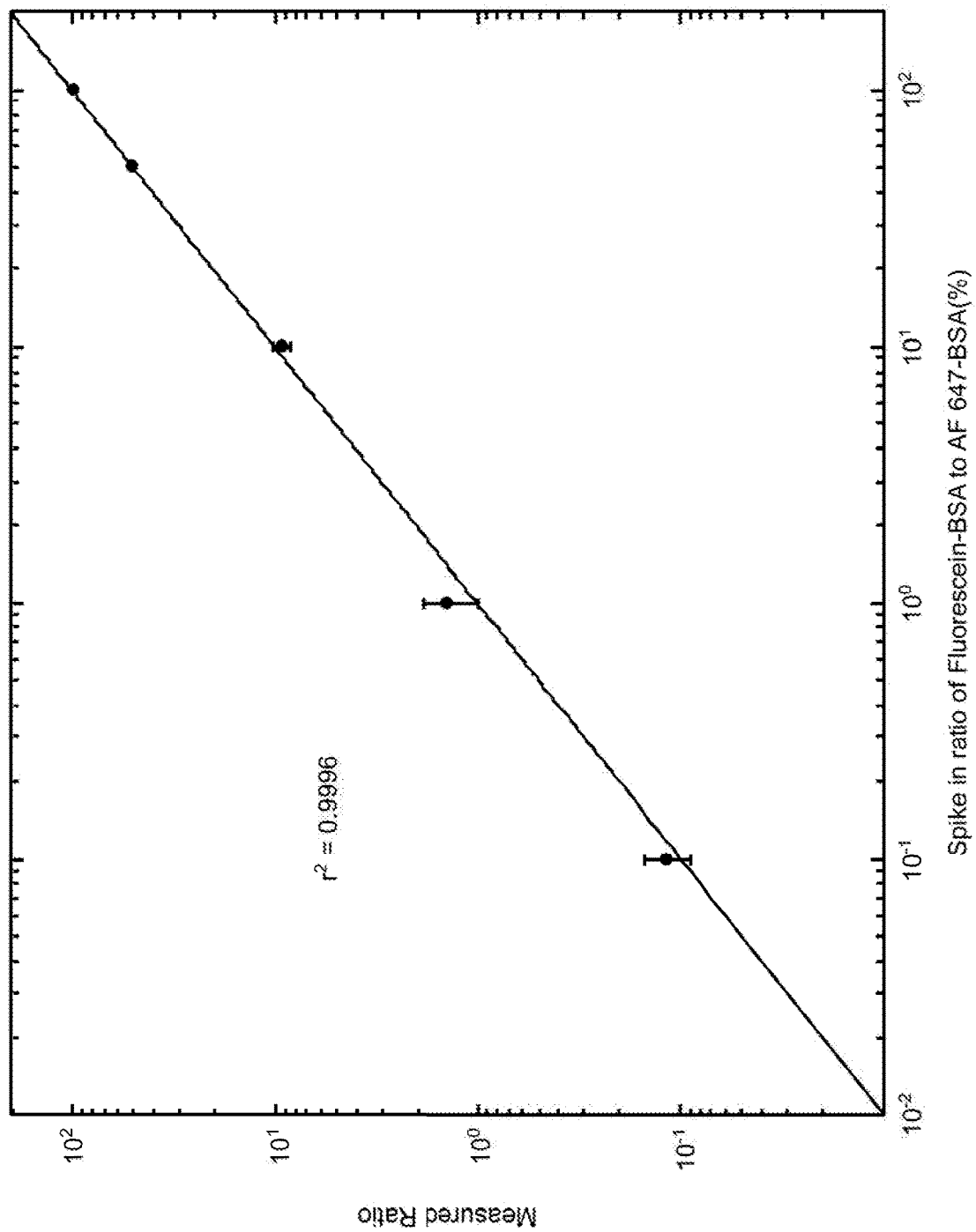
FIG. 46 shows the results of an experiment designed to test the detection rate of the FACS-run drops. Two populations of drops were created, one with labeled BSA fluorescent at 520 nm, and another with BSA fluorescent at 647 nm. The two populations were then mixed in defined ratios and the samples were run on FACS. The measured ratio was found to agree with the known ratio, demonstrating that the FACS measurements are accurate over this range.
Figure 50:
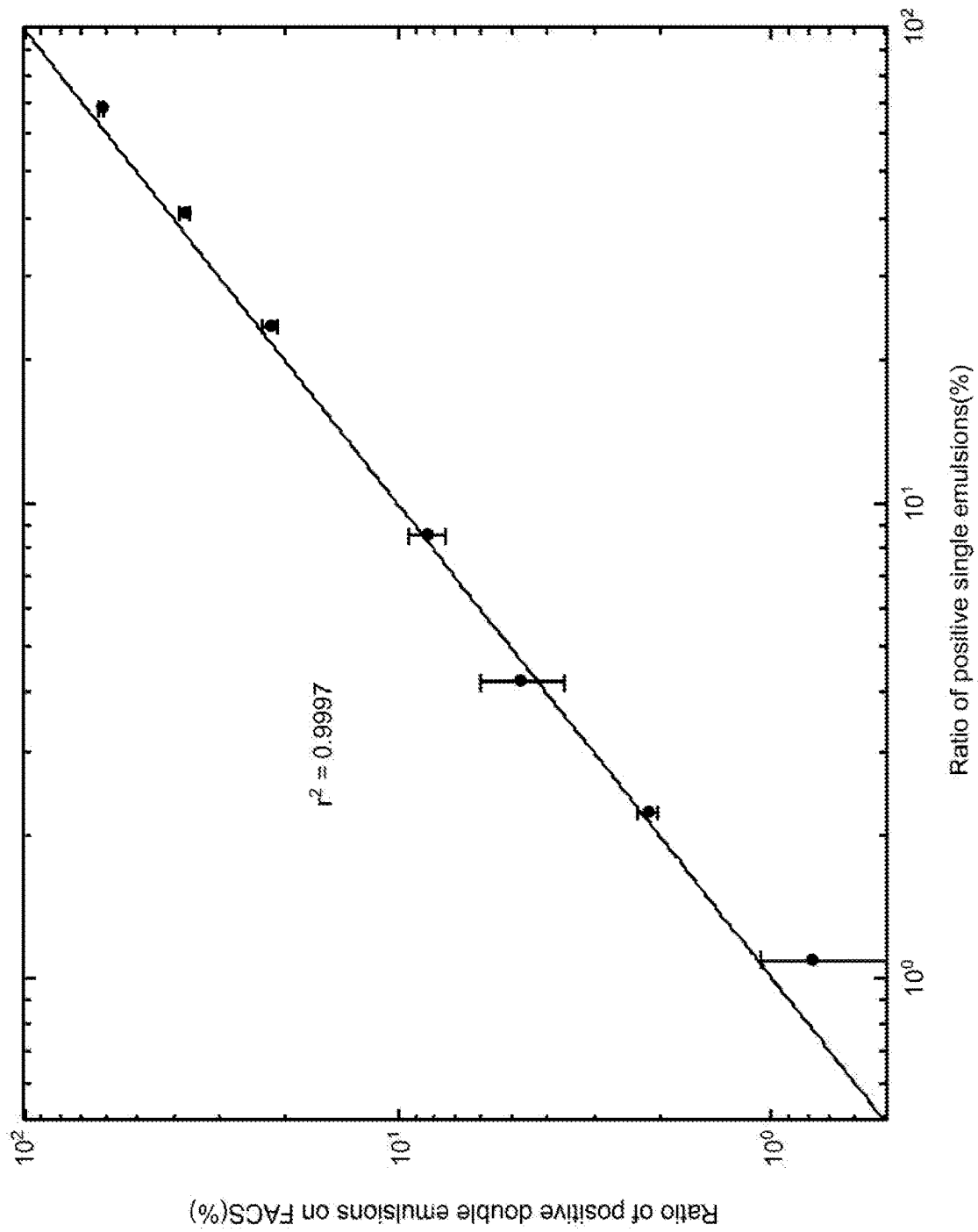
FIG. 50 shows a plot of the detected number of positives by FACS analysis of double emulsions plotted versus the number of positives detected by imaging the drops before double emulsification using a fluorescent microscope. The results agree with one another over the two decades tested.
Figure 51:
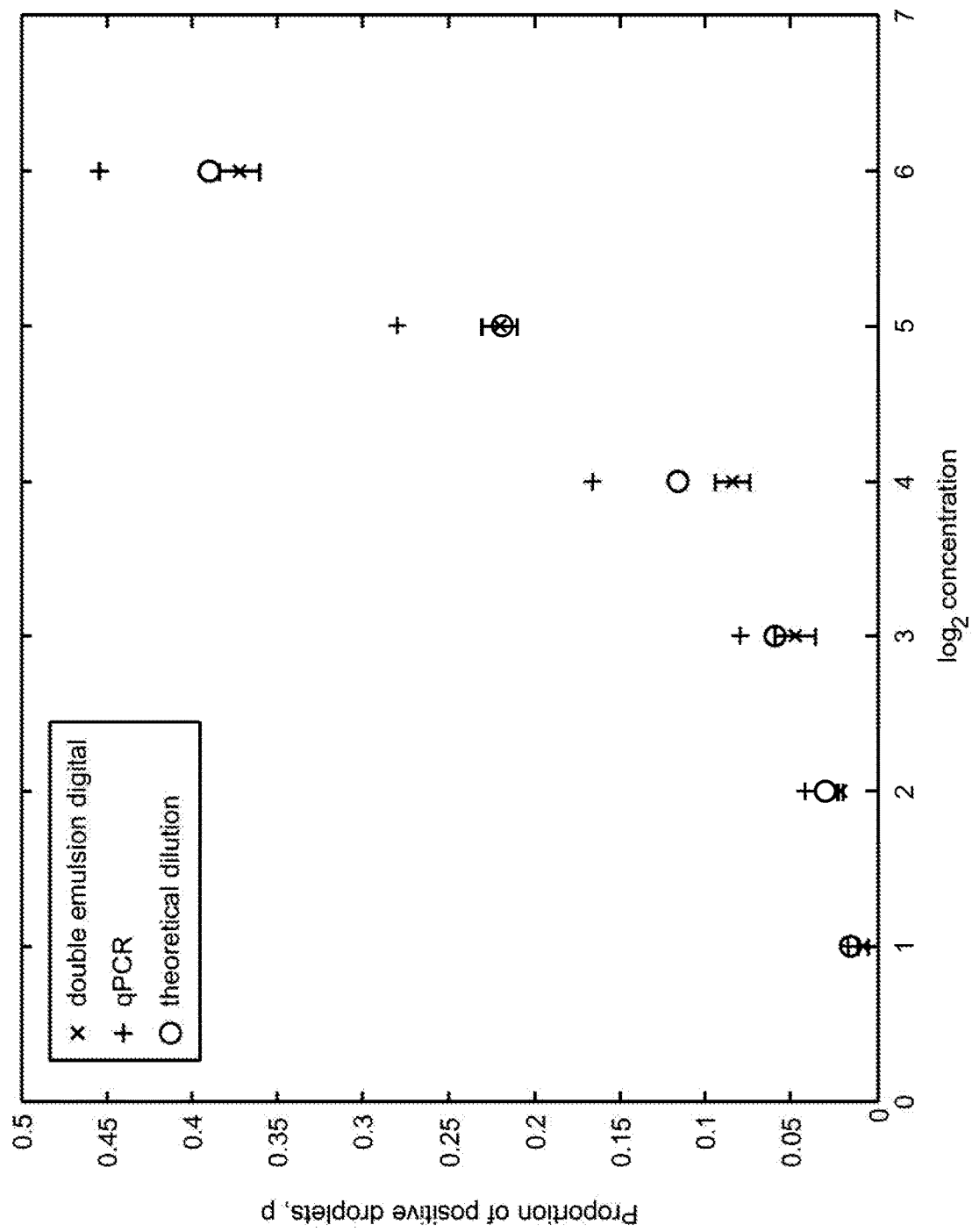
FIG. 51 provides a plot showing the fraction of drops that are positive as a function of the log-2 concentration. As the concentration of DNA goes up, more drops become fluorescent because more of them contain at least a single molecule.

As described herein, in some embodiments, a coaxial flow-focusing device may be utilized to prepare double emulsions suitable for FACS analysis. The device may include a channel which is, e.g., approximately 50 μm tall, into which single emulsion drops are introduced as a close pack; close packing minimizes interstitial oil, allowing the formation of thin-shelled double emulsions. The double emulsification junction includes a channel taller and wider than the single emulsion channel; aqueous carrier fluid is introduced into the Y-shaped channel, as shown in FIGS. 38 and 40. The single emulsion channel is centered horizontally and vertically in the carrier phase channel; when the aqueous carrier phase is introduced at a sufficient velocity, this geometry ensures that the oil encapsulating the single emulsion lifts from the walls, forming a "cone" suspended in the flowing aqueous phase, as shown in FIGS. 38 and 40. This non-planar geometry allows for the formation of double emulsions in a device that is uniformly hydrophobic.

Downstream of the cone is a constriction centered vertically and horizontally in the channel, as shown in the schematic of FIG. 38. This feature allows for the formation of thin-shelled double emulsions with just one core: as the cone extends into the constriction, it is hydrodynamically focused by the rushing carrier phase; this generates sufficient shear to rip individual drops from the tip of the cone, as illustrated in FIG. 38. Without the constriction, the double emulsions would likely contain multiple cores.

Suitable Subjects

The subject methods may be applied to biological samples taken from a variety of different subjects. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects (that is, in "non-human subjects") such as, but not limited to, birds, mice, rats, dogs, cats, livestock and horses. Accordingly, it is to be understood that any subject in need of assessment according to the present disclosure is suitable.

Moreover, suitable subjects include those who have and those who have not been diagnosed with a condition, such as cancer. Suitable subjects include those that are and are not displaying clinical presentations of one or more cancers. In certain aspects, a subject may one that may be at risk of developing cancer, due to one or more factors such as family history, chemical and/or environmental exposure, genetic mutation(s) (e.g., BRCA1 and/or BRCA2 mutation), hormones, infectious agents, radiation exposure, lifestyle (e.g., diet and/or smoking), presence of one or more other disease conditions, and the like.

As described more fully above, a variety of different types of biological samples may be obtained from such subjects. In certain embodiments, whole blood is extracted from a subject. When desired, whole blood may be treated prior to practicing the subject methods, such as by centrifugation, fractionation, purification, and the like. The volume of the whole blood sample that is extracted from a subject may be 100 mL or less, e.g., about 100 mL or less, about 50 mL or less, about 30 mL or less, about 15 mL or less, about 10 mL or less, about 5 mL or less, or about 1 mL or less.

The subject methods and devices provided herein are compatible with both fixed and live cells. In certain embodiments, the subject methods and devices are practiced with live cells. In other embodiments, the subject methods and devices are practiced with fixed cells. Fixing a cellular sample allows for the sample to be washed to extract small molecules and lipids that may interfere with downstream analysis. Further, fixing and permeabilizing cells allows the cells to be stained with antibodies for surface proteins as well as intracellular proteins. Combined with the RT-PCR methods described herein, such staining can be used to achieve high levels of multiplexing because the antibodies are localized to the cell sample, while RT-PCR products are free within a microdroplet. Such a configuration allows for dyes of the same color to be used for antibodies and for amplicons produced by RT-PCR. Any suitable method can be used to fix cells, including but not limited to, fixing using formaldehyde, methanol and/or acetone.

RT-PCR carried out on a fixed cell encapsulated in a microdroplet can be carried out by first diluting the microdroplet and performing the RT-PCR reaction on a sample of the diluted microdroplet. Such dilution of the cellular sample can help to limit any cellular compounds that would interfere with RT-PCR. In other embodiments, the RT-PCR reagents are added directly to the microdroplet containing the fixed cell in a "one pot" reaction without any dilution of sample. In certain embodiments, fixed cells are solubilized prior to the RT-PCR using proteases and detergents.

Genotyping Cells

As summarized above, aspects of the invention also include methods for genotyping components from biological samples. By "genotyping" it is meant the detection of two or more oligonucleotides (e.g., oncogenes) in a particular cell. Aspects include methods for genotyping cells, e.g., tumor cells, including CTCs.

In certain such aspects, the methods involve encapsulating in a microdroplet a cell obtained from a subject's blood sample, wherein one cell is present in the microdroplet; introducing a lysing agent into the microdroplet and incubating the microdroplet under conditions effective for cell lysis; introducing polymerase chain reaction (PCR) reagents and a plurality PCR primers into the microdroplet, and incubating the microdroplet under conditions allowing for PCR amplification to produce PCR amplification products, wherein the plurality of PCR primers include one or more primers that each hybridize to one or more oncogenes; introducing a plurality of probes into the microdroplet, wherein the probes hybridize to one or more mutations of interest and fluoresce at different wavelengths; and detecting the presence or absence of specific PCR amplification products by detection of fluorescence of a probe, wherein detection of fluorescence indicates the presence of the PCR amplification products; wherein one or more of steps are performed under microfluidic control.

In other aspects, the methods may involve encapsulating in a microdroplet a cell obtained from a subject's blood sample, wherein one cell is present in the microdroplet; introducing a lysing agent into the microdroplet and incubating the microdroplet under conditions effective for cell lysis; introducing polymerase chain reaction (PCR) reagents and a plurality PCR primers into the microdroplet, and incubating the microdroplet under conditions allowing for PCR amplification to produce PCR amplification products, wherein the plurality of PCR primers include one or more primers that each hybridize to one or more oncogenes, said primers including forward primers including a label, and reverse primers including a capture sequence; introducing a fluorescent bead into the microdroplet, wherein the bead includes a nucleotide sequence complementary to a capture sequence; and detecting the presence or absence of the PCR amplification products by detection of fluorescence of the bead and fluorescence of a primer, wherein detection of fluorescence indicates the presence of the PCR amplification products; wherein one or more of steps are performed under microfluidic control.

In practicing the methods for genotyping cells, any variants to the general steps described herein, such as the number of primers that may be added, the manner in which reagents are added, suitable subjects, and the like, may be made.

Detecting Cancer

Methods according to the present invention also involve methods for detecting cancer. Such methods may include encapsulating in a microdroplet oligonucleotides obtained from a biological sample from the subject, wherein at least one oligonucleotide is present in the microdroplet; introducing polymerase chain reaction (PCR) reagents, a detection component, and a plurality of PCR primers into the microdroplet and incubating the microdroplet under conditions allowing for PCR amplification to produce PCR amplification products, wherein the plurality of PCR primers include one or more primers that each hybridize to one or more oncogenes; and detecting the presence or absence of the PCR amplification products by detection of the detection component, wherein detection of the detection component indicates the presence of the PCR amplification products.

Detection of one or more PCR amplification products corresponding to one or more oncogenes may be indicative that the subject has cancer. The specific oncogenes that are added to the microdroplet may vary. In certain aspects, the oncogene(s) may be specific for a particular type of cancer, e.g., breast cancer, colon cancer, and the like.

Moreover, in practicing the subject methods the biological sample from which the components are to be detected may vary, and may be based at least in part on the particular type of cancer for which detection is sought. For instance, breast tissue may be used as the biological sample in certain instances, if it is desired to determine whether the subject has breast cancer, and the like.

In practicing the methods for detecting cancer, any variants to the general steps described herein, such as the number of primers that may be added, the manner in which reagents are added, suitable subjects, and the like, may be made.

Devices

As indicated above, embodiments of the invention employ microfluidics devices. Microfluidics devices of this invention may be characterized in various ways. In certain embodiments, for example, microfluidics devices have at least one "micro" channel. Such channels may have at least one cross-sectional dimension on the order of a millimeter or smaller (e.g., less than or equal to about 1 millimeter). Obviously for certain applications, this dimension may be adjusted; in some embodiments the at least one cross-sectional dimension is about 500 micrometers or less. In some embodiments, again as applications permit, the cross-sectional dimension is about 100 micrometers or less (or even about 10 micrometers or less—sometimes even about 1 micrometer or less). A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that micro-channels employed in this invention may have two dimensions that are grossly disproportionate—e.g., a rectangular cross-section having a height of about 100-200 micrometers and a width on the order or a centimeter or more. Of course, certain devices may employ channels in which the two or more axes are very similar or even identical in size (e.g., channels having a square or circular cross-section).

In some embodiments, microfluidic devices of this invention are fabricated using microfabrication technology. Such technology is commonly employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. A microfluidics "system" may include one or more microfluidic devices and associated fluidic connections, electrical connections, control/logic features, etc. Aspects of microfluidic devices include the presence of one or more fluid flow paths, e.g., channels, having dimensions as discussed herein.

In certain embodiments, microfluidic devices of this invention provide a continuous flow of a fluid medium. Fluid flowing through a channel in a microfluidic device exhibits many interesting properties. Typically, the dimensionless Reynolds number is extremely low, resulting in flow that always remains laminar. Further, in this regime, two fluids joining will not easily mix, and diffusion alone may drive the mixing of two compounds.

Various features and examples of microfluidic device components suitable for use with this invention will now be described.

Substrate

Substrates used in microfluidic systems are the supports in which the necessary elements for fluid transport are provided. The basic structure may be monolithic, laminated, or otherwise sectioned. Commonly, substrates include one or more microchannels serving as conduits for molecular libraries and reagents (if necessary). They may also include input ports, output ports, and/or features to assist in flow control.

In certain embodiments, the substrate choice may be dependent on the application and design of the device. Substrate materials are generally chosen for their compatibility with a variety of operating conditions. Limitations in microfabrication processes for a given material are also relevant considerations in choosing a suitable substrate. Useful substrate materials include, e.g., glass, polymers, silicon, metal, and ceramics.

Polymers are standard materials for microfluidic devices because they are amenable to both cost effective and high volume production. Polymers can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated device of this invention are poly(dimethylsiloxane) (PDMS), polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidics devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Surface Treatments and Coatings

Surface modification may be useful for controlling the functional mechanics (e.g., flow control) of a microfluidic device. For example, it may be advantageous to keep fluidic species from adsorbing to channel walls or for attaching antibodies to the surface for detection of biological components.

Polymer devices in particular tend to be hydrophobic, and thus loading of the channels may be difficult. The hydrophobic nature of polymer surfaces also make it difficult to control electroosmotic flow (EOF). One technique for coating polymer surface is the application of polyelectrolyte multilayers (PEM) to channel surfaces. PEM involves filling the channel successively with alternating solutions of positive and negative polyelectrolytes allowing for multilayers to form electrostatic bonds. Although the layers typically do not bond to the channel surfaces, they may completely cover the channels even after long-term storage. Another technique for applying a hydrophilic layer on polymer surfaces involves the UV grafting of polymers to the surface of the channels. First grafting sites, radicals, are created at the surface by exposing the surface to UV irradiation while simultaneously exposing the device to a monomer solution. The monomers react to form a polymer covalently bonded at the reaction site.

Glass channels generally have high levels of surface charge, thereby causing proteins to adsorb and possibly hindering separation processes. In some situations, it may be advantageous to apply a polydimethylsiloxane (PDMS) and/or surfactant coating to the glass channels. Other polymers that may be employed to retard surface adsorption include polyacrylamide, glycol groups, polysiloxanes, glyceroglycidoxypropyl, poly(ethyleneglycol) and hydroxyethylated poly(ethyleneimine). Furthermore, for electroosmotic devices it is advantageous to have a coating bearing a charge that is adjustable in magnitude by manipulating conditions inside of the device (e.g. pH). The direction of the flow can also be selected based on the coating since the coating can either be positively or negatively charged.

Specialized coatings can also be applied to immobilize certain species on the channel surface—this process is known by those skilled in the art as "functionalizing the surface." For example, a polymethylmethacrylate (PMMA) surface may be coated with amines to facilitate attachment of a variety of functional groups or targets. Alternatively, PMMA surfaces can be rendered hydrophilic through an oxygen plasma treatment process.

Microfluidic Elements

Microfluidic systems can contain a number of microchannels, valves, pumps, reactors, mixers and other components. Some of these components and their general structures and dimensions are discussed below.

Various types of valves can be used for flow control in microfluidic devices of this invention. These include, but are not limited to passive valves and check valves (membrane, flap, bivalvular, leakage, etc.). Flow rate through these valves are dependent on various physical features of the valve such as surface area, size of flow channel, valve material, etc. Valves also have associated operational and manufacturing advantages/disadvantages that should be taken into consideration during design of a microfluidic device.

Micropumps as with other microfluidic components are subjected to manufacturing constraints. Typical considerations in pump design include treatment of bubbles, clogs, and durability. Micropumps currently available include, but are not limited to electric equivalent pumps, fixed-stroke microdisplacement, peristaltic micromembrane and pumps with integrated check valves.

Macrodevices rely on turbulent forces such as shaking and stirring to mix reagents. In comparison, such turbulent forces are not practically attainable in microdevices, mixing in microfluidic devices is generally accomplished through diffusion. Since mixing through diffusion can be slow and inefficient, microstructures are often designed to enhance the mixing process. These structures manipulate fluids in a way that increases interfacial surface area between the fluid regions, thereby speeding up diffusion. In certain embodiments, microfluidic mixers are employed. Such mixers may be provide upstream from (and in some cases integrated with) a microfluidic separation device of this invention.

Micromixers may be classified into two general categories: active mixers and passive mixers. Active mixers work by exerting active control over flow regions (e.g. varying pressure gradients, electric charges, etc.). Passive mixers do not require inputted energy and use only "fluid dynamics" (e.g. pressure) to drive fluid flow at a constant rate. One example of a passive mixer involves stacking two flow streams on top of one another separated by a plate. The flow streams are contacted with each other once the separation plate is removed. The stacking of the two liquids increases contact area and decreases diffusion length, thereby enhancing the diffusion process. Mixing and reaction devices can be connected to heat transfer systems if heat management is needed. As with macro-heat exchangers, micro-heat exchanges can either have co-current, counter-current, or cross-flow flow schemes. Microfluidic devices frequently have channel widths and depths between about 10 μm and about 10 cm. A common channel structure includes a long main separation channel, and three shorter "offshoot" side channels terminating in either a buffer, sample, or waste reservoir. The separation channel can be several centimeters long, and the three side channels usually are only a few millimeters in length. Of course, the actual length, cross-sectional area, shape, and branch design of a microfluidic device depends on the application as well other design considerations such as throughput (which depends on flow resistance), velocity profile, residence time, etc.

Microfluidic devices described herein may include electric field generators to perform certain steps of the methods described herein, including, but not limited to, picoinjection, droplet coalescence, selective droplet fusion, and droplet sorting. In certain embodiments, the electric fields are generated using metal electrodes. In particular embodiments, electric fields are generated using liquid electrodes. In certain embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel. In particular embodiments, the liquid electrodes are used in picoinjection, droplet coalescence, selective droplet fusion, and/or droplet sorting aspects of a microfluidic device described herein. Liquid electrodes may find use, for example, where a material to be injected via application of an electric field is not charged.

Liquid electrodes as described herein also have applicability outside of the specific microfluidic device applications discussed herein. For example, liquid electrodes may be utilized in a variety of devices in which metal electrodes are generally used. In addition, liquid electrodes may be particularly well suited for use in flexible devices, such as devices that are designed to be worn on the body and/or devices that must flex as a result of their operation.

In certain embodiments, one or more walls of a microfluidic device channel immediately down-stream of a junction with one or more of an input microchannel, pairing microchannel and/or picoinjection microchannel includes one or more ridges. Such ridges in the walls of the microchannel are configured to trap a layer of a suitable phase, e.g., a suitable hydrophobic phase (e.g., oil) and thereby prevent an immiscible phase, e.g., an aqueous phase, from touching the walls of the microchannel, which can cause wetting of the channel walls. Such wetting may be undesirable as it may lead to unpredictable drop formation and/or allow fluids to transfer between drops, leading to contamination. In certain embodiments, the ridges allow for the formation of drops at higher flow rate ratios R ($Q_{aq}/Q_{sum}$).

In certain embodiments, the width of one or more of the microchannels of the microfluidic device (e.g., input microchannel, pairing microchannel, pioinjection microchannel, and/or a flow channel upstream or downstream of one or more of these channels) is 100 microns or less, e.g., 90 microns or less, 80 microns or less, 70 microns or less, 60 microns or less, 50 microns or less, e.g., 45 microns or less, 40 microns or less, 39 microns or less, 38 microns or less, 37 microns or less, 36 microns or less, 35 microns or less, 34 microns or less, 33 microns or less, 32 microns or less, 31 microns or less, 30 microns or less, 29 microns or less, 28 microns or less, 27 microns or less, 26 microns or less, 25 microns or less, 20 microns or less, 15 microns or less, or 10 microns or less. In some embodiments, the width of one or more of the above microchannels is from about 10 microns to about 15 microns, from about 15 microns to about 20 microns, from about 20 microns to about 25 microns, from about 25 microns to about 30 microns, from about 30 microns to about 35 microns, from about 35 microns to about 40 microns, from about 40 microns to about 45 microns, or from about 45 microns to about 50 microns, from about 50 microns to about 60 microns, from about 60 microns to about 70 microns, from about 70 microns to about 80 microns, from about 80 microns to about 90 microns, or from about 90 microns to about 100 microns.

In certain embodiments, the base of each of the one or more ridges is from about 10 microns to about 20 microns in length, e.g., from about 11 to about 19 microns in length, from about 12 to about 18 microns in length, from about 13 to about 17 microns in length, from about 14 to about 16 microns in length, or about 15 microns in length.

In certain embodiments, the peak of each of the one or more ridges has a width of about 1 to about 10 microns, e.g., from about 1 to about 9 microns, from about 2 to about 8 microns, from about 3 to about 7 microns, from about 4 to about 6 microns, or about 5 microns. In certain embodiments, the peak of each of the one or more ridges has a width of from about 1 micron to about 2 microns, from about 2 microns to about 3 microns, from about 3 microns to about 4 microns, from about 4 microns to about 5 microns, from about 5 microns to about 6 microns, from about 6 microns to about 7 microns, from about 7 microns to about 8 microns, from about 8 microns to about 9 microns, or from about 9 microns to about 10 microns.

In certain embodiments, the height of each of the one or more ridges is from about 5 microns to about 15 microns, e.g., about 6 microns to about 14 microns, about 7 microns to about 13 microns, about 8 microns to about 12 microns, about 9 microns to about 11 microns, or about 10 microns.

In certain embodiments, the ratio of the base of each of the one or more ridges to the height of each of the one or more ridges is from about 1.0:0.75 to about 0.75:1.0. In certain embodiments, the ratio of the base of each of the one or more ridges to the width of the peak of each of the one or more ridges is about 1.0:0.5 to about 1.0:0.1, e.g, from about 1.0:0.2, from about 1.0:0.3, or from about 1.0:0.4.

In certain embodiments, the ratio of the base of each of the one or more ridges to the height of each of the one or more ridges to the width of the peak of the one or more ridges is about 1:0.75:0.5.

In certain embodiments, a channel as described herein is provided with a plurality of ridges which extend for a distance along the channel wall. This distance may be, for example, from about 50 microns to about 500 microns, e.g., from about 50 microns to about 450 microns, from about 100 microns to about 400 microns, from about 150 microns to about 350 microns, from about 200 microns to about 300 microns, or about 250 microns. In certain embodiments, a plurality of ridges may be provided which extend for a distance along the channel wall, wherein the ratio between the distance along the channel wall and the width of the channel is from about 10:1 to about 1:2, e.g., about 10:1, about 9:1, about 8:1, about 7:1, about 6:1 about 5:1, about 4:1, about 3:1, about 2:1, about 1:1, or about 1:2.

It should be noted that one or more of the various dimensions discussed above may be scaled up or down as appropriate for a particular application, for example each of the above dimensions may be scaled up or down by a factor of 2, 5, 10 or more as appropriate.

In some embodiments, one or more channel junctions, e.g., one or more droplet forming junctions, such as a picoinjector junction, include a "step-down" structure. This is depicted, for example, in FIG. 26, wherein the portion of the flow channel at the picoinjector junction and downstream of the picoinjector junction is wider than the portion of the flow channel upstream of the picoinjector junction. This step-down structure facilitates the pinching-off of droplets and thus facilitates droplet formation. The step size may be chosen based on the desired size of the droplet to be formed, with larger steps creating larger droplets. Such structures may also help to avoid dripping of material from the picoinjector following injection from the picoinjector into a droplet. In some embodiments, the width of the flow channel at the picoinjector junction and downstream of the picoinjector junction is from about 5% to about 50% wider than the width of the flow channel immediately upstream of the picoinjector junction, e.g., about 5 to about 10% wider, about 10 to about 20% wider, about 20 to about 30% wider, about 30 to about 40% wider or about 40 to about 50% wider.

Methods of Fabrication

Microfabrication processes differ depending on the type of materials used in the substrate and the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition)

The combination of lithography, etching and deposition techniques may be used to make microcanals and microcavities out of glass, silicon and other "hard" materials. Technologies based on the above techniques are commonly applied in for fabrication of devices in the scale of 0.1-500 micrometers.

Microfabrication techniques based on current semiconductor fabrication processes are generally carried out in a clean room. The quality of the clean room is classified by the number of particles <4 μm in size in a cubic inch. Typical clean room classes for MEMS microfabrication are 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 μm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate— area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physico-chemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 μm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features are usually sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used should ideally have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100° C.

Polymers/Plastics

A number of techniques may be employed for micromachining plastic substrates in accordance with embodiments of this invention. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In micro-injection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is well suited for microchannels between about 5 and 500 µm. Specific properties of PDMS make it particularly suitable for microfluidic purposes:

1) It is optically clear which allows for visualization of the flows;
2) PDMS when mixed with a proper amount of reticulating agent has elastomeric qualities that facilitates keeping microfluidic connections "watertight;"
3) Valves and pumps using membranes can be made with PDMS because of its elasticity;
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. But it's also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180° C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials such as stainless steel make very durable mold inserts and can be micromachined to form structures down to the 10-µm range. Various other micromachining techniques for microfabrication exist including µ-Electro Discharge Machining (µ-EDM), µ-milling, focused ion beam milling. µ-EDM allows the fabrication of 3-dimensional structures in conducting materials. In µ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices must be closed up before they can become functional. Common problems in the bonding process for microfluidic devices include the blocking of channels and changes in the physical parameters of the channels. Lamination is one method used to seal plastic microfluidic devices. In one lamination process, a PET foil (about 30 µm) coated with a melting adhesive layer (typically 5-10 µm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65° C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

It should be noted that while the nucleic acid amplification techniques described herein are frequently described with reference to polymerase chain reaction (PCR) amplification techniques, such description is not intended to be limiting. In certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA). Accordingly, wherever technically feasible, one or more suitable non-PCR amplification techniques, e.g., one or more isothermal nucleic acid amplification techniques, may be substituted for one or more of the PCR amplification techniques described herein.

Regarding PCR amplification modules, it will be necessary to provide to such modules at least the building blocks for amplifying nucleic acids (e.g., ample concentrations of four nucleotides), primers, polymerase (e.g., Taq), and appropriate temperature control programs). The polymerase and nucleotide building blocks may be provided in a buffer solution provided via an external port to the amplification module or from an upstream source. In certain embodiments, the buffer stream provided to the sorting module contains some of all the raw materials for nucleic acid amplification. For PCR in particular, precise temperature control of the reacting mixture is extremely important in order to achieve high reaction efficiency. One method of on-chip thermal control is Joule heating in which electrodes are used to heat the fluid inside the module at defined locations. The fluid conductivity may be used as a temperature feedback for power control.

In certain aspects, the microdroplets, e.g., drops, containing the PCR mix may be flowed through a channel that incubates the droplets under conditions effective for PCR. Flowing the microdroplets through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the microdroplets move through such zones, their temperature cycles, as needed for PCR. The precise number of zones, and the respective temperature of each zone, may be readily determined by those of skill in the art to achieve the desired PCR amplification.

In other embodiments, incubating the microdroplets, e.g., drops, may involve the use of a Megadroplet Array. In such a device, an array consists of channels in which the channel ceilings are indented with millions of circular traps that are about 25 µm in diameter. Drops are distributed into the trapping channels using distribution plates—large channels connecting the inlets of the trapping channels (FIG. 12, Panel A). Due to the large size of the distribution channels compared to the trapping channels—the distribution channels are about 100×500 µm in height and width, compared to only about 15×100 µm for the droplet trapping channels—the hydrodynamic resistance of the distribution channels is 1500 times lower than that of the trapping channels; this ensures that the distribution channel fills with drops before the trapping channels begin to fill, allowing even distribution of the drops into the trapping channels. When the drops flow into the trapping channels, they are slightly pancaked in shape because the vertical height of the channel is 15 µm, or 10 µm shorter than the drops, as illustrated in FIG. 12, Panel B. When a drop nears a trap, its interface adopts a larger, more energetically favorable radius of curvature. To minimize its surface energy, the drop entirely fills the trap, allowing it to adopt the lowest, most energetically favorable, average radius of curvature. After a trap is occupied by a drop, no other drops are able to enter because the trap is large enough to fit only one drop; additional drops are diverted downstream, to occupy the first vacant trap they encounter. Because the array is filled using a close-packed emulsion, every trap will be occupied by a drop, since this is the most energetically favorable state under low flow conditions. After the droplet array is filled, oil is injected to remove excess drops and the array is thermal cycled and imaged.

A variety of different ways can be used to fill the traps of the device. For instance, buoyancy effects and centrifugation can also be used to fill and empty the traps by flipping the device with respect to the earth's gravitational field, since the droplet density is 63% that of the fluorocarbon carrier oil. That is, if the drops were heavier than the oil phase, then the wells could be imprinted into the "floor" of the device so that when the emulsion was flowed over it, the drops would sink into the wells. The flow rate of the emulsion could be adjusted to optimize this and the drop size would be made to be approximately the same size as the well so that the well could only fit a single drop at a time. In other aspects, the drops could also, or instead, be stored in a large chamber with no wells.

The device may achieve thermal cycling using a heater consisting of a Peltier plate, heat sink, and control computer (FIG. 12, Panel A; FIG. 13). The Peltier plate allows heating and/or cooling the chip above or below room temperature by controlling the applied current. To ensure controlled and reproducible temperature, a computer monitors the temperature of the array using integrated temperature probes, and adjusts the applied current to heat and cool as needed. A metallic (e.g., copper) plate allows uniform application of heat and dissipation of excess heat during cooling cycles, enabling cooling from 95° C. to 60° C. in under 1 min execution. In order to image microdroplets, certain embodiments may incorporate a scanner bed. In certain aspects, the scanner bed is a Canoscan 9000F scanner bed.

In order to effectively amplify nucleic acids from target components, the microfluidics system may include a cell lysing or viral protein coat-disrupting module to free nucleic acids prior to providing the sample to an amplification module. Cell lysing modules may rely on chemical, thermal, and/or mechanical means to effect cell lysis. Because the cell membrane consists of a lipid double-layer, lysis buffers containing surfactants can solubilize the lipid membranes. Typically, the lysis buffer will be introduced directly to a lysis chamber via an external port so that the cells are not prematurely lysed during sorting or other upstream process. In cases where organelle integrity is necessary, chemical lysis methods may be inappropriate. Mechanical breakdown of the cell membrane by shear and wear is appropriate in certain applications. Lysis modules relying mechanical techniques may employ various geometric features to effect piercing, shearing, abrading, etc. of cells entering the module. Other types of mechanical breakage such as acoustic techniques may also yield appropriate lysate. Further, thermal energy can also be used to lyse cells such as bacteria, yeasts, and spores. Heating disrupts the cell membrane and the intracellular materials are released. In order to enable subcellular fractionation in microfluidic systems a lysis module may also employ an electrokinetic technique or electroporation. Electroporation creates transient or permanent holes in the cell membranes by application of an external electric field that induces changes in the plasma membrane and disrupts the transmembrane potential. In microfluidic electroporation devices, the membrane may be permanently disrupted, and holes on the cell membranes sustained to release desired intracellular materials released.

Single Cell RT-PCR Microfluidic Device

Figure 32:
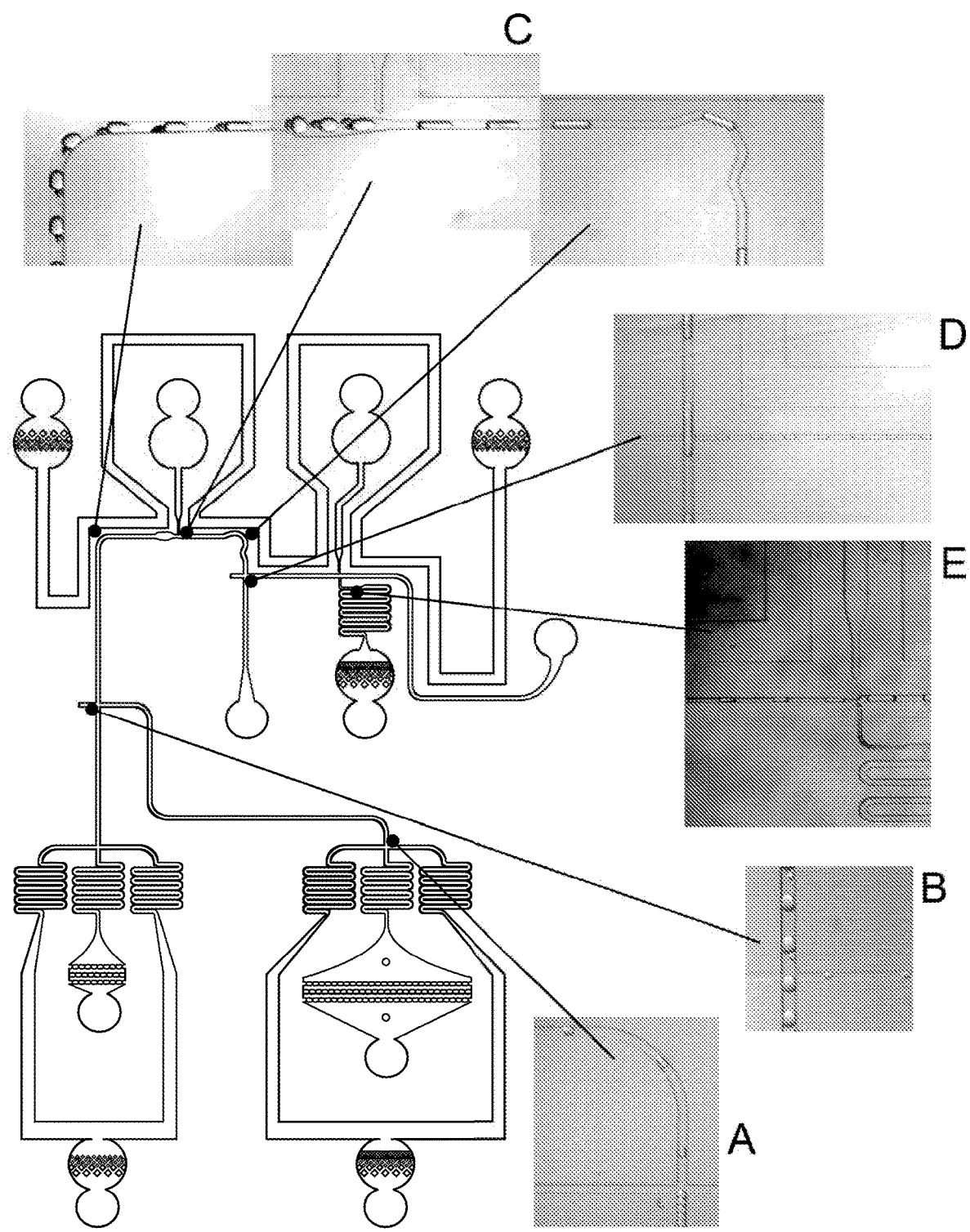
FIG. 32 shows an embodiment of a single cell RT-PCR microfluidic device as described herein.

In another aspect, provided herein is a single cell RT-PCR microfluidic device, described in greater detail below with reference to FIG. 32. In certain embodiments, the single cell RT-PCR microfluidic device includes an input microchannel, which may be coupled to a flow focus drop maker, for introducing microdroplets into the microfluidic device, wherein the flow focus drop maker spaces the microdroplets in the input microchannel, e.g., by a volume of a suitable hydrophobic phase, e.g., oil, wherein each microdroplet may include a cell lysate sample. An exemplary embodiment is shown in FIG. 32 (Panel A).

The microfluidic device may further include a pairing microchannel in fluidic communication with the input microchannel and a dilution buffer drop maker in fluidic communication with the pairing microchannel. In such embodiments, a microdroplet from the input microchannel flows into the pairing microchannel where the dilution buffer drop maker produces a drop of dilution buffer that is larger than and paired with each microdroplet. In certain embodiments, the dilution buffer drop maker is a T-junction drop maker. An exemplary embodiment is shown in FIG. 32 (Panel B).

The microfluidic device may also include a merging microchannel in fluidic communication with the pairing microchannel, the merging microchannel including an electric field generator positioned in proximity thereto. In such embodiments, the paired microdroplet and drop of dilution buffer enter the merging microchannel from the pairing microchannel and are merged upon passing through an electric field produced by the electric field generator to produce a diluted microdroplet. Any suitable electric field generator can be used to produce the diluted microdroplet. In certain embodiments, the electric field is created by metal electrodes. In other embodiments, the electric field is created by liquid electrodes as discussed herein. An exemplary embodiment is shown in FIG. 32 (Panel C).

The microfluidic device may also include a series of mixing microchannels in fluidic communication with the merging microchannel. Such mixing microchannels allow for the mixing of the contents of the diluted microdroplet.

The microfluidic device may also include a drop sampler in fluidic communication with the mixing microchannels. Such a drop sampler is capable of taking a sample of the diluted microdroplet, e.g., to be used in a subsequent RT-PCR reaction carried out in the microfluidic device. An exemplary embodiment is shown in FIG. 32 (Panel D).

The microfluidic device may also include a picoinjection microchannel including a picoinjector, wherein the picoinjection microchannel may be a pressurized microchannel capable of receiving the sample of the diluted microdroplet produced by the drop sampler and allowing the picoinejctor to picoinject RT-PCR reagents into the sample. In certain embodiments the picoinjection is assisted by an electric field applied to the picoinjection microchannel. Any electric field generator can be used to create an electric field for picoinjection. In certain embodiments, the electric field is created by metal electrodes. In other embodiments, the electric field is created by liquid electrodes as discussed herein. An exemplary embodiment is shown in FIG. 32 (Panel E).

Samples of the diluted microdroplet that have been picoinjected with RT-PCR reagents can then be subjected to conditions for RT-PCR using any of the approaches described herein. The single cell RT-PCR microfluidic device advantageously allows for the dilution of the cell lysate sample prior to addition of RT-PCR agents. Such dilution helps in prevent inhibition of RT-PCR that may be caused by components of the cell lysate. In certain embodiments, the microfluidic device also includes an encapsulating chamber in fluidic communication with the input microchannel, for encapsulating a cell and lysis regeant into a microdroplet. In such embodiments, the input micochannel is capable of receiving the microdroplet from the encapsulating chamber.

Although the above device is described with respect to an RT-PCR reaction, such is for exemplary purposes only. The device could be used in connection with a variety of other reaction types, including, e.g., PCR.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1: Microfluidic System for Performing Single-Cell PCR Reactions

Device Manufacturing:

The chips were made using the same photolithographic processes in polydimethylsiloxane as the other devices described above. A general schematic of the chips is shown in FIG. 1. The general approach carried out by such chips is depicted in FIG. 6.

Sample Preparation:

5-25 mL whole blood samples were extracted from a subject via syringe. Nucleated cells were separated using on-chip pinched-flow fractionation, as generally described in Lab on a Chip, 2005, 5, 778-784; the disclosure of which is incorporated herein by reference. Nucleated cells were collected for subsequent analysis.

Figure 7:
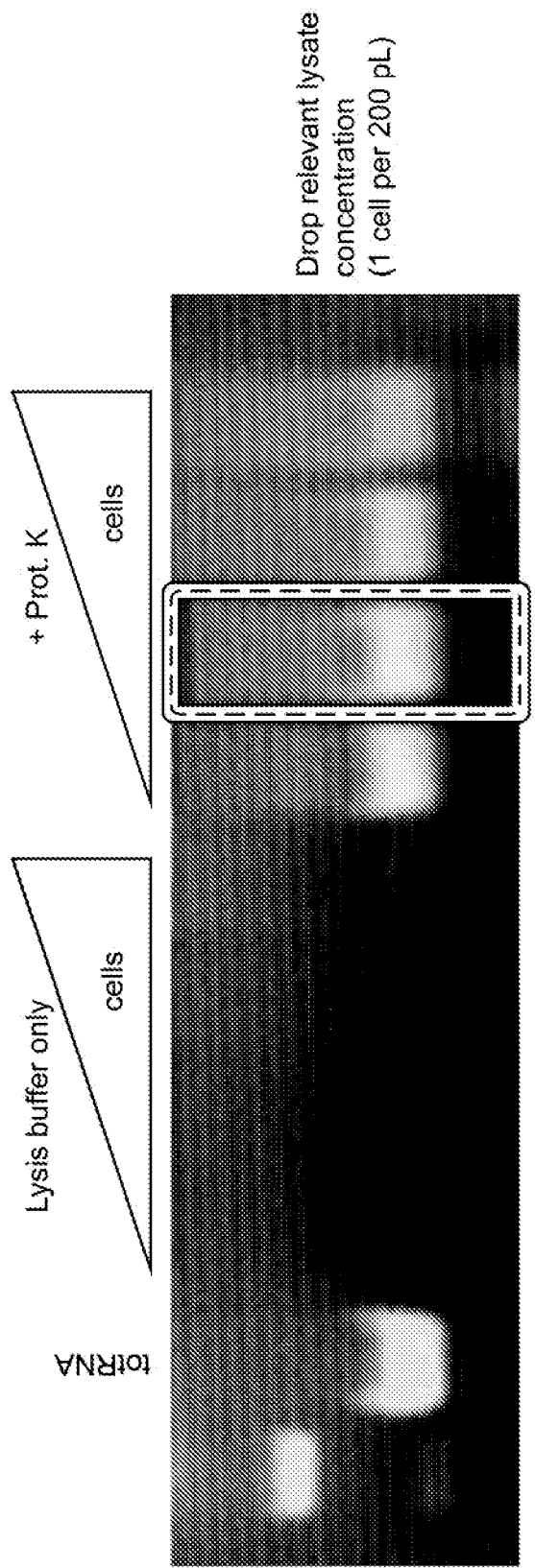
FIG. 7 shows relief of cell lysate-mediated inhibition of RT-PCR by proteinase K treatment. Increasing concentrations of cells were either treated with proteinase K and lysis buffer or lysis buffer only. Cells were then incubated at 55° C. followed by 95° C. Whole cell lysates were added directly to RT-PCR reactions at several drop relevant concentrations. Strong relief of lysate inhibition on PCR was seen at final cell concentrations of 1 cell per 200 pL in Proteinase K treated lysates but not in lysis buffer only lysates. PCR products are visualized on an ethidium bromide stained agarose gel.

PCR Reactions:

The assay requires the execution of an RT-PCR reaction in drops containing concentrated cell lysates; however, cell lysates inhibit RT-PCR (FIG. 7). To overcome this inhibition, a protocol has been developed that utilizes proteinase K to digest inhibitory proteins in cell lysates. Using proteinase K allows efficient amplification in lysates at concentrations as high as 1 cell in 50 pL, with optimal amplification occurring at 1 cell in 200 pL (FIG. 7). Thus, the system operates at this concentration.

Figure 8:
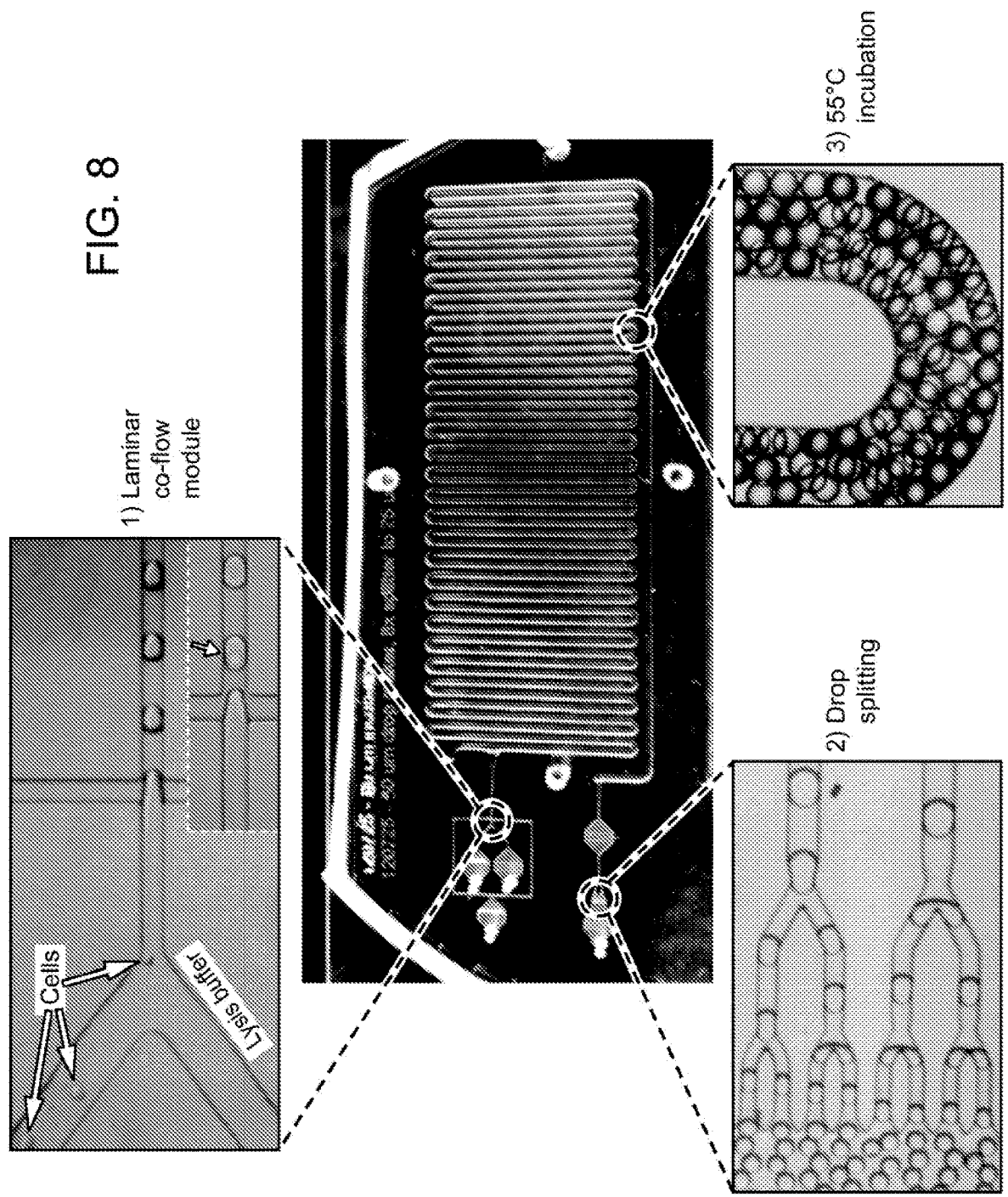
FIG. 8, Panels 1-3, show an integrated microfluidic system for cell encapsulation/dilution, lysis and drop splitting (center image). Panel 1: Co-flow module relies on laminar flow of Proteinase K containing lysis buffer and cell suspension solutions to encapsulate cells in drops without premature lysis or mixing of cells prior to drop formation; a laminar flow boundary is just visible between the cell and lysis buffer streams. Panel 2: Drops containing cells flow through a 55° C. incubation channel for 20 minutes to lyse cells and digest inhibitory proteins. Panel 3: Drops are split to allow for efficient picoinjection of 2×RT-PCR reagents and imaging on the droplet array FIG. 9, Panels A-C, show TaqMan® RT-PCR in drops following picoinjection. Drops containing a limiting dilution of total RNA from the prostate cancer cell line PC3 were injected with an equal volume of 2×RT-PCR reagents and a TaqMan® probe targeting EpCAM, (Panel A). Following picoinjection, drops were thermocycled and imaged for fluorescence, (Panel B). The number of fluorescent drops was found to be in agreement with the prediction of a Poisson distribution, demonstrating adequate sensitivity to detect single transcript molecules in drops. Panel C: To further confirm the results, the drops from Panel B were chemically ruptured and their contents run on an agarose gel to observe the presence of PCR products in negative control drops that were injected without RT-PCR enzymes (−) and experimental drops that received both RT and Taq (+). Both control reactions performed in a tube with no picoinjection and picoinjected reactions produced bands of similar intensity, demonstrating that the reaction efficiency was comparable. White stars mark picoinjected drops.

Cell encapsulation, lysis, and proteinase K digestion are accomplished using an integrated microfluidic system (FIG. 8, Panels 1-3). Cells are co-encapsulated in 70 μm drops (200 pL) with lysis buffer containing non-ionic detergents and proteinase K using a 30×30 μm flow focus device. Importantly, the cells are not exposed to lysis buffer until they are encapsulated in drops, ensuring that no lysis occurs prior to encapsulation. This is enabled by the laminar flow conditions in the microfluidic channels, which ensure that diffusive mixing is negligible compared to the convection of the fluids. Following encapsulation, the close-packed drops move through a 55° C. incubation channel for 20 min, to allow the cells to lyse and the proteinase K to digest inhibitory proteins. The drops are then split into equally-sized drops using a hierarchical splitter (FIG. 5; FIG. 8, Panel 3), producing drops of the ideal small size for picoinjection and Megadroplet Array imaging (FIGS. 12-13).

Figure 9:
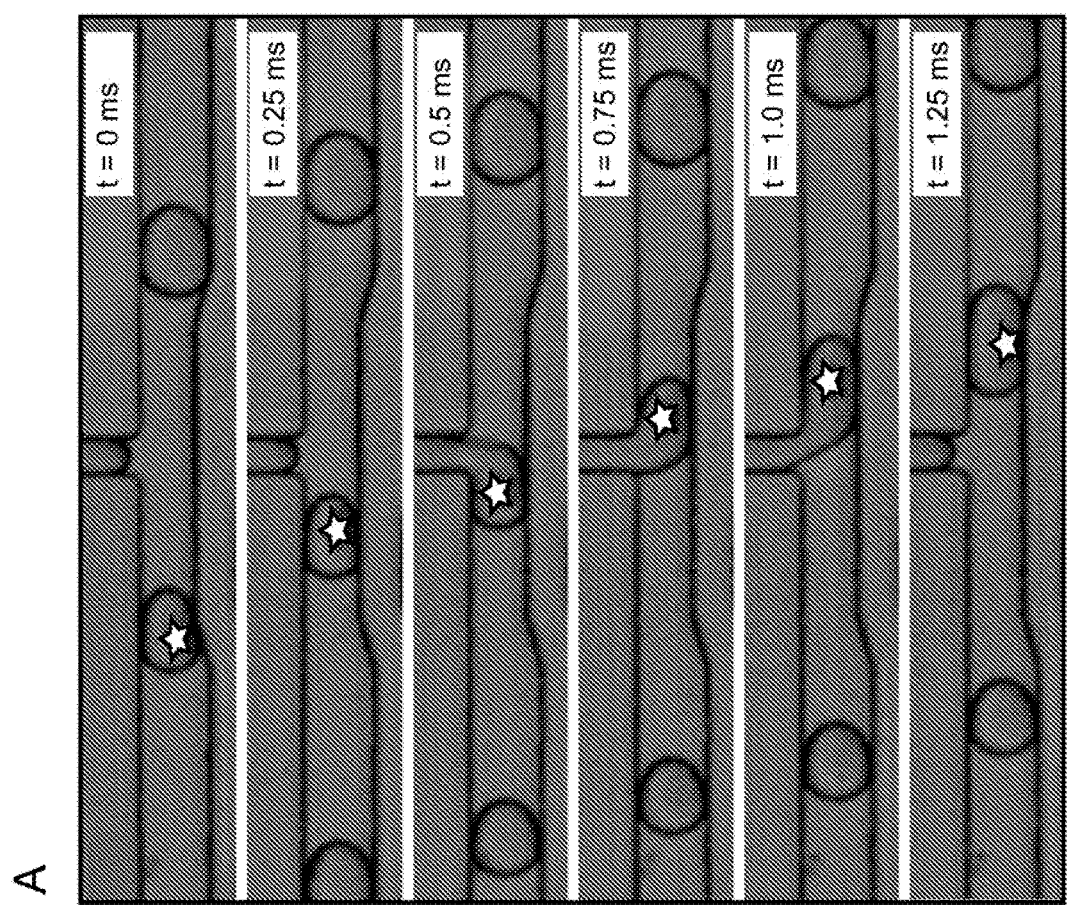
Figure 10:
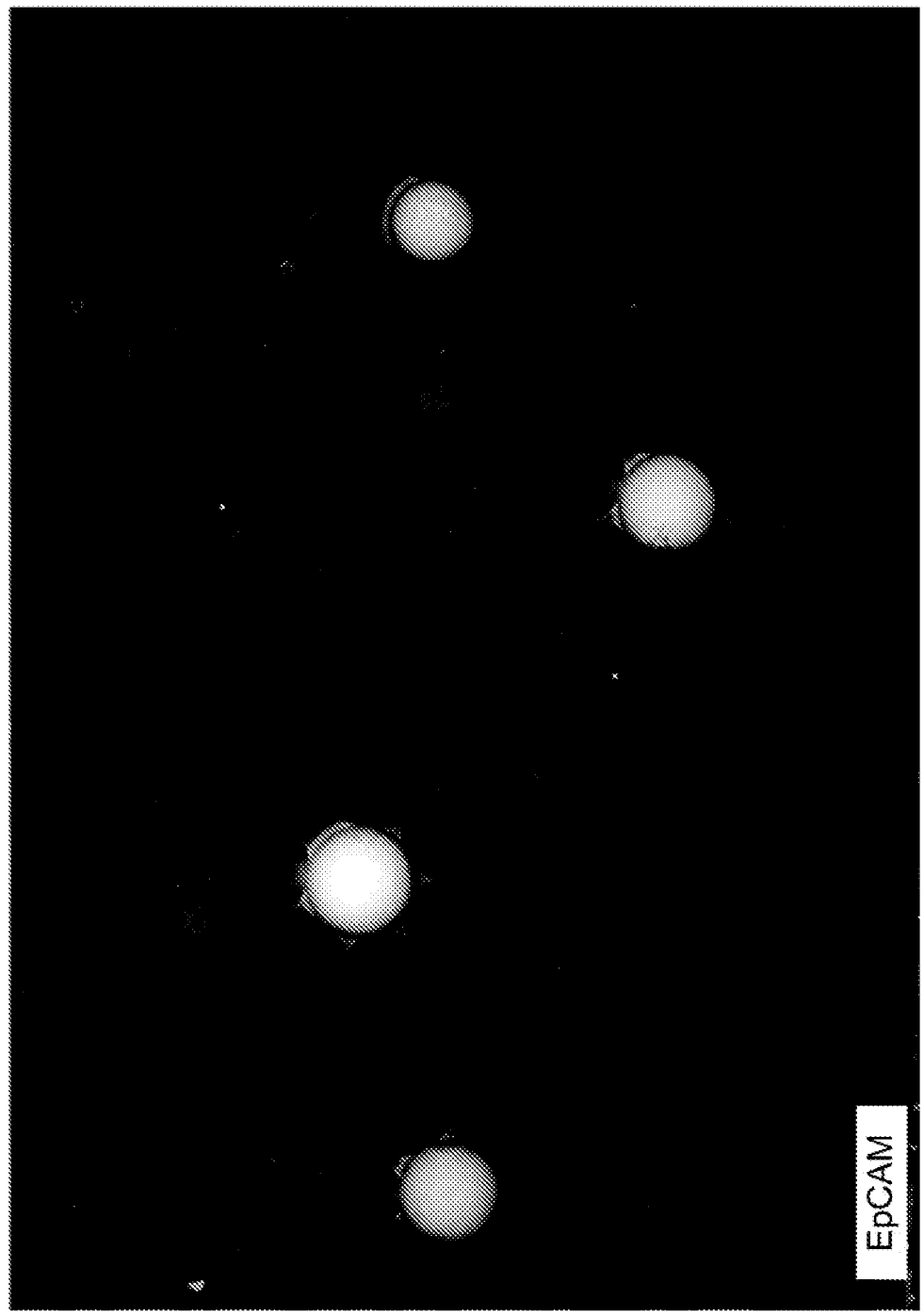
FIG. 10 shows detection of EpCAM transcripts from droplet encapsulated MCF7 breast cancer cells. Using the device depicted in FIG. 8, Panels 1-3, MCF7 cells were encapsulated in drops, lysed and drops were split. Lysate containing drops were then picoinjected with RT-PCR reagents and TaqMan® probes. Drops were then thermocycled and imaged for fluorescence. Brightfield and fluorescent channels are shown merged.

Prior to injection of the RT-PCR reagents and enzymes, the proteinase K is inactivated by heating the drops to 95° C. for 10 min. The drops are then injected with an equal volume of 2× primers and RT-PCR reagents (FIG. 9, Panel A). After picoinjection, the emulsion is collected into a PCR tube and thermal cycled. To determine whether a drop contains a cancer cell, TaqMan® probes are also included that hybridize to the EpCAM amplicons; this allows the probes to be hydrolyzed by the 5'-3' nuclease activity of Taq DNA polymerase, liberating the 5' fluorophore from the quenching 3' end modification making the drop fluorescent. By contrast, drops not containing cancer cells do not have EpCAM amplicons, so that the TaqMan® probes remain quenched and non-fluorescent (FIG. 4, Panels A-B). Hence, a bright drop relates the presence of an EpCAM positive cancer cell (FIG. 9, Panels B-C; FIG. 10). The thermocycled drops are injected into a flow cell 30 μm in height and 54 cm² in area; the narrow vertical gap of the flow cell forces the emulsion into a monolayer, allowing unobstructed epi-fluorescence visualization of every drop. For the fluorescence imaging, an automated microscope captures a mosaic of the entire flow cell and stores the images on a hard drive. The images are processed with custom Matlab code to identify fluorescent drops and measure their brightness. All data is stored digitally and analyzed using custom algorithms.

Example 2: Quantitative Multiplexed Assay

Figure 11:
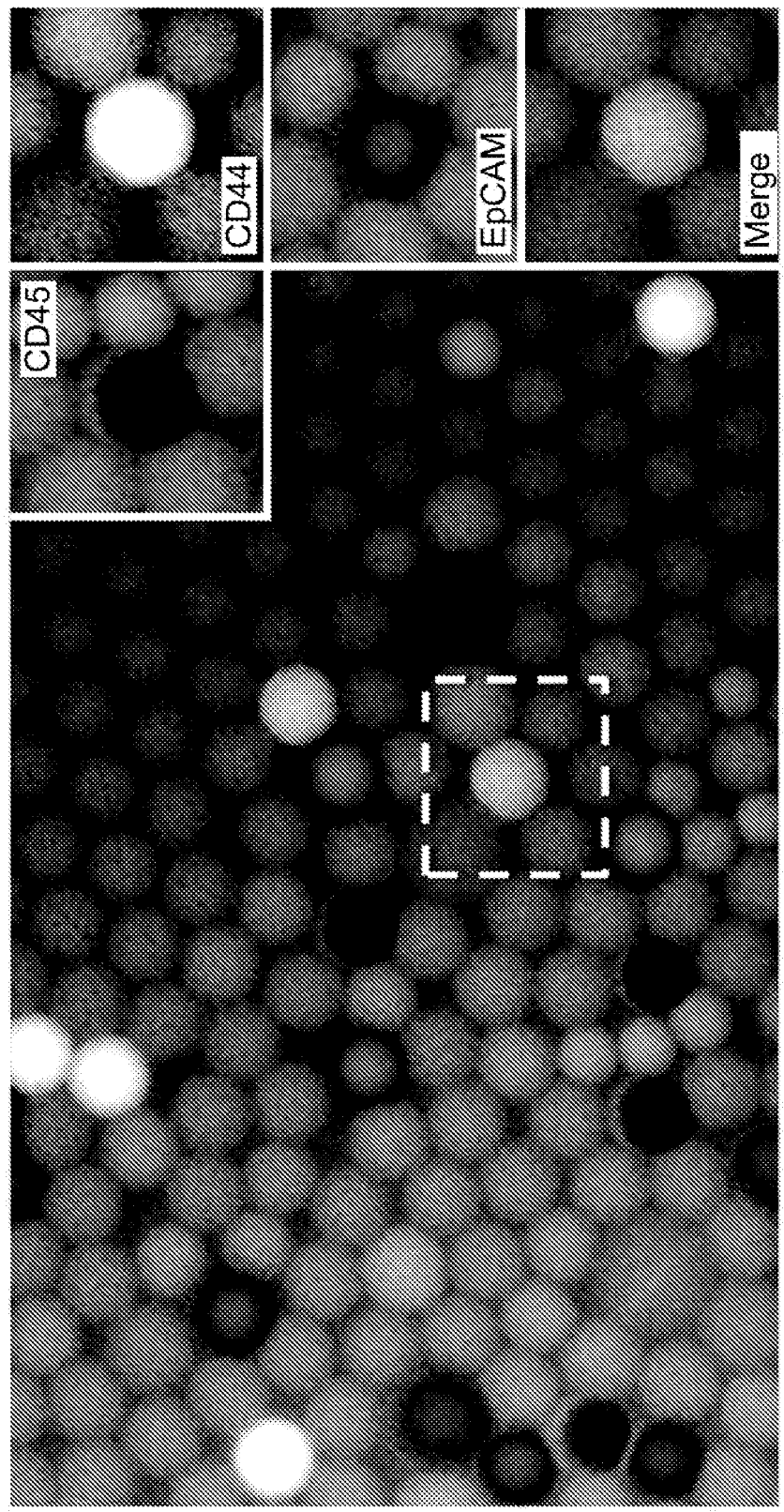
FIG. 11 depicts digital droplet RT-PCR multiplexing with TaqMan® probes. Limiting dilutions of total RNA from both Raji cells (B-lymphocytes) and PC3 prostate cancer cells were encapsulated in drops together with RT-PCR reagents and TaqMan® probes specific to CD45 (blue), CD44 (red) and EpCAM (green). Orange drops indicate the presence of both CD44 and EpCAM transcripts detected by a multiplex reaction. Other probe multiplexing combinations have also been seen (data not shown). Fluorescent channels are shown individually as a magnified inset for the dashed box region.

To screen more than one gene simultaneously, a multiplexed qPCR reaction may be utilized. Reactions were initially performed in bulk with PCR tubes to optimize reaction conditions. Using these methods, successful multiplexing was achieved during digital droplet RT-PCR for three TaqMan® probes, EpCAM, CD44 and CD45. An example of this multiplexing is shown in FIG. 11, where EpCAM and CD44 probes were multiplexed in drops containing both target transcripts. All PCR primer sets were designed to span large introns, making these larger genomic PCR products highly unlikely in multiplex reactions. Additionally, all TaqMan® probes are designed to hybridize to exon-exon junctions. The current probe sets do not recognize gDNA.

Single-Cell qPCR with Megadroplet Arrays:

To perform qPCR analysis on single cells, the drops are imaged as they are thermal cycled. This requires that the drops be held at fixed positions during thermal cycling so they can be repeatedly imaged. The microfluidic system used to prepare the drops was prepared as described above and in Example 1. After the drops are formed and loaded with cells and qPCR reagents, they are introduced into a Megadroplet Array (FIG. 12, Panels A-C; FIG. 13). The array consists of channels in which the channel ceilings are indented with millions of circular traps 25 μm in diameter. When the drops flow into the array, they are slightly pan-caked in shape because the vertical height of the flow channel is 15 μm, or 10 mm shorter than the drops. When a drop nears a trap, its interface adopts a larger, more energetically favorable radius of curvature. To minimize its surface energy, the drop will entirely fill the trap, allowing it to adopt the lowest, most energetically favorable, average radius of curvature. The capillary pressure of the drop is several orders of magnitude larger than the shear exerted by the flow, ensuring that the drops remain intact and confined in the traps. After a trap is occupied by a drop, no other drops are able to enter because the trap will be large enough to fit only one drop; additional drops are diverted downstream, to occupy the first vacant trap they encounter. The array is filled using a close-packed emulsion, and thus every trap is occupied by a drop. After the droplet array is filled, oil is injected to remove excess drops and the array is thermal cycled and imaged.

Thermal System for Temperature Cycling and Imaging:

Once the array is filled with drops and cells, the device is thermal cycled while simultaneously imaging the drops, to obtain the time-dependent information necessary for qPCR. The thermal cycling is accomplished using a custom heater consisting of a Peltier plate, heat sink, and control computer (FIG. 13). The Peltier plate permits heating or cooling the chip above or below room temperature by controlling the applied current. To ensure controlled and reproducible temperature, a computer monitors the temperature of the array using integrated temperature probes, and adjusts the applied current to heat and cool as needed. A copper-plate allows uniform application of heat and dissipation of excess heat during cooling cycles, enabling cooling from 95° C. to 60° C. in under 1 min execution of the qPCR assay in under two hours. To image the droplets during temperature cycling, a customized Canoscan 9000F scanner bed having a resolution of 9600 dpi by 9600 dpi is utilized. For 10 million hexagonally-packed 25 μm drops (54 cm²), 800 million pixels are required at highest resolution. With a resolution of 20 pixels per drop, the full image may be captured in 3s. The array is imaged several times per cycle with different excitation and emission filters to visualize the different dyes for the multiplexed TaqMan® probes.

Example 3: Electrode-Free Picoinjection of Drops of Microfluidic Drops

Microfluidic devices were fabricated in poly(dimethylsiloxane) (PDMS) using soft photolithographic techniques. The devices had channel heights of 30 μm, optimal for the picoinjection of water-in-oil droplets that are 50 μm in diameter. The device design is similar to those described previously by Abate, et al. *Proc. Natl. Acad. Sci. U.S.A.*, 2010, 107, 19163; the disclosure of which is incorporated herein by reference. An important difference, however, is that the channels for the metal solder electrodes are removed. Further, a "Faraday Mote"—an empty channel filled with a conducting aqueous solution—is implemented that runs between the injection site and the droplet spacer, as shown in FIG. 15, Panel B. The mote electrically isolates re-injected drops upstream of the picoinjection site from electric fields emanating from the picoinjector, preventing unintended merging. The emulsion that was picoinjected consists of monodisperse droplets of 3.8 mM fluorescein sodium salt ($C_{20}H_{10}Na_2O_5$) dissolved in Milli-Q $H_2O$. The droplets are suspended in a carrier oil of Novec HFE-7500 fluorinated oil with 2% (wt/wt) dissolved biocompatible surfactant. The picoinjection fluids consist of a dilution series of NaCl ranging from 0 to 500 mM, each containing 3.8 mM fluorescein sodium salt. This range of concentrations reflects the molarities of dissolved ions present in most biological buffers and reagents. Thus, since in most applications the fluids will already contain the requisite ions, the technique can be used without adding additional reagents to the solutions.

Droplets and carrier oil were introduced via syringe pumps (New Era) and spaced using the same carrier oil and surfactant mixture described above (FIG. 15, Panels A-B). The picoinjection fluid was contained in a BD Falcon tube. Through the cap of the Falcon tube was submerged a wire electrode into the fluid, as illustrated in FIG. 15, Panel A. Gaps in the cap were sealed with LocTite UV-cured epoxy. The picoinjection fluid was charged using a function generator outputting a 10 kHz sinusoidal signal ranging from 0 to 5 volts. This output was amplified 1000× by a Trek 609E-6 model HV amplifier. The positive output of the amplifier was attached via an alligator clip to the wire submerged in the picoinjection fluid. The ground electrode of the amplifier was attached to the metal needle of a syringe containing a 1 M solution of NaCl, introduced into the Faraday Mote (FIG. 15, Panel A). The two electrodes were never in electrical contact and the emulsions exiting the device were collected into separate, electrically isolated containers to avoid a closed circuit and prevent current flow.

The picoinjected reagent was infused into the device through PE-2 tubing (Scientific Commodities) using an air pressure pump (ControlAir Inc.) controlled by custom LabVIEW software. The injection fluid was pressurized such that the oil/water interface at the picoinjection orifice is in mechanical equilibrium with the droplet channel; the pressure difference across the interface is equal to the Laplace pressure, causing the injection fluid to bulge into the droplet channel without budding off and forming its own drops (FIG. 15, Panel C). For this device, drops and spacer oil were injected the at flow rates of 200 and 400 $\mu L\ hr^{-1}$, respectively. At these flow rates, the picoinjection fluid interface is in mechanical equilibrium for an applied pressure of ~13 psi. The lengths of the tubing carrying the injection fluid and solution serving as a Faraday mote was controlled, since longer tubes have higher electrical resistance and may attenuate the AC signal applied to trigger picoinjection.

To picoinject drops with reagent, the previously formed monodisperse emulsion was re-injected into the picoinjection device. The emulsion was introduced at a high volume-fraction such that there is little carrier oil and the drops are packed together. The packed drops traveled through a narrowing channel that forced them single file. Additional oil with surfactant is added from two perpendicular channels, spacing the drops evenly, as shown in FIG. 15, Panel B. A simple T-junction spacer was also found to work. The droplets then passed the picoinjector, a narrow channel containing the reagent to be added. To trigger picoinjection, the voltage signal was applied to the electrode submerged in the injection fluid, generating an electric field at the picoinjector as the drops pass the injection site. This caused the drops to coalesce with the injection fluid. As they traveled past, fluid was injected into them through a liquid bridge formed after the two fluids coalesce. The applied signal must have zero offset to prevent electrophoretic migration of charged particles in the solutions. Additionally, the frequency of the signal must be high enough to ensure that during the act of injecting, the sign of the field switches many times between positive and negative, so that the net charge of the fluid added to the droplets is approximately zero. This ensured that the droplets leaving the injector have zero net charge, which was important for ensuring that they remain stable. A 10 kHz signal was applied.

To analyze the behavior of the picoinjector, the injection site was observed under a microscope. In the absence of an electric field, a distinct boundary was observed between the droplet and the injection fluid, as shown in FIG. 16, Panel A. When a 250 V signal was applied to the picoinjector, the boundary vanishes and droplet coalescence is visible, as demonstrated in FIG. 16, Panel B. Thus, electrification of the injection fluid is adequate to trigger picoinjection, demonstrating that electrically-isolated electrodes are not needed.

To determine if it were possible to vary the injection volume using the applied voltage, voltage was varied between 0-5000V and the volume change of the resulting droplets was measured. Injection volume was quantified with an optical fluorescence detection setup. As the drops passed a 472 nm wavelength laser focused on the droplet channel ~1 cm downstream of the picoinjector, the emitted fluorescence signal from the dissolved fluorescein contained within the drops was amplified by a photomultiplier tube (PMT) and converted to a voltage signal analyzed with LabVIEW FPGA. As the drops passed the laser, their fluorescence signals resembled square waves as a function of time, with amplitudes and widths that corresponded to the drop intensity and length, respectively. The drops had a spherical diameter larger than the dimensions of the channel, causing them to be cylindrical in shape. Thus, the drop volume is approximately linear as a function of length. To calculate the volume fractional (Vf) increase, the ratio of the drop length before and after picoinjection was measured. These measurements were repeated for a range of applied voltages and molarities of NaCl in the injection fluid.

The increase in volume was plotted as a function of applied voltage for three representative molarities of injection fluid in FIG. 17, Panels A-C. In all cases the injection volume increased with the applied voltage, though this effect is most prominent for the 100 mM injection solution shown in FIG. 17, Panel A. The dependence of the droplet volume on the applied voltage may be attributed to the observation that the droplets are not perfect cylinders as they travel past the picoinjector; instead they have a "bullet" shape, with the leading edge having a smaller radius of curvature than the trailing edge. Consequently, as the drops pass the picoinjector, the thickness of the oil layer separating their interface from the bulge of the picoinjection fluid decreases. For an electrically-induced thin-film instability, the threshold voltage required to rupture the interface depends on the thickness of the film, decreasing as the film gets thinner. Hence, because the film thickness decreases as the drops pass the picoinjector, the moment of coalescence depends on electric field magnitude: for higher fields it is possible to rupture thicker films, leading to picoinjection at an earlier point; conversely, for lower fields thinner films are ruptured, causing picoinjection to start at a later point. Because the volume injected depends on the duration of picoinjection, it therefore also depends on applied voltage. This is supported by data which shows a dependence on applied voltage for all molarities (FIG. 17, Panels A-C). It was also observed that the curves relating volume injected to applied voltage are lower for lower molarities, as shown for the 50 mM and 25 mM data in FIG. 17, Panels B and C, respectively. This may be attributable to the fact that lower molarity solutions have a lower conductivity, and can thus attenuate the AC signals used to trigger injection, reducing the volume injected for a particular applied voltage.

Above 3000V and 100 mM, the injected volume begins to decrease and the variability in drop size increases. In images of these systems at these voltages, it was observed that the picoinjection fluid is no longer held at equilibrium in the picoinjection orifice, but instead wets the channel walls and buds off small drops into the flow channel.

Figure 18:
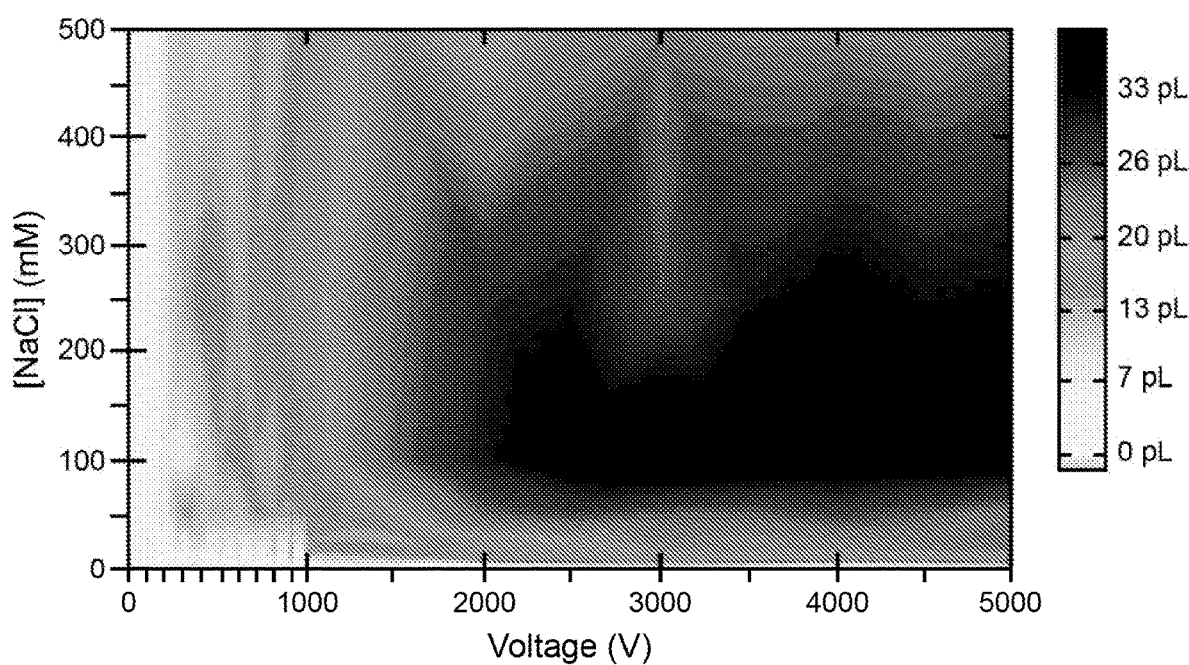
FIG. 18 is a heat map showing injection volume as a function of applied voltage and the molarity of dissolved NaCl in the injection fluid. Arrows/ticks indicate data points. The injection volume can be adjusted in the range of 0-36 pL with a resolution of ~2.6 pL 5 (4% Vf) with 100V increments of the applied signal. The largest injected volumes were 3000 V with the 100 mM fluid. Increasing electric field above this allows for electrowetting, causing drops to spontaneously form at the picoinjector, adversely affecting injection efficacy and consistency.
Figure 19:
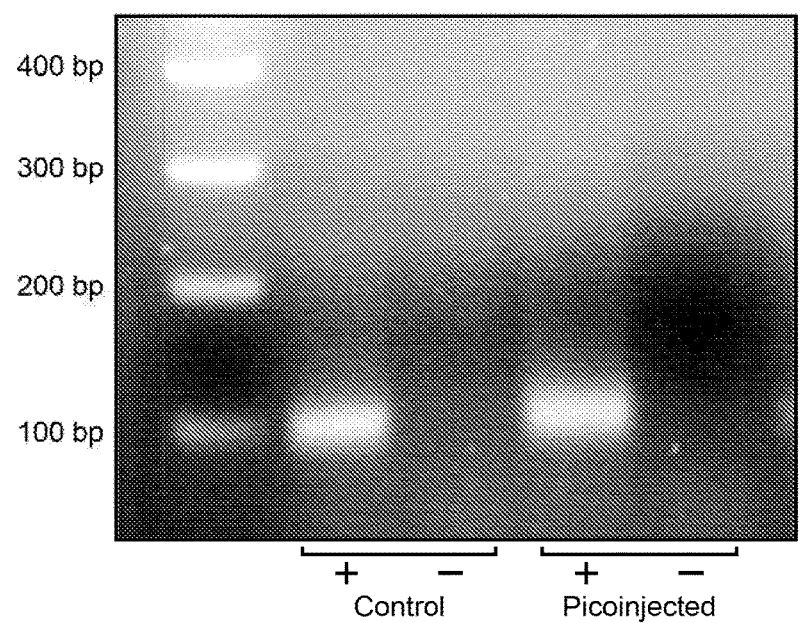
FIG. 19 shows ethidium bromide stained 2% agarose gel. Total RNA isolated from an MCF7 human cell line was encapsulated in drops and picoinjected with an RT-PCR reaction mixture either with (+) or without 50 (−) reverse transcriptase (RT) and Taq DNA polymerase. Non-emulsified control reactions were performed in parallel. Only reactions receiving enzyme generated the expected 100 bp amplicon. Both positive control and picoinjected reactions produced PCR products, demonstrating that the electric field generated during picoinjection is 55 biologically compatible with DNA, reverse transcriptase, and Taq.

To characterize the behavior of the electrode-free picoinjector for all parameters, injection volume was measured as a function of molarity and applied voltage and the resulting data was plotted on a 2D heat-map (FIG. 18). This data demonstrates that the technique should allow controlled picoinjection for most biological buffers, which commonly have molarities within the tested range.

To investigate whether the electric fields and currents generated by the high-voltage signal may disrupt biomolecules needed for downstream assays, the picoinjector was used to prepare droplets for an RT-PCR reaction. Drops containing total RNA isolated from an MCF7 human cell line were picoinjected with an RT-PCR reaction mixture containing the enzymes reverse transcriptase (RT) and Taq DNA polymerase. Negative-control drops were injected with a mixture containing no enzymes. Additional non-emulsified positive and negative control reactions were performed in parallel with the same RT-PCR mixture. Following thermocycling, the emulsions were broken and the amplification products visualized on an ethidium bromide-stained 2% agarose gel. The positive control and picoinjected drops showed PCR bands of comparable intensity for the expected 100 bp amplicon length, as visible in FIG. 19. In contrast, the negative controls showed no amplification, demonstrating that applying the triggering signal to the picoinjection fluid is sufficiently biocompatible so as to allow downstream RT-PCR reactions in drops.

Example 4: Coalescing Triple-Emulsions to Add Reagent to Droplets

One step, which may be important in running a droplet reaction, is the ability to add reagents to pre-existing drops. As an example, drop addition might be beneficial if a final drop reaction requires a reagent that could be denatured in a prior heating step. If no drop-stabilizing surfactants are used, adding reagent can be as simple as bringing a drop in contact with a second reagent-filled one. Standard drop processing and storage often require surfactant-stabilized drops, however, and localized electric fields have been utilized to selectively disrupt and merge pairs of drops. Merging involves timing the flow of original and reagent drops so that they pair up and are in contact. A second strategy uses electric fields to destabilize a passing drop so it can be injected with reagent from a side channel. This avoids the issue of synchronization, but has the disadvantage that each drop is potentially cross-contaminated when joined with the side channel. Furthermore, only a volume less than or equal to the passing drop can be injected.

Rather than merging or injecting reagents with a drop, presented here is a different scheme where the original drop is enveloped within a larger reagent droplet and then both are coalesced via application of an electric field. In some embodiments, this enveloping facilitates the pairing of one original drop with one reagent envelope. The contained nature of the mixing may also limit cross-contamination and facilitate the addition of arbitrary volumes as compared with a droplet injector.

The drop-envelope pairing is made possible with surface chemistry. To reduce interfacial energy, a hydrophilic channel encapsulates an oil-coated drop in aqueous reagent if available. A subsequent hydrophobic channel then encapsulates it in oil, creating a stable water-in-oil drop in a water-in oil drop, or triple emulsion (E3). This technique of alternating channel hydrophobicity has each low-order emulsion triggering the formation of the next higher one, with reliable quintuple emulsions even possible. The triggering leads to the proper pairing of one original drop per envelope. Once there, the original drop surface is in maximal contact with the inner surface of the reagent envelope, facilitating later electro-coalescence. This contact means that any volume of reagent could be added to the original drop, from a thin-shelled reagent envelope of fractional volume to an envelope $10^2$, $10^3$, $10^4$ or more times larger.

Figure 23:
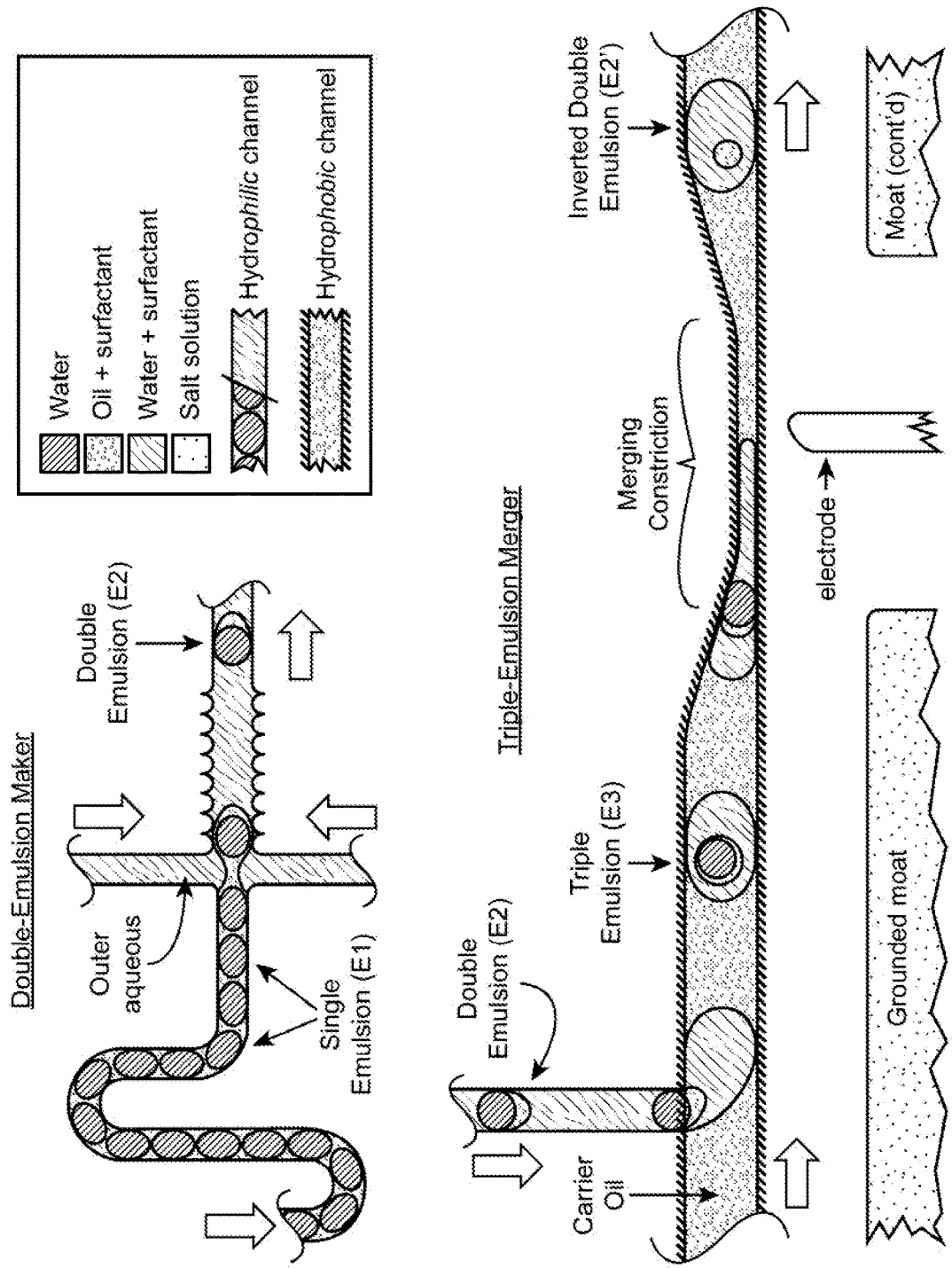
FIG. 23 shows a schematic of a coalescence process, starting with the formation of double emulsions (E2) from a reinjected single emulsion (E1) in a hydrophilic channel (top, left). These are turned into triple emulsions (E3) at a hydrophobic junction (bottom, left), which are then coalesced using an electric field into an inverted E2 (E2', bottom, right).

A detailed schematic of the E3 scheme is shown in FIG. 23. First, a premade, water-in-oil emulsion (E1) was reinjected into the device through a hydrophilic channel (FIG. 23, top left). The drops met a junction where co-flowing reagent pinched them off individually, surrounding them to reduce surface repulsion. The oil of the E1 formed thin, stable shells that housed each original drop. The channel immediately after the junction was designed to include ridges as described herein to traps pockets of aqueous fluid. This prevented oil from contacting the walls during budding and potentially altering their hydrophobicity. The water-in-oil-in water double emulsion (E2) then traveled to a second junction where it met a hydrophobic channel carrying oil (FIG. 23, bottom left) (Additional description and characterization of double emulsions and their formation are provided in the descriptions of FIGS. 38-51). Here, the aqueous reagents were repelled from the walls, and formed an E3 drop. In the figure, the E2 is shown in the process of seeding the E3 by weakening the adhesion of the reagent fluid to the hydrophilic channel. The volume ratio of reagent to the original E1 drops was determined by the flow rates at the first junction.

After formation, the E3 was passed into a narrow constriction and coalesced with an electric field. The electric field was generated between two salt-solution containing channels, an electrode carrying a high, alternating voltage and a grounded moat (FIG. 23, bottom). The constriction may have facilitated application of the electric field to the drops because the reagent envelope likely contained mobile ions that could screen the interior from the electric field. As seen in the figure, constricting the E3 forces the inner drop to the channel wall. After coalescing, the oil shell collapsed and became the innermost phase of an inverted oil-water-oil double emulsion (E2').

The device itself was constructed using conventional PDMS fabrication techniques. First, a master was made by spinning layers of SU-8 resist onto a silicon wafer and sequentially exposing them with UV light (Blakray) and a patterned mylar mask (Fineline Imaging) After developing in CD-30, the SU-8 master was covered in PDMS (PDMS manufacturer) with a 10:1 polymer to cross-linker mix, placed in vacuum to remove trapped air, and baked for 1 hour at 75° C. The device was then extricated and given access holes with a 0.75 mm biopsy punch. Next, the device was bonded to a 1 mm-thick glass slide by exposing both to 1 mbar $O_2$ in a 300 W plasma cleaner for 20s, attaching, and then baking for 10 min at 75° C.

The final processing steps created the hydrophilic and hydrophobic channels. First, Aquapel® was flowed backwards through the device, into the drop outlet and out the carrier oil inlet. At the same time, the drop reinjector inlet was pressurized with 15 psi air to prevent the Aquapel® from entering the double-emulsion, hydrophilic section of the device. Next, the same inlets exposed to Aquapel® were plugged with PEEK tubing (Resolution Systems, TPK.515-5M) and the device was re-exposed to 1 mbar $O_2$ plasma in the same cleaner for 1 min. The plasma made exposed channels hydrophilic, while the plugs kept the hydrophobic channels as they were. This hydrophilic treatment was only semi-permanent, and other methods not used here are capable of creating robust hydrophilic channels.

To operate, syringes filled with the appropriate fluids were connected to the finished device via PE-2 tubing (Scientific Commodities, #BB31695) and the same PEEK tubing and pressurized using syringe pumps (New Era). The reinjected drops consisted of Milli-Q water in a fluorinated oil (Novec HFE 7500) with a 1% w/w biocompatiable surfactant. The drops were flowed at a relatively slow flow rate of 20 µL/hr, and a snaking channel was used (FIG. 23, top left) to add flow resistance and filter any pressure fluctuations. The test reagent was PBS buffer (model #) with 0.1% pluronic surfactant (model #), and the carrier oil was the same as with the reinjected drops. These were flowed at equal rates between 200 µL/hr and 1200 µL/hr. The electrodes and moat were filled with 3.0 NaCl solution. The electrode, which was a dead end, was pressurized with a solution-filled syringe until air in the channel was absorbed by the PDMS. It was connected to a 20 kHz high voltage oscillator (JKL Components Corp, BXA-12579) running at 500 V. Such large voltages applied to merge or inject drops have been shown to be biologically compatible.

Figure 24:
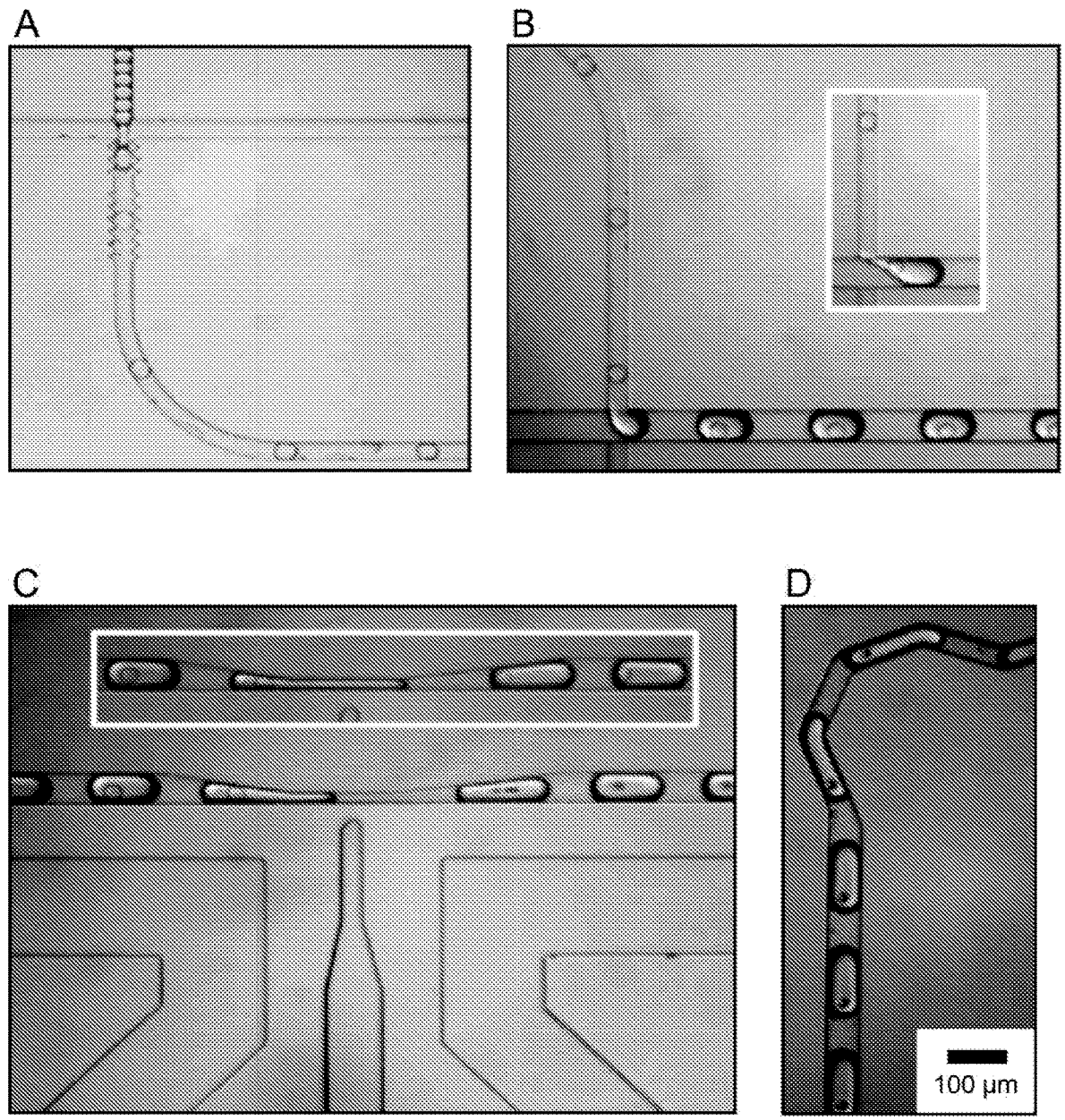
FIG. 24, Panels A-D, show microscope images of (a) double emulsions (E2) formation, (b) triple emulsion (E3) formation, (c) E3 coalescence, and (d) the final inverted E2 (E2') products. The scale bar applies to all images.

FIG. 24 shows microscope images of the running E3 device. The reinjected E1 travelling from the top of FIG. 24, Panel A, are starkly outlined because the disparate oil and water indices of refraction bent the back lighting. After the E1 was encapsulated at the junction by reagent flowing from the sides and became an E2, the inner and outer indices of refraction matched and the borders became much fainter. This is an indication of the thinness of the oil shell, which did not appreciably refract. In FIG. 24, Panel A, the E1 consisted of 30 µm-diameter drops (15 pL), and all channels here were hydrophilic and square, 30 µm to a side.

At the next junction, seen in FIG. 24, Panel B, the E2 exited the hydrophilic channel as an E3 in a large square, hydrophobic channel, 60 µm to a side. As with the initial emulsion, the edges of these E3 drops were clearly visible due to refractive mismatch. Conceivably, this step could have caused timing issues because the inner E1 needed to synchronize with the large drop formation. However, this problem was avoided because the arrival of the E1 at the junction weakened the adhesion of the reagent phase to the hydrophilic channel and induced budding. The process is shown in the inset of FIG. 24, Panel B, and caused a very regular loading of E1 into the E3.

The coalescence of the E3 is shown in FIG. 24, Panel C. The 60 µm-wide channel narrowed to 15 nm, squeezing the E1 against the walls where the electric field from the electrode could penetrate. The new E2' product of coalescing can be seen on the right. The collapsed oil remnants appear in high contrast and have a volume of roughly 2 pL, corresponding to an original oil shell that was 1 nm thick. The remnants could conceivably have merged with the carrier oil during coalescence except for the fact that the E3 was squeezed against the channel wall where there is no oil. In the inset, the constriction is shown without electric field. No coalescence occurred and the constriction moved the inner phases to the rear. The regularity of coalescence is demonstrated in FIG. 24, Panel D, the top of which shows a mixing channel for homogenizing the aqueous contents of the drop.

Figure 25:
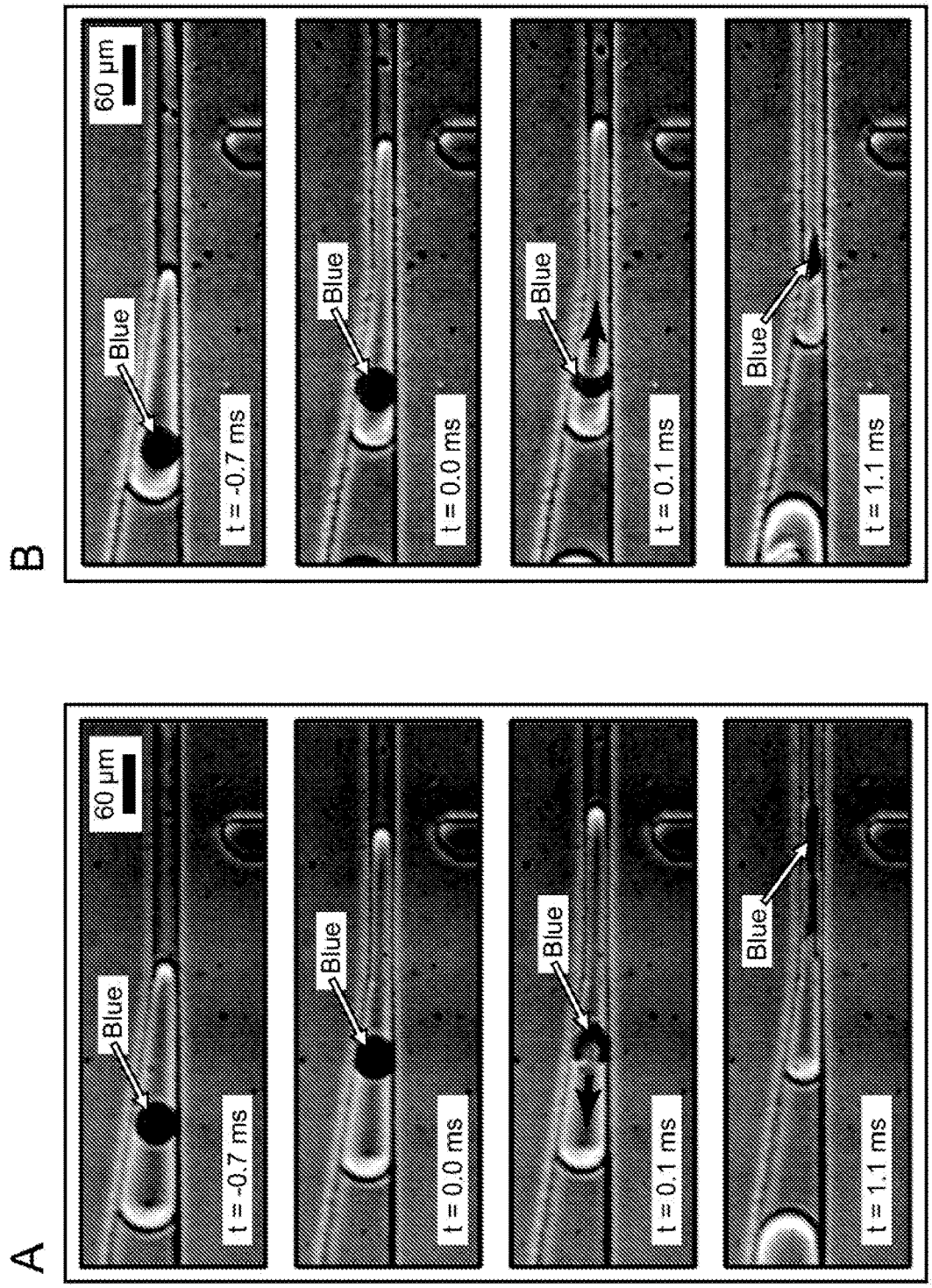
FIG. 25, Panels A-B, show two fast-camera time series showing E3 coalescence into E2'. The oil shell of the inner E1 is false-colored blue.

The precise dynamics of E3 coalescing were determined using a fast camera. Two time series are shown in FIG. 25, with the oil shell of the inner E1 highlighted in blue (indicated by arrows in FIG. 25). Each starts out at a time t=−0.7 ms where the inner E1 was not yet constricted and was spherical. Time t=0.0 ms was set immediately before rupturing when the E1 was pinned against the constriction walls and slightly flattened. By next frame, t=0.1 ms, the E1 ruptured. In FIG. 25, Panel A, the rupturing ejected contents of the E1 to the back of the drop, whereas in FIG. 25, Panel B, the contents were ejected forward. In high-order emulsions, the unconstrained surface of an inner phase will be tangent somewhere with the surface of the next outermost phase to reduce interfacial energy (i.e. the phases are never perfectly concentric). This randomly positioned contact point helps merging and may determine where the drop ruptures. After rupturing, the oil shells collapsed as shown in the frame at t=1.1 ms.

The robustness of this process depends on the appropriate channels being hydrophilic or hydrophobic. If the first section of the device is not sufficiently hydrophilic, the oil of E1 may wet the channel walls immediately after the junction. Instead of travelling as spheres down the center of the channel as in FIG. 24, Panel A, they may travel as hemispheres down the side and slip into the carrier fluid at the next junction as a single emulsion rather than enveloped. If the second section of the device is not sufficiently hydrophobic, there may be electro-wetting at the constriction and small satellite drops will buff off at the tail of the passing E3. As is, this scheme produces aqueous drops with oil in them (E2') as opposed to the pure aqueous drops (E1) of the merger and injector strategies mentioned previously. Depending on the desired product, this might be acceptable; otherwise, various techniques like microfluidic centrifuges or drop splitting can be employed to remove the oil.

From the study described, a triple emulsion coalescence strategy was demonstrated to be a robust method for adding a reagent to a collection of drops. Such triple emulsion coalescence was carried out without loss of drops or drop

Example 5: Picoinjection Enables Digital Detection of RNA Molecules with Droplet RT-PCR Most biological assays require the stepwise addition of reagents at different times. For microfluidic techniques to be most widely useful, a robust procedure for adding reagents to drops is therefore important. One technique for accomplishing this is electrocoalescence of drops, in which the reagent is added by merging the drop with a drop of the reagent using an electric field. Another technique is picoinjection, which injects the reagent directly into the drops by flowing them past a pressurized channel and applying an electric field. An advantage of picoinjection is that it does not require the synchronization of two streams of drops, making it easier to implement and more robust in operation. However, variability in the volume injected from drop to drop and the potential degradation of reagents by the electric field may interfere with assays. In addition, during picoinjection, the drops temporarily merge with the reagent fluid, potentially allowing transfer of material between drops, and cross-contamination.

This study investigated the impact of picoinjection on biological assays performed in drops and the extent of material transfer between drops. Using sensitive digital RT-PCR assays, it is shown that picoinjection is a robust method for adding reagents to drops, allowing the detection of RNA transcripts at rates comparable to reactions not incorporating picoinjection. It was also determined that there is negligible transfer of material between drops. The benefit of workflows incorporating picoinjection over those that do not is that picoinjection allows reagents to be added in a stepwise fashion, opening up new possibilities for applying digital RT-PCR to the analysis of heterogeneous populations of nucleic acids, viruses, and cells.

Materials and Methods
Microfluidic Device Fabrication

The microfluidic devices consisted of polydimethylsiloxane (PDMS) channels bonded to a glass slide. To make the PDMS mold, a device master was first created by spinning a 30 mm-thick layer of photoresist (SU-8 3025) onto a silicon wafer, followed by a patterned UV exposure and resist development. Next, an uncured mix of polymer and crosslinker (10:1) was poured over the master and baked at 80° C. for 1 hour. After peeling off the cured mold, access holes were punched in the PDMS slab with a 0.75 mm biopsy coring needle. The device was washed with isopropanol, dried with air, and then bonded to a glass slide following a 20 s treatment of 1 mbar $O_2$ plasma in a 300 W plasma cleaner. To make the devices hydrophobic, the channels were flushed with Aquapel® and baked at 80° C. for 10 min.

RNA Isolation

Human PC3 prostate cancer or Raji B-lymphocyte cell lines were cultured in appropriate growth medium supplemented with 10% FBS, penicillin and streptomycin at 37° C. with 5% $CO_2$. Prior to RNA isolation, Raji cells were pelleted and washed once in phosphate buffered saline (PBS). Confluent and adhered PC3 cells were first trypsinized prior to pelleting and washing. Total RNA was isolated from cell pellets using an RNeasy Mini Kit (Qiagen). Total RNA was quantified using a spectrophotometer and the indicated amounts (between 150 and 1000 ng) of RNA were used in subsequent 25 ml RT-PCR reactions.

TaqMan® RT-PCR Reactions

The sequence of amplification primers used for the RT-PCR reactions were as follows: EpCAM Forward 5'-CCTATGCATCTCACCCATCTC-3' (SEQ ID NO:1), EpCAM Reverse 5'-AGTTGTTGCTGGAATTGTTGTG-3' (SEQ ID NO:2); CD44 Forward 5'-ACGGTTAACAATAGTTATGGTAATTGG-3' (SEQ ID NO:3), CD44 Reverse 5'-CAACACCTCCCAGTATGACAC-3' (SEQ ID NO:4); PTPRC/CD45 Forward 5'-CCATATGTTTGCTTTCCTTCTCC-3' (SEQ ID NO:5), PTPRC/CD45 Reverse 5'-TGGTGACTTTTGGCAGATGA-3' (SEQ ID NO:6). All PCR primers were validated prior to use in microfluidic droplet experiments with tube-based RT-PCR reactions. Products from these reactions were run on agarose gels and single bands of the predicted amplicon size were observed for each primer set. The sequence of the TaqMan® probes was as follows: EpCAM 5'-/6-FAM/ATCTCAGCC/ZEN/TTCTCATACTTTGCCATTCTC/IABkFQ/-3' (SEQ ID NO:7); CD44 5'-/Cy5/TGCTTCAATGCTTCAGCTCCACCT/IAbRQSp/-3' (SEQ ID NO:8); PTPRC/CD45 5'-/HEX/CCTGGTCTC/ZEN/CATGTTTCAGTTCTGTCA/IABkFQ/-3' (SEQ ID NO:9). Pre-mixed amplification primers and TaqMan® probes were ordered as a PrimeTime Standard qPCR assay from Integrated DNA Technologies (IDT) and were used at the suggested 1× working concentration. Superscript III reverse transcriptase (Invitrogen) was added directly to PCR reactions to enable first stand cDNA synthesis. Following emulsification or picoinjection of RT-PCR reagents, drops were collected in PCR tubes and transferred to a T100 Thermal Cycler (BioRad). Reactions were incubated at 50° C. for 15 min followed by 93° C. for 2 min and 41 cycles of: 92° C., 15 s and 60° C., 1 min.

Emulsion Generation and Picoinjection

The reaction mixtures were loaded into 1 mL syringes and injected into microfluidic T junction drop makers using syringe pumps (New Era) controlled with custom LabVIEW software. The dimensions of the device and flow rates of the reagents were adjusted to obtain the desired 30 mm drop size. To apply the electric field for picoinjection, the electrode and surrounding moat channels were filled with a 3M NaCl solution, having a conductivity of ~0.1 S/cm. The electrode was energized using 20 kHz, 300 VAC signals generated by a fluorescent light inverter (JKL Components Corp) attached via an alligator clip to the syringe needle.

Immunofluorescence Imaging

To image the thermocycled droplets, 10 mL of emulsion were pipetted into Countess chambered coverglass slides (Invitrogen). The slides were imaged on a Nikon Eclipse Ti inverted microscope using conventional widefield epifluorescence and a 4× objective. Fluorescence filters were chosen to optimize the signal intensity and to mitigate background fluorescence due to spectral overlapping of the dyes used in the multiplexed reactions. The images were captured using NIS Elements imaging software from Nikon.

Data Analysis

The droplet images were analyzed using custom MATLAB software. For each field of view, brightfield and fluorescence images were captured. The software first located all drops in the brightfield image by fitting circles to the drop interfaces. Next, the light background in the fluorescence images was subtracted using a smooth polynomial surface constrained to vary over size scales much larger than the drops. The software then measured the average fluorescence intensity within each droplet's circular boundary. The resultant intensity values were offset so that the cluster of lowest intensity (empty) had an average of zero. Drops were determined to be "positive" or "negative" based on whether their intensity fell above or below, respectively, a defined threshold.

Results

Detection of RNA Transcripts in Picoinjected Drops.

Figure 26:
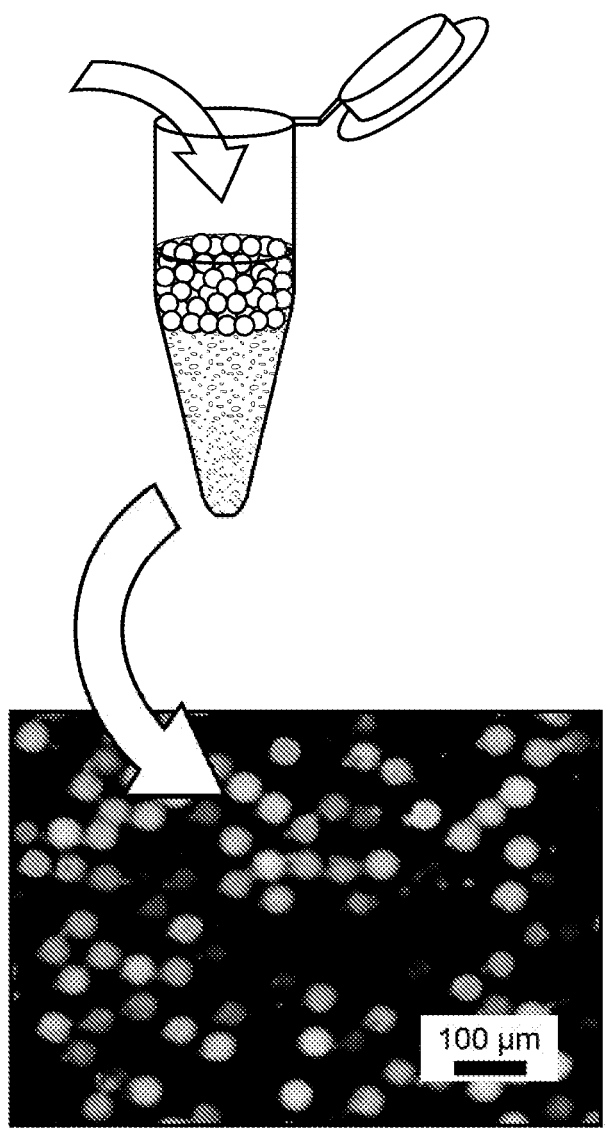
FIG. 26, Panels A-C, show microfluidic devices and digital RT-PCR workflow used in the study of Example 5. (A) Drops containing RNA and RT-PCR reagents are created with a microfluidic T-junction and carrier oil. Brightfield microscopy images of the drop formation are shown below, the middle image showing the generation of one population of drops from a single reaction mixture, and the lower the generation of two populations from two mixtures. (B) After formation, the drops are picoinjected with reverse transcriptase using a picoinjection channel triggered by an electric field, applied by an electrode channel immediately opposite the picoinjector. (C) The picoinjected drops are collected into a tube, thermocycled, and imaged with a fluorescent microscope.

A potential concern when using picoinjection for RT-PCR assays is the possibility that it may interfere with reactions in the drops; for example, the process may result in variability in the amount of reagents between the drops or degradation of key components upon exposure to the electric field. To investigate these issues, the detection of two cancer-relevant human transcripts, EpCAM and CD44, was compared in picoinjected and non-picoinjected drops using TaqMan® RT-PCR, (FIG. 26). The TaqMan® probe for detecting EpCAM was conjugated to the fluorophore 6 carboxyfuoroscein (FAM) and the probe for CD44 to the dye Cy5. The probe mix also contained primers that flank the TaqMan® probes and yield ~150 base amplicons from these genes.

Figure 27:
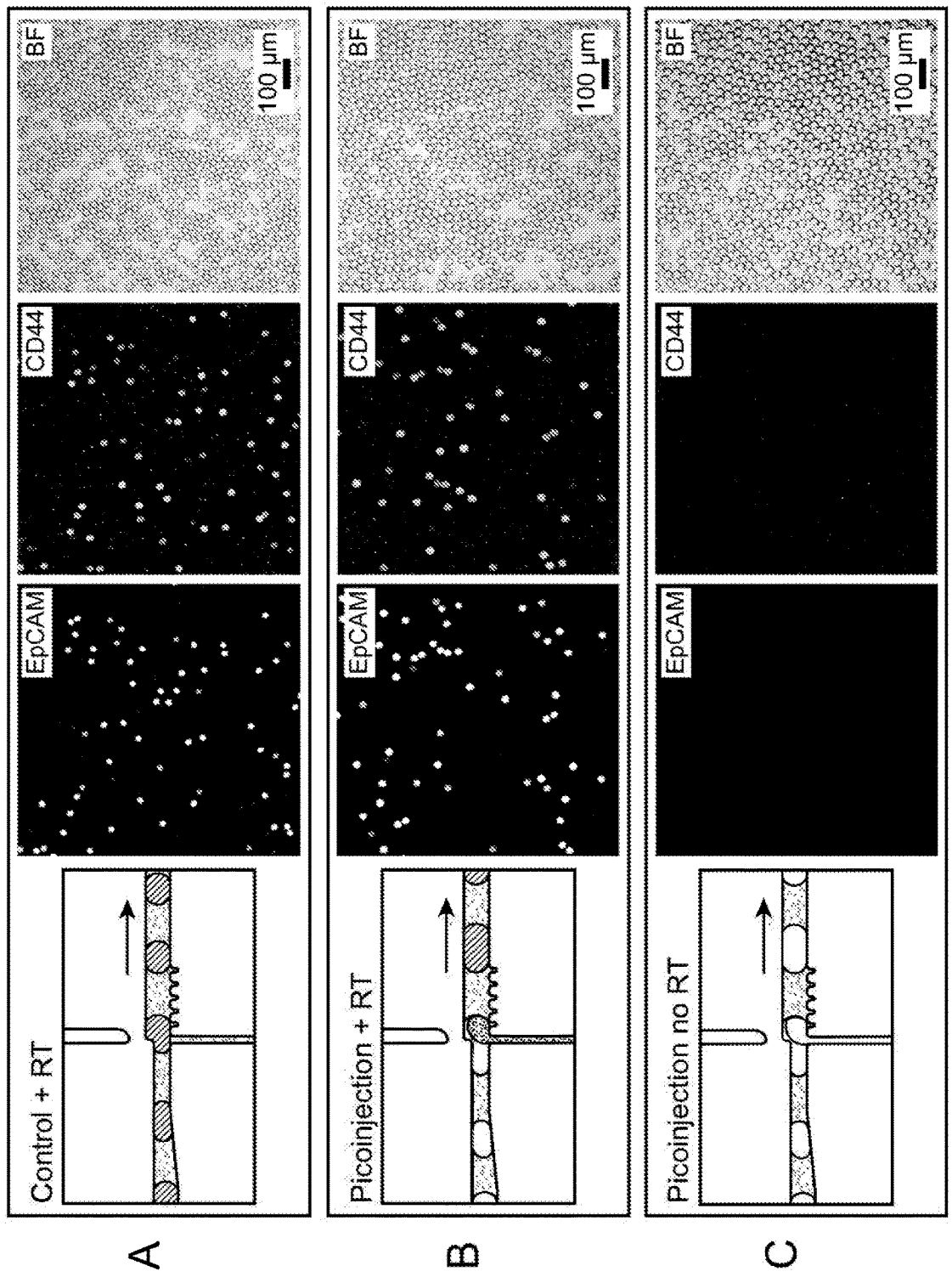
FIG. 27, Panels A-C, show digital RT-PCR TaqMan® assays in microfluidic drops following picoinjection of reverse transcriptase. (A) Control RT-PCR reactions containing PC3 cell total RNA were emulsified on a T-junction drop maker, thermocycled, and imaged. FAM (green) fluorescence indicates TaqMan® detection of an EpCAM transcript and Cy5 (red) indicates detection of CD44 transcripts. Brightfield images (BF) of the same drops are shown in the image panel on the far right. (B) RT-PCR reactions lacking reverse transcriptase were emulsified on a T-junction drop maker and subsequently picoinjected with reverse transcriptase. Picoinjection fluid is pictured as dark gray in the schematic diagram on the left. Brightfield images demonstrate that the drops roughly doubled in size after picoinjection. (C) RT-PCR reactions subjected to picoinjection omitting the reverse transcriptase show no TaqMan® signal for EpCAM and CD44, demonstrating the specificity of the TaqMan® assay. The red arrows indicate the direction of emulsion flow in the illustrations. Scale bars=100 μm.

To prepare the non-picoinjected control drops, the probe mix was added to a 25 ml RT-PCR master mix reaction containing 150 ng of total RNA isolated from the human PC3 prostate cancer cell line. The RT-PCR solution was the emulsified into monodisperse 30 mm (14 pL) drops with a T-junction drop maker, and the drops were collected into PCR tubes and thermocycled (FIG. 26, Panel A and 26, Panel C). During thermocycling, drops containing at least one EpCAM or CD44 transcript were amplified, becoming fluorescent at the wavelengths of the associated FAM and Cy5 dyes. By contrast, drops without a molecule did not undergo amplification and remained dim, as in standard TaqMan®-based digital droplet RT-PCR. Following thermocycling, the drops were pipetted into chambered slides and imaged with a fluorescence microscope. To measure the concentrations of EpCAM and CD44 in the original solution, the number of drops with FAM or Cy5 fluorescence were counted. The reactions showed a digital fluorescent signal for both the EpCAM and CD44 probes, indicating that these transcripts were present at limiting concentrations in the drops, as shown in FIG. 27, Panel A. Control reactions where reverse transcriptase was omitted failed to produce a fluorescent signal, indicating that the TaqMan® assays were specific and not the result of non-specific cleavage of TaqMan® probes caused by the emulsification process.

To test the impact of picoinjection on TaqMan® RT-PCR, a similar experiment as above was performed, but the RT-PCR reagents were separated into two solutions added at different times. Total RNA, RT-PCR buffer, primers, probes, and DNA polymerase were emulsified into 30 mm diameter drops; these drops were not capable of RT-PCR, since they lacked reverse transcriptase. Using picoinjection, an equal volume of 2× reverse transcriptase was introduced in PCR buffer and the drops were thermocycled. Just as with the non-picoinjected control, this emulsion showed a robust digital signal and had an equivalent ratio of fluorescent-to-non-fluorescent drops, as shown in FIG. 27, Panels A and B. To confirm that the fluorescence was not due to background hydrolysis of the TaqMan® probes, disruption of the probes by the electric field, or some other factor, additional reactions were performed where a picoinjection fluid lacking reverse transcriptase was added to RNA-containing drops. In these drops, no fluorescence was evident following thermocycling (FIG. 27, Panel C), demonstrating that the signal was indeed a result of digital detection of RNA molecules, and that these assays were specific.

Quantification of RT-PCR Detection Rates in Picoinjected Drops

Figure 28:
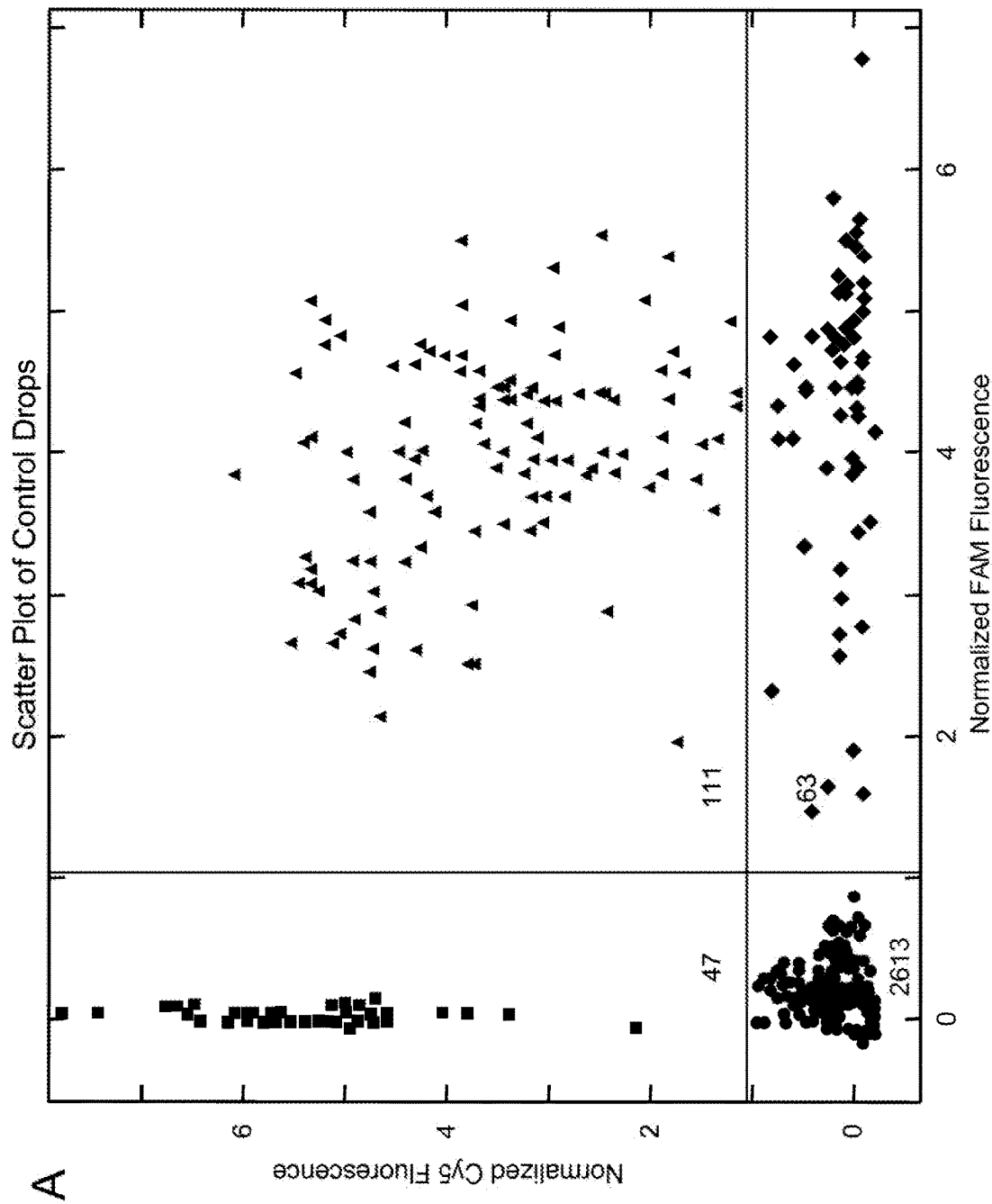
FIG. 28, Panels A-B, show a comparison of digital RT-PCR detection rates between control drops and drops that were picoinjected with reverse transcriptase. (A) Scatter plots of FAM and Cy5 drop intensities for a control sample (left) and picoinjected sample (right). The gating thresholds used to label a drop as positive or negative for TaqMan® signal are demarcated by the lines, and divide the scatter plot into quadrants, (−,−), (−,+), (+,−), (+,+). (B) The bar graph shows the average TaqMan® positive drop count with picoinjection relative to the normalized count for CD44 and EpCAM TaqMan® assays for control populations. The data represent the average of four independent experimental replicates.
Figure 28:
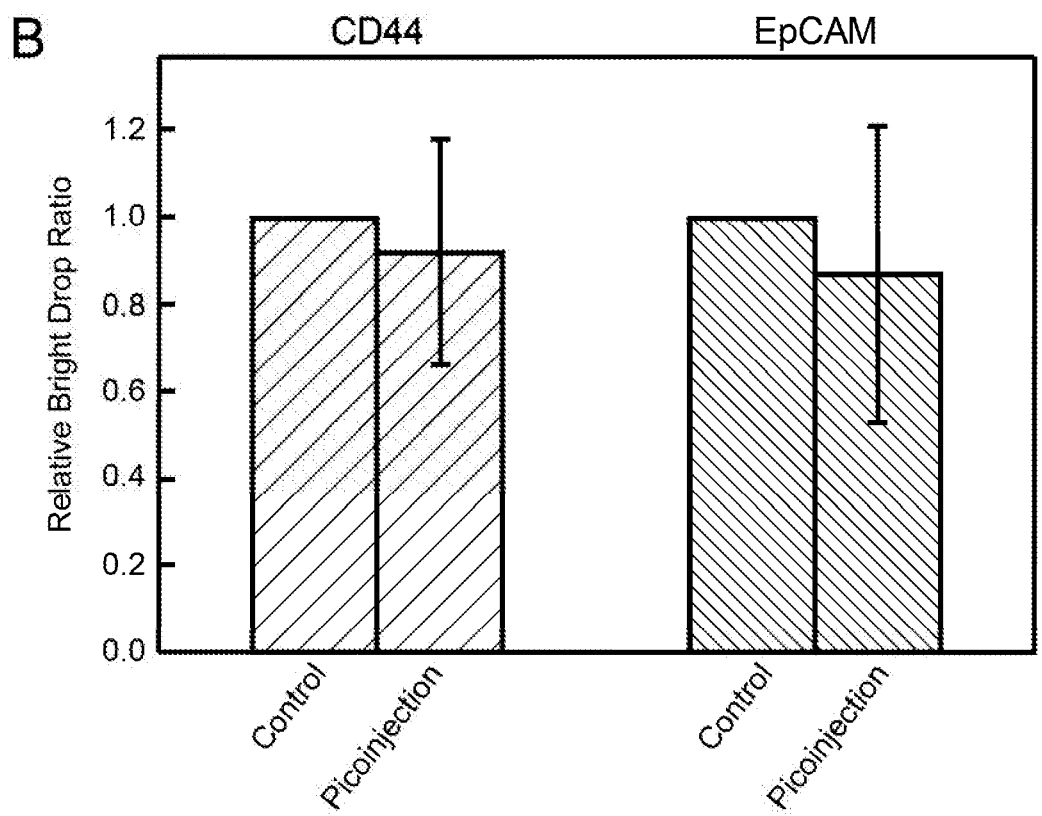

To precisely quantify the impact of picoinjection on TaqMan® RT-PCR transcript detection, four independent replicates of the picoinjected and non-picoinjected drops were collected. To automate data analysis, a custom MATLAB software was used to locate the drops in the images and measure their fluorescence intensities. For a particular channel (FAM or Cy5), the fluorescence intensity within each drop was averaged; all drop values were subsequently offset so that the cluster of empty drops had an average of zero (See Materials and Methods). Using one threshold for both channels, each drop was labeled as positive or negative for EpCAM and CD44 based on whether it was above or below the threshold, respectively, as shown in FIG. 28, Panel A. In total, 16,216 control drops and 14,254 picoinjected drops were analyzed from the four experimental replicates. To determine the TaqMan® detection rate of picoinjected drops relative to non-picoinjected controls, the total number of CD44 (Cy5) and EpCAM (FAM) positive control drops in each replicate was normalized. Following picoinjection of reverse transcriptase, 92% (+/−26%) of CD44 positive drops and 87% (+/−34%) of EpCAM positive drops were detected relative to the control drops (FIG. 28, Panel B). Although the average transcript detection rate for picoinjected drops was slightly lower than that of control drops for a given RNA concentration, the difference was not statistically significant, and some experimental replicates had detection rates for picoinjected drops higher than for the controls. Based on these results, it was conclude that picoinjection affords transcript detection rates equivalent to that of digital RT-PCR, with the benefit of allowing the reaction components to be added at different times.

Discrete Populations of Drops can be Picoinjected with Minimal Cross-Contamination An important feature when adding reagents to drops is maintaining the unique contents of each drop and preventing the transfer of material between drops. Unlike the merger of two discrete drops, the contents of a picoinjected drop become momentarily connected with the fluid being added, as illustrated in FIG. 26, Panel B. After the drop disconnects from the fluid, it may leave material behind that, in turn, may be added to the drops that follow. This could lead to transfer of material between drops, and cross-contamination. To examine the extent to which picoinjection results in cross-contamination, TaqMan® RT-PCR reactions were again used because they are extremely sensitive and capable of detecting the transfer of just a single RNA molecule. A FAM-conjugated TaqMan® probe was used for targeting the EpCAM transcript and a hexachlorofluorescein (HEX) conjugated TaqMan® probe was used for recognizing the B-lymphocyte-specific transcript PTPRC. Total RNA was isolated from PC3 cells expressing EpCAM but not PTPRC, and a B-lymphocyte derived cell line (Raji) expressing PTPRC but not EpCAM. For a control set of drops, the RNA from both cell types was mixed, TaqMan® probes and RT-PCR reagents were added, and the solutions were emulsified into 30 mm drops. The drops were collected into a tube, thermocycled, and imaged, FIG. 29A. In the images, a large number of drops displayed FAM and HEX fluorescence, indicative of multiplexed TaqMan® detection of PTPRC and EpCAM transcripts. A smaller fraction had pure green or red fluorescence, indicating that they originally contained just one of these molecules, while even fewer were dim and were thus devoid of these transcripts.

Figure 29:
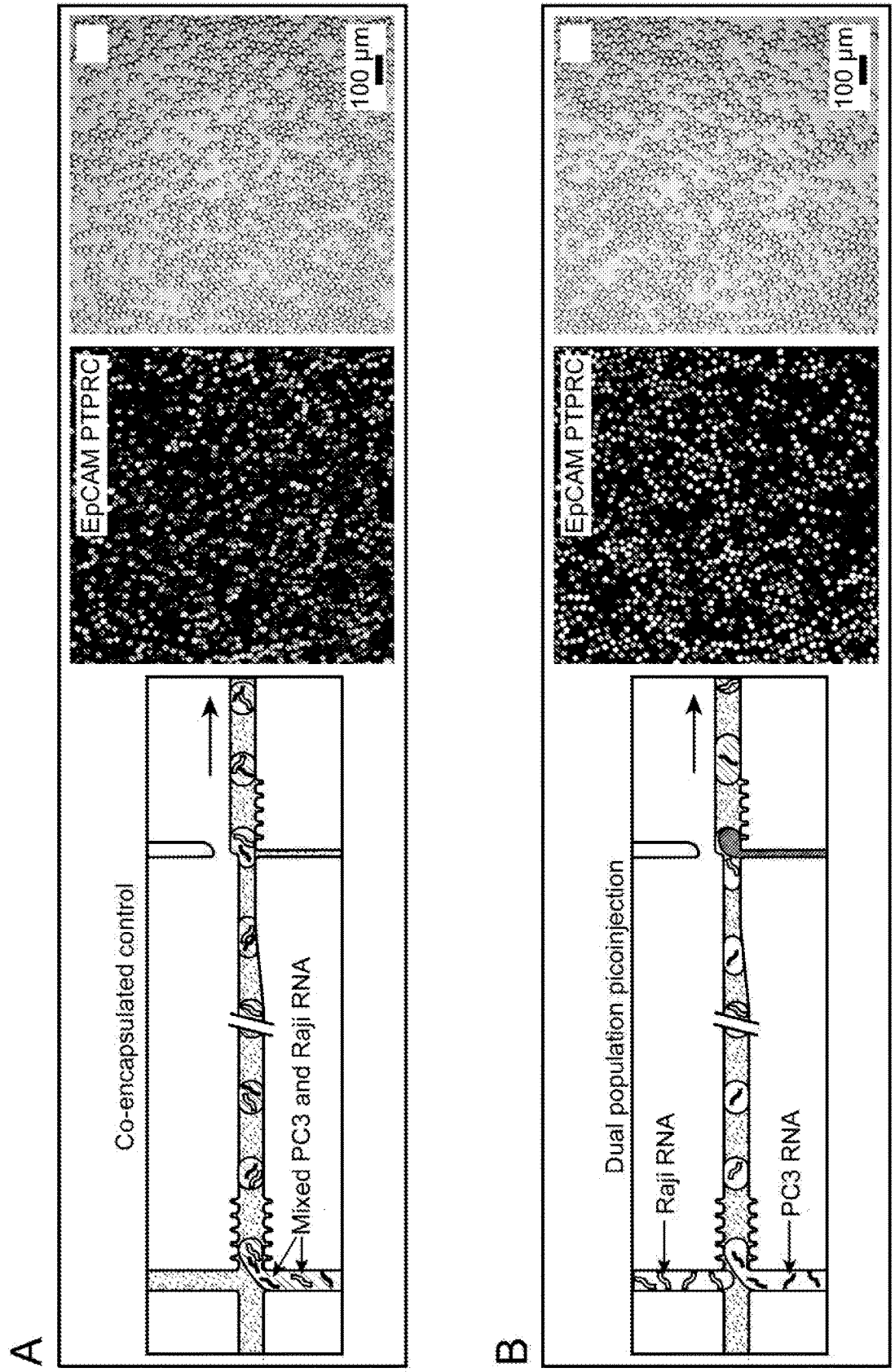
FIG. 29, Panels A-B, shows that picoinjection enables analysis of discrete drop populations. (A) Non-picoinjected drops. Control RT-PCR reactions containing mixed PC3 cell total RNA and Raji cell total RNA were emulsified with a T-junction drop maker, thermocycled, and imaged. Merged FAM and HEX fluorescent images are shown with FAM (green) fluorescence indicating TaqMan® detection of an EpCAM transcript and HEX (red) indicating the presence of PTPRC transcripts. The yellow drops indicate the presence of multiplexed TaqMan® assays, where EpCAM and PTPRC transcripts were co-encapsulated in the same drop. The brightfield images (BF) are shown in the panel on the right. (B) Picoinjected drops. A double T-junction drop maker simultaneously created two populations of drops that were immediately picoinjected. One drop maker created drops containing only Raji cell RNA, and the other drops containing only PC3 cell RNA. Both drop types initially lack reverse transcriptase, which is added via picoinjection just downstream of the drop makers. The overwhelming majority of drops display no multiplexing, demonstrating that transfer of material during picoinjection is very rare. The red arrows indicate the direction of emulsion flow in the illustrations. Scale bars=100 μm.

To observe the rate of picoinjector cross-contamination, a microfluidic device was used that synchronously produced two populations of drops from opposing T-junctions, pictured in FIG. 29, Panel B. One population contained only Raji cell RNA and PTPRC transcripts; the other, only PC3 cell RNA and EpCAM transcripts, as illustrated in FIG. 29, Panel B. Both populations contained primers and TaqMan® probes for EpCAM and PTPRC and were therefore capable of signalling the presence of either transcript. Immediately after formation, the drops were picoinjected with the 2× reverse transcriptase, thereby enabling first strand cDNA template synthesis for the TaqMan® assay, and an opportunity for contamination. If RNA was transferred between drops, some of the drops should have displayed a multiplexed TaqMan® signal, whereas in the absence of contamination, there should have been two distinct populations and no multiplexing. In the fluorescence images, two distinct populations were observed, one positive for EpCAM (FAM) and the other for PTPRC (HEX), with almost no yellow multiplexed drops that would be indicative of a multiplexed signal, as shown in FIG. 29, Panel B. This demonstrated that cross-contamination during picoinjection is rare.

Figure 30:
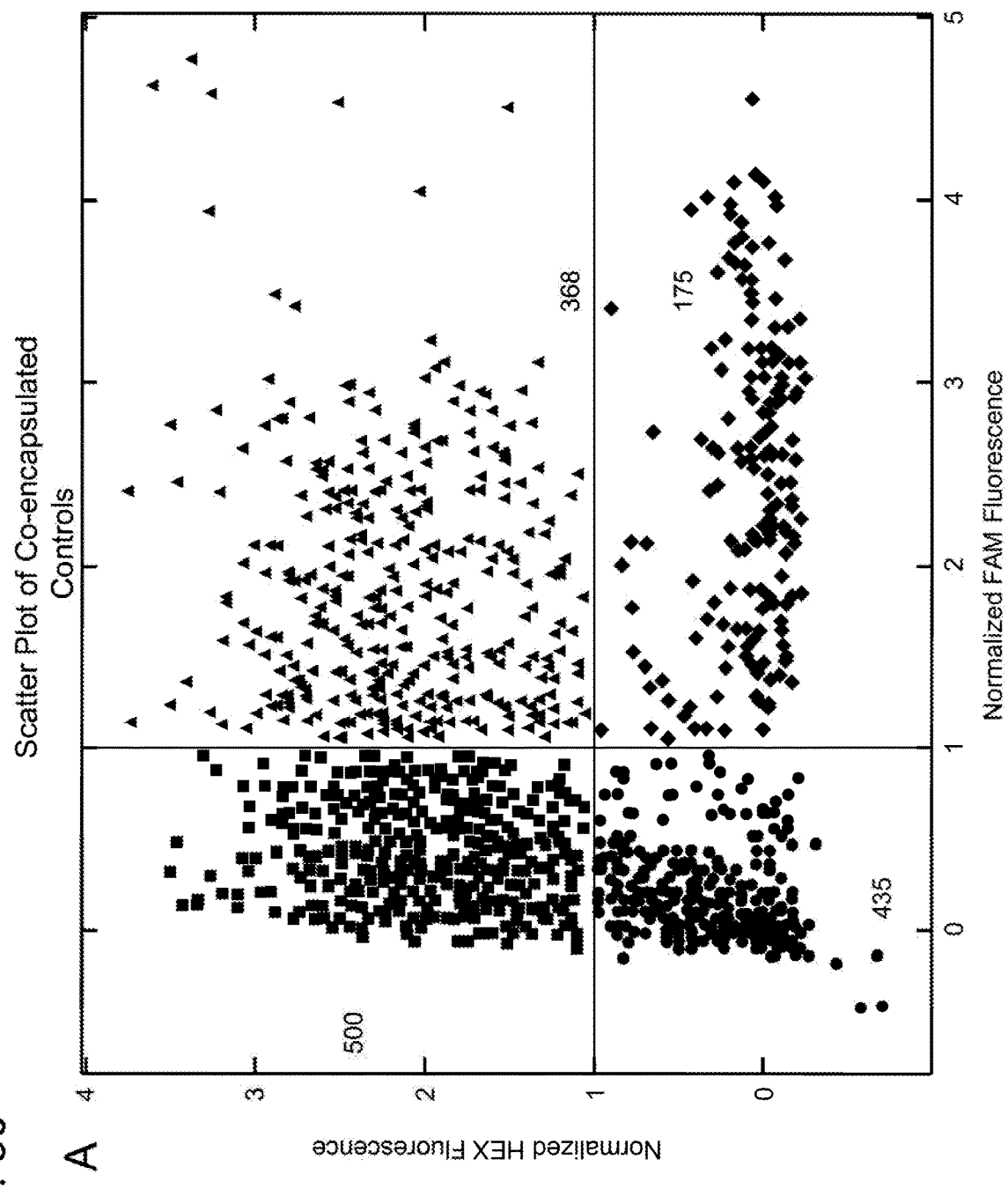
FIG. 30, Panels A-B, shows a dual transcript detection analysis, indicating minimal cross-contamination during picoinjection. (A) Scatter plots of FAM and HEX drop intensities for a co-encapsulated control sample (left) and dual population picoinjected sample (right). Using this analysis, large numbers of TaqMan® multiplexed drops were identified in the co-encapsulated controls that were virtually absent in the dual population picoinjected drops (upper right quadrants of gated scatter plots). (B) A bar graph of different bright drop populations relative to the total bright count for co-encapsulation control and for dual population picoinjection. The data represent the average of three experimental replicates.
Figure 30:
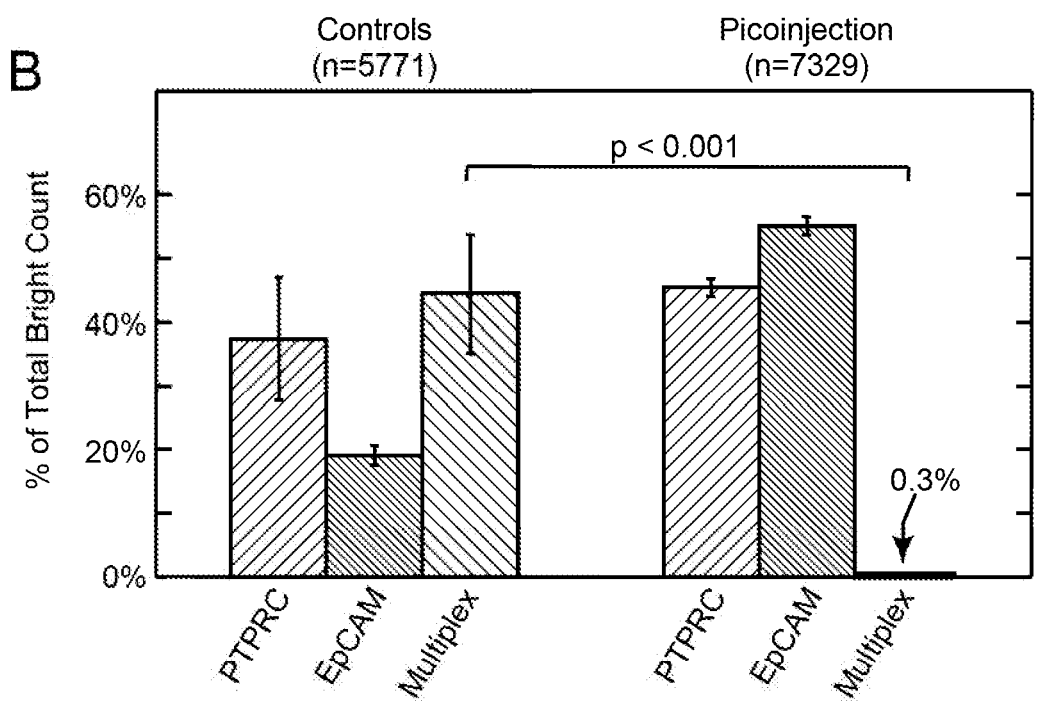

To measure the precise rate of cross-contamination, automated droplet detection software was used to analyze thousands of drops, FIG. 30, Panel A, and the results were plotted as a percentage of the total number of TaqMan® positive drops, FIG. 30, Panel B. A total of 5771 TaqMan® positive control drops and 7329 TaqMan® positive picoinjected drops were analyzed from three independent experimental replicates. For the control drops, in which the Raji and PC3 RNA were combined, a multiplexing rate 44% (+/−9.26) was observed. By contrast, for the picoinjected drops, only 0.31% (+/−0.14) multiplexed drops were observed, as shown in FIG. 30, Panel B. Hence, with picoinjection, there was some multiplexing, although the rate was so low it cannot be ruled out as resulting from other sources of RNA transfer, such as merger of drops during thermocycling or transport of RNA between droplet interfaces.

Figure 31:
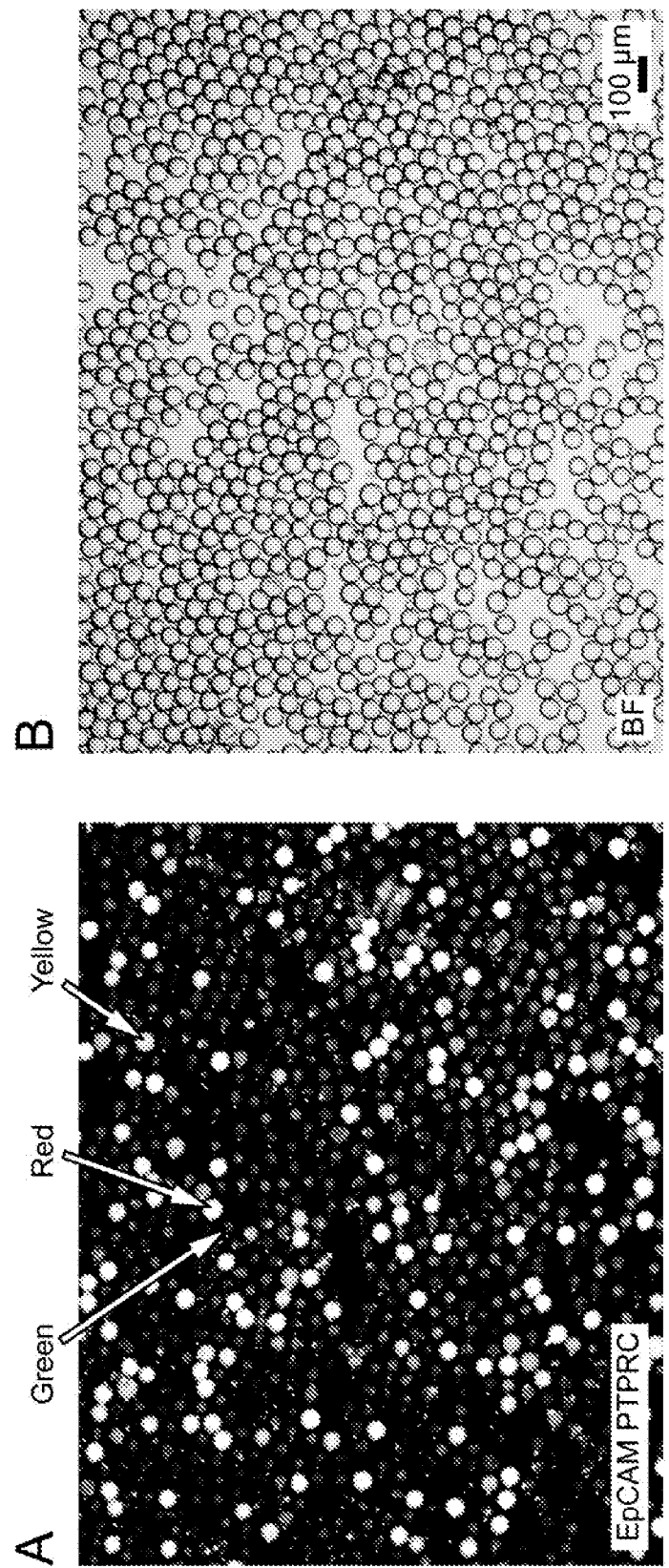
FIG. 31 Panels A-B, shows that dual populations of RNA drops can be stored offline and picoinjected at a later time. (A) An emulsion was made consisting of two populations of drops, one containing RNA recovered from Raji cells, and the other from PC3 cells. The drops were collected into a syringe, incubated off chip, and then re-introduced into a microfluidic device to picoinject. The drops were then collected, thermocycled, and imaged. These drops are somewhat more polydisperse and displayed higher multiplexing rates (1%) than the drops picoinjected on the same device on which they were formed, which is most likely due to merger of some of the drops during incubation and reinjection. The ability to reinject emulsions following incubation to add reagents may be important for numerous droplet-based molecular biology assays. (B) Brightfield images of picoinjected emulsions. Scale bars=100 μm.

The dual population experiments in which the drops were picoinjected immediately after being formed allowed for the estimation of the precise amount of cross-contamination, but in most actual implementations of picoinjection for biological assays, the drops will be formed on one device, removed offline for incubation or thermocycling, and then reinjected into another device for picoinjection. To demonstrate that picoinjection is effective for digital RT-PCR reactions performed under these conditions, and to estimate the rate of cross contamination, a dual population of drops was again created, but this time the drops were pulled offline and stored in a 1 mL syringe before reinjecting and picoinjecting them. Just as before, it was observed that nearly all drops were pure green or red, indicating minimal cross contamination, as shown in FIG. 31. However, some drops with a multiplexed signal were also observed, as shown by the rare yellow drops in the image. In this experiment, the multiplexing rate was 1%, higher than with the drops that were picoinjected immediately after formation. While cross-contamination at the picoinjector cannot be ruled out, it is suspected that the higher multiplexing rate was the result of merger of drops during offline storage and reinjection, during which the drops may be subjected to dust, air, and shear forces that can increase the chances for merger. This is supported by the observation that during reinjection of the emulsion there were occasional large merged drops, and also that the picoinjected emulsion was somewhat polydisperse, as shown in FIG. 31. Nevertheless, even under these rough conditions, the vast majority of drops displayed no multiplexing, indicating that they retained their integrity as distinct reactors.

From these studies, it was demonstrated that picoinjection is compatible with droplet digital RT-PCR and affords single RNA molecule detection rates equivalent to workflows not incorporating picoinjection. This showed that picoinjection is compatible with reactions involving common biological components, like nucleic acids, enzymes, buffers, and dyes. It was also observed that there was negligible transfer of material between drops during picoinjection. These results support picoinjection as a powerful and robust technique for adding reagents to drops for ultrahigh-throughput biological assays.

Example 6: Single Cell RT-PCR Microfluidic Device

FIG. 32 shows one embodiment of a single cell RT-PCR microfluidic device as provided herein. The cells of interested were first encapsulated in drops with lysis reagent including proteases and detergents and incubated offline. These drops were then introduced into this device and spaced by oil using an input microchannel and a flow focus drop maker for introducing microdroplets (Panel A). In a pairing microchannel, the spaced drops were then paired with large drops containing a dilution buffer that were created by a dilution buffer drop maker in fluidic communication with the pairing microchannel (Panel B). The big and small drops were then merged in a merging microchannel with an electric field (Panel C), adding the contents of the small drop to the large drop. The merged drops passed through mixing microchannels and then a small portion was sampled from them by a drop sampler (Panel D). The small portion was then passed by a picoinjection microchannel where the small portion was then picoinjected with the RT-PCR reagent (Panel E). The drops were then thermocycled for the RT-PCR reaction.

This system facilitated single cell RT-PCR because it allowed for the performance of the cell lysis and protein digestion in one step (not shown) and subsequent dilution of the lysate in the drop prior to addition of the RT-PCR reagent. Without the dilution, the lysate could have inhibited the RT-PCR reaction.

The device worked robustly, at least in part, because the timing of each microfluidic component was set by the periodicity of the large drop maker making the dilution drops. Without this periodic drop formation, the device might operate less stably and potentially produce polydisperse drops.

Figure 33:
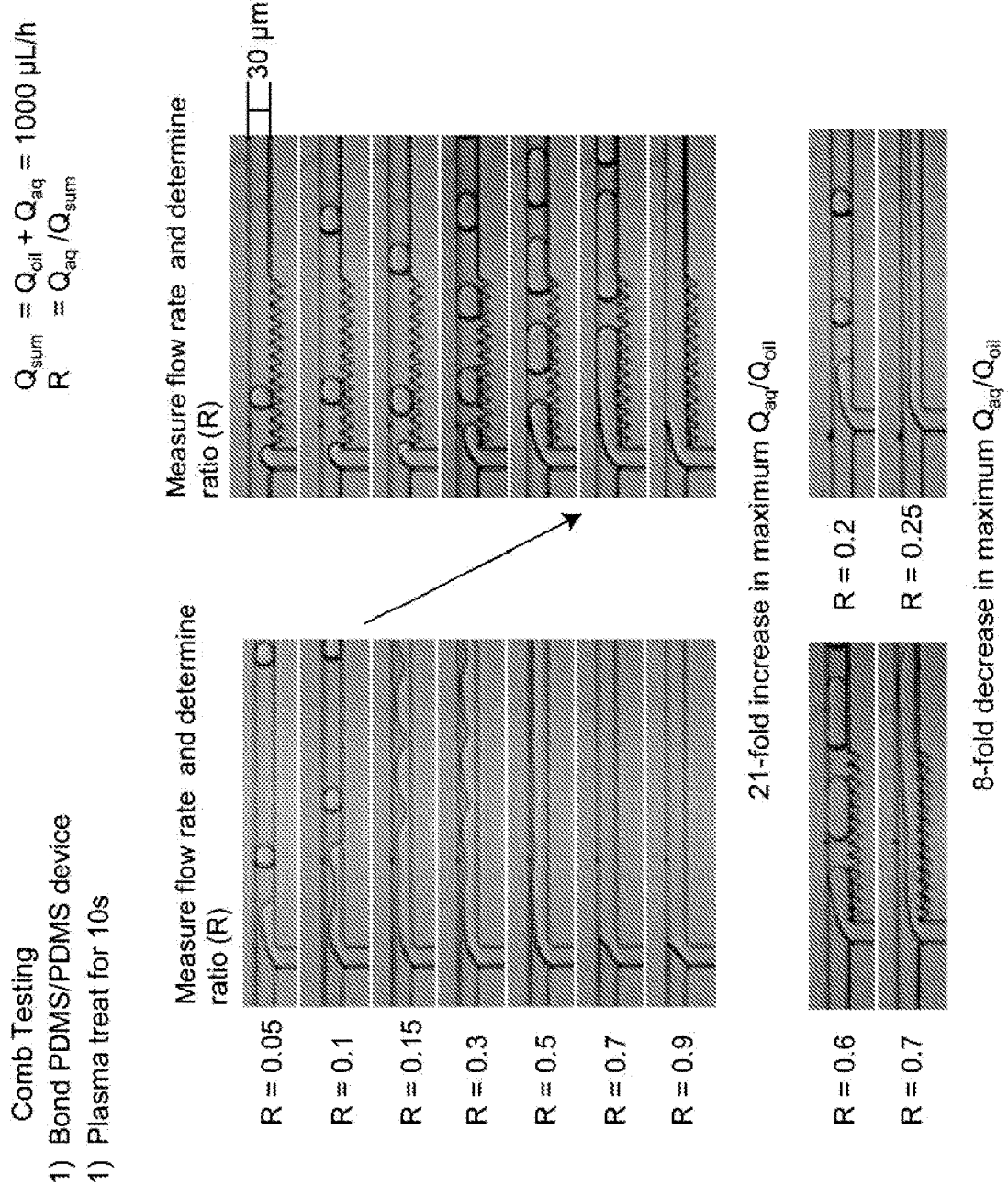
FIG. 33 shows the effect of including ridge structures in a microfluidic device channel downstream of a droplet forming junction. A T-junction drop maker without ridges is shown to the left. As the flow rate ratio is increased, the drop maker stops forming drops and instead forms a long jet. This is due to the jet wetting the channel walls and adhering, preventing the formation of drops. On the right, a similar T-junction is shown with ridge structures. The ridges trap a suitable phase, e.g., a hydrophobic oil phase, near the walls, making it difficult for the aqueous phase to wet. This allows the device to form drops at much higher flow rate ratios before it eventually wets at R=0.9. This shows that inclusion of the ridges allows the drop maker to function over a much wider range than if the ridges are omitted. The channel widths are 30 microns and the peaks of the ridges are about 5-10 microns. The top and bottom sets of images correspond to experiments performs with different microfluidic devices.

Example 7: Testing of Microfluidic Droplet Forming Devices Utilizing Channels Including Ridges T-junction drop makers with and without channel ridges positioned downstream of the T-junction were tested to determine the effect of including such ridges on droplet formation performance. The channel widths were about 30 microns and the width of the ridge peaks were from about 5 to about 10 microns. See FIG. 33.

PDMS microfluidic devices were prepared generally as described herein and plasma treated for 10 seconds. The flow rate ratio was monitored, wherein the sum ($Q_{sum}$) of individual flow rates ($Q_{oil}+Q_{aq}$) was approximately 1000 µl/hr, and the ratio (R)=$Q_{aq}/Q_{sum}$, and droplet formation was visualized.

As the flow rate ratio was increased for the device lacking ridges, the drop maker stopped forming drops and instead formed a long jet. Without intending to be bound by any particular theory, it is believe that this was due to the jet wetting the channel walls and adhering, preventing the formation of drops. See FIG. 33, left side. For the device which included the ridges, the ridges successfully trapped oil near the walls, making it difficult for the aqueous phase to wet. This allowed the device to form drops at much higher flow rate ratios before it eventually wet at R=0.9. This demonstrated that the ridges allow the drop maker to function over a much wider range than would be possible without the ridges. The top and bottom sets of images in FIG. 33 correspond to experiments performs with different devices. When the experiment was performed with the first pair of devices, a 21-fold increase in maximum $Q_{aq}/Q_{oil}$ was achieved. When the same experiment was performed with a second set of devices, an 8-fold increase in maximum $Q_{aq}/Q_{oil}$ was achieved. This discrepancy may be attributed to experimental variability because the wetting properties that lead to jetting are somewhat unpredictable, hysteretic, and prone to variability.

Example 8: Fabrication and Testing of Liquid Electrodes

Many microfluidic devices utilize metal electrodes to create electric fields when such fields are called for in a particular microfluidic device application. However, there may be disadvantages to using such metal electrodes including an increased number of fabrication steps and the potential for failure of the electrodes.

Advantageously, the present disclosure describes the fabrication and use of liquid electrodes, which simplify the fabrication process and provide similar and/or improved capabilities relative to metal electrodes.

Figure 34:
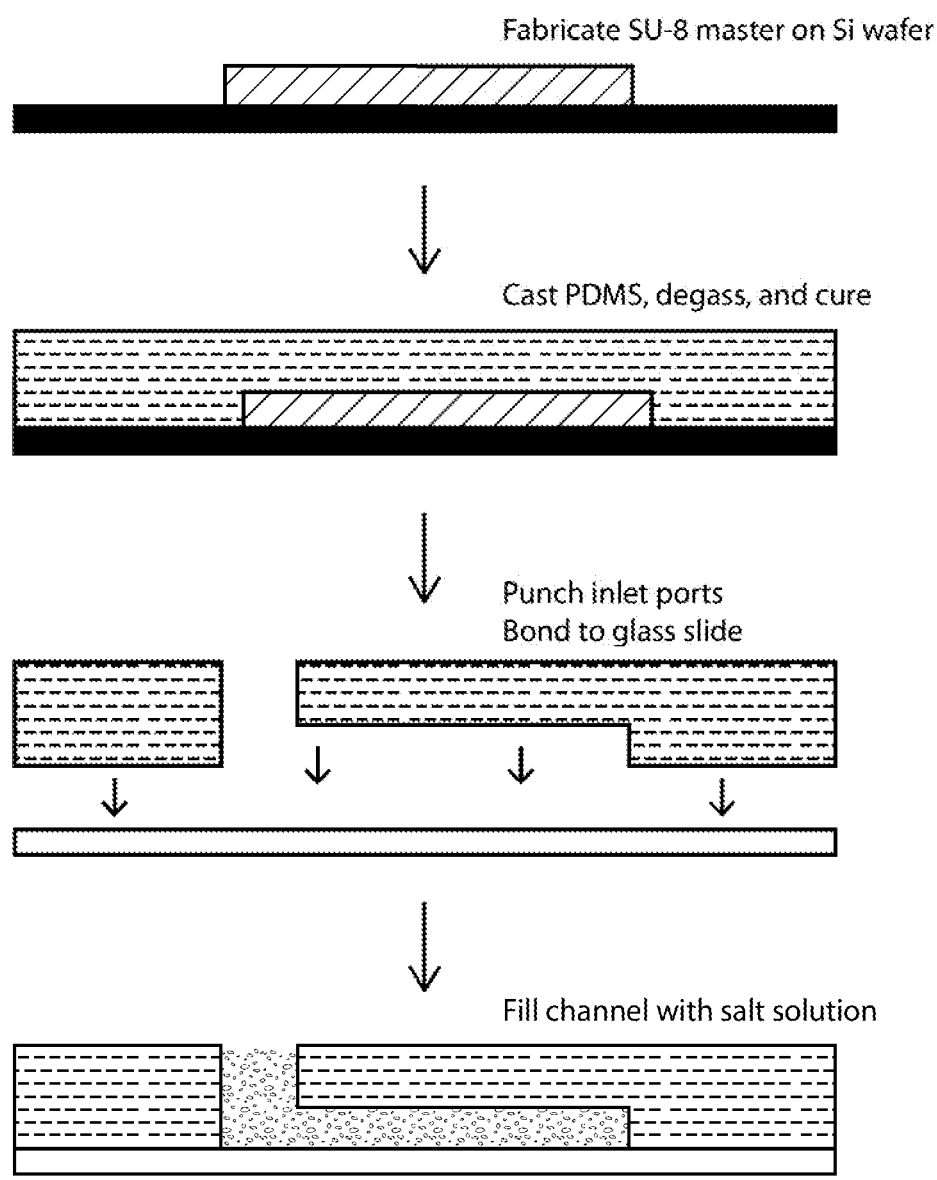
FIG. 34 provides a flow diagram showing a general fabrication scheme for an embodiment of a liquid electrode as described herein.
Figure 35:
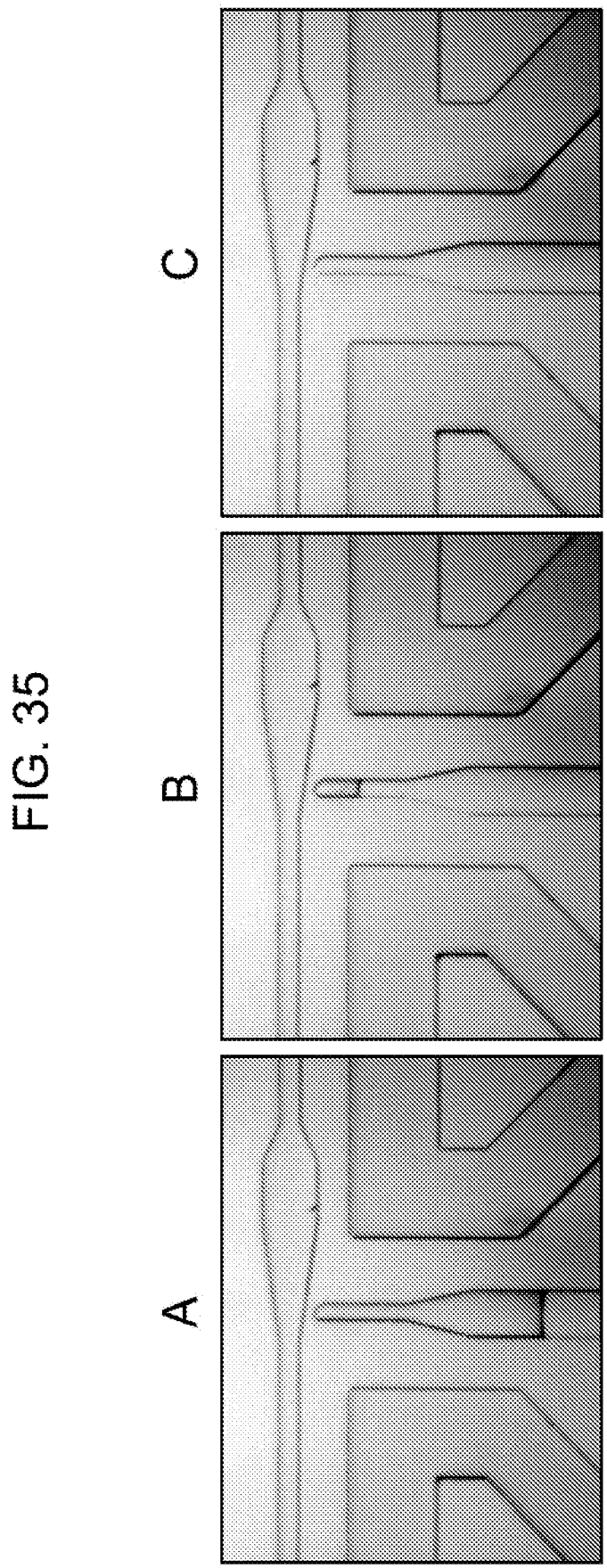
FIG. 35 provides a sequence of three images taken at different times as an electrode channel is being filled with salt water (time course proceeds from left to right; Panels A-C). The salt water is introduced into the inlet of the channel and pressurized, causing it to slowly fill the channel. The air that is originally in the channel is pushed into the PDMS so that, by the end, it is entirely filled with liquid.

FIG. 34 provides an overview of an exemplary liquid electrode fabrication method. Initially, an SU-8 photoresist master was fabricated on an Si wafer (A). PDMS was then cast, degassed and cured (B). Inlet ports were punched in the PDMS, and the PDMS was bonded to a glass slide (C). Finally, the channel was filled with a NaCl solution. FIG. 35 provides a sequence of three images taken at different times as an electrode channel was being filled with salt water (time course proceeds from left to right). The salt water was introduced into the inlet of the channel and pressurized, causing it to slowly fill the channel. The air that was originally in the channel was pushed into the PDMS so that, by the end, it was entirely filled with liquid.

Figure 36:
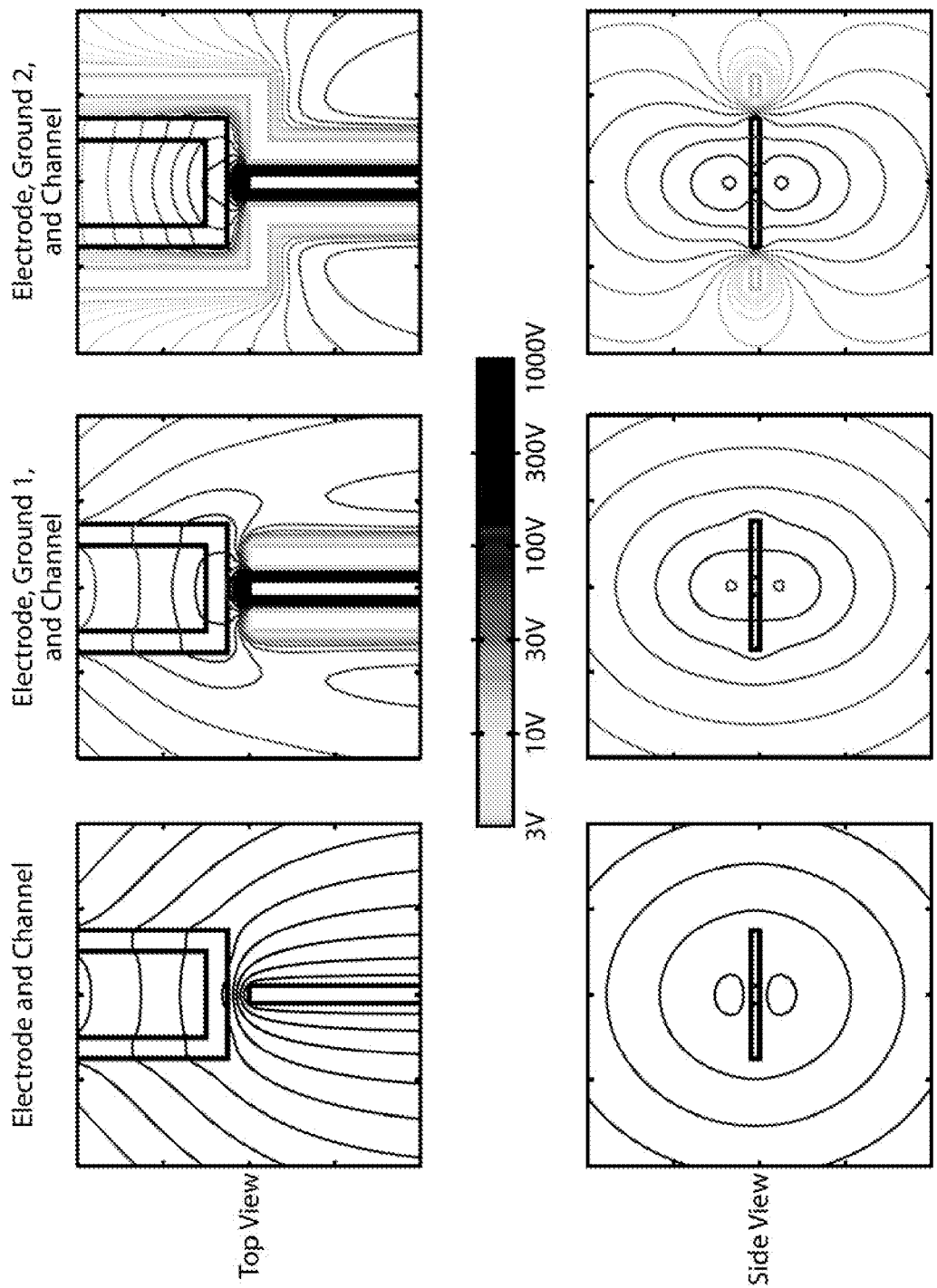
FIG. 36 shows electric field lines simulated for various liquid electrode configurations. The simulations are of positive and ground electrodes showing equipotential lines for three different geometries.

Electric field lines for various liquid electrode configurations were simulated as shown in FIG. 36. The simulations are of positive and ground electrodes showing equipotential lines for three different geometries.

Figure 37:
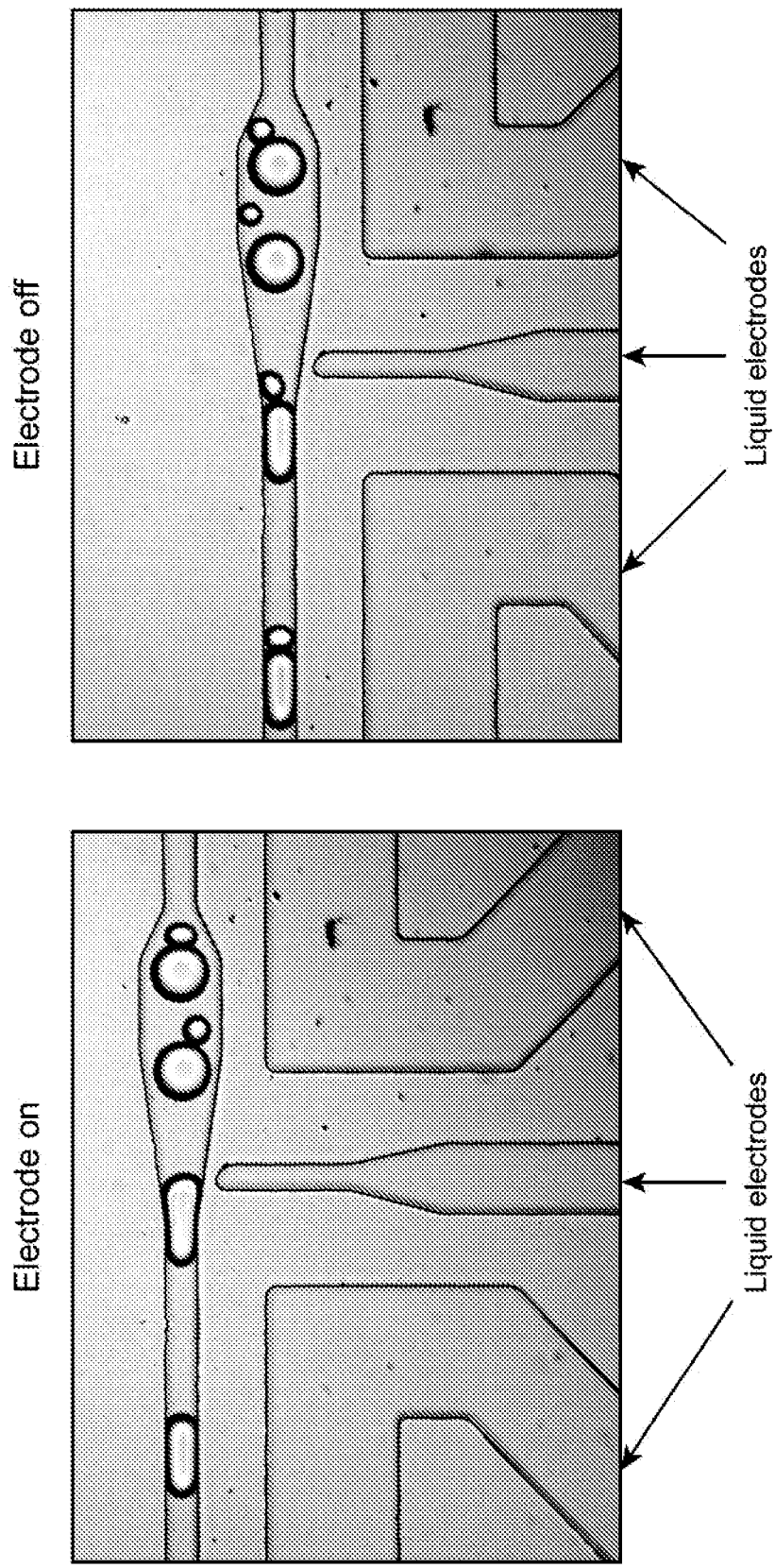
FIG. 37 provides two images of a droplet merger device that merges large drops with small drops utilizing liquid electrodes. To merge the drops, an electric field is applied using a salt-water electrode. When the field is off, no merger occurs (right) and when it is on, the drops merge (left).

The liquid electrodes were capable of merging drops through application of an electric field as shown in FIG. 37, which provides two images of a droplet merger device that merges large drops with small drops utilizing liquid electrodes. To merge the drops, an electric field was applied using a salt-water electrode. When the field was off, no merger occurred (right) and when it was on, the drops merged (left).

Example 9: PCR Analysis and FACS Sorting of *Azopira/E. coli* Mixture

Figure 52:
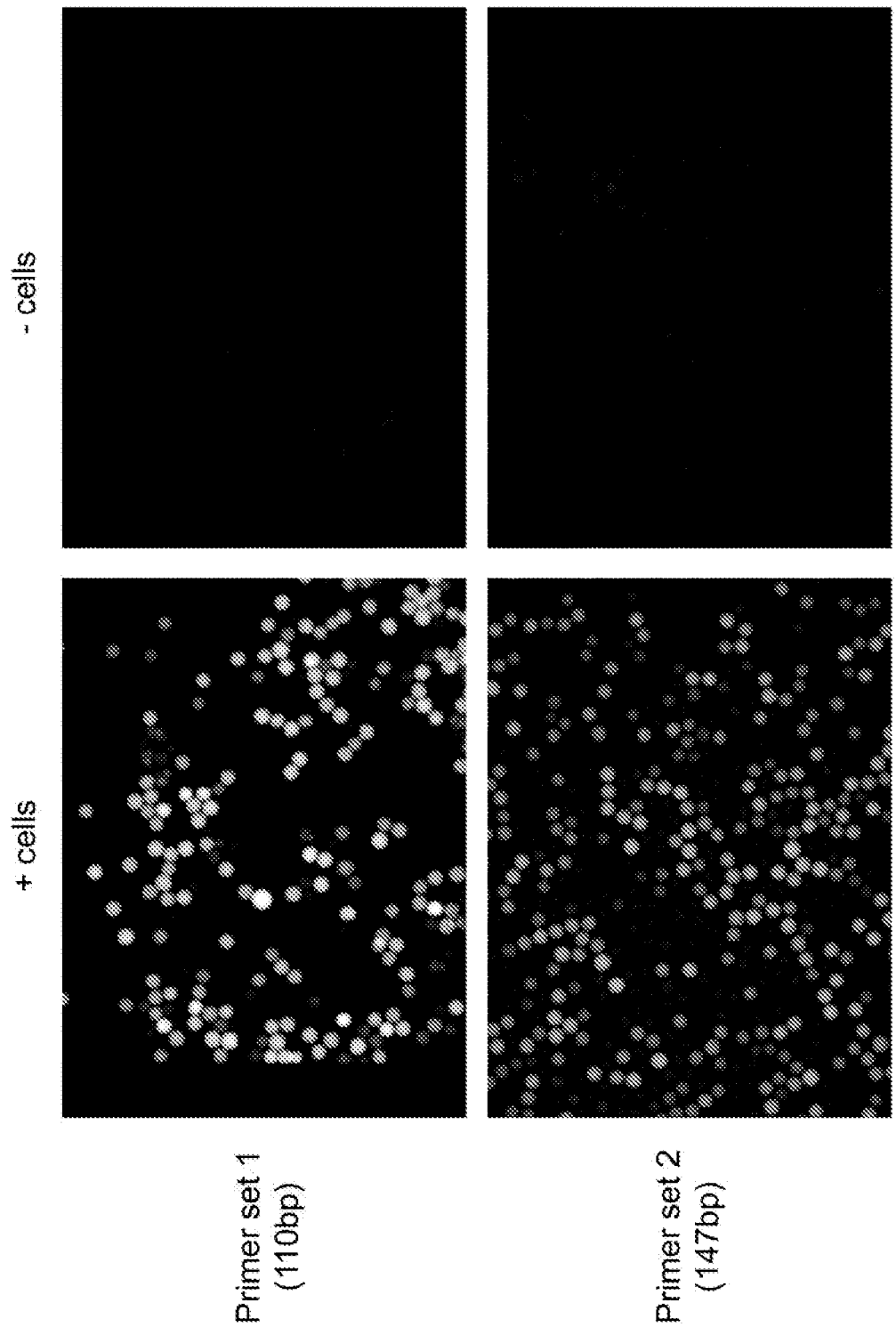
FIG. 52 provides images showing drops in which a TaqMan® PCR reaction has been performed with encapsulated Azospira. The upper images correspond to a reaction in which a 110 bp amplicon was produced, whereas the lower images correspond to a 147 bp amplicon.
Figure 53:
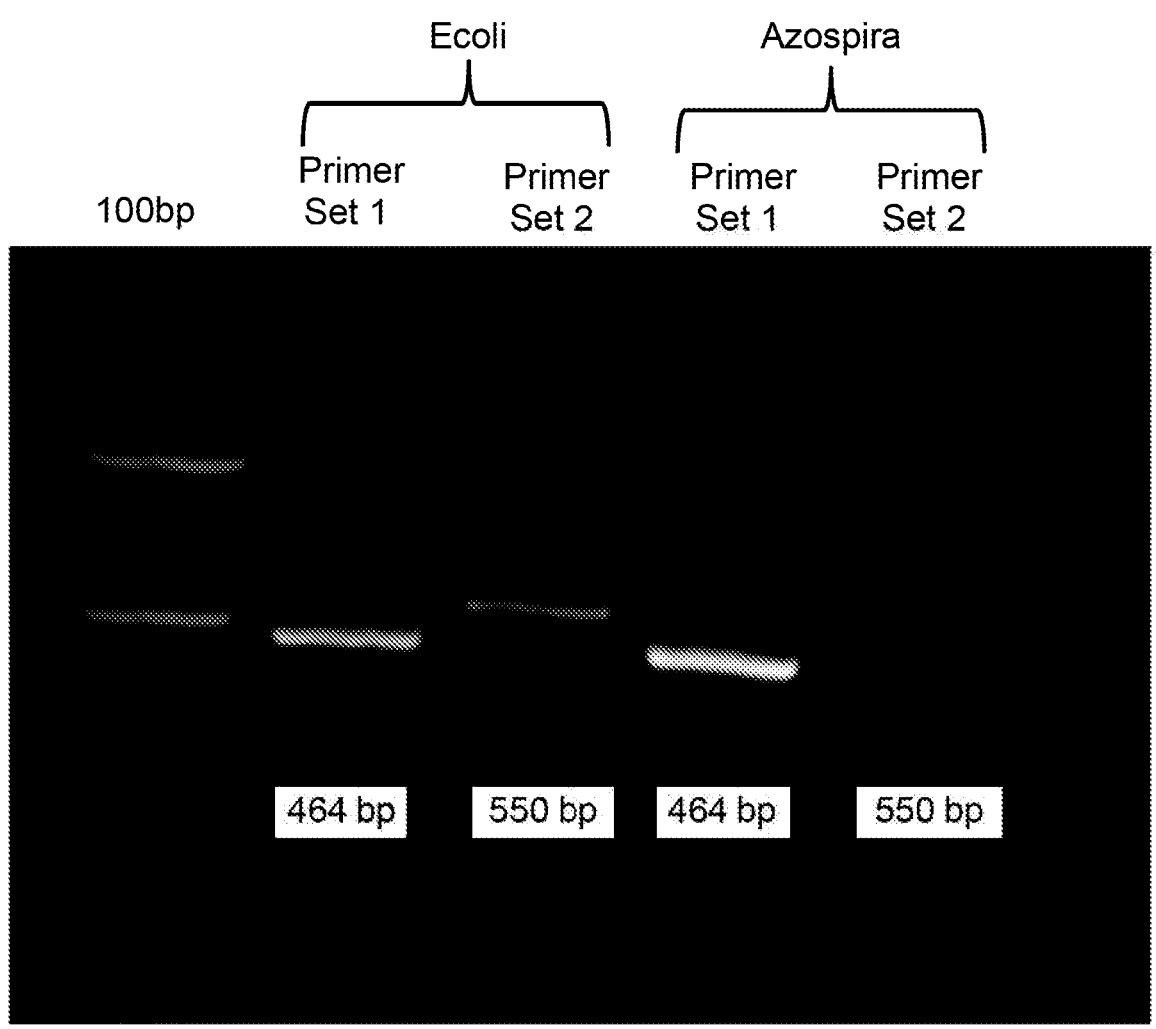
FIG. 53 shows a picture of a gel showing bands corresponding to the amplicons of two TaqMan® PCR reactions, one for a 464 bp amplicon and one for a 550 bp amplicon.
Figure 54:
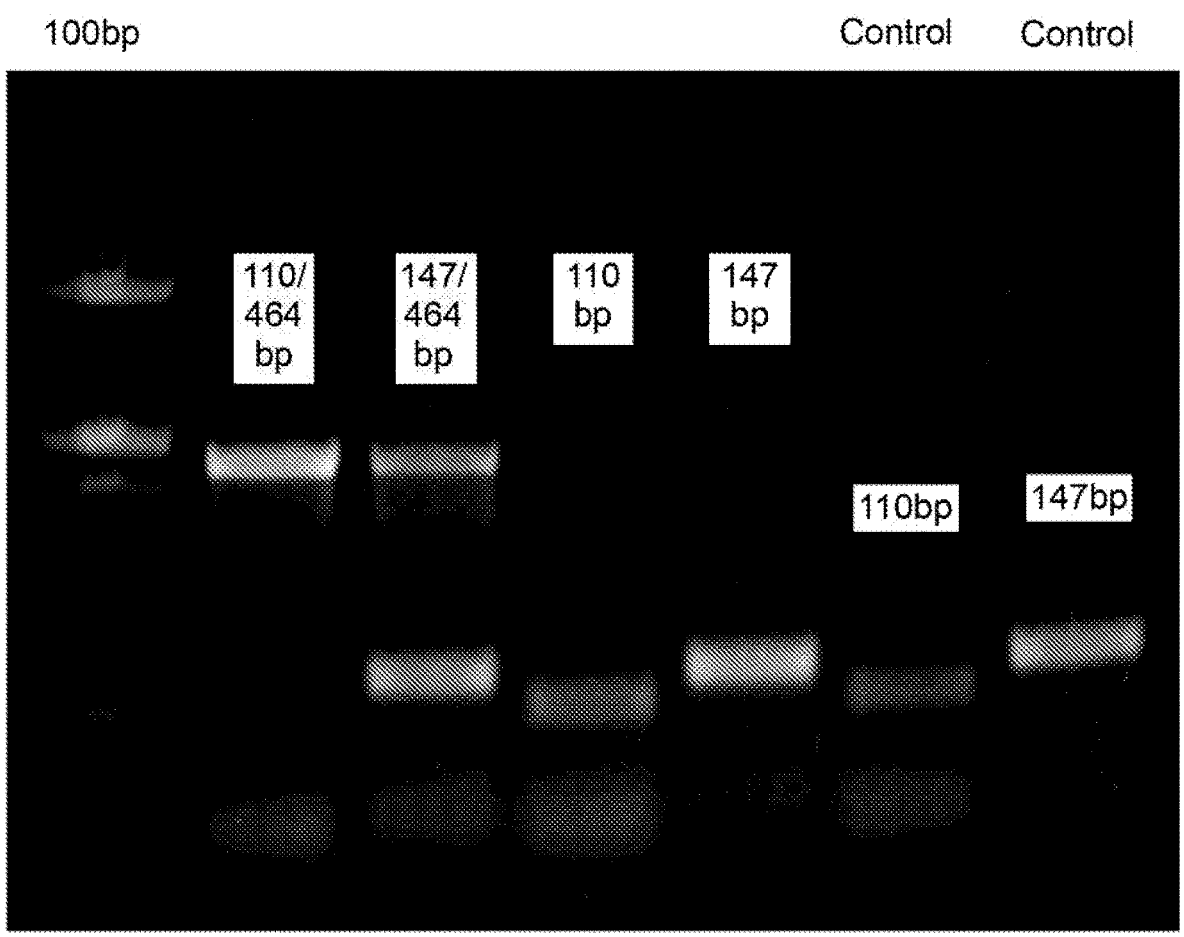
FIG. 54 shows a picture of a gel validating that PCR reactions can be multiplexed by adding multiple primer sets to a sample containing bacteria.
Figure 55:
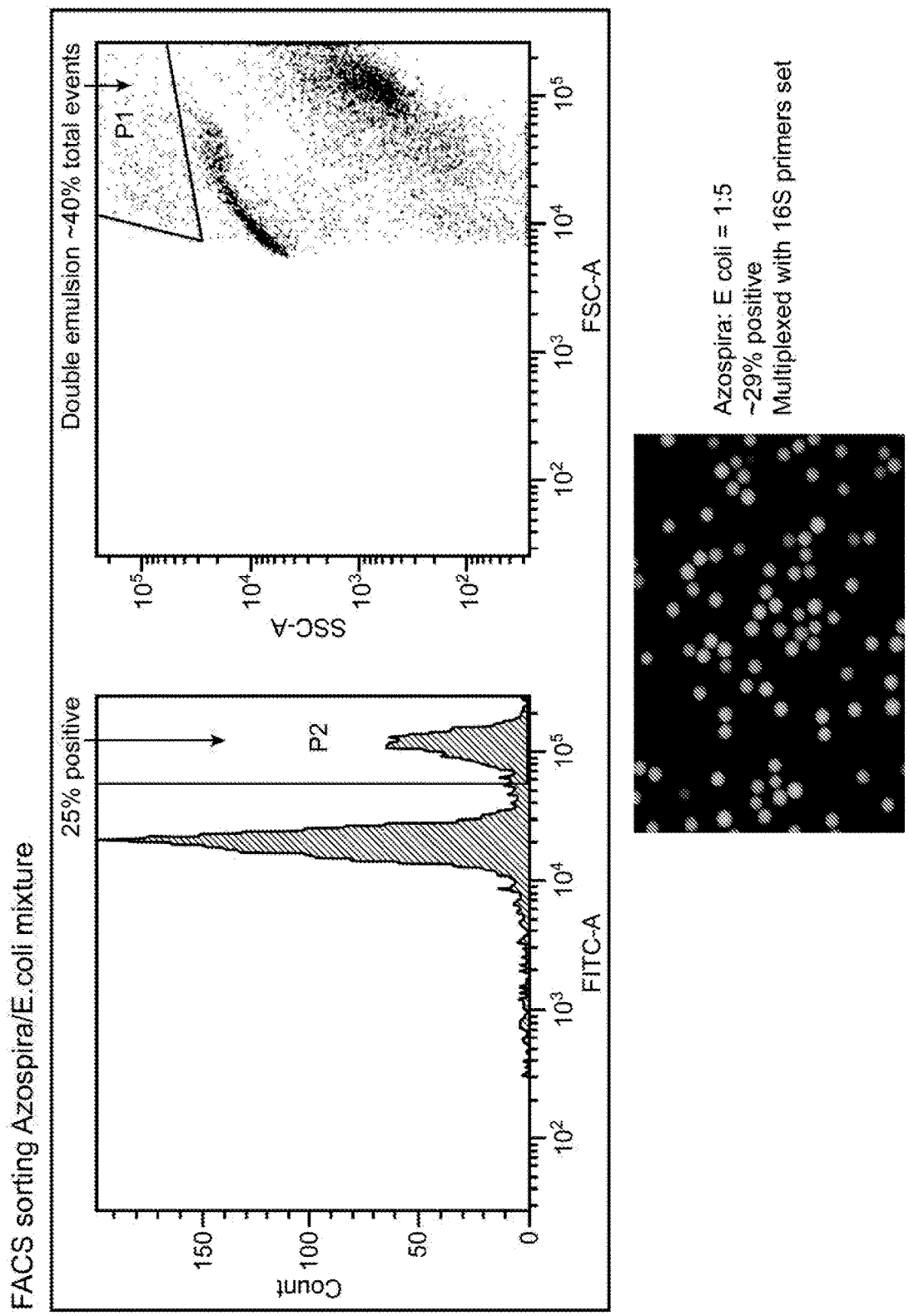
FIG. 55 shows results for the PCR amplification of Azospira amplicons (left) and FACS analysis of Azospira containing double emulsions (right).

Two different species of microbes, Azospira and *E. coli*. Were encapsulated in microdrops. In-droplet PCR was performed using TaqMan® and primers for Azospira and/or *E. coli*. FIG. 52 provides images showing drops in which a TaqMan® PCR reaction was performed with encapsulated Azospira. The upper images correspond to a reaction in which a 110 bp amplicon was produced, whereas the lower images to a 147 bp amplicon. FIG. 53 shows a picture of a gel testing 16S primers for Azospira and *E. coli*. The gel shows the bands corresponding to the amplicons of two TaqMan® PCR reactions, one for a 464 bp amplicon and one for a 550 bp amplicon. FIG. 54 provides a picture of a gel validating that the in-droplet PCR reactions can be multiplexed by adding multiple primer sets to a sample containing bacteria. FIG. 55 shows results for an experiment where the TaqMan® reaction had primers and probes only for Azospira, so only the drops containing one of these microbes underwent amplification and became fluorescent, while the empty drops or the ones with *E. coli* remained dim. The emulsion was then encapsulated into double emulsions using a microfluidic device and sorted on FACS. The plots to the right in FIG. 55 show the FACS data. The upper plot shows the scattering cross section plotted as a function of the drop fluorescence. Based on this, a population was gated out by drawing boundaries (shown above), and this population was sorted based on the drop intensity. The gating allowed erroneous events due to small oil drops or dust to be discarded. When looking at only the double emulsions, the population had two distinct peaks which corresponded to the fluorescent and non-fluorescent drops, shown in the lower histogram. An attempt to re-amplify the amplicons created during the in-droplet PCRs was unsuccessful, potentially due to their chemical structure since they may contain analogue bases or due to an inhibitory effect of the carrier oil.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Example 10: Identification and Genetic Analysis of Cancer Cells with PCR-Activated Cell Sorting (PACS)

Prostate cancer cells were identified and sorted from a heterogeneous population as described in greater detail below.

Materials and Methods

Cell Culture and Staining

Human DU145 prostate cancer and Raji B-lymphocyte cell lines were cultured in RPMI 1640 supplemented with 10% FBS, penicillin and streptomycin at 37° C. with 5% $CO_2$. Prior to cell staining, Raji cells were pelleted and washed once in phosphate buffered saline (PBS). Adherent DU145 cells were trypsinized prior to pelleting and washing. Cells were stained in 1 ml Hank's balanced salt solution (HBSS) with 2 µl %/1 Calcein Violet AM or Calcein Green AM for 30 minutes at room temperature. Following staining, cells were washed with PBS and then resuspended in PBS that was density matched with OptiPrep solution prior to encapsulation in microfluidic droplets.

To generate cell suspensions with known ratios of cell types, cell counting and viability analysis was performed on individual cell lines. This was done by combining a 10 aliquot of each cell type with an equal volume of trypan blue and placing the mixture into a chamber slide. Live cell numbers were determined by reading the chamber slides with the Countess Automated Cell Counter (Invitrogen).

Fabrication and Operation of Microfluidic Devices

The poly(dimethylsiloxane) (PDMS) devices were fabricated using standard soft lithographic techniques. Fluid flow was regulated via computer-controlled syringe pumps (New-Era) connected to the PDMS devices with polyethylene tubing. Fluorinated oil (FC40) with 5% PEG-PFPE amphiphilic block copolymer was used to generate the initial microdroplet emulsion. Lysis buffer (100 mM Tris pH 8.0, 2% Tween-20, proteinase K 1.5 mg/mL) was introduced at the time of cell encapsulation using a co-flow drop maker to prevent premature rupture of cells.

Microdroplet TaqMan RT-PCR

Amplification primers for the vimentin RT-PCR reactions were as follows: Primer1 5'-GTGAATCCAGATT-AGTTTCCCTCA-3' (SEQ ID NO:10), Primer2 5'-CAA-GACCTGCTCAATGTTAAGATG-3' (SEQ ID NO:11); The sequence of the vimentin TaqMan probe was: 5'-HEX/CGCCTTCCA/ZEN/GCAGCTTCCTGTA/IABkFQ-3' (SEQ ID NO:12). TaqMan reaction primers and probes were purchased as a pre-mixed assay from Integrated DNA Technologies (IDT). Superscript III reverse transcriptase and Platinum Taq DNA polymerase (Invitrogen) were used for the microdroplet single-cell TaqMan reactions. Thermocycling conditions were 50° C. for 15 min followed by 93° C. for 2 min and 45 cycles of: 92° C., 15 s and 60° C., 1 min. Thermocycled droplets were either imaged on a fluorescent microscope to confirm specificity of TaqMan reactions or transferred to a 1 ml syringe and reinjected into a microfluidic droplet sorter.

Ultrahigh-Throughput Detection and Sorting of Droplets

Droplets were sorted dielectrophoretically using custom LabVIEW code controlling an FPGA card (National Instruments). Two lasers (405 and 532 nm) were focused onto the channel upstream of the sorting junction, allowing the droplets to be scanned for fluorescence. The FPGA card analyzed the emitted fluorescence measured with spectrally-filtered PMTs (Hamamatsu Photonics) and outputted a train of 1 kV, 30 kHz pulses to the microfluidic electrode via a high voltage amplifier (Trek) to direct appropriate droplets into a collection channel. Droplets that had merged prior to sorting were measurably large and automatically discarded. During detection, the average HEX and calcein violet fluorescence of each droplet were recorded and plotted with MATLAB code. To quantify sorting efficiency, sorted droplets were analyzed with MATLAB code which identified droplets based on their circular boundary in brightfield images and then measured their fluorescence in the associated epifluorescence images.

DNA Sequencing of PACS-Sorted Genomic DNA

Following collection of sorted droplets, emulsions were broken using perfluoro-1-octanol and the aqueous fraction was diluted in 10 mM Tris pH 8.0. The aqueous layer containing the pooled cellular lysate was then purified using a DNeasy Blood and Tissue Kit (Qiagen). CDKN2A and RB1 were PCR amplified from gDNA isolated from both pre-sorted and vimentin sorted emulsions. Amplicons were analyzed on agarose gels and extracted with a Qiagen Gel Extraction kit. 50 ng of gel extracted DNA was sent for Sanger sequencing and the data was analyzed on 4Peaks sequencing and chromatogram analysis software.

For next-generation sequencing, 1 ng of each amplicon was subsequently used for sequencing library preparation using the Nextera XT library kit (Illumina). Sequencing was done on a HiSeq2500 sequencer with 50 bp reads. Each library was indexed with a barcode and reads were automatically partitioned post sequencing. Next-generation sequence analysis was performed using the Galaxy web-based platform. The workflow consisted of quality checking sequence data with FASTQ Groomer, mapping the data to a reference sequence with Bowtie, converting the mapped data to a SAM file and then generating a pileup of the sequence data. Pileup data was analyzed for the presence of Raji or DU145-specific SNPs at the relevant positions. More than 15,000 base reads were analyzed for RB1 and CDKN2A SNP positions from both the pre-sorted and vimentin-positive PACS amplicon libraries.

Quantitative RT-PCR Analysis of PACS-Sorted RNA

After breaking the emulsions with perfluoro-1-octanol, aqueous fractions from the droplets were collected and purified on an RNA binding column (Qiagen). Following elution, the extracted RNA was analyzed with TaqMan RT-PCR assays (Integrated DNA Technologies). Amplification reagents were from the SuperscriptIII One-Step RT-PCR System (Invitrogen). Three replicates were performed for each reaction and GAPDH was used to verify that equal amounts of RNA were used in each of the CD9 reactions. Quantitative reactions were carried out using an MX3005p Real-Time PCR System (Stratagene). Normalized fluorescence values from the instrument were plotted using Prism software. For control reactions, total RNA was first isolated from Raji and DU145 cell lines using an RNeasy purification kit (Qiagen). 80 ng of total RNA was used as template for each qRT-PCR reaction. Differences in expression levels were calculated using normalized Ct values obtained from the amplification plots.

Results

PACS Workflow

Figure 56:
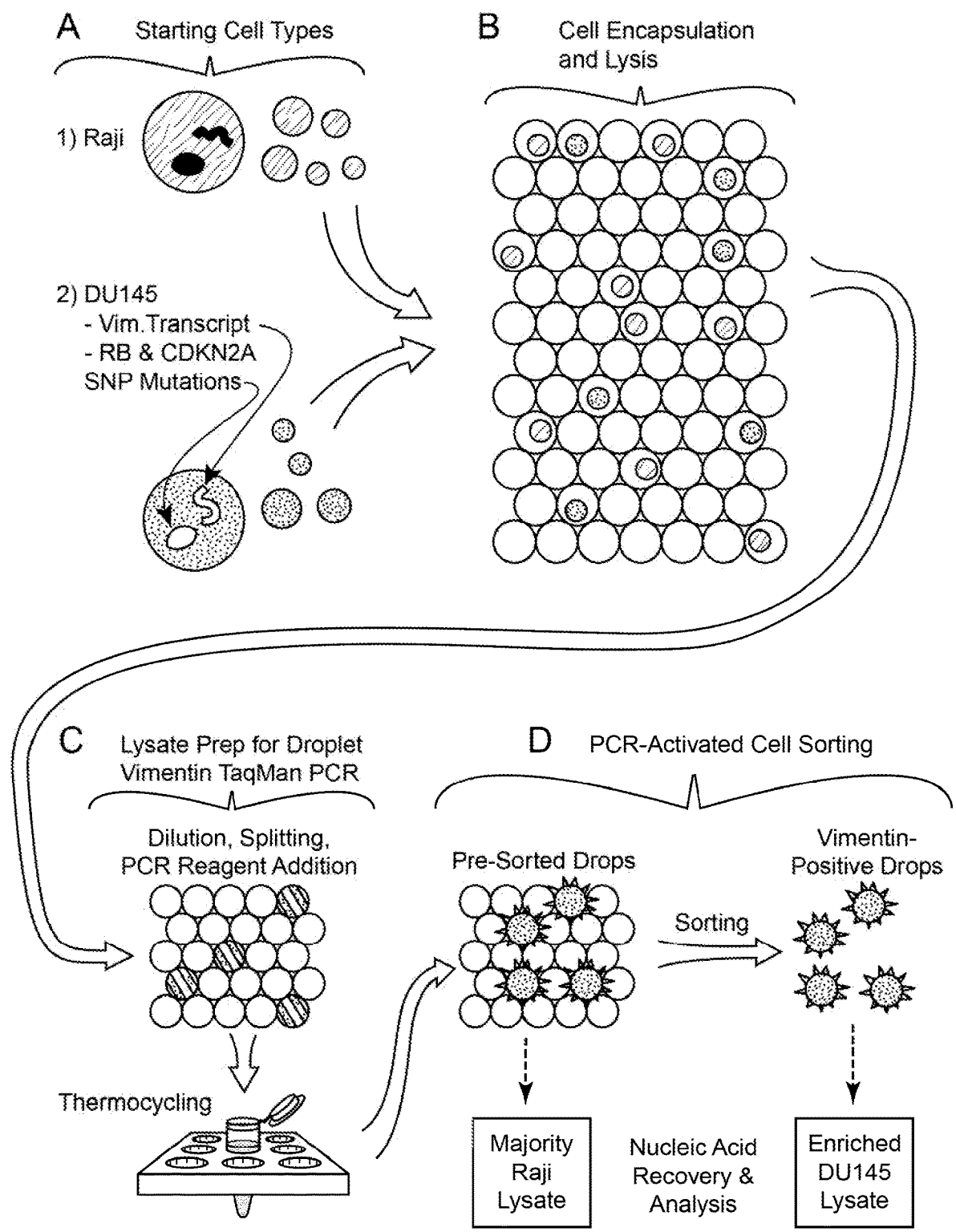
FIG. 56, Panels a-d, show a workflow for PCR-activated cell sorting according to certain embodiments. Although specific cell types and reagents are listed, these are for purposes of illustration only and are not intended to be limiting.

Factors weighing against the effective sorting of cells using TaqMan PCR as an assay readout include both the difficulty of preparing and handling stable, single-cell containing droplets and also lysate-mediated inhibition of the reaction in subnanoliter volumes. Development of a robust microfluidic workflow that maintains compartmentalization of single-cell lysates at all times while also overcoming mammalian cell lysate-mediated inhibition of PCR has contributed to the PACS method described herein. Cells are first encapsulated in aqueous droplets with Tween-20 and proteinase K lysis reagents (FIG. 56, Panels A and B). The compartmentalized lysates of single cells are then diluted by droplet merger and TaqMan RT-PCR reagents added by droplet picoinjection (FIG. 56, Panel C). The droplets, now prepared for efficient, uninhibited single-cell TaqMan RT-PCR, are collected and thermocycled for amplification to identify cells expressing target transcripts. This technique has been used to achieve a single-cell RT-PCR throughput of 47,000 mammalian cells. Additionally, this approach is highly specific, enabling the unambiguous detection of Raji cells in a mixed suspension containing PC3 cancer cells. To enable lysate recovery of cells positive for the nucleic acid biomarker, sorting of the microfluidic droplets was implemented based on the presence of the fluorescent signal produced from the TaqMan reaction (FIG. 56, Panel D). TaqMan positive droplets containing cell lysate of interest are then collected and the nucleic acids extracted for downstream sequencing.

Vimentin-Based Prostate Cancer Cell Detection

TaqMan PCR assays offer single molecule sensitivity and can be precisely targeted to a wide variety of gene transcripts, making them ideal for distinguishing between and sorting cells. To demonstrate the utility of PACS-based TaqMan PCR to identify specific cells in a heterogeneous population, expression of vimentin was targeted in DU145 prostate cancer cells spiked into Raji B-lymphocyte-derived cells. Vimentin is an intermediate filament protein known to participate in epithelial-to-mesenchymal transitions and can serve as a biomarker for some cancer cell types. It is robustly expressed in DU145 cells, but not in Raji cells. The Raji cells thus serve as both an essential control for the specificity of the TaqMan reactions and as a more abundant "background" cell type to assess the effectiveness of PACS enrichment of DU145 cells.

To measure the specificity and detection rate of PACS sorting based on vimentin expression, DU145 cells were labeled with calcein violet and Raji cells with calcein green viability stains. The vimentin TaqMan probe was labeled with HEX fluorescent dye having minimal spectral overlap with the calcein dyes. This three-color detection strategy enabled the correlation of vimentin mRNA detection with the presence of a specific cell type, and thereby measurement of the rate at which droplet TaqMan PCR was able to correctly distinguish between cells.

Figure 57:
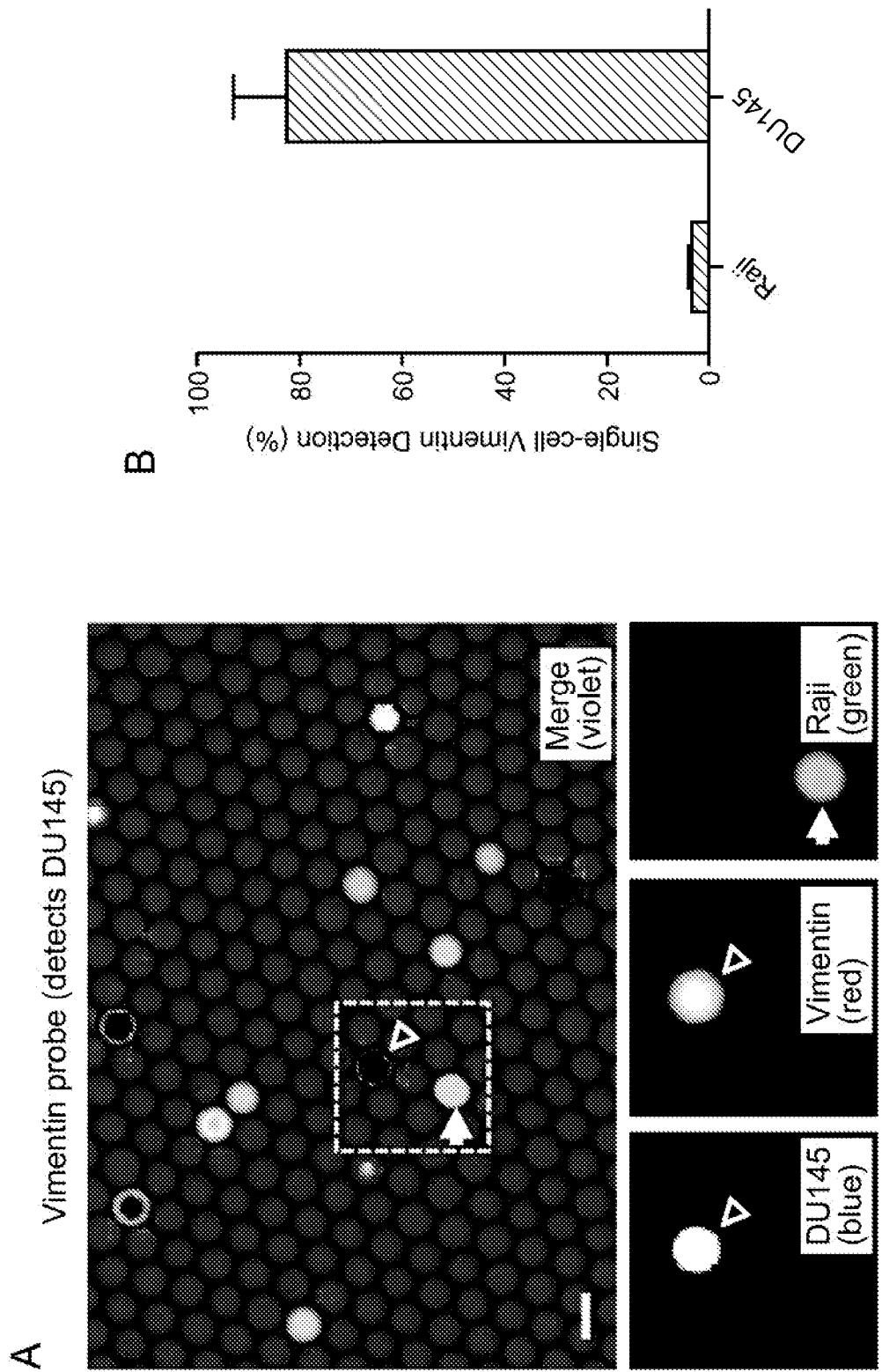
FIG. 57, Panels a-b, show single-cell vimentin TaqMan assays that are specific for DU145 cancer cells according to certain embodiments.
Figure 58:
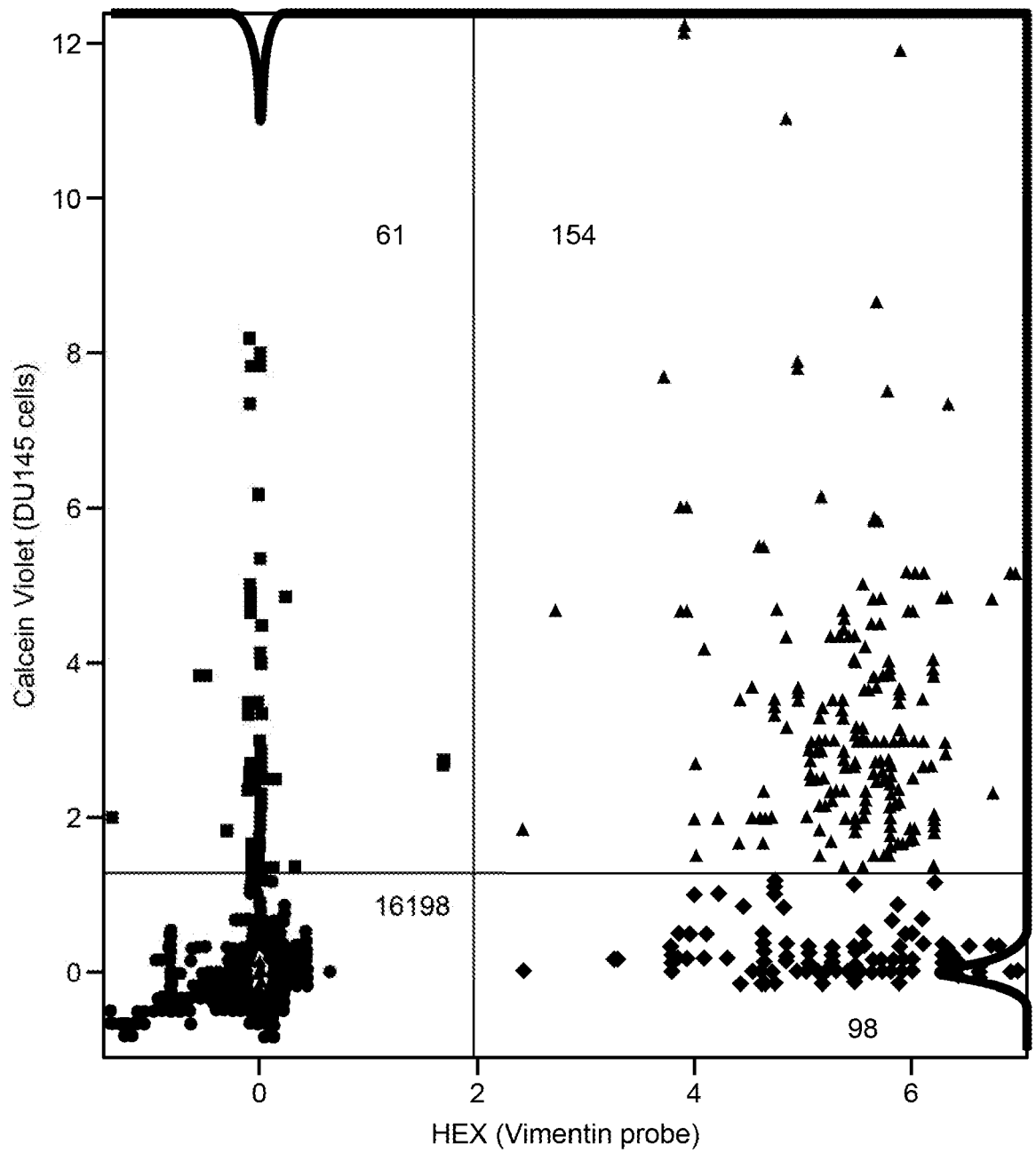
FIG. 58, Panels a-d, depicts correlation analysis between calcein violet and green cell stains according to certain embodiments.
Figure 58:
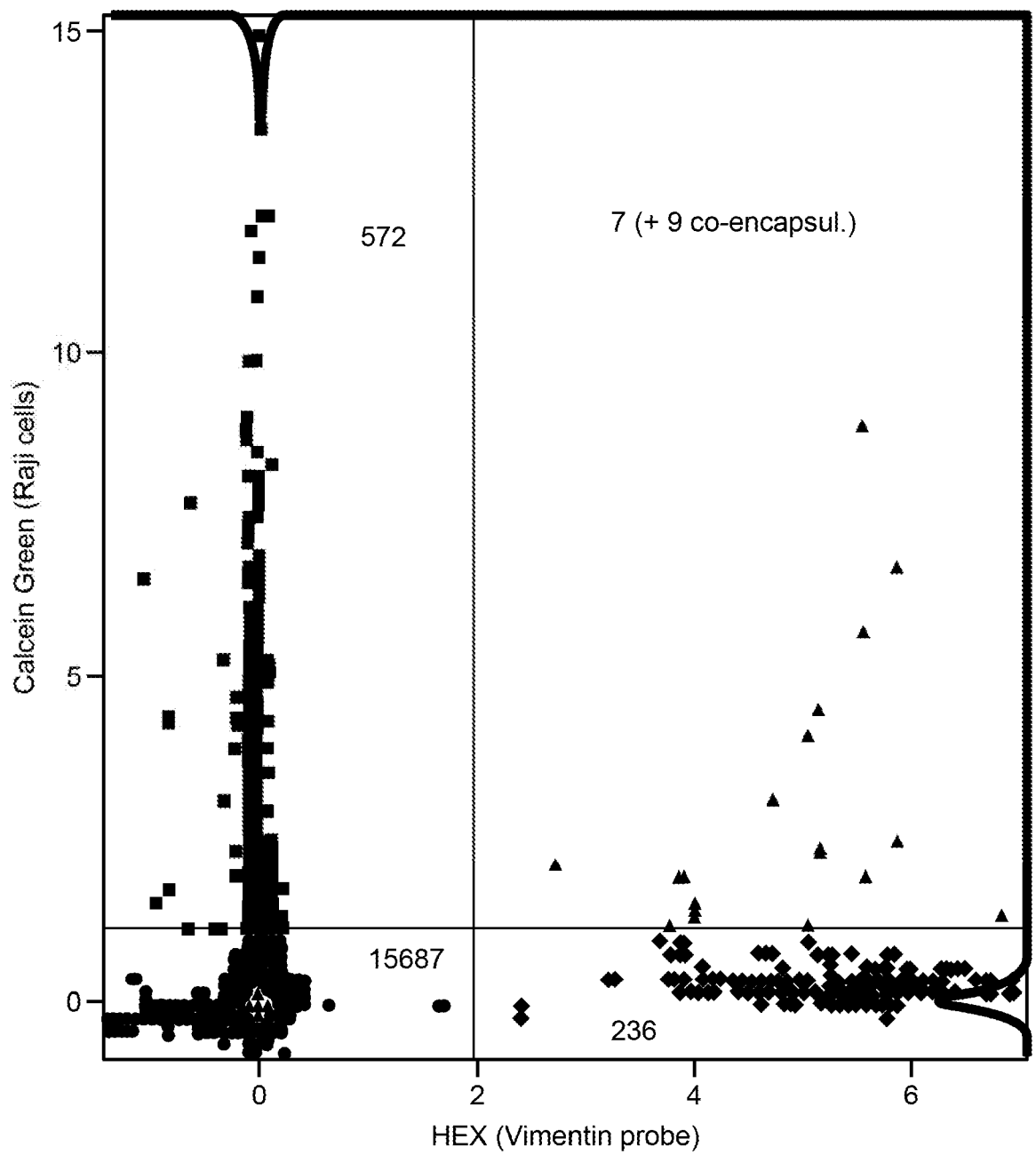
Figure 58:
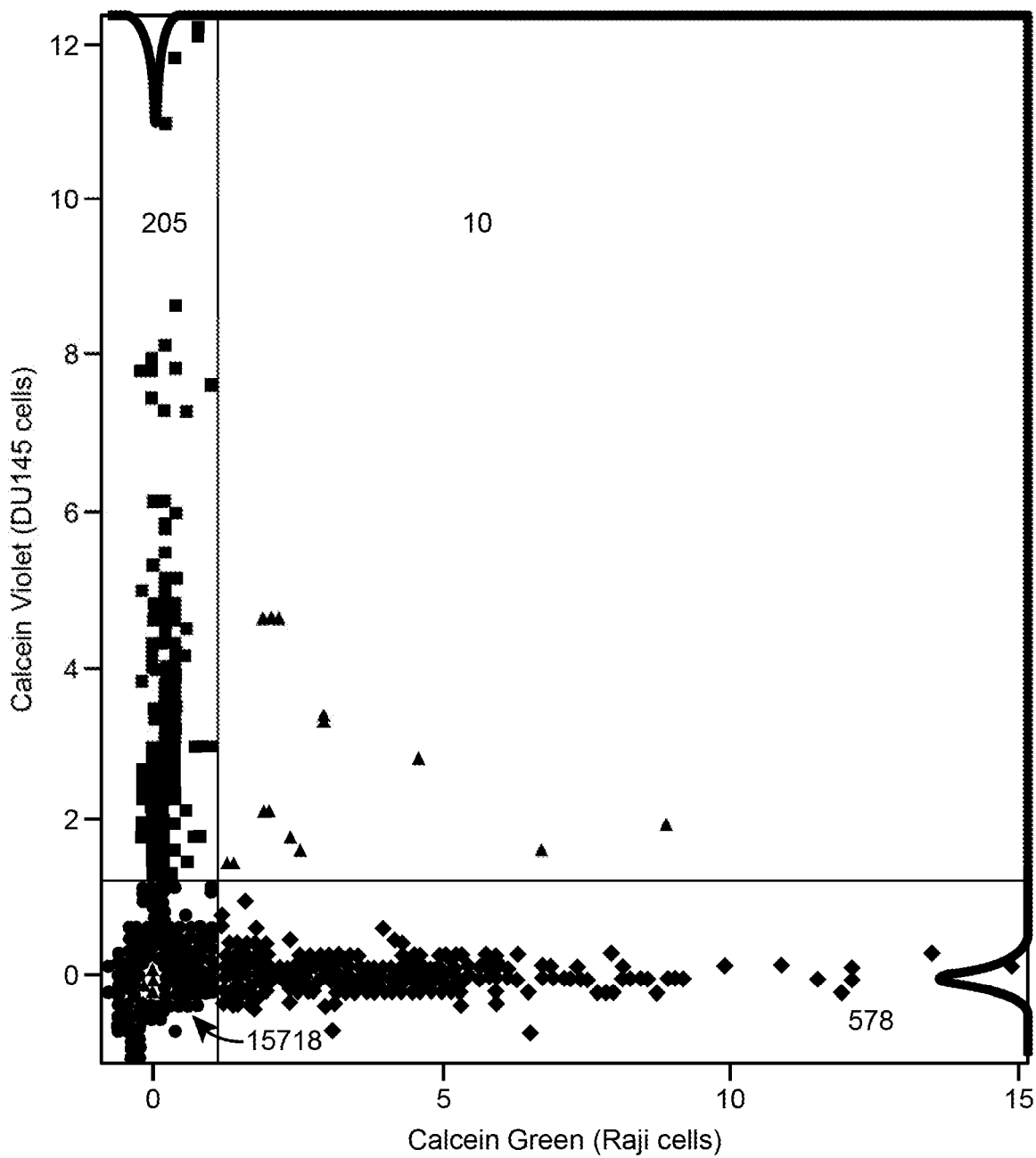
Figure 58:
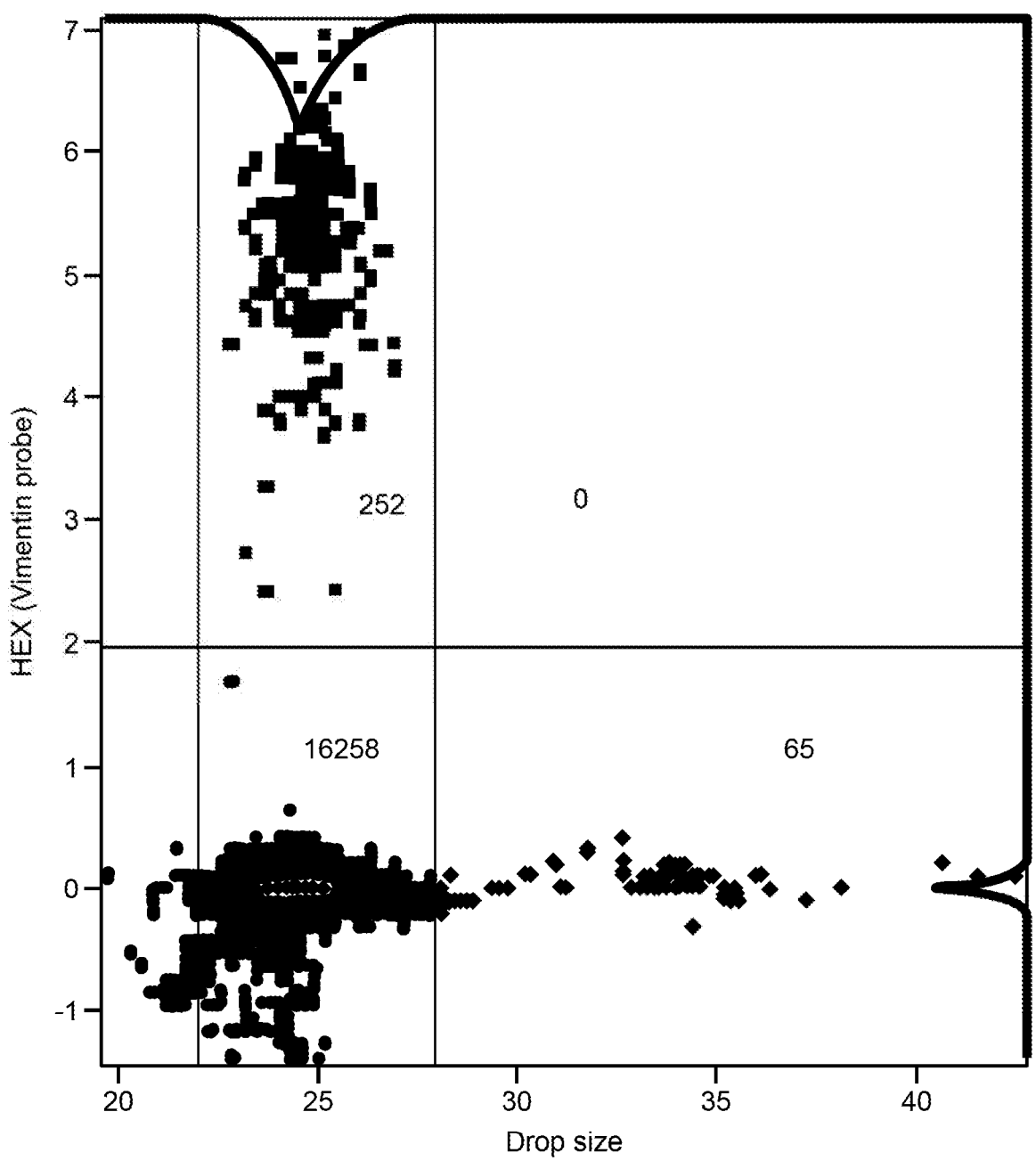

Calcein-labeled DU145 and Raji cells were mixed in roughly equal ratios and encapsulated in droplets for lysis. The droplets were then processed on the disclosed microfluidic system to prepare them for RT-PCR and add TaqMan reagents. Following droplet collection and thermocycling, the droplets were imaged on a fluorescence microscope to measure the intensities of the channels corresponding to the calcein dyes and HEX TaqMan probe (FIG. 57, Panel a). The images were subsequently analyzed using a custom MATLAB script to measure the correlation between the two calcein dyes and the TaqMan probe signal (FIG. 58, Panels a-d). This enabled determination of the percentage of Raji and DU145 cells detected with the vimentin TaqMan reaction (FIG. 57, Panel b). The detection rate for DU145 cells was 82.3% (+/−15.1) and for Raji cells 3.4% (+/−1.0). Although a low percentage of Raji cells appear to be vimentin-positive, correlation analysis between calcein violet and green cell stains indicates that the majority of these events occur from both Raji and DU145 cells being in the same droplet during cell encapsulation, a result of random Poisson loading (FIG. 58, Panels a-d). The ability to detect multiple transcript types in Raji cells with high efficiency has been demonstrated, indicating that the extremely low number of Raji cells determined to express vimentin is not an artifact of reduced RT-PCR efficiency in the presence of Raji cell lysate. Together, these results demonstrate that vimentin expression is a specific biomarker for DU145 cells compared to Raji cells, and that by interrogating for vimentin it will be possible to identify and recover these cells out of a heterogeneous population.

Enrichment of DU145 Cells Out of a Mixed Population with PCR-Activated Cell Sorting In addition to detecting cells based on nucleic acid analysis, in some embodiments, one of the goals of PACS is to recover the lysates of the positive cells. To demonstrate this capability, another sample was prepared in which DU145 cells were spiked into Raji cells at 20% and 80%, respectively. The cells were then labeled with calcein violet, which acted as a fluorescent indicator for droplets that originally contained a live cell; this internal control allows for the identification of false positive droplets undergoing amplification due to the presence of vimentin transcripts but that did not contain a single cell ("digital background"). Following staining, cells were encapsulated, lysed, and run through the PCR addition device, taking ~4 hours. The droplets were collected, thermocycled, stored overnight at 4° C., and sorted the following day. During sorting, droplets containing cell lysates positive for vimentin expression were recovered by gating. This was accomplished by discarding all droplets which were below the gating thresholds for either the HEX or calcein signals (uncolored, FIG. 59, Panel a) and recovering all droplets above the thresholds for both signals (pseudo-colored purple, FIG. 59, Panel a).

During sorting, statistics were collected on droplet fluorescence. A scatter plot of HEX versus calcein fluorescence reveals that over 132,000 single cells were interrogated and over 1.2 million droplet RT-PCRs were performed, FIG. 59, Panel b. The dashed red lines demarcate the sorting thresholds used to recover positive droplets. Of droplets containing cell lysate, 16.4% were also positive for TaqMan fluorescence (upper-right quadrant, FIG. 59, Panel b). This measured value is in good agreement with the number of DU145 cells expected (16.5%) based on the controlled spike-in value (20%) and the detection rate independently measured in the previous experiment (82.3%, FIG. 57, Panel b). A small fraction of droplets were devoid of calcein stain but nevertheless exhibited TaqMan signal. We have observed and reported this previously and attribute it to free vimentin transcripts released into suspension during cell encapsulation, which is likely due to inevitable cell death during this step 8. These "digital background" droplets are discarded by the sorter, since they fall below the cell stain threshold (vertical dashed line, FIG. 59, Panel b).

Figure 59:
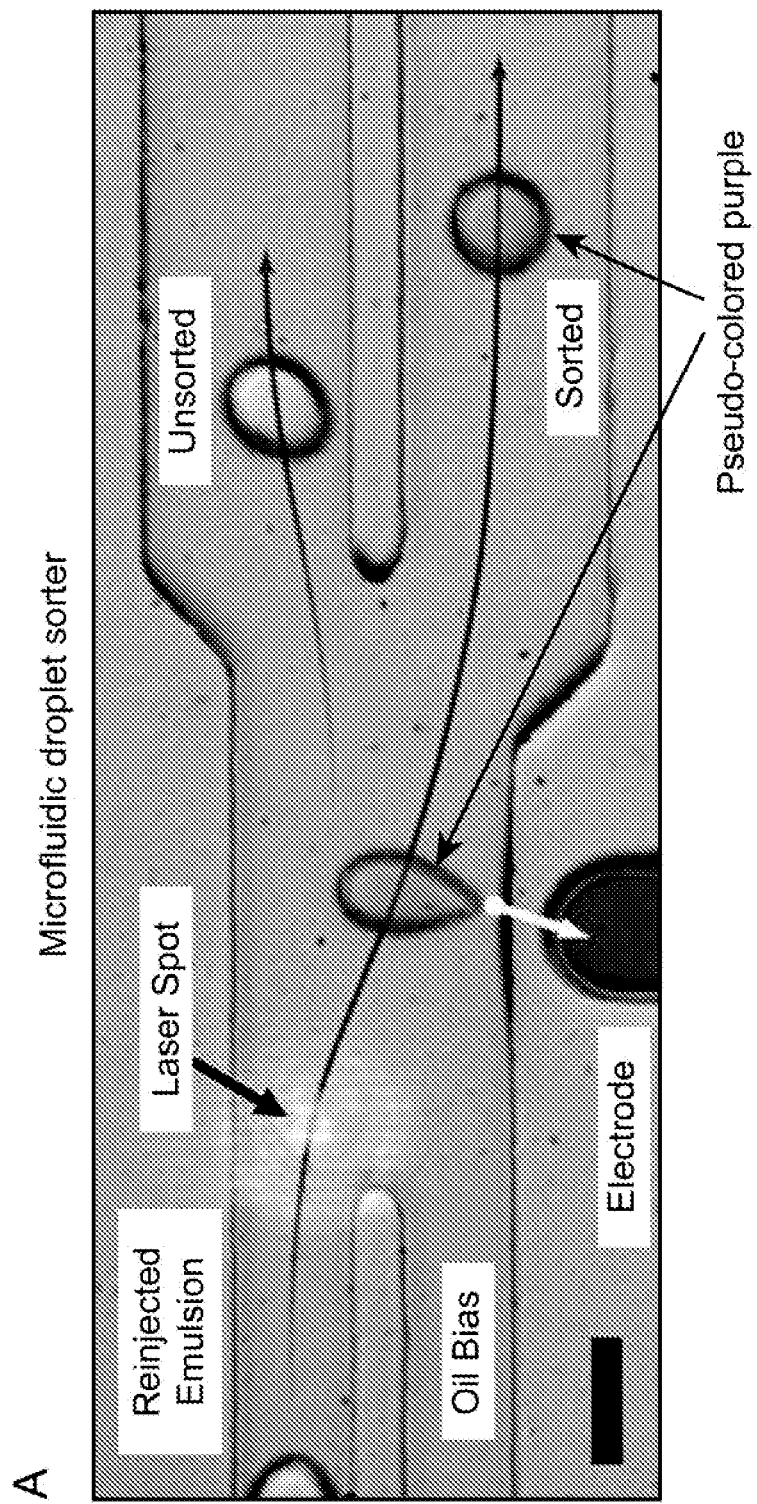
FIG. 59, Panels a-c, depicts ultrahigh-throughput detection and PCR-activated sorting of droplets according to certain embodiments.
Figure 59:
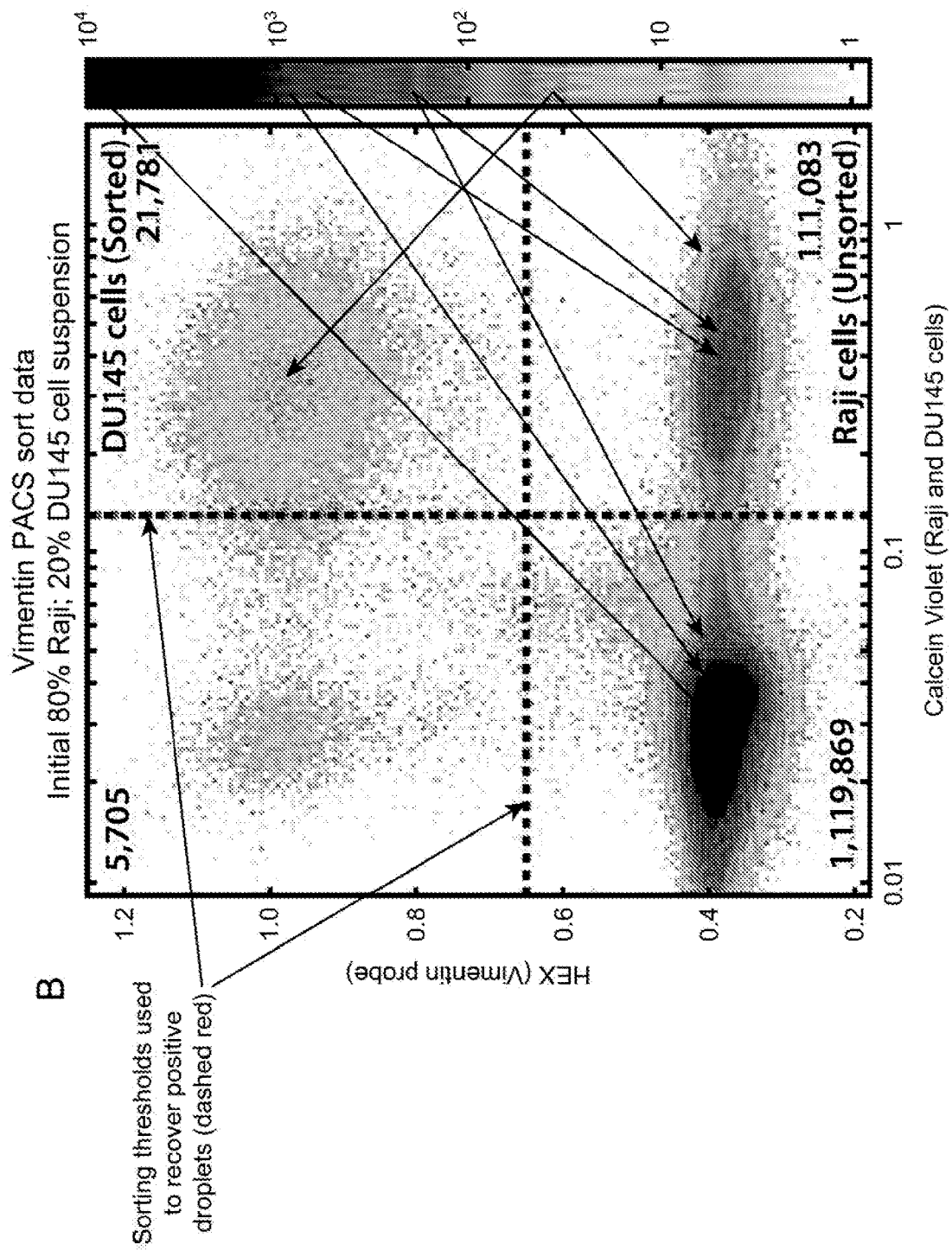
Figure 59:
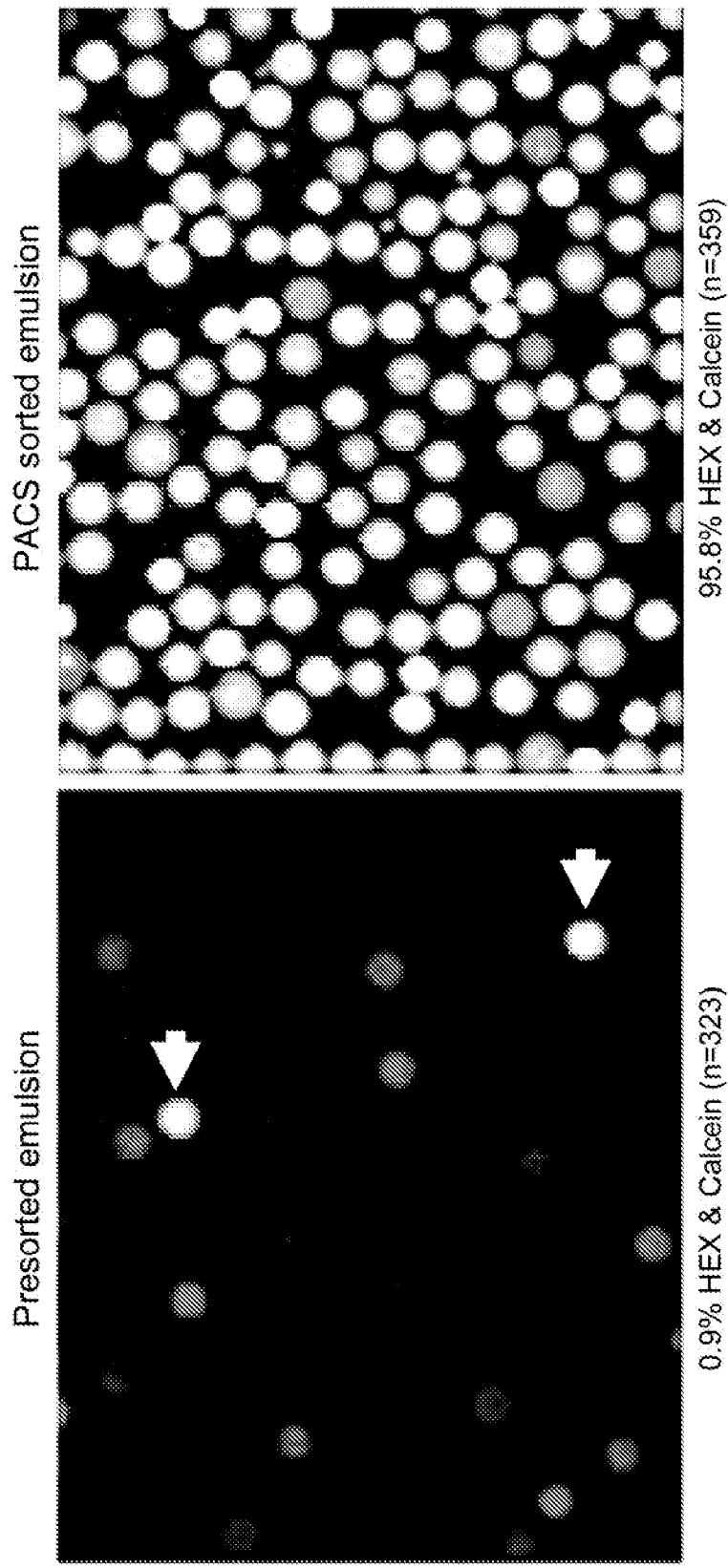
Figure 60:
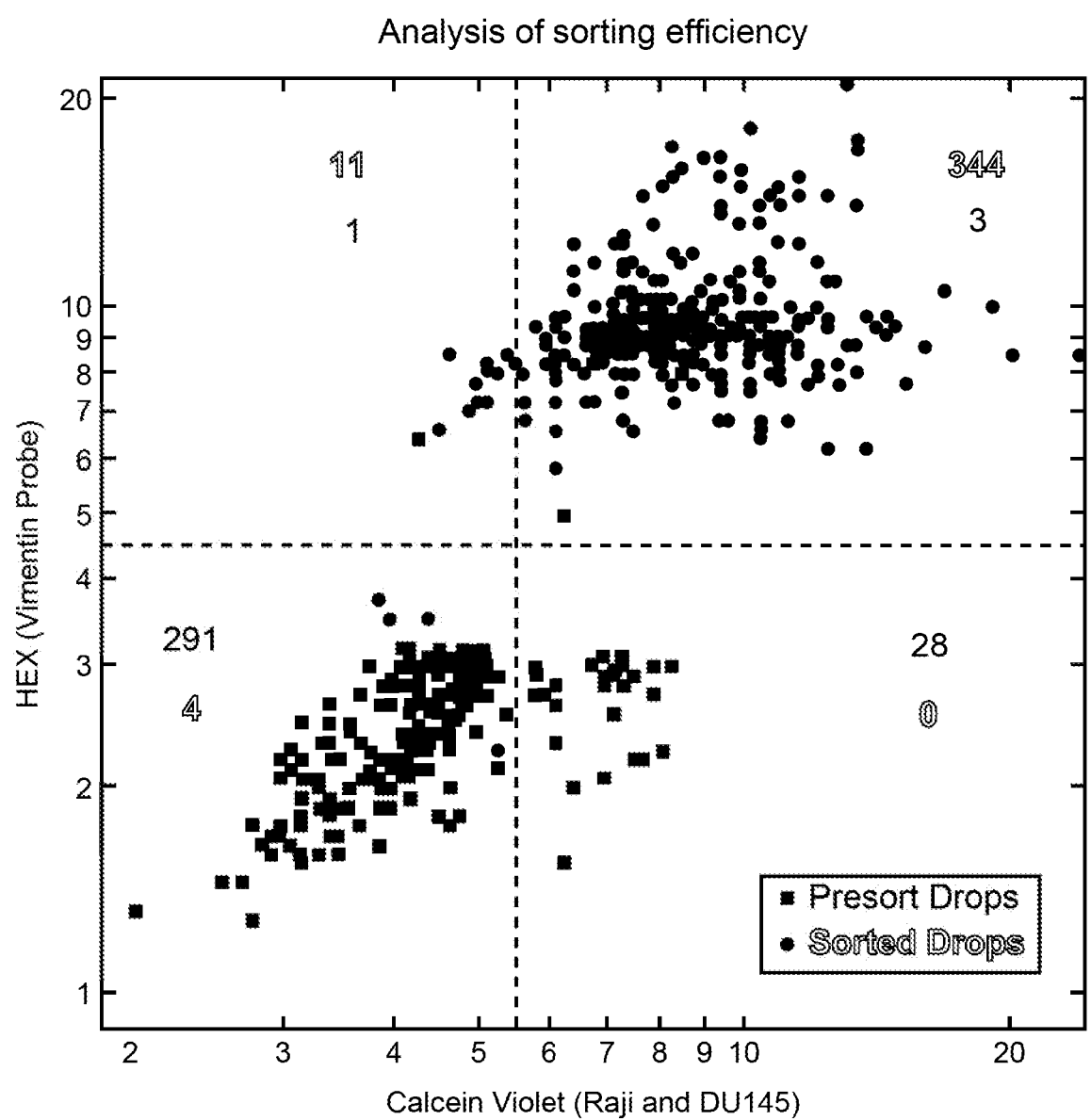
FIG. 60 depicts a scatterplot of HEX and calcein fluorescence according to certain embodiments.

To confirm the function of the sorter and appropriate selection of sorting gates, the sorted droplets and a small portion of the original pre-sorted emulsion were examined (FIG. 59, Panel c). A scatterplot of the HEX and calcein fluorescence values revealed that 95.8% of positively-sorted droplets had significant calcein and HEX fluorescence (FIG. 60). Conversely, only 0.9% of pre-sorted droplets were positive for both signals. This constitutes a more than 100-fold increase in the double-positive droplet ratio following sorting, and confirms the ability of PACS to enrich specific cells from a heterogeneous population.

Genetic Analysis of PACS-Sorted Cancer Cells

A major advantage of PACS over FISH-FC is that it does not require chemical fixation, enabling facile analysis of nucleic acids recovered with sorting. To more thoroughly characterize the ability of PACS to specifically sort target cells out of a heterogeneous population and sequence the recovered material, a suspension containing 10% DU145 and 90% Raji cells was sorted. DU145 cells have genetic mutations in two commonly mutated tumor suppressor genes, RB1 and CDKN2A, which likely contribute to the transformation of this prostate cancer cell line. These two mutations are homozygous SNPs residing at genetically unlinked genomic loci and are not found in Raji cells (upper panels, FIG. 61, Panels a-b); consequently, they represent clear genetic biomarkers with which to estimate the fraction of DU145 and Raji DNA in the recovered material.

Figure 61:
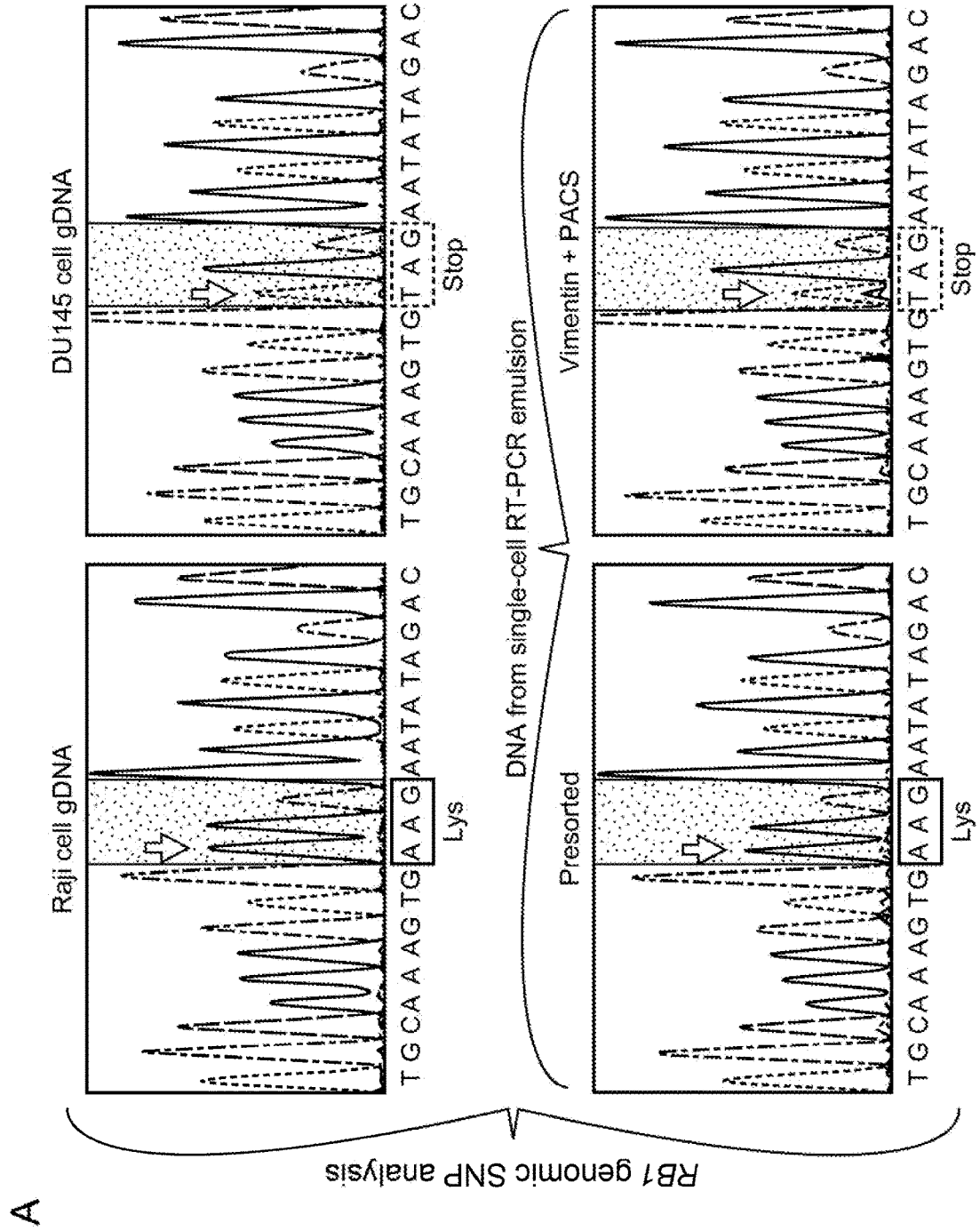
FIG. 61, Panels a-b, show Sanger sequencing of PACS enriched genomic DNA according to certain embodiments.
Figure 61:
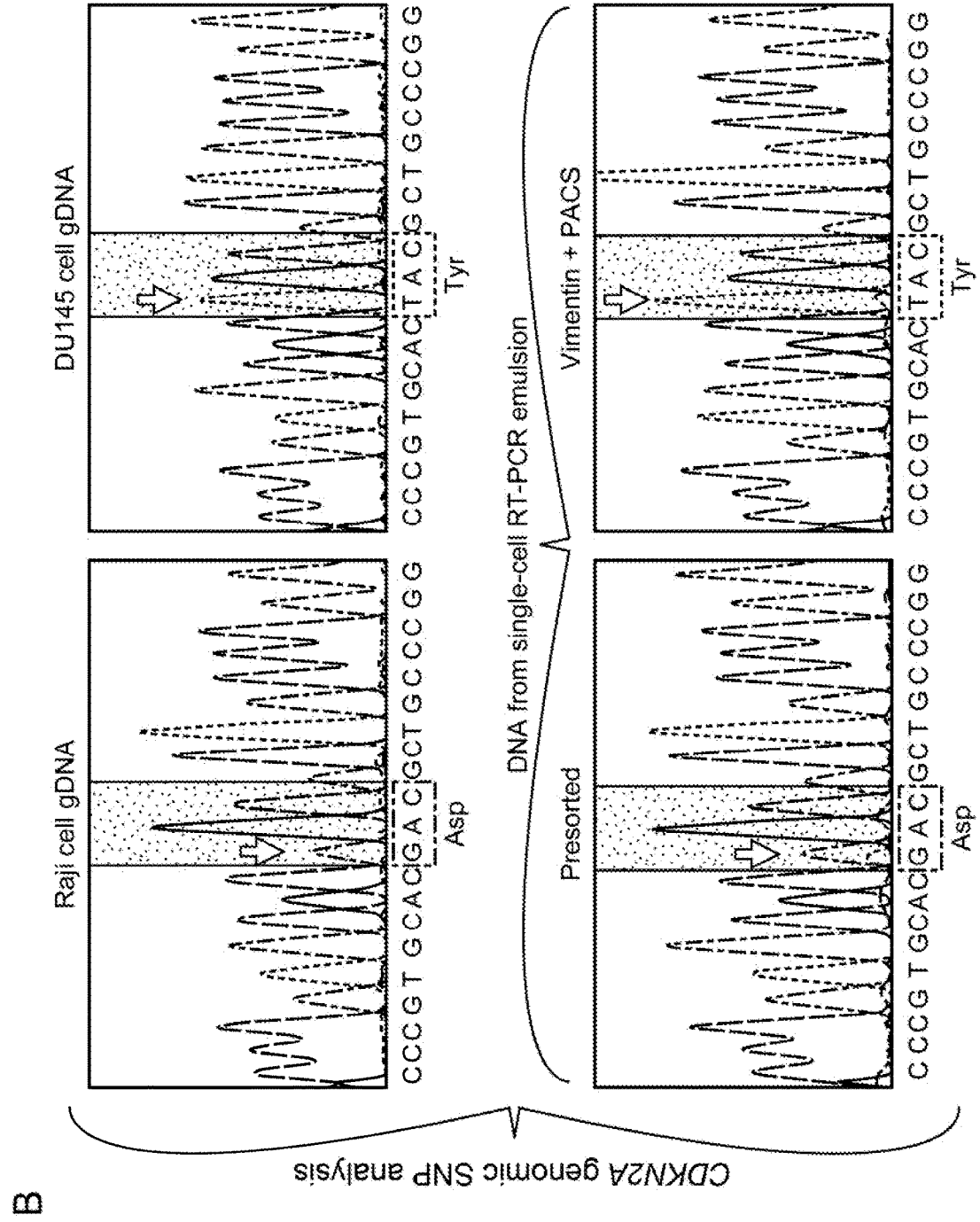

In this experiment, 92,996 individual cells were analyzed, of which 10.8% (10,099) were positive for vimentin and cell stain. To perform the genomic analysis, DNA was isolated from the pre- and post-sorted emulsions. Purified genomic DNA from a total of 1,326 (~13% of total droplets positively sorted) was used to amplify RB1 and CDKN2A, and the SNP regions for both genes were analyzed by Sanger sequencing (FIG. 61). In the pre-sorted emulsion, both RB1 and CDKN2A contain Raji SNP sequences and only a weak DU145-specific nucleotide peak, reflecting the relatively minor (10%) contribution of DU145 DNA in this emulsion. By contrast, after sorting, sequences associated with DU145 cells dominate, with only trace Raji sequences still present, as illustrated in FIG. 61, Panels a-b, lower chromatograms. This shows that PACS can identify the genotype of an initially undetectable cancer cell population by sorting the heterogeneous cells based on expression of a cancer-associated gene.

The Sanger sequencing chromatograms provided a measurement of DU145 enrichment. In addition, next-generation sequencing was performed to measure the exact proportion of SNPs associated with the two different cell types in the sorted pool. Nextera libraries were generated from the RB1 and CDKN2A amplicons obtained in the previous experiment. Following next-generation sequencing, the percentage of reads containing SNPs were measured from the two different cell types (FIG. 62, Panels a-b). In the pre-sorted emulsion, for RB1, DU145-specific codons made up 6.2% of the total reads. Following vimentin-positive PACS, this codon variant was 87.7% of all reads. Similar results were obtained for the CDKN2A locus, with DU145 codons accounting for 13.5% of total reads pre-sorting and 74.2% post-sorting. The differences between the RB1 and CDKN2A percentages may be due to bias introduced during sequencing library preparation with Nextera and PCR. These results are consistent with the expected SNP percentages in the original 10% DU145 and 90% Raji cell suspension, and provide a quantitative validation of successful enrichment of DU145 cells with PACS.

Gene Expression Analysis of PACS-Sorted Cells

Figure 63:
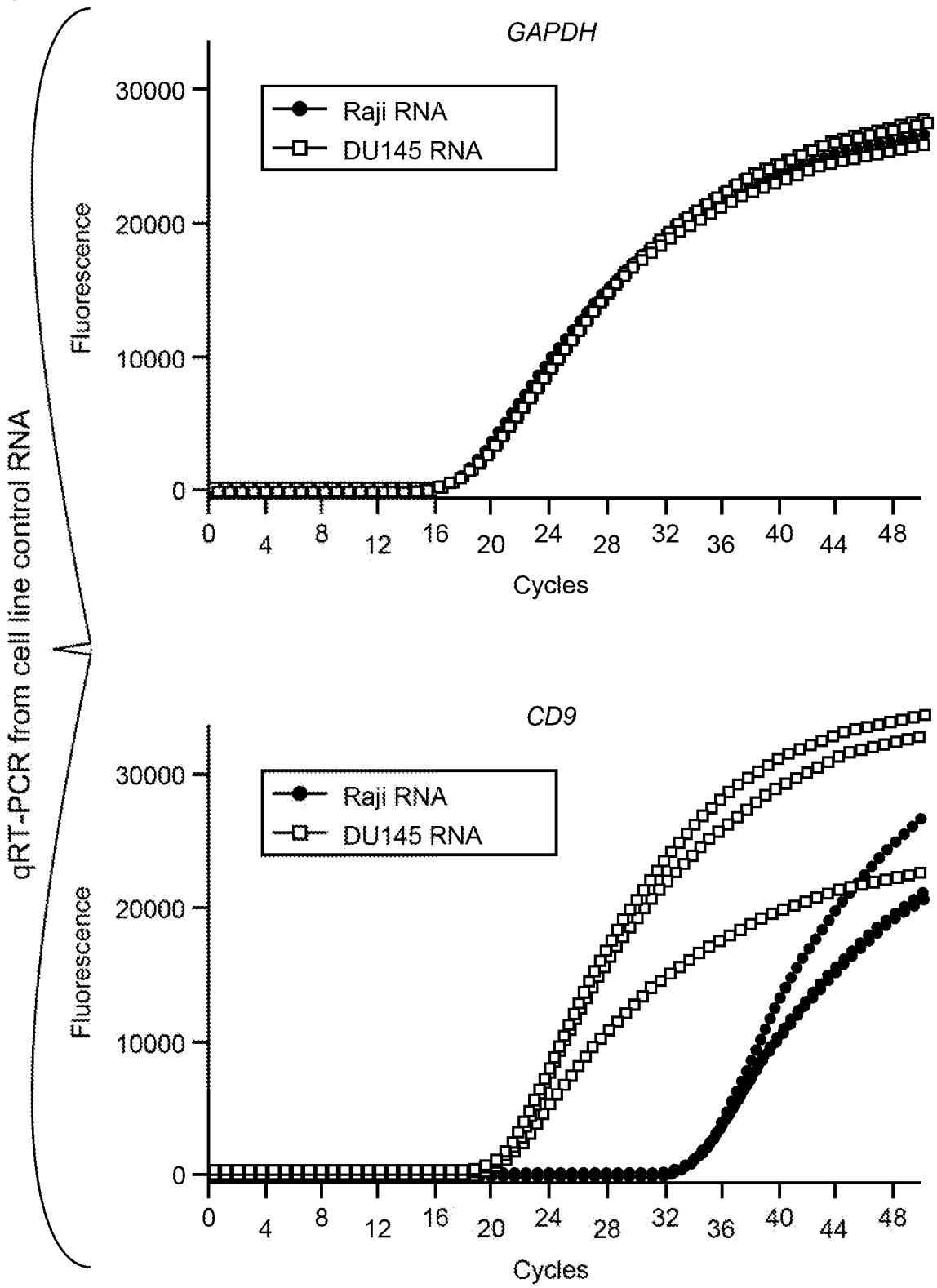
FIG. 63, Panels a-b, show mRNA expression analysis following PACS enrichment according to certain embodiments.
Figure 63:
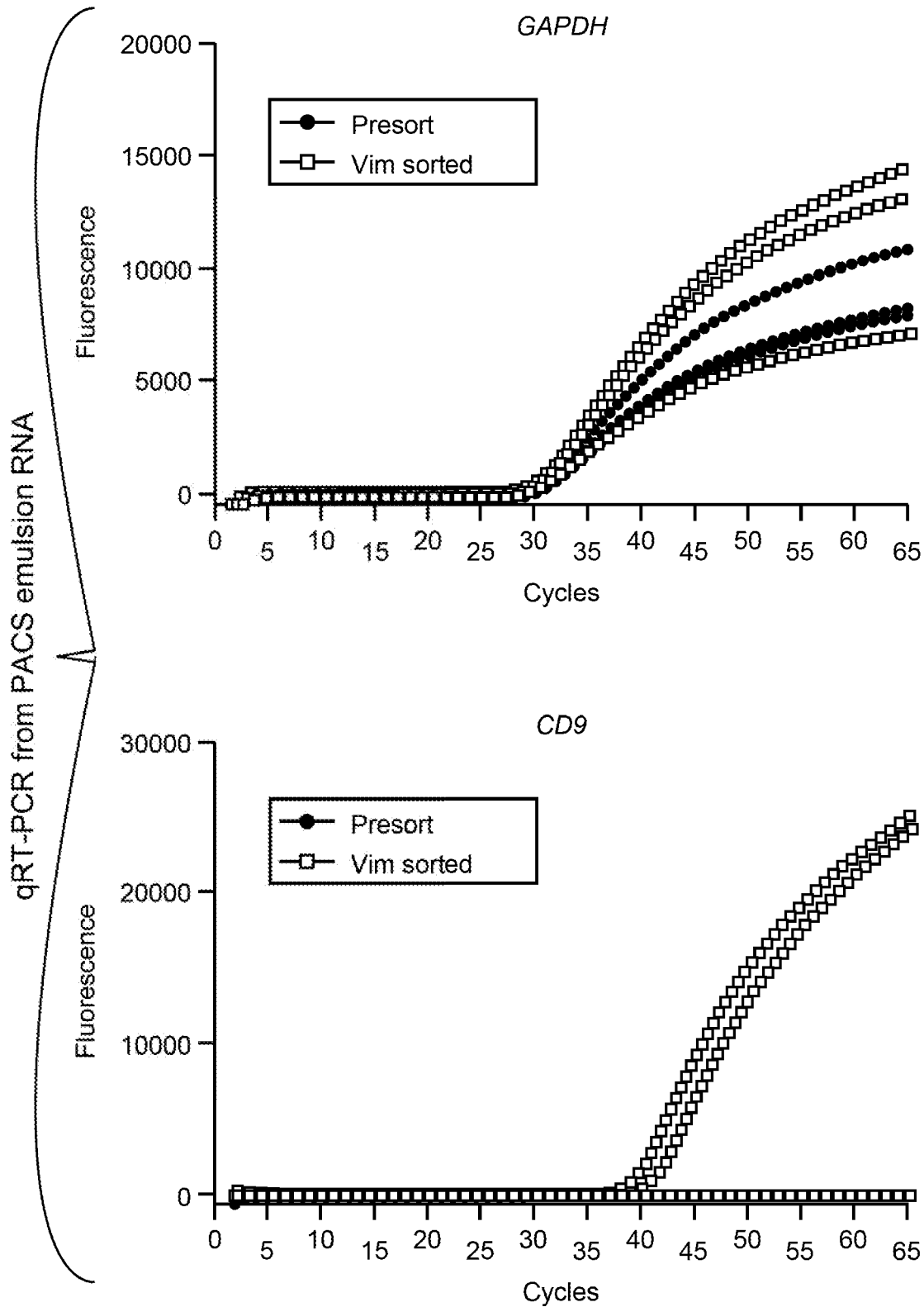

RNA recovered from vimentin-positive droplets for the enrichment of transcripts differentially expressed in DU145 cells compared to Raji cells were examined to investigate the ability of PACS to enable downstream gene expression analysis of sorted cells. Analysis of control RNA isolated from individual Raji and DU145 cells demonstrated that CD9 expression is more than 16,000 times higher in DU145 cells than in Raji cells when normalized to GAPDH expression (FIG. 63, Panel a). Following vimentin-positive PACS on the DU145 and Raji cell suspension, RNA recovered from 4,659 TaqMan sorted droplets was divided and used for GAPDH and CD9 qRT-PCR replicates (FIG. 63, Panel b). RNA input for pre-sorted and PACS sorted samples were normalized with GAPDH controls. CD9 was detected in PACS sorted droplets and absent from the pre-sorted emulsion. This indicates that downstream gene expression analysis on lysates recovered with PACS is feasible. An additional benefit of PACS is that it can use RT-PCR to detect the cell types of interest; implementation of first strand cDNA synthesis in this step facilitates pan-transcriptome analysis, including with RNA-Seq and microarrays.

The above results demonstrate the preparation of single-cell lysates for RT-PCR in microfluidic droplets and the use of TaqMan reactions for sorting. The use of single-cell TaqMan reactions not only provided specific and sensitive detection of cells, but is also compatible with multiplexing and analyzing non-coding RNAs, transcript splice variants, genetic mutations and other nucleic acid biomarkers undetectable with antibodies.

The results above show that embodiments of the present disclosure provide for analysis of single cells with RT-PCR high throughput. As discussed above, RT-PCR analysis and sorting of 132,000 cells was demonstrated in a single experiment. Likewise, scalability was demonstrated where certain instances showed at least a ten-fold increase in single-cell throughput. A throughput of >100,000 cells per experiment showed that PACS provided for analysis of heterogeneous cell populations, including immune cells, large tumors, and even circulating tumor and fetal cells, especially when combined with cell pre-enrichment or depletion strategies. In certain instances, antibody fluorescence at the time of encapsulation was used to sort cells with PACS.

As demonstrated above, PACS can be used to recover nucleic acids for downstream analysis. The genomes of PACS-sorted cells can be sequenced in a targeted fashion and as can whole genome sequencing with the implementation of appropriate library preparation steps downstream. PACS can be used to identify and enumerate cells based on many different nucleic acid biomarkers for a given behaviour or cell state and can subsequently be used to study the genetic drivers behind that behaviour. In addition to genomic analysis, PACS-recovered cells can be analyzed in gene expression analysis, which is important to the investigation of regulatory networks and effector proteins behind cell states and behaviour.

Example 11: PCR-Activated Cell Sorting (PACS) for Cultivation-Free Enrichment and Sequencing of Rare Microbes The use of PACS for the cultivation-free enrichment of rare microbes is described in greater detail below. In this example, microbes from a diverse ecosystem are individually encapsulated in picoliter-volume aqueous droplets and subjected to TaqMan PCR, followed by interrogation for the presence of specific nucleic acid sequences. If the sequences are present, TaqMan amplification yields a bright fluorescent signal that fills the droplet encapsulating the cell, allowing for the recovery of the cell's whole genome by sorting the entire droplet.

Materials and Methods

Microfabrication of Devices

Fluidic chips were fabricated using standard photolithography techniques in poly(dimethylsiloxane) (PDMS). To produce a master, a layer of SU-8 photoresist (Microchem) was first spun onto a silicon wafer, and then exposed to UV light from a Blakray device under a mylar mask (Fineline Imaging) The wafer was then baked at 95° C. on a hotplate for 1 min and then developed in Propylene glycol monomethyl ether acetate (PGMEA). The PDMS polymer was poured and crosslinker mixed in a 11:1 ratio over the master and then baked at 75° C. for 4 hours. The device was then peeled from the master and holes were punched using a 0.75 mm biopsy coring needle. After that, the device was bonded to a glass slide following oxygen plasma treatment. To make the device channels hydrophobic, Aquapel was flushed into the channels, after which the device was baked in an oven for 20 mins at 65° C. For the devices (DEP and flow focusing) in this example, the thickness of the photoresist was maintained at 25 μm while the channel widths at the flow-focusing junctions were 20 μm.

Bacterial Strain Construction and Growth

The parental wild type strain was BW25113. The entire 1poA ORF was deleted and replaced with a sacB-cat cassette using lambda Red recombinase-mediated allelic exchange. The Red recombinase was expressed using plasmid pKD46. The sacB-cat cassette was generated by PCR using plasmid pDS132 as template and primers ANG188 and ANG189. Transformants were selected on LB Cam10 and verified by diagnostic PCR.

Next, the mutant 1poA allele was generated by two-step overlap-extension PCR. The first-round PCR products were generated using primers ANG065 and AG4 together with AG3 and ANG066, with BW25113 genomic DNA as template. The PCR products were treated with DpnI and gel-purified to get rid of the initial template DNA. The final PCR product was generated using primers ANG065 and ANG066, with the first-round PCR products as template (present in equimolar amounts). This PCR product was used to replace the sacB-cat cassette as above, with selection on LB 0% NaCl 7% (w/v) sucrose. The sacB gene confers sucrose sensitivity, allowing counterselection. Transformants were screened for chloramphenicol sensitivity (indicating loss of cassette) and verified by diagnostic PCR and sequencing. The strain produced is the LpoA K168A *E. coli*.

A ΔtolA::kan insertion was introduced into wild type strain BW25113 by sequential P1 transductions, with selection on LB with 10 mM sodium citrate and ampicillin at 50 μgml$^{-1}$, and LB with 10 mM Na citrate and kanamycin at 30 μgml$^{-1}$, respectively. The ΔtolA::kan allele is from the Keio collection *E. coli* gene knock-out library. The strain produced has TolA knocked out but with a wild-type copy of the BW25113 LpoA gene.

The bacteria were grown in 2% Luria-Bertani (LB) broth at 37° C. for around 10 hours. The bacterial cultures were then assayed for their optical density (OD) via spectrophotometrical measurement of absorption at 600 nm. The correlation between OD and bacterial number is taken to be that 1 OD is equivalent to 5×10$^8$ bacteria.

Primer Sequences for the Construction of Mutant Bacterial Strains

The primer sequences used for the construction of the bacterial strains were as follows: ANG188 5'-TGCCGATT-TAATATTGAGCATTGCGTAAAAAAAATATCACTG-GATACATTGCCCGTA GTCTGCAAATCC-3' (SEQ ID NO:13) (50 bp upstream of 1poA and forward sacB-cat cassette primer; the 50 bp upstream of 1poA allows homologous recombination to replace the gene), ANG189 5'-CAGCCAGCGACGCGCTTGTGCTTCCCACG-CATCGCCGGTCTGTTTGGTGGCCATGAC CCGG-GAATTACG-3' (SEQ ID NO:14) (50 bp downstream of 1poA (reverse-complement) and rev sacB-cat cassette primer), ANG065 5'-CGCAAACAACCGGGCATTAATC-3' (SEQ ID NO:15) (forward upstream 1poA primer, anneals 256 bp upstream of 1poA), ANG066 5'-TTTGCTGCGGGT-CACACTG-3' (SEQ ID NO:16) (reverse downstream 1poA primer, anneals 209 bp downstream of 1poA), AG3 5'-gctgcttggcgcgGCagaaaaacagcag-3' (SEQ ID NO:17) (forward 1poA(K168A) mutagenesis primer; upper-case letters represent changes for 1poA(K168A) point mutation), AG4 5'-ctgctgtttttctGCcgcgccaagcagc-3'(SEQ ID NO:18) (reverse 1poA(K168A) mutagenesis primer).

Encapsulation of Bacteria in Monodisperse Droplets

Before mixing bacteria together with the other components of the reaction, the bacterial suspension was washed 3 times by centrifugation at 3000 rpm (Eppendorf) followed by resuspension of the pellet in distilled water. The bacteria was mixed together with primers, Taqman probe and PCR mix (2×ddPCR MasterMix, Biorad). The primers and Taqman probe were used at a working concentration of 1 μM and 250 nM respectively. This mix was loaded into a 1 ml syringe back-filled with HFE-7500 oil, which was connected to a coaxial flow-focus device. The oil used for the carrier phase was the droplet generation oil for probes (Biorad). The oil flow rate was set at 400 μlhr$^{-1}$ while the aqueous flow rate was set at 200 μlhr$^{-1}$. The emulsion was collected into PCR tubes and thermal-cycled on a T100 thermocycler (Bio-Rad), with the following conditions: 10 min at 95° C., 35 cycles of 10 seconds at 95° C., 15 seconds at 72° C. and 30 seconds at 55° C. To verify that the PCR reactions were specific, both bacterial samples were electrophoresed on a 2% agarose gel. No non-specific product was observed after imaging.

Primer and Probe Sequences for Taqman PCR, LpoA Amplification and Sequencing

The primers for the detection of TolA were: TolA Forward 5'-GTTGATTCAGGTGCGGTAGTT-3' (SEQ ID NO:19), TolA Reverse 5'-GCCTGCTGTTCCTTCATCTT-3' (SEQ ID NO:20). The TolA probe sequence was 5'-/6-FAM/ATCAAACCT/ZEN/GAAGGTGGCGATCCC/3IABkFQ/-3'(SEQ ID NO:21). The primers for LpoA amplification were: LpoA Forward 5'-TTTACTGCGCGCGTTAATTG-3' (SEQ ID NO:22), LpoA Reverse 5'-TTGCGGCT-GAGGTTGTT-3' (SEQ ID NO:23). The primer for TOPO Vector sequencing was: M13 Forward (−20) 5'-GTAAAACGACGGCCAG-3' (SEQ ID NO:24).

DEP Sorting

Thermalcycled drops were collected into a syringe filled with HFE-7500 (3M) fluorinated oil, and left to cream for 10 minutes before starting the syringe pump. The drops are then re-injected into the DEP device at a flow rate of 50 μlhr$^{-1}$, with the spacer oil flow rate set at 1000 μlhr$^{-1}$. The flow rate for the 2nd oil spacer at the sorting junction was set at 100 μlhr$^{-1}$. All the oil used for spacing droplets was HFE-7500. The moat was filled with 2M NaCl salt solution, as were the salt electrodes. The PMTs were connected to a computer with LABVIEW software and a FPGA data acquisition card (National Instruments) for droplet fluorescence intensity recording and electrode activation. Custom LABVIEW software was written to enable dynamic adjustments of PMT gain, droplet fluorescence intensity thresholds for sorting, electrode AC voltage pulse frequency and magnitude. The data acquisition rate for this system was 200 kHz.

LpoA Sequencing Verification

Droplets from the positive DEP sort were collected into 1.5 ml Eppendorf tubes. Chloroform (Sigma-Aldrich) and distilled water were pipetted over the oil, with 20 μL of water used for every 200 μL of chloroform and 200 μL of oil. The droplets were then vortexed for 10 minutes on a shaker, and then centrifuged at 14,000 rpm. The top layer of immiscible water was then extracted, of which 9 μL was used for PCR amplification. The PCR amplification mixture included 1 μM forward and reverse LpoA sequencing primers, 1× Toptaq PCR master mix (Qiagen), and template from the broken drops in a total volume of 20 μL. The mixture was then thermal-cycled with the following conditions: 10 minutes at 95° C., 35 cycles of 10 seconds at 95° C., 15 seconds at 72° C. and 30 seconds at 50° C. The PCR product was then cloned into a pCR4-TOPO vector (Life Technologies) using a TOPO TA cloning kit for sequencing (Life Technologies), following the manufacturer's instructions. This vector was transformed into electrocompetent *E. coli* TOP10 bacteria and streaked onto LB plates with 50 μgml$^{-1}$ kanamycin for growth at 37° C. overnight. Colonies were picked at random for overnight growth in LB with 50 μgml-1 kanamycin at 37° C., DNA extracted using a Qiagen miniprep kit, and then sent for Sanger sequencing (Quintara Biosciences). The primer used for sequencing was the M13 Forward (−20) primer.

Results

Strategy of PACS

PACS provides single cell nucleic acid analysis and ultrahigh-throughput sorting of cells. PCR is a powerful technique for detecting microbes because it enables the use of temperatures near the boiling point of water to lyse cells and denature DNA; this allows PCR probes to anneal to their complementary targets with higher efficiency and sequence specificity than methods that rely on room-temperature hybridization alone. Moreover, PCR results in exponential amplification of the target DNA, yielding a bright signal that can be detected rapidly, as needed for ultrahigh-throughput screening and FACS sorting. Additionally, by implementing TaqMan PCR, it is possible to differentiate between sequences with high specificity and to multiplex reactions to interrogate several genomic regions within each microbe; this limits false-positive identification and enables fine differentiation between species of similar type.

In these examples, microfluidic droplets are utilized. With microfluidic devices, droplets can be generated and sorted at kilohertz rates and each droplet utilizes just tens of picoliters of reagent, allowing millions of PCR reactions to be performed with microliters of total reagent. Moreover, because the aqueous droplets are suspended in an inert liquid oil, they can be flowed through microfluidic devices, which allows multiple steps of processing, such as sampling fluid from, adding reagents to, and incubating and sorting the droplets; this allows multistep reactions to be performed in the droplets that are not otherwise possible.

Small genomic regions including hundreds of bases in length serve as "sequence biomarkers" to identify cells of interest. Based on the PCR signal produced when a cell containing the sequence biomarker is present, droplet sorting is used to recover the entire genome of the cell.

Targeted Recovery of Microbial Genomes with PACS

PACS may be used to rapidly screen a large and diverse population of microbes to identify and recover the genomes of those microbes that contain particular nucleic acids. This may be accomplished by performing a PCR reaction on each individual cell and then sorting the cells based on the outcomes of the reactions.

Figure 64:
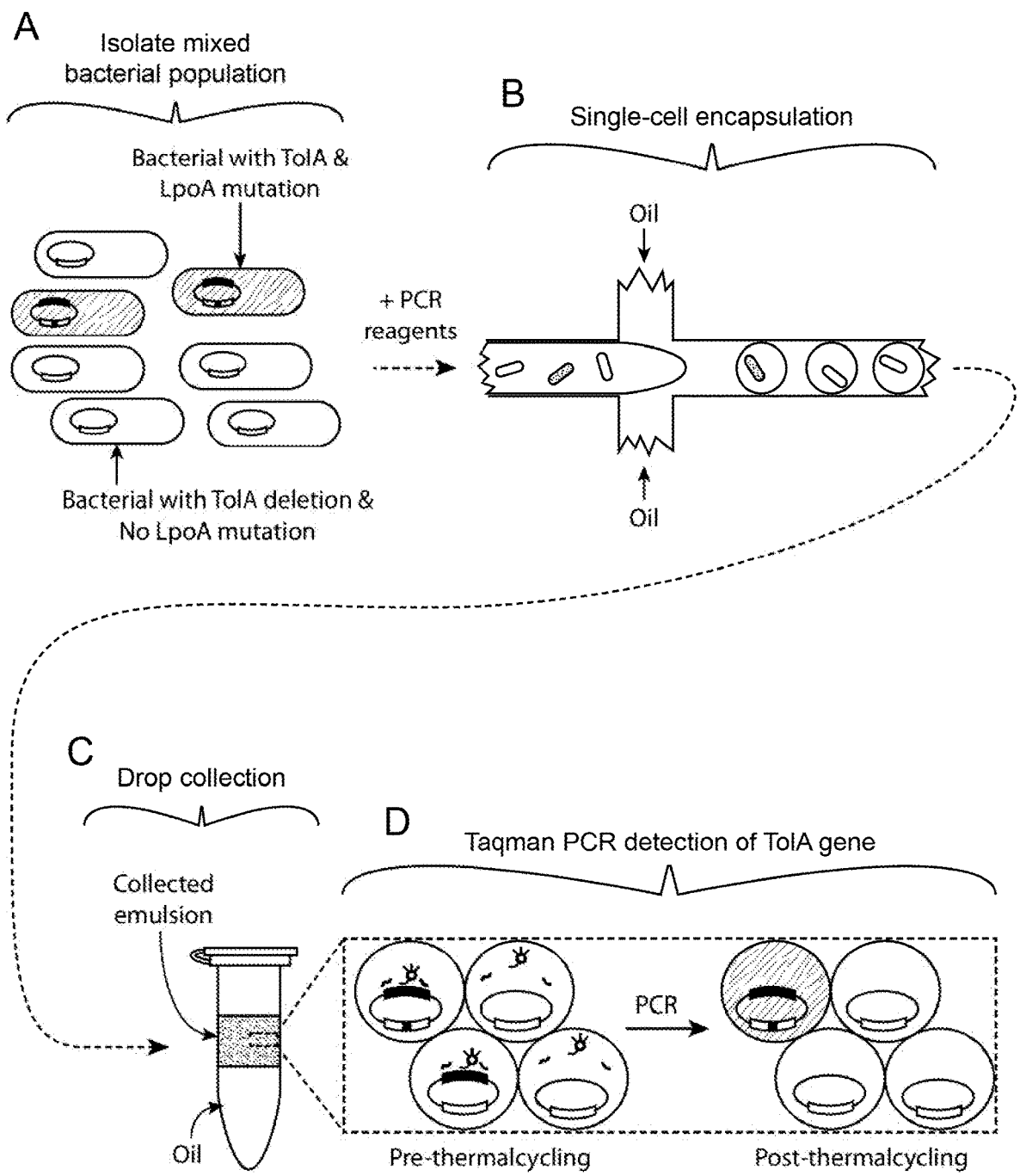
FIG. 64, Panels a-f, show PACS workflow applied to a model microbial system according to certain embodiments.

FIG. 64 provides one example of a general workflow which may be utilized for the targeted recovery of microbial genomes with PACS. In some embodiments, first step in such experiments is to encapsulate the microbes (FIG. 64, Panel a) in individual water-in-oil droplets using microfluidic emulsification (FIG. 64, Panel b). PCR reagent may be included in the microbial suspension, but in certain embodiments, the microbes and PCR reagent, which can include detergents to enhance lysis, may be combined on-chip via laminar co-flow followed by droplet generation. The microbes may be diluted so that there are on average less than one per droplet, with the droplets loaded randomly in accordance with a Poisson distribution. In some embodiments, the droplets are ~35 pL in volume, however in certain instances the volume varied by greater than 5× up or down, and are collected into a PCR tube and thermo-cycled (FIG. 64, Panel c). Thermocycling may be performed on a standard PCR system, although on-chip thermocyclers may also be used for an unbroken workflow in some instances. During PCR, the elevated temperature lyses the microbes and disrupts DNA-protein and DNA-DNA interactions, providing the PCR primers with access to the cell's DNA. Droplets containing the genetic sequences being assayed for will result in TaqMan PCR amplification, yielding a droplet that is bright with fluorescence at the emission wavelength of the TaqMan probe due to its degradation by the 5' exonuclease activity of Taq polymerase. At this point in the process, a large quantity (e.g. millions) of droplets may be present, some of which are fluorescent (e.g., contain a microbe with the sequence targeted by the assay). Next, the droplets may be screened using ultrahigh-throughput dropometry and the positives may be recovered with dielectrophoretic (DEP) sorting (FIG. 64, Panel d). The sorted droplets can be loaded into individual wells or pooled together and chemically ruptured to access their contents, providing genomic DNA of the target microbes.

Validation of PACS

To validate recovery of specific microbes with PACS, target cells were spiked into a background of non-target cells and the workflow depicted in FIG. 64 was implemented. Two different E. coli strains having two differences in their genome were employed: The first strain had the genetic sequence for the membrane protein TolA knocked out (ΔTolA), whereas the second had TolA intact but was a double mutant on the LpoA gene, which is an outer membrane lipoprotein (LpoA K168A). The mixed population was then run through PACS as described herein (FIG. 64, Panels a-f) sorting based on the presence of TolA, which should only recover the LpoA double mutants. To characterize the efficiency of the PACS sorting, the genomic DNA of the sorted microbes was recovered and PCR-amplified and the portion of the LpoA gene containing the mutations was sequenced (FIG. 64, Panel f). By comparing the number of sequences containing the double mutant and those without it, the efficiency with which PACS can discriminate between these cell types based on TolA was estimated. This experiment demonstrated that cells may be differentiated based on the presence of a gene (TolA) at one location of the genome, and then correct sorting confirmed by analyzing a different gene (LpoA) far away on the same genome. The sequences analyzed post-sorting were found not to be the product of the first PCR; they were present in the sorted mixture because they existed in the same genome that contained TolA and, thus, were sorted with it.

Efficiency of Single Cell Droplet PCR

Figure 66:
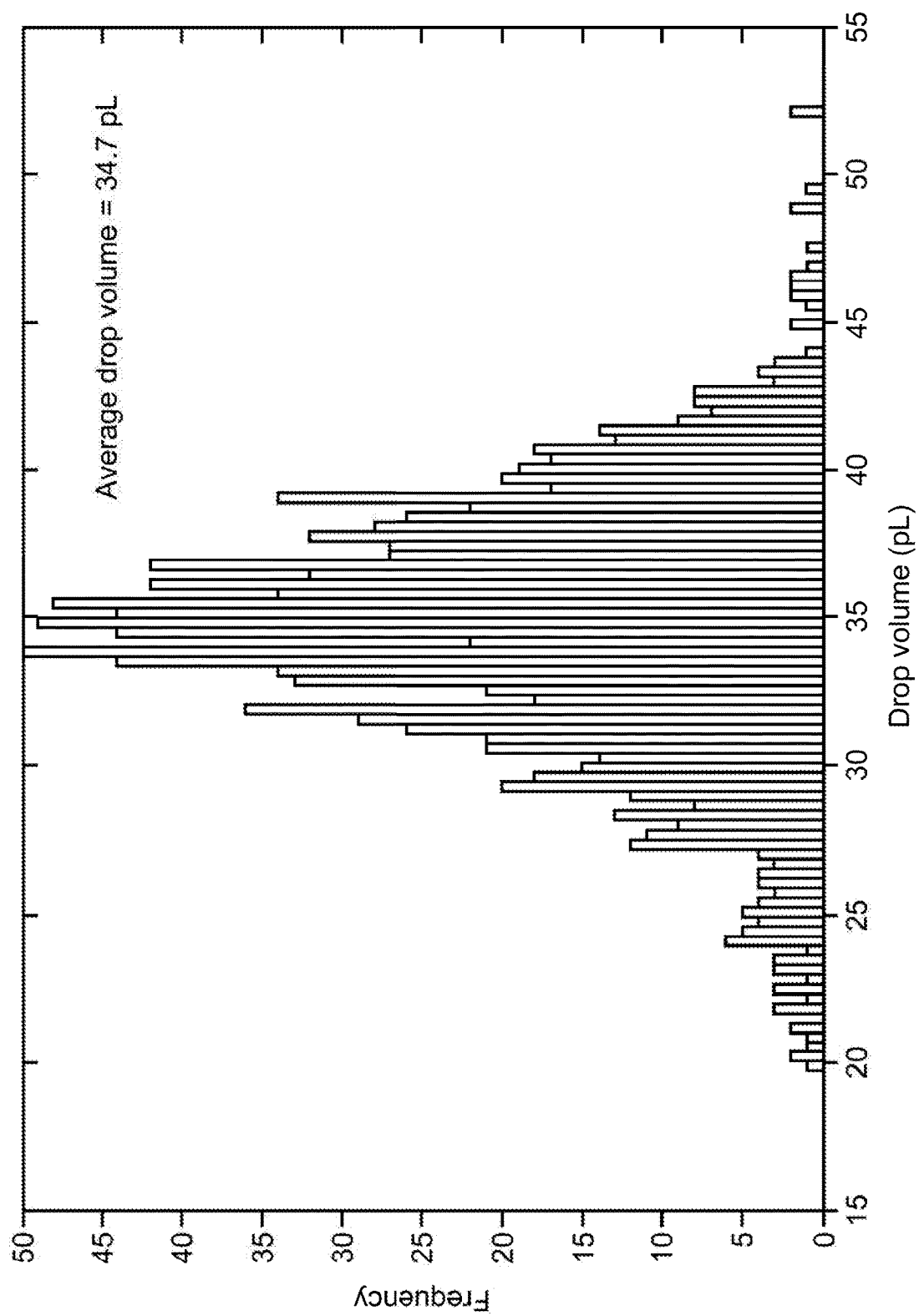
FIG. 66 depicts droplet size distribution according to certain embodiments. In this example, single emulsion droplet diameters were quantified using ImageJ, with a total of 1200 drops measured for all concentrations of bacteria. The average drop volume was calculated to be 34.7 pL.

To investigate the specificity of the TaqMan assay, control experiments were performed in which clonal populations of the two cell types were emulsified separately, and then analyzed using droplet single cell TaqMan PCR with primers and probes for the TolA gene, the results of which are shown in FIG. 65, Panel a. For the droplets containing the double mutants (LpoA K168A), in which TolA is present, a "digital" fluorescence signal is observed, in which a small fraction of the droplets are bright, and the remainder exhibit no fluorescence, as illustrated in FIG. 65, Panel a, upper; the fluorescent droplets contain individual K168A microbes, while the dim droplets are devoid of any cells and thus constitute what is expected when the target sequence (TolA) is not present within the droplet. To confirm this, the same experiment was performed with the knockout population (ΔTolA), the results of which are shown in FIG. 65, Panel a, lower. Even though the stoichiometry of the ΔTolA cells is comparable to that of the K168A cells in the first experiment, such that similar loading rates were expected into the droplets, no fluorescent droplets were observed. This demonstrates that the TaqMan assay is specific to cells that have sequences targeted by the selected primers. This is consistent with control experiments performed in bulk on large numbers of the cells and also with the properties of TaqMan PCR. To validate that the positive droplets in the K168A experiment correspond to "digital" amplification resulting from a TolA positive cell, the experiment was repeated for different concentrations of K168A cells. For Poisson loading of the cells in droplets, the probability that a given droplet has x cells is given by:

$$P(x; \lambda) = \frac{e^{-\lambda}\lambda^x}{x!}, \tag{1}$$

where λ is the average number of cells per 35 pL droplet (FIG. 66). Bright drops correspond to x≥1, whereas x=0 relates to dark drops. The proportion p of bright to dark drops depends on λ according to, $$p=1-e^{-\lambda} \tag{2}$$

This is a simple statement that as the concentration of cells in suspension increases, more of the droplets contain at least one cell. To relate the number of cells in the droplets to the number of fluorescent droplets observed at the conclusion of the assay, the fact that not all droplets containing single cells undergo amplification should be accounted for. That is, due to inefficiencies in the PCR, the probability that the reaction undergoes amplification is less than unity. We can account for this by rewriting the equation as $$p=1-e^{-5\lambda}, \tag{3}$$

where k is the probability that a droplet containing a target cell yields a fluorescent signal. To measure, k, an important parameter that describes the sensitivity with which positive cells are detected, the experiment is repeated at different concentrations, (FIG. 65, Panel b). For k=1, the TaqMan reaction can be said to be perfectly efficient so that every drop containing a cell yields a fluorescent signal. For k<1, the reaction is imperfect so that some droplets containing positive cells do not yield a fluorescent signal. Based on the current data, it is determined that 0.6<k<0.7, indicating that approximately 65% of the positive cells are detected in the sample. This inefficiency may be a consequence of the natural stochasticity of PCR, particularly in picoliter volumes in which reagents may be limiting. Another explanation is that cell lysis is not perfectly efficient and in some of the droplets the cells remain intact or the DNA targets inaccessible to the amplification primers, inhibiting the reaction. This effect can be mitigated by including PCR-compatible detergents in the droplets, which aid cell lysis and solubilization of DNA targets and may improve single cell PCR efficiency. Using more sophisticated multistep microfluidic techniques, it is also possible to include PCR incompatible lysis reagents, such as alkaline buffers, lysozyme, or proteases, to enable lysis of particularly durable microbes.

Recovery of Whole Bacterial Genomes with Droplet Sorting

At the conclusion of single cell droplet PCR, a collection of millions of droplets may be present, some of which contain target microbes and are fluorescent. To recover the positive droplets and the genomes of the cells they contain, ultrahigh-throughput dielectrophoretic (DEP) droplet sorting may be used. An example of a suitable droplet sorter configuration is provided in FIG. 67. The droplet sorter includes a droplet reinjection inlet, a spacing inlet, and a sorting junction. The device is surrounded by conducting aqueous "moats" that shield the injected droplets from stray electric fields, which can unintentionally coalesce droplets. These "moats" are designed so that they surround the oil channels, as illustrated in (FIG. 67).

Figure 67:
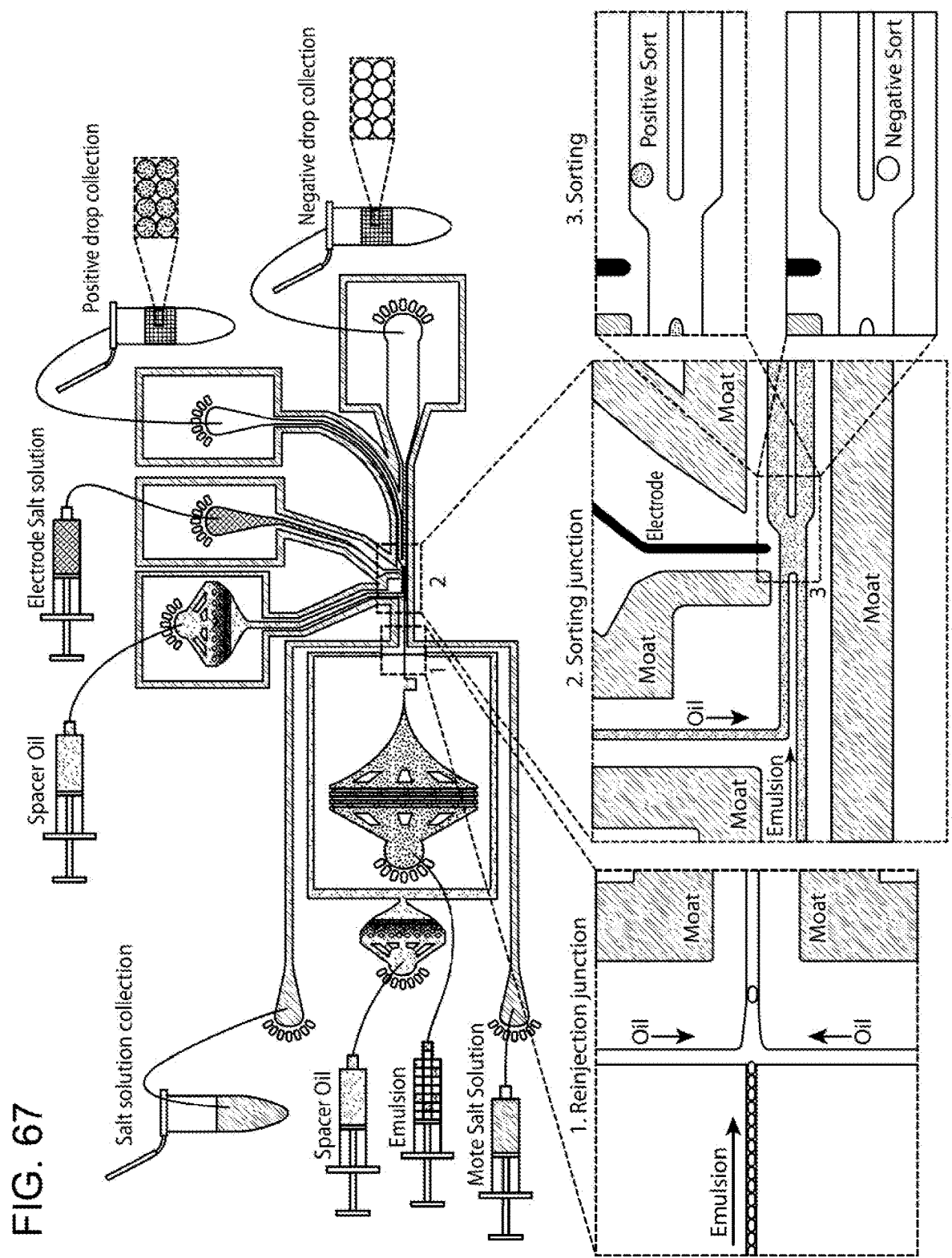
FIG. 67 depicts a DEP droplet sorting device according to certain embodiments.
Figure 68:
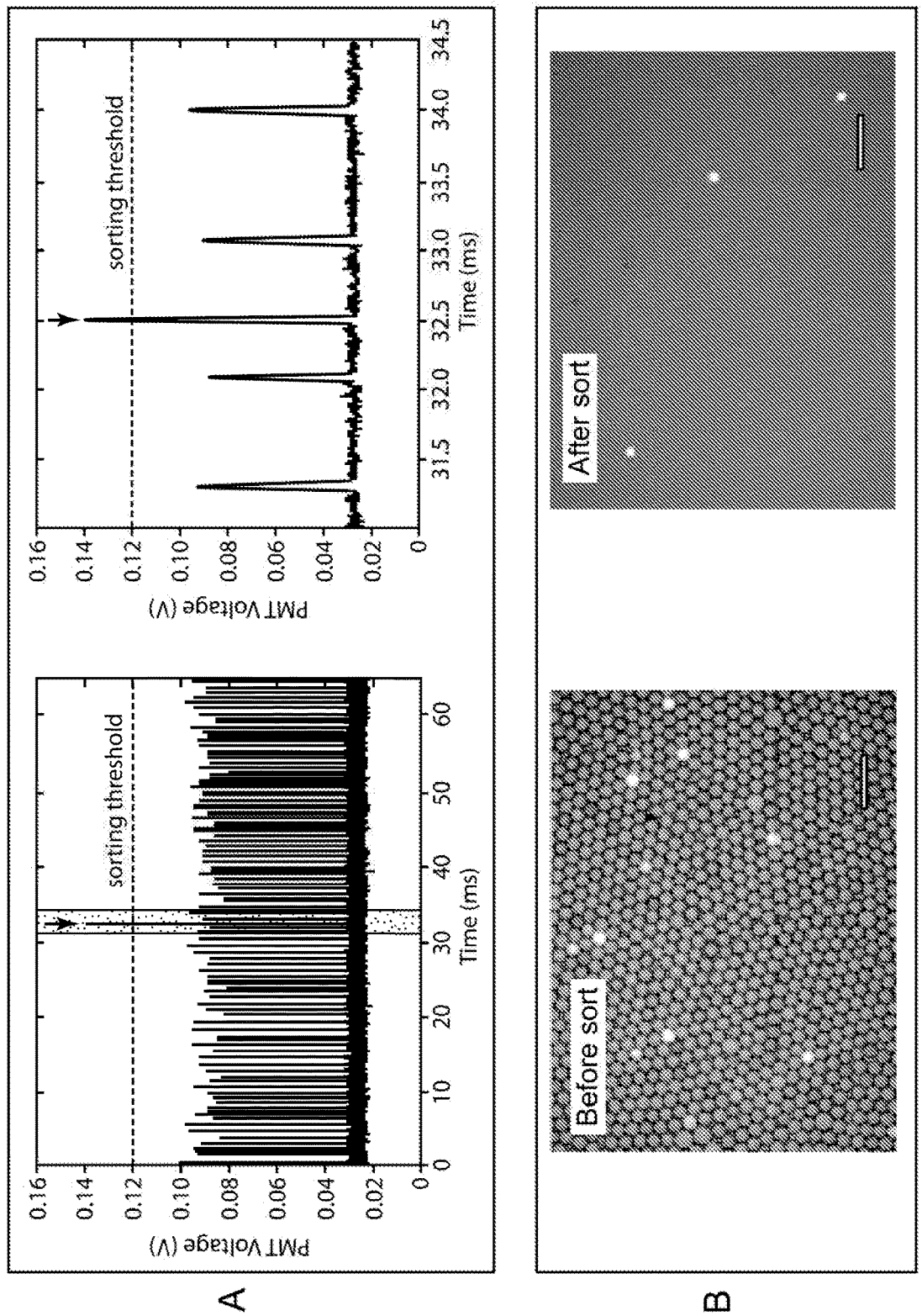
FIG. 68, Panels a-b, depicts droplet detection and sorting of drops according to certain embodiments.

Upon injection into the device, the thermocycled droplets are close packed and spaced by oil in the spacing junction, as shown in FIG. 67, left. Spacing ensures that the droplets pass the detection region (FIG. 67, middle) one at a time, so that the fluorescence of each droplet can be measured individually. It also ensures that the droplets do not crowd the sorting junction (FIG. 67, right), which can result in droplet collisions that interfere with controlled sorting. After spacing, the droplets pass through the detection region (FIG. 67, middle) and pass through a focused laser beam; the laser excites the fluorescent dyes in the droplets, causing them to emit light in proportion to the amount of cleaved TaqMan probes they contain. Droplets that underwent successful TaqMan amplification emit bright fluorescent light, while those that did not appear dim. The fluorescent light is captured by the objective of a microscope, filtered through dichroic mirrors and bandpass filters, and focused onto the sensor of a photomultiplier tube (PMT). The PMT outputs a voltage proportional to the intensity of the fluorescent light. The oil surrounding each droplet is not fluorescent; hence, when a droplet passes through the detection laser, the PMT records a peak as a function of time, as shown in FIG. 68, Panel a; each peak in the time trace corresponds to a distinct droplet. The amplitude of a given peak is proportional to the intensity of the droplet, allowing bright TaqMan positive droplets to be differentiated from dim TaqMan negative droplets, as illustrated by the bright droplet at t=32.5 ms.

To recover the bright droplets, a threshold voltage of 0.12 was set; this value varies between runs depending on the focusing optics and PMT gains and cleanly distinguishes between positive and negative droplets, as shown in FIG. 68, Panel a. Above this value, the computer is instructed to sort the droplet, which it does by outputting an alternating current (AC) pulse that is amplified to 1500 V and applied to a conducting aqueous electrode in the sorting junction, as illustrated in FIG. 67, middle. Energizing the electrode generates an electric field that polarizes the droplet in the sorting junction; this produces a dielectrophoretic attraction that pulls the droplet towards the electrode, deflecting it into streamlines that carry it into the collection channel. When the electrode is not energized, the geometry of the sorting junction is designed so that the droplet follows streamlines that carry it into the waste channel. By selectively energizing the electrodes based on the measured fluorescence of the droplets, TaqMan positive droplets were recovered and the negative droplets discarded, as shown in the images in FIG. 68, Panel b.

Sequence Verification of Sorted Genomes

Epifluorescence microscopy images (FIG. 68, Panel b) demonstrate that the dielectrophoretic sorter accurately sorts the bright from the dim drops. To validate that PACS enables accurate single cell sorting based on nucleic acid sequences, genomic DNA was recovered from the positively sorted droplets for Sanger sequencing. The sorted droplets were chemically ruptured with the addition of chloroform and application of mechanical shear, and the microbial genomes dispersed into aqueous buffer. The K168A cell line has a double amino acid mutation of "AAA" encoding lysine to "GCA" encoding alanine, as seen in FIG. 69, Panel a. Since errors in the PCR preparation or the Sanger sequencing are rare, the above provides a high confidence read out with which to validate the PACS sorting. Two mixed ratios of the ATolA and TolA bacteria were tested, one where the mutant was present at 20% in the total population, and the other at 1%. For the 20% spike-in, 5 of 10 sequences before PACS were positive for the mutant, whereas 9 of 10 were positive after PACS, as shown in FIG. 69, Panel b. The high pre-PACS frequency of the mutant may be the result of random sampling variation, since only ten molecules were sequenced. Similarly, the 1% spike-in yielded no pre-PACS positives in the ten molecule sample, while the post-PACS library was 9 of 10. Thus, for both spike-in ratios, a reasonable number of mutants pre-PACS and mostly mutants post-PACS were observed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
    obtaining a heterogeneous sample comprising nucleic acids;
    encapsulating, in a plurality of microdroplets, one or more of the nucleic acids, nucleic acid synthesis reagents, and at least one detection component, the plurality of microdroplets comprising an aqueous phase fluid in an immiscible phase carrier fluid;
    incubating the plurality of microdroplets under conditions that promote nucleic acid synthesis reagent activity;
    sorting the plurality of microdroplets based on identifying the at least one detection component, to produce sorted microdroplets; and
    analyzing at least one unamplified nucleic acid in at least one sorted microdroplet of the sorted microdroplets.

2. The method of claim 1, further comprising lysing a cell to release the nucleic acids prior to encapsulating the nucleic acid synthesis reagent and detection component to the plurality of microdroplets.

3. The method of claim 1, wherein analyzing comprises analyzing epigenetic marks.

4. The method of claim 1, wherein identifying the at least one detection component indicates presence of a sequence biomarker.

5. The method of claim 1, wherein the at least one detection component is a fluorescent detection component.

6. The method of claim 5, wherein the fluorescent detection component hybridizes with a mutation of interest in nucleic acids encapsulated in the plurality of microdroplets.

7. The method of claim 5, wherein the fluorescent detection component is a fluorescent bead comprising a nucleotide sequence capable of hybridizing with a capture sequence associated with a mutation of interest in nucleic acids encapsulated in the plurality of microdroplets.

8. The method of claim 1, wherein sorting comprises sorting the plurality of microdroplets via flow cytometry.

9. The method of claim 1, further comprising pooling target nucleic acids from the sorted microdroplets to provide an enriched pool of target nucleic acids.

10. A method comprising:
- encapsulating, in at least one microdroplet of a plurality of microdroplets, a nucleic acid and a nucleic acid synthesis reagent, the plurality of microdroplets comprising an aqueous phase fluid in an immiscible phase carrier fluid;
- introducing a detection component into the at least one microdroplet;
- incubating the plurality of microdroplets under conditions that promote nucleic acid synthesis reagent activity using the at least one nucleic acid and the at least one nucleic acid synthesis reagent;
- sorting the plurality of microdroplets comprising the at least one microdroplet based on identifying the at least one detection component; and
- analyzing at least one unamplified nucleic acid from the at least one sorted microdroplet of the sorted plurality of microdroplets.

11. The method of claim 10, further comprising lysing a cell to release the nucleic acid prior to encapsulating the nucleic acid synthesis reagent into the at least one microdroplet.

12. The method of claim 10, wherein analyzing comprises analyzing epigenetic marks.

13. The method of claim 10, wherein identifying the at least one detection component indicates presence of a sequence biomarker.

14. The method of claim 10, wherein the at least one detection component is a fluorescent detection component.

15. The method of claim 14, wherein the fluorescent detection component hybridizes with a mutation of interest in nucleic acids encapsulated in the plurality of microdroplets.

16. The method of claim 14, wherein the fluorescent detection component is a fluorescent bead comprising a nucleotide sequence capable of hybridizing with a capture sequence associated with a mutation of interest in nucleic acids encapsulated in the plurality of microdroplets.

17. The method of claim 10, wherein sorting comprises sorting the plurality of microdroplets via flow cytometry.

18. The method of claim 10, further comprising pooling target nucleic acids from the sorted microdroplets to provide an enriched pool of target nucleic acids.

19. The method of claim 18, wherein analyzing at least one unamplified nucleic acid comprises sequencing one or more target nucleic acids.

20. A method of enriching nucleic acids, the method comprising:
- encapsulating, in at least one microdroplet of a plurality of microdroplets, at least one nucleic acid and at least one nucleic acid synthesis reagent, the plurality of microdroplets comprising an aqueous phase fluid in an immiscible phase carrier fluid;
- introducing a detection component into the at least one microdroplet;
- incubating the plurality of microdroplets under conditions that promote nucleic acid synthesis reagent activity;
- positioning the plurality of microdroplets in an aqueous phase carrier fluid to provide a plurality of aqueous phase-in-immiscible phase-in aqueous phase microdroplets; and
- sorting the plurality of aqueous phase-in-immiscible phase-in aqueous phase microdroplets based on identifying the at least one detection component, wherein identification of the detection component indicates the presence of nucleic acid amplification products; and
- analyzing at least one unamplified nucleic acid in at least one sorted microdroplet of the sorted microdroplets.

* * * * *